United States Patent
Shah et al.

(10) Patent No.: US 12,371,673 B2
(45) Date of Patent: *Jul. 29, 2025

(54) ALDEHYDE DEHYDROGENASE VARIANTS AND METHODS OF USING SAME

(71) Applicant: Genomatica, Inc., San Diego, CA (US)

(72) Inventors: Amit Shah, San Diego, CA (US); Joseph Warner, Oceanside, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/191,774

(22) Filed: Mar. 28, 2023

(65) Prior Publication Data
US 2023/0416698 A1 Dec. 28, 2023

Related U.S. Application Data

(63) Continuation of application No. 17/280,181, filed as application No. PCT/US2019/052829 on Sep. 25, 2019, now Pat. No. 11,634,692.

(60) Provisional application No. 62/740,830, filed on Oct. 3, 2018, provisional application No. 62/737,053, filed on Sep. 26, 2018.

(51) Int. Cl.
| | |
|---|---|
| C12N 9/02 | (2006.01) |
| C12N 15/90 | (2006.01) |
| C12P 7/04 | (2006.01) |
| C12P 7/62 | (2022.01) |
| C12P 13/02 | (2006.01) |

(52) U.S. Cl.
CPC ........... *C12N 9/0008* (2013.01); *C12N 15/90* (2013.01); *C12P 7/04* (2013.01); *C12P 7/62* (2013.01); *C12P 13/02* (2013.01); *C12Y 102/01003* (2013.01)

(58) Field of Classification Search
None
See application file for complete search history.

(56) References Cited

U.S. PATENT DOCUMENTS

| | | | |
|---|---|---|---|
| 7,127,379 B2 | 10/2006 | Palsson et al. | |
| 7,135,315 B2 * | 11/2006 | Hoshino | C12P 7/60 435/254.2 |
| 7,858,350 B2 | 12/2010 | Burk et al. | |
| 8,067,214 B2 | 11/2011 | Burk et al. | |
| 8,129,169 B2 | 3/2012 | Van Dien et al. | |
| 8,377,666 B2 | 2/2013 | Haselbeck et al. | |
| 9,017,983 B2 | 4/2015 | Burgard et al. | |
| 2002/0012939 A1 | 1/2002 | Palsson | |
| 2002/0168654 A1 | 11/2002 | Maranas et al. | |
| 2003/0059792 A1 | 3/2003 | Palsson et al. | |
| 2003/0224363 A1 | 12/2003 | Park et al. | |
| 2003/0233218 A1 | 12/2003 | Schilling | |
| 2004/0009466 A1 | 1/2004 | Maranas et al. | |
| 2004/0029149 A1 | 2/2004 | Palsson et al. | |
| 2004/0072723 A1 | 4/2004 | Palsson et al. | |
| 2009/0047719 A1 | 2/2009 | Burgard et al. | |
| 2012/0021478 A1 | 1/2012 | Osterhout et al. | |
| 2013/0029381 A1 | 1/2013 | Haselbeck et al. | |
| 2013/0066035 A1 | 3/2013 | Burgard et al. | |
| 2014/0030779 A1 | 1/2014 | Pharkya et al. | |
| 2014/0371417 A1 | 12/2014 | Pharkya et al. | |
| 2015/0148513 A1 | 5/2015 | Pharkya et al. | |

FOREIGN PATENT DOCUMENTS

| | | |
|---|---|---|
| WO | WO 2002/055995 | 7/2002 |
| WO | WO 2003/106998 | 12/2003 |
| WO | WO 2008/115840 | 9/2008 |
| WO | WO 2009/094485 | 7/2009 |
| WO | WO 2010/030711 | 3/2010 |
| WO | WO 2010/127319 | 11/2010 |
| WO | WO 2010/141920 | 12/2010 |
| WO | WO 2011/047101 | 4/2011 |
| WO | WO 2012/018624 | 2/2012 |
| WO | WO 2012/177619 | 12/2012 |
| WO | WO 2013/036764 | 3/2013 |
| WO | WO 2013/150153 | 10/2013 |
| WO | WO 2013/184602 | 12/2013 |
| WO | WO 2014/176514 | 10/2014 |
| WO | WO 2014/190251 | 11/2014 |
| WO | WO 2014/200994 | 12/2014 |
| WO | WO 2018/183664 | 10/2018 |

OTHER PUBLICATIONS

Uniprot Accession No. A0A1I1SDY2, Nov. (Year: 2017).*
Altschul et al., "Basic local alignment search tool," *J. Mol. Biol.* 215(3):403-410 (1990).
Bergquist et al., "Degenerate oligonucleotide gene shuffling (DOGS) and random drift mutagenesis (RNDM): two complementary techniques for enzyme evolution," *Biomol. Eng.*, 22:63-72 (2005).
Bergquist et al., "Degenerate oligonucleotide gene shuffling," *Methods Mol. Biol.*, 352:191-204 (2007).
Burgard et al., "Minimal reaction sets for *Escherichia coli* metabolism under different growth requirements and uptake environments," *Biotechnol. Prog.*, 17(5):791-797 (2001).

(Continued)

*Primary Examiner* — Richard G Hutson
(74) *Attorney, Agent, or Firm* — Greenberg Traurig, LLP

(57) ABSTRACT

The invention provides polypeptides and encoding nucleic acids of aldehyde dehydrogenase variants. The invention also provides cells expressing aldehyde dehydrogenase variants. The invention further provides methods for producing 3-hydroxybutyraldehyde (3-HBal) and/or 1,3-butanediol (1,3-BDO), or an ester or amide thereof, comprising culturing cells expressing an aldehyde dehydrogenase variant or using lysates of such cells. The invention additional provides methods for producing 4-hydroxybutyraldehyde (4-HBal) and/or 1,4-butanediol (1,4-BDO), or an ester or amide thereof, comprising culturing cells expressing an aldehyde dehydrogenase variant or using lysates of such cells.

25 Claims, 9 Drawing Sheets

Specification includes a Sequence Listing.

(56) References Cited

OTHER PUBLICATIONS

Burgard et al., "Optknock: a bilevel programming framework for identifying gene knockout strategies for microbial strain optimization," *Biotechnol. Bioeng.*, 84(6):647-657 (2003).
Coco et al., "DNA shuffling method for generating highly recombined genes and evolved enzymes," *Nat. Biotechnol.*, 19(4):354-359 (2001).
Colonna et al., "Synthesis and radiocarbon evidence of terephthalate polyesters completely prepared from renewable resource," *Green Chem.*, 13:2543-2548 (2011).
Currie et al., "Authentication and dating of biomass components of industrial materials; links to sustainable technology," *Nucl. Instrum. Methods Phys. Res. B*, 172:281-287 (2000).
Database RefSeq [Online] Aug. 18, 2017, "aldehyde dehydrogenase EutE [Petroclostridium xylanilyticum]", XP093010778, retrieved from NCBI accession No. WP 094548529.1, Database accession No. WP 094548529.
Database RefSeq [Online] Feb. 27, 2017, "aldehyde dehydrogenase EutE [Clostridium puniceum]", retrieved from NCBI accession No. WP_077849585.1, Database accession No. WP 077849585.
Database RefSeq [Online] Jul. 28, 2017, "aldehyde dehydrogenase EutE [Clostridium gasigenes]", retrieved from NCBI accession No. WP_089969691.1, Database accession No. WP 089969691.
EBI Accession No. GSP: BBP76764, "*Mycobacterium smegmatis* alpha-ketoglutarate decarboxylase SEQ:439" (2014).
EBI Accession No. GSP: BBR45068, "L. brevis coenzyme-A-acylating propionaldehyde dehydrogenase, SEQ 48" (2015).
EBI Accession No. GSP: BFS48689, "Mutant *Clostridium saccharoperbutylacetinicum* ALD-1 protein #49" (2018).
EBI Accession No. Uniprot: A0A1H0T3I8, "Propionaldehyde dehydrogenase" (2017).
Fujii et al., "Error-prone rolling circle amplification: the simplest random mutagenesis protocol," *Nat. Protoc.*, 1(5):2493-2497 (2006).
Fujii et al., "One-step random mutagenesis by error-prone rolling circle amplification," *Nucleic Acids Res.*, 32(19):e145 (2004).
Gibbs et al., "Degenerate oligonucleotide gene shuffling (DOGS): a method for enhancing the frequency of recombination with family shuffling," *Gene*, 271(1):13-20 (2001).
Goswami et al., "Enzymatic strategies and biocatalysts for amide bond formation: tricks of the trade outside of the ribosome," *Mol. Biosyst.*, 11(2):338-353 (2015).
Hayes et al., "Combining computational and experimental screening for rapid optimization of protein properties," *Proc. Natl. Acad. Sci. USA*, 99(25):15926-15931 (2002).
Hibbert et al., "Directed evolution of biocatalytic processes," *Biomol. Eng.*, 22(1-3):11-19 (2005).
Hoffmeister et al., "Mitochondrial trans-2-enoyl-CoA reductase of wax ester fermentation from Euglena gracilis defines a new family of enzymes involved in lipid synthesis," J. Biol. Chem., 280(6):4329-4338 (2005).
Houghten, "General method for the rapid solid-phase synthesis of large numbers of peptides: specificity of antigen-antibody interaction at the level of individual amino acids," *Proc. Natl. Acad. Sci. USA*, 82(15):5131-5135 (1985).
Huisman et al., "Enzyme Evolution for Chemical Process Applications" *Biocatalysis in the Pharmaceutical and Biotechnology Industries*, Patel ed., CRC Press, pp. 717-742 (2007).
Karlen et al., "Absolute determination of the activity of two $C^{14}$ dating standards," *Arkiv Geofysik*, 4:465-471 (1968).
Kretz et al., "Gene site saturation mutagenesis: a comprehensive mutagenesis approach," *Methods Enzymol.*, 388:3-11 (2004).
Lee et al., "A new approach to directed gene evolution by recombined extension on truncated templates (RETT)," *J. Molec. Catalysis*, 26:119-129 (2003).
Lin et al., "Fed-batch culture of a metabolically engineered *Escherichia coli* strain designed for high-level succinate production and yield under aerobic conditions," Biotechnol. Bioeng., 90(6):775-779 (2005).
Low et al., "Mimicking somatic hypermutation: affinity maturation of antibodies displayed on bacteriophage using a bacterial mutator strain," *J. Mol. Biol.*, 260(3):359-368 (1996).
Lutz et al., "Creating multiple-crossover DNA libraries independent of sequence identity," *Proc. Natl. Acad. Sci. USA*, 98(20):11248-11253 (2001).
Lutz et al., "Rapid generation of incremental truncation libraries for protein engineering using alpha-phosphothioate nucleotides," *Nucleic Acids Res.*, 29(4):E16 (2001).
Mann, "An International Reference Material for Radiocarbon Dating," *Radiocarbon*, 25(2):519-527 (1983).
Merrifield, "Solid Phase Peptide Synthesis. I. The Synthesis of a Tetrapeptide," *J. Am. Chem. Soc.* 85:2149-2154 (1964).
Muller et al., "Nucleotide exchange and excision technology (NExT) DNA shuffling: a robust method for DNA fragmentation and directed evolution," *Nucleic Acids Res.*, 33(13):e117 (2005).
Ness et al., "Synthetic shuffling expands functional protein diversity by allowing amino acids to recombine independently," *Nat. Biotechnol.*, 20(12):1251-1255 (2002).
Ngo et al., *The Protein Folding Problem and Tertiary Structure Prediction*, Mertz et al. ed., Birkhauser, Boston, MA, pp. 433 and 492-495 (1994).
Ostermeier et al., "A combinatorial approach to hybrid enzymes independent of DNA homology," *Nat. Biotechnol.*, 17(12):1205-1209 (1999).
Ostermeier et al., "Combinatorial protein engineering by incremental truncation," *Proc. Natl. Acad. Sci. USA*, 96(7):3562-3567 (1999).
Otten et al., "Directed evolution: selecting today's biocatalysts," *Biomol. Eng.*, 22:1-9 (2005).
Pritchard et al., "A general model of error-prone PCR," *J. Theor. Biol.*, 234(4):497-509 (2005).
Rajpal et al., "A general method for greatly improving the affinity of antibodies by using combinatorial libraries," *Proc. Natl. Acad. Sci. USA*, 102(24):8466-8471 (2005).
Reetz et al., "Directed Evolution of an Enantioselective Enzyme through Combinatorial Multiple-Cassette Mutagenesis," *Angew. Chem. Int. Ed Engl.*, 40(19):3589-3591 (2001).
Reetz et al., "Iterative saturation mutagenesis (ISM) for rapid directed evolution of functional enzymes," *Nat. Protoc.*, 2(4):891-903 (2007).
Reetz et al., "Iterative saturation mutagenesis on the basis of B factors as a strategy for increasing protein thermostability," *Angew. Chem. Int. Ed Engl.*, 45(46):7745-7751 (2006).
Reidhaar-Olson et al., "Combinatorial cassette mutagenesis as a probe of the informational content of protein sequences," *Science*, 241(4861):53-57 (1988).
Reidhaar-Olson et al., "Random mutagenesis of protein sequences using oligonucleotide cassettes," *Methods Enzymol.*, 208:564-586 (1991).
Selifonova et al., "Rapid evolution of novel traits in microorganisms," *Appl. Environ. Microbiol.*, 67(8):3645-3649 (2001).
Sen et al., "Developments in directed evolution for improving enzyme functions," *Appl. Biochem. Biotechnol.*, 143(3):212-223 (2007).
Shao et al., "Random-priming in vitro recombination: an effective tool for directed evolution," *Nucleic Acids Res.*, 26(2):681-683 (1998).
Sieber et al., "Libraries of hybrid proteins from distantly related sequences," *Nat. Biotechnol.*, 19(5):456-460 (2001).
Stemmer, "DNA shuffling by random fragmentation and reassembly: in vitro recombination for molecular evolution," *Proc. Natl. Acad. Sci. USA*, 91(22):10747-10751 (1994).
Stemmer, "Rapid evolution of a protein in vitro by DNA shuffling," *Nature*, 370(6488):389-391 (1994).
Uniprot Accession No. A0A1I1SDY2, Nov. 22, 2017.
Volkov et al., "Random chimeragenesis by heteroduplex recombination," *Methods Enzymol.*, 328:456-463 (2000).
Volkov et al., "Recombination and chimeragenesis by in vitro heteroduplex formation and in vivo repair," *Nucleic Acids Res.*, 27(18):e18 (1999).
Wong et al., "Sequence saturation mutagenesis (SeSaM): a novel method for directed evolution," *Nucleic Acids Res.*, 32(3):e26 (2004).
Wong et al., "Sequence saturation mutagenesis with tunable mutation frequencies," *Anal. Biochem.*, 341(1):187-189 (2005).

(56) References Cited

OTHER PUBLICATIONS

Wong et al., "Transversion-enriched sequence saturation mutagenesis (SeSaM-Tv+): a random mutagenesis method with consecutive nucleotide exchanges that complements the bias of error-prone PCR," *Biotechnol. J.*, 3(1):74-82 (2008).
Zhao et al., "Molecular evolution by staggered extension process (StEP) in vitro recombination," *Nat. Biotechnol.*, 16(3):258-261 (1998).
U.S. Appl. No. 14/262,461, 2014/0371417, filed Apr. 25, 2014, Microorganisms and Methods for Production of 4-Hydroxybutyrate, 1,4-Butanediol and Related Compounds.
U.S. Appl. No. 15/191,421, 2017/0183694, filed Jun. 23, 2016, Paul J Holland, Microorganisms and Methods for Production of 4-Hydroxybutyrate, 1,4-Butanediol and Related Compounds.
U.S. Appl. No. 16/499,531, 2020/0040312, filed Sep. 30, 2019, Aldehyde Dehydrogenase Variants and Methods of Use, U.S. Pat. No. 11,299,716
U.S. Appl. No. 17/697,504, 2022/0325254, filed Mar. 17, 2022, Aldehyde Dehydrogenase Variants and Methods of Use.

\* cited by examiner

```
ALD-1    1   ------MIKDTLVSITKDLKLKTNVENANLKNYKDDSSCFGVFENVENAISNAVHAQKILSLHYTKEQREKIITEIRKAA
ALD-2    1   ---MNTENIEQAIRKILSEELSNPQSSTATNTTVPGKN----GIFKTVNEAIAATKAAQENYA-DQPISVRNKVIDAIREGF
ALD-3    1   MTVNEQLVQDIIKNVVASMQL-TQTNKTEL----------GVFDDMNQAIEAAKEAQLVVK-KMSMDQREKIISAIRKKT

ALD-1   75   LENKEILATMILEETHMGRYEDKILKHELVAKYTPGTEDLTTAWSGDNGLTVVEMSPYGVIGAITPSTNPTETVICNSI
ALD-2   75   RPYIEDMAKRIHDETGMGTVSAKIAKLNNALYNTPGPEILQPEAETGDGGLVMYEYAPFGVIGAVGPSTNFSETVIANAI
ALD-3   69   IEHAETLARMAVEETGMGNVGHKILKHQLVAEKFPGTEDITTAWSGDRGLFLVEMGPFGVIGAITPCTNPSETIICNTI

ALD-1  155   GMIAAGNTVVFNGHPGAKKCVAFAVEMINKAIISC-GGPENLVTTIKNPTMDSLDAIIKHPSIKLLCGTGGPGMVKTLLN
ALD-2  155   MMLAGGNTLFFGAHPGAKNITRWTIEKLNELVADATGLHNLVV-SLETPSIESVQEVMQHPDVAMLSITGGPAVVHQALI
ALD-3  149   GMLAGGNTVVFNPHPAAIKTSNFAVQLINEASLSA-GGPVNIACSVRKPTLDSSKIMMSHQDIPLIAATGGPGVVTAVLQ

ALD-1  234   SGKKAIGAGAGNPPVIVDDTADIEKAGKSIIEGCSFDNNLPCIAEKEVFVFENVADDLISNMLIKNNAV-IINEDQVSKLI
ALD-2  234   SGKKAVGAGAGNPPAMVDATANIALAAHNIVDSAAFDNNILCTAEKEVVVEAAVKDELIMRMQQEGAFLVTDSADIEKLA
ALD-3  228   SGKRGIGAGAGNPPVLVDETADIRKAAEDIINGCTFDNNLPCIAEKEVVAIDAIANELMNYMVKEQGCYAITKEQQERLT

ALD-1  313   DLVLQKNNETQEYSINKKWVGKDAKLFLDEIDVESPSSVKCIICEVSASHPFVMTELMMPILPIVRVKDIDEAIEYAKIA
ALD-2  314   QMTIGPKGAP-------DRKFVGKDATYILDQAGISYTGTPTLIILEAAKDHPLVTTEMLMPILPVVCCPDEDSVLATATEV
ALD-3  308   NLVITPKG-----LNRNCVGKDARTLLGMIGIDVPSNIRCIIFEGEKEHPLISEELMMPILGIVRAKSFDDAVEKAVWL

ALD-1  393   EQNRKHSAYIYSKNIDNLNRFEREIDTTIFVKNAKSFAGVGYEAE-------GFTFFTIAGSTGEGITSARNFTQRRCVLAG
ALD-2  389   EGGLHHTASIHSENLPHINKAAHRLNTSIFVVNGPTYCGTGVATNGAHSGASALTIATPTGEGTATSKTYTRRRLNSPE
ALD-3  382   EHGNRHSAHIHSKNVDRITTYAKAIDTAILVKNAPSYAAIGFGGE-----GFCTFTIASRTGEGLTSASTFFTKRRPCVMSD

ALD-1
ALD-2  469   GFSLRTWEA     477
ALD-3  458   SLCIR-----    462
```

FIG. 3

```
ALD-1     1    M-------------------------------------IKDTLVSITKDLKLKTNVENANLKNYKDDSSCF----
SEQ 13    1    M-----------------------------------------SVNERMVQDI---------VQEVVAKM-------
SEQ 20    1    M-----------------------------------------PINENMVQEI---------VQEVMAKM-------
SEQ 24    1    MNDGQTAAAVAKVLEAYGVPADPSAAAPAPAAPVAPAAPTAGSVSEMIARGIAKASSDDQIAQIVAKVVGDYSAQAAKPA

ALD-1    35    ---------GVFENVENAISNAVHAQKILSLHYTKEQREKIITEIRKAALEN---KEILATMILEETHMGRYEDKIL
SEQ 13   20    QIASDVTGNHGVFQDMNAAIEAAKKTQKVA-RMSMDQREKIISNIRAKIKEH---AEIFARMGVQETGMGNVGHKIL
SEQ 20   20    QIADAPTGKHGIFKEMNDAIEAAKKSQLIVK-KMSMDQREKIITCIRKKIKEN---AEVMARMGVEETGMGNVGDKIL
SEQ 24   81    VVPGAAASTEAGDGVFDTMDAAVDAAVLAQQYL-LCSMTDRQRFVDGIREVILQKDTLELISRMAAEETGMGNYEHKLI

ALD-1   100    KHELVAKYTPGTEDLTTAWSGDNGLTVVEMSPYGVIGATTPSTNPTETVICNSIGMIAAGNTVVFNGHPGAKKCVAFAV
SEQ 13   94    KHQLVAEKTPGTEDIQTTAWSGDRGLTLIEMGPFGVIGAITPCTNPSETVLCNTIGMLAGGNTVFNPHPAAIKTSIYAV
SEQ 20   94    KHHLVADKTPGTEVITTTAWSGDRGLTLIEMGPFGVIGAITPCTNPSETILCNTMGMLAGGNTVFNPHPAAIKTSIYAI
SEQ 24  160    KNRLAAEKTPGTEDLTTEAFSGDDGLTLVEYSPFGAIGAVAPTTNPTETIICNSIGMLAAGNSVIFSPHPRATKVSLLTV

ALD-1   180    EMINKAIISCGGPENLVTTIKNPTMDSLDAIIKHPSIKLLCGTGGPGMVKTLLNSGKKAIGAGAGNPPVIVDDTADIEKA
SEQ 13  174    NLINEASLEAGGPDNIACTVENPTLESSNIMMKHKDIPLIAATGGPGVVTAVLSSGKRGIGAGAGNPPALVDETADIRKA
SEQ 20  174    NLLNEASLESGGPDNIAVTVEKPTLETSNVMMKHKDIPLIAATGGPGVVTAVLSSGKRGIGAGAGNPPALVDETADIRKA
SEQ 24  240    KLINQKLACLGAPANLVVTVSKPSVENTNAMMAHPKIRMLVATGGPGIVKAVMSTGKKAIGAGAGNPPVVVDETADIEKA

ALD-1   260    GKSIIEGCSFDNNLPCIAEKEVFVFEENVADDLISNMLKNNAV-IINEDQVSKLIDLVLQKNNETQEYSINKKWVGKDAKL
SEQ 13  254    AEDIVNGCTFDNNLPCIAEKEIVAVDSIADELMHYMISEQGCYLASKEEQDALTEVVLKG--GR------LNRKCVGRDAKT
SEQ 20  254    ATDIVNGCTFDNNLPCIAEKEIVAVSSIVDELMHYLVTENDCYLASKEEQDKLTEVVLAG--GK------LNRKCVGRDART
SEQ 24  320    ALDEINGCSFDNNLPCIAEKEIIAVAQIADYLIFSMKKQGAYQITDPAVLRKLQDLVLTAKGG------PQTSCVGKSAVW

ALD-1   339    FLDEIDVESPSSVKCIICEVSASHPFVMTELMMPILPIVRKDIDEAIEYAKIAEQNRKHSAYIYSKNIDNLNRFEREID
SEQ 13  328    LLGMIGVTVPDNIRCITFEGPKEHPLIAEELMMPILGVVRAKDFDDAVEQAVWLEHGNRHSAHIHSKNVDNITKYAKAID
SEQ 20  328    LLSMIGVNAPANIRCIVFEGPKEHPLITTELMMPILGVVRARDEFDDAVEQAVWLEHGNRHSAHIHSKNIDNITKYAKAID
SEQ 24  395    LLNKIGIEVDSSVKVILMEVPKEHPFVQEELMMPILPLVRVSDVDEAIAVAIEVEHGNRHTAIMHSTNVRKLTKMAKLIQ

ALD-1   419    TTIFVRNAKSFAGVGYEAEGFTTFTIAGSTGEGITSARNFTRQRPCVLAG-------                        468
SEQ 13  408    TAILVKNGPSYAAIGFGEGEFCTFTIASRTGEGLTSASAFTKRRRCVMCDSLCIR                          462
SEQ 20  408    TAILVKNAPSYAALGFGEGYCTFTIASRTGEGLTCASTFTKRRRCVMADSLCIR                           462
SEQ 24  475    TTIFVKNGPSYAGLGVGGEGYTTFTIAGPTGEGLTSAKSFARKRKCVMVEALNIR                          529
```

FIG. 4A

```
ALD-1     1    MIKD-TLVS----I-TKDLKLKTNVENANLKNYKDDSSCFGVFENVENAISNAVHAQKILSLHYTKEQREKITTEIRKAA
SEQ 30    1    MNNN-LFVS------PETKDLKLRTNVENLKFKGCEGGSTYIGVFENAETAIDEAVNAQKRLSLYYTKEQRERIITEIRKVT
SEQ 33    1    MERNLSVLS----Q-TNDLKITKRTEGDKSNNKE---SYLGVFKKVENAITKAIYAQKKLSLYYTKEDRERIIKSIRKAT
SEQ 37    1    MDVDVVLVEKLVRQAIEEVKNKNLLNLDKFESVKN------YGIFGTMDAAVEASFVAQKQL-LNASMTDKQKYVDTIKATI

ALD-1    75    L---ENKEILATMILEETHMGRYEDKILKHELVAKYTPGTEDLTTAWSGDNGLTVVEMSPYGVIGAITPSTNPTETVICN
SEQ 30   76    L---KNKEILAQMILEETHMGRYEDKILKHELVAKYTPGTEDLATTAWSGDNGLTVVEMSPYGVIGAITPSTNPTETIICN
SEQ 33   73    L---ENKEILAKMIVDETHMGRYEDKILKHELVAKYTPGTEDLITTAWSGDQGLTLVEMSPYGVIGAITPSTNPTETVICN
SEQ 37   76    LKKENLELISRMSVEETEIGKYEHKLIKNRVAAEKTPGIEDLTTEAMTGDNGLTLVEYCPFGVIGAITPTNPTETIICN

ALD-1   153    SIGMIAAGNTVVFNGHPGAKKCVAFAVEMINKAISCGGPENLVTTIKNPTMDSLDAIIKHPSIKLLCGTGGPMVKTLL
SEQ 30  154    SIGMIASGNAVVFNGHPGAKKCVAFAVDMINRAIISCGGPRNLVTAIKNPTMESLDAIIKHPAIKLLCGTGGPMVKTLL
SEQ 33  151    SIGMIAAGDSVVFNGHPGAKKCVAFAVDMINKAVIREGGPENLVTTVENPTMESLNVIMKHPYIKLLCGTGGPGLIKTLL
SEQ 37  156    SISMIAGGNTVVFSPHPRAKNVSIKLVTMLNKALEEAGAPDNLIATVKEPSIENTNIMMEHPKIRMLVATGGPAIVNKVM

ALD-1   233    NSGKKAIGAGAGNPPVIVDDTADIEKAGKSIIEGCSFDNNLPCIAEKEVFVFENVADDLISNMLKNNAVIINE-DQVSKL
SEQ 30  234    SSGKKSIGAGAGNPPVIVDDTADIEKAGKSIIEGCSFDNNLPCIAEKEVFVFENVADDLIKNMLKNNAVIINK-DQVSRL
SEQ 33  231    NSGKKAIGAGAGNPPVIVDDSADIDKAAKNIIEGCSFDNNLPCIAEKEVFVFENVANDLIQNMIKNNAVLIENE-NQVSKL
SEQ 37  236    STGKKAIGAGAGNPPVVVDETADIVNGCSFDNNVPCIAEKEVFAVDQVCDYLIHYMKLNGAYEIKDRDLIQKL

ALD-1   312    IDLV-LQKNNETQEYSINKKWVGKDAKLFLDEIDVESPSSVKCIICEVSASHPFVMTELMPILPIVRVKDIDEAIEYAK
SEQ 30  313    VNLV-LQKNNETSEYTINKKWVGKDAKLFLDEIDVESSSDVRCIICEVDADHPFVMTELMPILPIVRVKDIDEAIKYAK
SEQ 33  310    LDLVLLERKDETLEYAINKKWVGKDAKLFLDKIGIKASDNVRCIICEVDANHPFVMTELMPILPIVRVKDVDEAIECAK
SEQ 37  316    LDLVITNENGGPKV------SFVGKRSAPYILNKLGISVDENIKVIIMEVEKNHHFVLEEMMPILPIVRTKDVDEAIECAY

ALD-1   391    IAEQNRKHSAYIYSKNIDNLNRFEREIDTTIFVKNAKSFAGVGYEAEGFTTFTIAGSTGEGITSARNFTRQRRCVLAG--
SEQ 30  392    IAEQNRKHSAYIYSKNIENLNRFEKEIDTTIFVKNAKSFAGVGYGAEGFTTFTIAGCTGEGITSARNFTRQRRCVFVG--
SEQ 33  390    TAEQRKRHSAYMYSKNIDNLNRFEKEIDTTIFVKNAKSFAGVGFGAEGFTTFTIAGPTGEGITSARNFTRQRRCVLAG--
SEQ 37  390    VAEHGNRHTAIMHSKNVDKLTKMARLLETTIFVKNSPSYAGIGVGGEGTTTFTIAGPTGEGLTTARSFCRKRRCVMVDAF

ALD-1          ----
SEQ 30         ----
SEQ 33         ----
SEQ 37   470   NIR
```

FIG. 4B

```
ALD-1    1    MIKDTLVSITKDLKLKTNVENANLKNYKDDSSCFGVFENVENAISNAVHAQKILSLHYTKEQREKIITEIRKAALENKEI
SEQ 38   1    MIKDTLVSITKDLKLKTNVENANLKNYKDDSSCFGVFENVENAISNAVHAQKILSLHYTKEQREKIITEIRKAALENKEI
SEQ 40   1    MIKDTLVSVTKDLKLKTNVENTNLKNYKDNSSCFGVFENAENAISNAVHAQKILSLHYTKEQREKINEIRKAALENKEV
SEQ 44   1    MNKDTLIPTTKDLRKVTNGENINLKNYKDNSSCFGVFENVENAISSAVHAQKILSLHYTKEQREKIITEIRKAALQNKEV

ALD-1    81   LATMILEETHMGRYEDKILKHELVAKYTPGTEDLTTAWSGDNGLTVVEMSPYGVIGAITPSTNPTETVICNSIGMIAAG
SEQ 38   81   LATMILEETHMGRYEDKILKHELVAKYTPGTEDLTTAWSGDNGLTVVEMSPYGVIGAITPSTNPTETVICNSIGMIAAG
SEQ 40   81   LATMILEETHMGRYEDKILKHELVAKYTPGTEDLTTAWSGDNGLTVVEMSPYGVIGAITPSTNPTETVLCNSIGMIAAG
SEQ 44   81   LATMILEETHMGRYEDKILKHELVAKYTPGTEDLTTAWSGDNGLTVVEMSPYGVIGAITPSTNPTETVICNSIGMIAAG

ALD-1    161  NTVVFNGHPGAKKCVAFAVEMINKAIISCGGPENLVTTIKNPTMDSLDAIIKHPSIKLLCGTGGPGMVKTLLNSGKKAIG
SEQ 38   161  NTVVFNGHPGAKKCVAFAVEMINKAIISCGGPENLVTTIKNPTMDSLDAIIKHPSIKLLCGTGGPGMVKTLLNSGKKAIG
SEQ 40   161  NAVVFNGHPGAKKCVAFAVEMINKAIVSCGGPENLVTTIKNPTMESLNAIIKHPSIELLCGTGGPGMVKTLLNSGKKAIG
SEQ 44   161  NAVVFNGHPGAKKCVAFAVEMINKAIISCGGPENLVTTIKNPTMESLDAIIKHPSIKLLCGTGGPGMVKTLLNSGKKAIG

ALD-1    241  AGAGNPPVIVDDTADIEKAGKSIIEGCSFDNNLPCIAEKEVFVFENVADDLISNMLKNNAVIINEDQVSKLIDLVLQKNN
SEQ 38   241  AGAGNPPVIVDDTADIEKAGKSIIEGCSFDNNLPCIAEKEVFVFENVADDLISNMLKNNAVIINEDQVSKLIDLVLQKNN
SEQ 40   241  AGAGNPPVIVDDTADIEKAGKSIIEGCSFDNNLPCIAEKEVFVFENIADDLISNMLKNNAVIINEDQVSKLIDLVLQKNN
SEQ 44   241  AGAGNPPVIVDDTADIEKAGRSIIEGCSFDNNLPCIAEKEVFVFENVADDLISNMLKNNAVIINEDQISKLIDLVLQKNN

ALD-1    321  ETQEYSINKKWVGKDAKLFLDEIDVESPSSVKCIICEVSASHPFVMTELMPILPIVRVKDIDEAIEYAKIAEQNRKHSA
SEQ 38   321  ETQEYSINKKWVGKDAKLFLDEIDVESPSSVKCIICEVSASHPFVMTELMPILPIVRVKDIDEAIEYAKIAEQNRKHSA
SEQ 40   321  ETQEYSINKKWVGKDAKLFLDEIDVESPSNVKCIICEVNANHPFVMTELMPILPIVRVKDIDEAIEYAKIAEQNRKHSA
SEQ 44   321  ETQEYFINKKWVGKDAKLFLDEIDIESPSNVKCIICEVNENHPFVMTELMPILPIVRVKDIDEAIRYAKIAEYNRKHSA

ALD-1    401  YIYSKNIDNLNRFEREIDTTIFVKNAKSFAGVGYEAEGFTTFTIAGSTGEGITSARNFTRQRRCVLAG    468
SEQ 38   401  YIYSKNIDNLNRFEREIDTTIFVKNAKSFAGVGYEAEGFTTFTIAGSTGEGITSARNFTRQRRCVLAG    468
SEQ 40   401  YIYSKNIDNLNRFEREIDTTIFVKNAKSFAGVGYEAEGFTTFTIAGSTGEGITSARNFTRQRRCVLAG    468
SEQ 44   401  YIYSKNIDNLNRFEREIDTTIFVKNAKSFAGVGYEAEGFTTFTIAGSTGEGITSARNFTRQRRCVLAG    468
```

FIG. 4C

ALDEHYDE DEHYDROGENASE VARIANTS AND METHODS OF USING SAME

CROSS-REFERENCE TO RELATED APPLICATIONS

This application is a continuation of U.S. application Ser. No. 17/280,181, filed Mar. 25, 2021, which is a U.S. National Stage Application under 35 U.S.C. § 371 of International Patent Application No. PCT/US2019/052829, filed Sep. 25, 2019, which claims the benefit of U.S. Provisional Application No. 62/737,053, filed Sep. 26, 2018, and the benefit of U.S. Provisional Application No. 62/740,830, filed Oct. 3, 2018, the entire contents of each of which are incorporated herein by reference.

Reference is made to the following provisional and international applications, which are incorporated herein by reference in their entireties: (1) U.S. Provisional Application No. 62/480,194 entitled "ALDEHYDE DEHYDROGENASE VARIANTS AND METHODS OF USE," filed Mar. 31, 2017; (2) U.S. Provisional Application No. 62/480,208 entitled "3-HYDROXYBUTYRYL-COA DEHYDROGENASE VARIANTS AND METHODS OF USE," filed Mar. 31, 2017; (3) U.S. Provisional Application No. 62/480,270 entitled "PROCESS AND SYSTEMS FOR OBTAINING 1,3-BUTANEDIOL FROM FERMENTATION BROTHS," filed Mar. 31, 2017; (4) International Patent Application No. PCT/US2018/025122 entitled "ALDEHYDE DEHYDROGENASE VARIANTS AND METHODS OF USE," filed Mar. 29, 2018; (5) International Patent Application No. PCT/US2018/025086 entitled "3-HYDROXYBUTYRYL-COA DEHYDROGENASE VARIANTS AND METHODS OF USE," filed Mar. 29, 2018; and (6) International Patent Application No. PCT/US2018/025068 entitled, "PROCESS AND SYSTEMS FOR OBTAINING 1,3-BUTANEDIOL FROM FERMENTATION BROTHS," filed on Mar. 29, 2018.

INCORPORATION BY REFERENCE OF SEQUENCE LISTING

The instant application contains a Sequence Listing, which has been submitted via Patent Center. The Sequence Listing titled 199683-129001_US_SL.xml, which was created on May 3, 2023 and is 173,073 bytes in size, is hereby incorporated by reference in its entirety.

FIELD

The present invention relates generally to organisms engineered to produce desired products, engineered enzymes that facilitate production of a desired product, and more specifically to enzymes and cells that produce desired products such as 3-hydroxybutyraldehyde, 1,3-butanediol, 4-hydroxybutyraldehyde, 1,4-butanediol, and related products and products derived therefrom.

BACKGROUND OF THE INVENTION

Various commodity chemicals are used to make desired products for commercial use. Many of the commodity chemicals are derived from petroleum. Such commodity chemicals have various uses, including use as solvents, resins, polymer precursors, and specialty chemicals. Desired commodity chemicals include 4-carbon molecules such as 1,4-butanediol and 1,3-butanediol, upstream precursors and downstream products. It is desirable to develop methods for production of commodity chemicals to provide renewable sources for petroleum-based products and to provide less energy- and capital-intensive processes.

Thus, there exists a need for methods that facilitate production of desired products. The present invention satisfies this need and provides related advantages as well.

SUMMARY OF INVENTION

The invention provides polypeptides and encoding nucleic acids of aldehyde dehydrogenase variants. The invention also provides cells expressing aldehyde dehydrogenase variants. The invention further provides methods for producing 3-hydroxybutyraldehyde (3-HBal) and/or 1,3-butanediol (1,3-BDO), or an ester or amide thereof, comprising culturing cells expressing an aldehyde dehydrogenase variant or using lysates of such cells. The invention additional provides methods for producing 4-hydroxybutyraldehyde (4-HBal) and/or 1,4-butanediol (1,4-BDO), or an ester or amide thereof, comprising culturing cells expressing an aldehyde dehydrogenase variant or using lysates of such cells.

BRIEF DESCRIPTION OF THE DRAWINGS

FIG. 1 shows pathways from acetoacetyl-CoA to 1,3-butanediol. The enzymes are: (A) acetoacetyl-CoA reductase (CoA-dependent, aldehyde forming); (B) 3-oxobutyraldehyde reductase (ketone reducing); (C) 3-hydroxybutyraldehyde reductase, also referred to herein as 1,3-butanediol dehydrogenase; (D) acetoacetyl-CoA reductase (CoA-dependent, alcohol forming); (E) 3-oxobutyraldehyde reductase (aldehyde reducing); (F) 4-hydroxy, 2-butanone reductase; (G) acetoacetyl-CoA reductase (ketone reducing); (H) 3-hydroxybutyryl-CoA reductase (aldehyde forming), also referred to herein as 3-hydroxybutyraldehyde dehydrogenase; and (I) 3-hydroxybutyryl-CoA reductase (alcohol forming).

FIG. 3 shows a sequence alignment of ALD-1, ALD-2 and ALD-3. The sequences correspond to SEQ ID NOS:1, 2 and 3, respectively. Underlined in the figure are 2 loop regions, the first designated A, the second B, both involved in substrate specificity and enantiomer specificity as determined herein. Loop A in ALD-1 is sequence LQKNNETQEYSINKKWVGKD (SEQ ID NO:124), in ALD-2 is sequence IGPKGAPDRKFVGKD (SEQ ID NO:125), and in ALD-3 is sequence IIPKGLNRNCVGKD (SEQ ID NO:126). Loop B in ALD-1 is sequence SFAGVGYEAE- GFTTFTIA (SEQ ID NO:127), in ALD-2 is sequence TYCGTGVATNGAHSGASALTIA (SEQ ID NO:128), and in ALD-3 is sequence SYAAIGFGGEGFCTFTIA (SEQ ID NO:129). The sequence and the length of the substrate specificity loop A and B from ALD-2 differ from those of ALD-1 and ALD-3; nevertheless the alignment shows sufficient conservation to facilitate identification of corresponding positions for substitution as described herein, and especially so if combined with 3D modeling as shown in FIG. 6. ALD-3 was used as the template for modeling of crystal structure; see FIG. 6 that shows the two loop regions interacting to affect substrate specificity and enantiomer specificity, especially when modified with exemplary substitutions as described herein. ALD-1 and ALD-3 are 51.9% identical. ALD-1 and ALD-2 are 35.9% identical. ALD-3 and ALD-2 are 40% identical. A consensus for Loop A based on alignment of ALD-1, ALD-2 and ALD-3 is IXPKG-----XXNRKXVGKD (SEQ ID NO:5). A consensus for Loop B based on alignment of ALD-1, ALD-2 and ALD-3 is SYAG-WOOCE----GFXTFTIA (SEQ ID NO:6). It is understood that the specifically identified amino acids in the consensus sequences are conserved residues, whereas the positions marked with "K" are variable, and can correspond to any amino acid, as desired and disclosed herein. It is further understood that "-----" can correspond to the presence or absence of a variable number of amino acid residues. An example of such a variable number of amino acid residues is shown in FIGS. 3 and 4A-4C. Further, it is understood that conserved residues in the consensus sequence can be substituted, for example, with conservative amino acids, as described herein (see, for example, FIGS. 4A-4C).

FIGS. 4A-4C show alignments of exemplary aldehyde deydrogenases (ALD), which representative alignments demonstrate identifying positions in ALDs that correspond to positions in the representative template ALD sequence where substitutions of the invention can be made. As in FIG. 3, underlined are 2 loop regions, the first designated A, the second B, both involved in substrate specificity and enantiomer specificity as determined herein. FIG. 4A shows an alignment of exemplary ALD sequences with a 40-55% cutoff compared to ALD-1. The sequences correspond to SEQ ID NOS: 1 (ALD-1), 13, 20 and 24 as indicated in FIG. 4A. FIG. 4B shows an alignment of exemplary ALD sequences with a 75-90% cutoff compared to ALD-1. The sequences correspond to SEQ ID NOS: 1 (ALD-1), 30, 33 and 37 as indicated in FIG. 4B. Loops A and B are underlined. FIG. 4C shows an alignment of exemplary ALD sequences with a 90% cutoff compared to ALD-1. The sequences correspond to SEQ ID NOS: 1 (ALD-1), 38, 40 and 44 as indicated in FIG. 4C. ALD-1 is 99%, 97%, and 95% identical to SEQ ID NOS: 38, 40 and 44, respectively. FIGS. 4A-4C demonstrate that corresponding positions for substitutions taught herein can be identified in ALDs that have at least 40% identity with ALD-1, especially the Loop A and B regions, and especially the very conserved Loop B region.

FIG. 5B shows the ratio of activity with the R to S form of 3-hydroxybutyraldehyde.

FIG. 6C shows the same orientation as 3-hydroxy-(R)-butyraldehyde (R3HB).

DETAILED DESCRIPTION OF THE INVENTION

Figure 1:
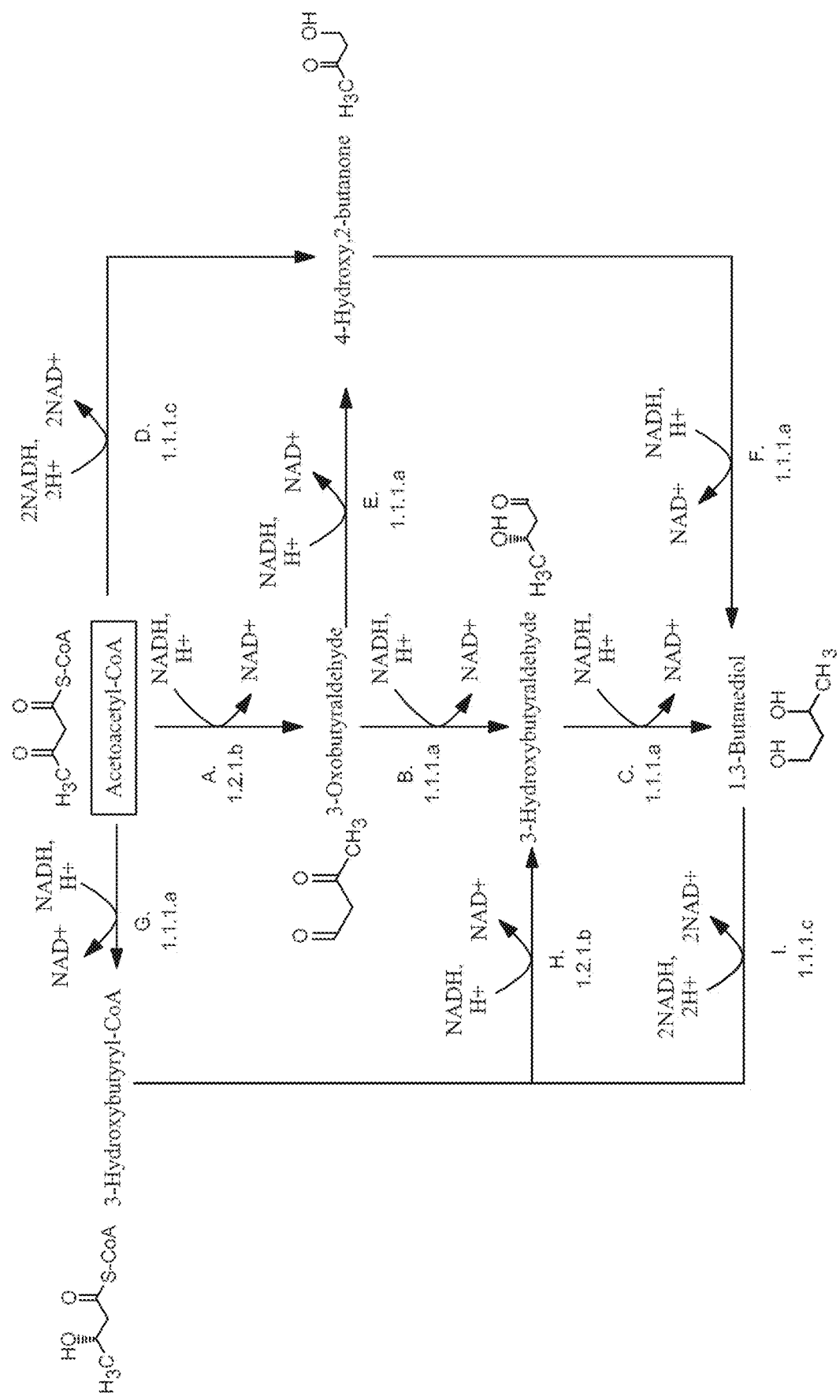
FIG. 1 shows an exemplary 1,3-butanediol (1,3-BDO) pathway that comprise an aldehyde dehydrogenase.

The invention relates to enzyme variants that have desirable properties and are useful for producing desired products. In a particular embodiment, the invention relates to aldehyde dehydrogenase variants, which are enzyme variants that have markedly different structural and/or functional characteristics compared to a wild type enzyme that occurs in nature. Thus, the aldehyde dehydrogenases of the invention or not naturally occurring enzymes. Such aldehyde dehydrogenase variants of the invention are useful in an engineered cell, such as a microbial organism, that has been engineered to produce a desired product. For example, as disclosed herein, a cell, such as a microbial organism, having a metabolic pathway can produce a desired product. An aldehyde dehydrogenase of the invention having desirable characteristics can be introduced into a cell, such as microbial organism, that has a metabolic pathway that uses an aldehyde dehydrogenase enzymatic activity to produce a desired product. Such aldehyde dehydrogenase variants are additionally useful as biocatalysts for carrying our desired reactions in vitro. Thus, the aldehyde dehydrogenase variants of the invention can be utilized in engineered cells, such as microbial organisms, to produce a desired product or as an in vitro biocatalyst to produce a desired product.

As used herein, the term "non-naturally occurring" when used in reference to a cell, a microbial organism or microorganism of the invention is intended to mean that the cell has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the cell's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a biosynthetic pathway for producing a desired product.

A metabolic modification refers to a biochemical reaction that is altered from its naturally occurring state. Therefore, non-naturally occurring cells can have genetic modifications to nucleic acids encoding metabolic polypeptides, or functional fragments thereof. Exemplary metabolic modifications are disclosed herein.

As used herein, the term "isolated" when used in reference to a cell or microbial organism is intended to mean a cell that is substantially free of at least one component as the referenced cell is found in nature, if such a cell is found in nature. The term includes a cell that is removed from some or all components as it is found in its natural environment. The term also includes a cell that is removed from some or all components as the cell is found in non-naturally occurring environments. Therefore, an isolated cell is partly or completely separated from other substances as it is found in nature or as it is grown, stored or subsisted in non-naturally occurring environments. Specific examples of isolated cells include partially pure cells, substantially pure cells and cells cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host cell. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the cell. When used in reference to a biosynthetic activity, the term refers to an activity that is introduced into the host reference organism. The source can be, for example, a homologous or heterologous encoding nucleic acid that expresses the referenced activity following introduction into the host cell. Therefore, the term "endogenous" refers to a referenced molecule or activity that is present in the host. Similarly, the term when used in reference to expression of an encoding nucleic acid refers to expression of an encoding nucleic acid contained within the cell. The term "heterologous" refers to a molecule or activity derived from a source other than the referenced species whereas "homologous" refers to a molecule or activity derived from the host cell. Accordingly, exogenous expression of an encoding nucleic acid of the invention can utilize either or both a heterologous or homologous encoding nucleic acid.

It is understood that when more than one exogenous nucleic acid is included in a cell that the more than one exogenous nucleic acids refers to the referenced encoding nucleic acid or biosynthetic activity, as discussed above. It is further understood, as disclosed herein, that such more than one exogenous nucleic acids can be introduced into the host cell on separate nucleic acid molecules, on polycistronic nucleic acid molecules, or a combination thereof, and still be considered as more than one exogenous nucleic acid. For example, as disclosed herein a cell can be engineered to express two or more exogenous nucleic acids encoding a desired enzyme or protein, such as a pathway enzyme or protein. In the case where two exogenous nucleic acids encoding a desired activity are introduced into a host cell, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

As used herein, the term "gene disruption," or grammatical equivalents thereof, is intended to mean a genetic alteration that renders the encoded gene product inactive or attenuated. The genetic alteration can be, for example, deletion of the entire gene, deletion of a regulatory sequence required for transcription or translation, deletion of a portion of the gene which results in a truncated gene product, or by any of various mutation strategies that inactivate or attenuate the encoded gene product. One particularly useful method of gene disruption is complete gene deletion because it reduces or eliminates the occurrence of genetic reversions in the non-naturally occurring cells of the invention. A gene disruption also includes a null mutation, which refers to a mutation within a gene or a region containing a gene that results in the gene not being transcribed into RNA and/or translated into a functional gene product. Such a null mutation can arise from many types of mutations including, for example, inactivating point mutations, deletion of a portion of a gene, entire gene deletions, or deletion of chromosomal segments.

As used herein, the term "growth-coupled" when used in reference to the production of a biochemical product is intended to mean that the biosynthesis of the referenced biochemical product is produced during the growth phase of a microorganism. In a particular embodiment, the growth-coupled production can be obligatory, meaning that the biosynthesis of the referenced biochemical is an obligatory product produced during the growth phase of a microorganism.

As used herein, the term "attenuate," or grammatical equivalents thereof, is intended to mean to weaken, reduce or diminish the activity or amount of an enzyme or protein. Attenuation of the activity or amount of an enzyme or protein can mimic complete disruption if the attenuation causes the activity or amount to fall below a critical level required for a given function. However, the attenuation of the activity or amount of an enzyme or protein that mimics complete disruption, for example, complete disruption for one pathway, can still be sufficient for a separate pathway to continue to function. For example, attenuation of an endogenous enzyme or protein can be sufficient to mimic the complete disruption of the same enzyme or protein for production of a desired product of the invention, but the remaining activity or amount of enzyme or protein can still be sufficient to maintain other pathways, such as a pathway that is critical for the host cell to survive, reproduce or grow. Attenuation of an enzyme or protein can also be weakening, reducing or diminishing the activity or amount of the enzyme or protein in an amount that is sufficient to increase yield of a desired product of the invention, but does not necessarily mimic complete disruption of the enzyme or protein.

The non-naturally occurring cells of the invention can contain stable genetic alterations, which refers to cells that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

In the case of gene disruptions, a particularly useful stable genetic alteration is a gene deletion. The use of a gene deletion to introduce a stable genetic alteration is particularly useful to reduce the likelihood of a reversion to a phenotype prior to the genetic alteration. For example, stable growth-coupled production of a biochemical can be achieved, for example, by deletion of a gene encoding an enzyme catalyzing one or more reactions within a set of metabolic modifications. The stability of growth-coupled production of a biochemical can be further enhanced through multiple deletions, significantly reducing the likelihood of multiple compensatory reversions occurring for each disrupted activity.

Those skilled in the art will understand that the genetic alterations, including metabolic modifications exemplified herein, are described with reference to a suitable host cell or organism such as *E. coli* and their corresponding metabolic reactions or a suitable source cell or organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring cell. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of *mycoplasma* 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring cells of the invention having biosynthetic capability for a desired product, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced cell that encode an enzyme catalyzing a similar or substantially similar metabolic reaction, those skilled in the art also can utilize these evolutionarily related genes. Similarly for a gene disruption, evolutionarily related genes can also be disrupted or deleted in a host cell to reduce or eliminate functional redundancy of enzymatic activities targeted for disruption.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST® alignment algorithm, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST® alignment algorithm, for example, can be as set forth below. Briefly, amino acid sequence alignments can be performed using BLASTPR alignment algorithm version 2.0.8 (Jan-05-1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN® alignment algorithm version 2.0.6 (Sept-16-1998) and the following parameters: Match: 1; mismatch:-2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In one embodiment, the invention provides an aldehyde dehydrogenase that is a variant of a wild type or parent aldehyde dehydrogenase. The aldehyde dehydrogenase of the invention converts an acyl-CoA to its corresponding aldehyde. Such an enzyme can also be referred to as an oxidoreductase that converts an acyl-CoA to its corresponding aldehyde. Such an aldehyde dehydrogenase of the invention can be classified as a reaction 1.2.1.b, oxidoreductase (acyl-CoA to aldehyde), where the first three digits correspond to the first three Enzyme Commission number digits which denote the general type of transformation independent of substrate specificity. Exemplary enzymatic conversions of an aldehyde dehydrogenase of the invention include, but are not limited to, the conversion of 3-hydroxybutyryl-CoA to 3-hydroxybutyraldehyde (also referred to as 3-HBal)(see FIG. 1), and the conversion of 4-hydroxybutyryl-CoA to 4-hydroxybutyraldehyde (see FIG. 2). An aldehyde dehydrogenase of the invention can be used to produce desired products such as 3-hydroxybutyraldehyde (3-HBal), 1,3-butanediol (1,3-BDO), 4-hydroxybutyraldehyde (4-HBal), 1,4-butanediol (1,4-BDO), or other desired products such as a downstream product, including an ester or amide thereof, in a cell, such as a microbial organism, containing a suitable metabolic pathway, or in vitro. For example, 1,3-BDO can be reacted with an acid, either in vivo or in vitro, to convert to an ester using, for example, a lipase. Such esters can have nutraceutical, medical and food uses, and are advantaged when R-form of 1,3-butanediol is used since that is the form (compared to S-form or the racemic mixture that is made from petroleum or from ethanol by the acetaldehyde chemical synthesis route) best utilized by both animals and humans as an energy source (e.g., a ketone ester, such as (R)-3-hydroxybutyl-R-1,3-butanediol monoester (which has Generally Recognized As Safe (GRAS) approval in the United States) and (R)-3-hydroxybutyrate glycerol monoester or diester). The ketone esters can be delivered orally, and the ester releases R-1,3-butanediol that is used by the body (see, for example, WO2013150153). Thus the present invention is particularly useful to provide an improved enzymatic route and microorganism to provide an improved composition of 1,3-butanediol, namely R-1,3-butanediol, highly enriched or essentially enantiomerically pure, and further having improved purity qualities with respect to by-products.

1,3-Butanediol, also referred to as butylene glycol, has further food related uses including use directly as a food source, a food ingredient, a flavoring agent, a solvent or solubilizer for flavoring agents, a stabilizer, an emulsifier, and an anti-microbial agent and preservative. 1,3-Butanediol is used in the pharmaceutical industry as a parenteral drug solvent. 1,3-Butanediol finds use in cosmetics as an ingredient that is an emollient, a humectant, that prevents crystallization of insoluble ingredients, a solubilizer for less-water-soluble ingredients such as fragrances, and as an anti-microbial agent and preservative. For example, it can be used as a humectant, especially in hair sprays and setting lotions; it reduces loss of aromas from essential oils, preserves against spoilage by microorganisms, and is used as a solvent for benzoates. 1,3-Butanediol can be use at concentrations from 0.1 percent or less to 50 percent or greater. It is used in hair and bath products, eye and facial makeup, fragrances, personal cleanliness products, and shaving and skin care preparations (see, for example, the Cosmetic Ingredient Review board's report: "Final Report on the Safety Assessment of Butylene Glycol, Hexylene Glycol, Ethoxydiglycol, and Dipropylene Glycol", *Journal of the American College of Toxicology*, Volume 4, Number 5, 1985, which is incorporated herein by reference). This report provides specific uses and concentrations of 1,3-butanediol (butylene glycol) in cosmetics; see for examples the report's Table 2 therein entitled "Product Formulation Data".

In one embodiment, the invention provides an isolated nucleic acid molecule selected from (a) a nucleic acid molecule encoding an amino acid sequence referenced as SEQ ID NO:1, 2 or 3 or in Table 4, wherein said amino acid sequence comprises an amino acid substitution corresponding to position I166; (b) a nucleic acid molecule that hybridizes to the nucleic acid of (a) under highly stringent hybridization conditions and comprises a nucleic acid sequence that encodes an amino acid substitution corresponding to position I66; and (c) a nucleic acid molecule that is complementary to (a) or (b).

In some embodiments of a nucleic acid of the invention, the amino acid substitution at position I66 is an amino acid substitution as set forth in Table 1, 2 and/or 3. In some embodiments, the amino acid sequence, in addition to the substitution at position I66, comprises one or more amino acid substitutions at other amino acid variant positions set forth in Table 1, 2 and/or 3. In some embodiments, the amino acid sequence, in addition to the substitution at position I66, comprises one or more of the amino acid substitutions set forth in Table 1, 2 and/or 3.

In some embodiments of a nucleic acid molecule of the invention, the amino acid sequence, other than the one or more amino acid substitutions, has at least 65%, 70%, 75%, 80%, 85%, 90%, 95%, 98% or 99% sequence identity, or is identical, to an amino acid sequence referenced in SEQ ID NO:1, 2 or 3 or in Table 4. In some embodiments, the amino acid sequence comprises at least 2, 3, 4, 5, 6, 7, 8, 9, 10, 11, 12, 13, 14, 15 or 16 of the amino acid substitutions set forth in Table 1, 2 and/or 3. In some embodiments, the amino acid sequence comprises the amino acid substitutions of a variant as set forth in Table 1, 2 and/or 3.

In one embodiment, an isolated nucleic acid molecule can be selected from: (a) a nucleic acid molecule encoding an amino acid sequence referenced as SEQ ID NO:1, 2 or 3 or in Table 4, wherein the amino acid sequence comprises one or more of the amino acid substitutions set forth in Table 1, 2 and/or 3; (b) a nucleic acid molecule that hybridizes to the nucleic acid of (a) under highly stringent hybridization conditions and comprises a nucleic acid sequence that encodes one or more of the amino acid substitutions set forth in Table 1, 2 and/or 3; (c) a nucleic acid molecule encoding an amino acid sequence comprising the consensus sequence of Loop A (SEQ ID NO:5) and/or Loop B (SEQ ID NO:6), wherein the amino acid sequence comprises one or more of the amino acid substitutions set forth in Table 1, 2 and/or 3; and (d) a nucleic acid molecule that is complementary to (a) or (b). In an embodiment, the amino acid sequence encoded by the nucleic acid molecule, other than the one or more amino acid substitutions, has at least 65%, 70%, 75%, 80%, 85%, 90%, 95%, 98% or 99% sequence identity, or is identical, to an amino acid sequence referenced in SEQ ID NO:1, 2 or 3 or in Table 4. The amino acid sequence can comprise at least 2, 3, 4, 5, 6, 7, 8, 9, 10, 11, 12, 13, 14, 15 or 16, or more, of the amino acid substitutions set forth in Table 1, 2 and/or 3, for example, 17, 18, 19, 20, 21, 22, 23, 24, 25, 26, 27, 28, 29, 30, 31, 32, 33, 34, 35, 36, 37, 38, 39, 40, 41, 42 or 43, i.e., up to all of the amino acid positions having a substitution.

The invention also provides a vector containing the nucleic acid molecule of the invention. In one embodiment, the vector is an expression vector. In one embodiment, the vector comprises double stranded DNA.

The invention also provides a nucleic acid encoding an aldehyde dehydrogenase polypeptide of the invention. A nucleic acid molecule encoding an aldehyde dehydrogenase of the invention can also include a nucleic acid molecule that hybridizes to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number. Hybridization conditions can include highly stringent, moderately stringent, or low stringency hybridization conditions that are well known to one of skill in the art such as those described herein. Similarly, a nucleic acid molecule that can be used in the invention can be described as having a certain percent sequence identity to a nucleic acid disclosed herein by SEQ ID NO, GenBank and/or GI number or a nucleic acid molecule that hybridizes to a nucleic acid molecule disclosed herein by SEQ ID NO, GenBank and/or GI number. For example, the nucleic acid molecule can have at least 65%, 70%, 75%, 80%, 85%, 90%, 91%, 92%, 93%, 94%, 95%, 96%, 97%, 98% or 99% sequence identity, or be identical, to a nucleic acid described herein.

Stringent hybridization refers to conditions under which hybridized polynucleotides are stable. As known to those of skill in the art, the stability of hybridized polynucleotides is reflected in the melting temperature (Tm) of the hybrids. In general, the stability of hybridized polynucleotides is a function of the salt concentration, for example, the sodium ion concentration, and temperature. A hybridization reaction can be performed under conditions of lower stringency, followed by washes of varying, but higher, stringency. Reference to hybridization stringency relates to such washing conditions. Highly stringent hybridization includes conditions that permit hybridization of only those nucleic acid sequences that form stable hybridized polynucleotides in 0.018M NaCl at 65° C., for example, if a hybrid is not stable in 0.018M NaCl at 65° C., it will not be stable under high stringency conditions, as contemplated herein. High stringency conditions can be provided, for example, by hybridization in 50% formamide, 5× Denhart's solution, 5×SSPE, 0.2% SDS at 42° C., followed by washing in 0.1×SSPE, and 0.1% SDS at 65° C. Hybridization conditions other than highly stringent hybridization conditions can also be used to describe the nucleic acid sequences disclosed herein. For example, the phrase moderately stringent hybridization refers to conditions equivalent to hybridization in 50% formamide, 5× Denhart's solution, 5×SSPE, 0.2% SDS at 42° C., followed by washing in 0.2×SSPE, 0.2% SDS, at 42° C. The phrase low stringency hybridization refers to conditions equivalent to hybridization in 10% formamide, 5× Denhart's solution, 6×SSPE, 0.2% SDS at 22° C., followed by washing in 1×SSPE, 0.2% SDS, at 37° C. Denhart's solution contains 1% Ficoll, 1% polyvinylpyrolidone, and 1% bovine serum albumin (BSA). SSPE (sodium chloride, sodium phosphate, ethylene diamine tetraacetic acid (EDTA)) contains 3M sodium chloride, 0.2M sodium phosphate, and 0.025 M (EDTA). Other suitable low, moderate and high stringency hybridization buffers and conditions are well known to those of skill in the art and are described, for example, in Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, MD (1999).

A nucleic acid molecule encoding an aldehyde dehydrogenase of the invention can have at least a certain sequence identity to a nucleotide sequence disclosed herein. Accordingly, in some aspects of the invention, a nucleic acid molecule encoding an aldehyde dehydrogenase of the invention has a nucleotide sequence of at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity, or is identical, to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number.

Sequence identity (also known as homology or similarity) refers to sequence similarity between two nucleic acid molecules or between two polypeptides. Identity can be determined by comparing a position in each sequence, which may be aligned for purposes of comparison. When a position in the compared sequence is occupied by the same base or amino acid, then the molecules are identical at that position. A degree of identity between sequences is a function of the number of matching or homologous positions shared by the sequences. The alignment of two sequences to determine their percent sequence identity can be done using software programs known in the art, such as, for example, those described in Ausubel et al., Current Protocols in Molecular Biology, John Wiley and Sons, Baltimore, MD (1999). Preferably, default parameters are used for the alignment. One alignment program well known in the art that can be used is BLAST® alignment algorithm set to default parameters. In particular, programs are BLASTN® and BLASTP® alignment algorithms, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+ PDB+GenBank CDS translations+SwissProtein+SPupdate+ PIR. Details of these programs can be found at the National Center for Biotechnology Information (see also Altschul et al., "J. Mol. Biol. 215:403-410 (1990)).

In some embodiments, the nucleic acid molecule is an isolated nucleic acid molecule. In some embodiments, the isolated nucleic acid molecule is a nucleic acid molecule encoding a variant of a reference polypeptide, wherein (i) the reference polypeptide has an amino acid sequence of SEQ ID NO: 1, 2 or 3 or those in Table 4 (SEQ ID NOS:7-123), (ii) the variant comprises one or more amino acid substitutions relative to SEQ ID NO: 1, 2 or 3 or those in Table 4, and (iii) the one or more amino acid substitutions are selected from the amino acid substitutions shown in Tables 1-3. Tables 1-3 provide non-limiting lists of exemplary variants of SEQ ID NO: 1, 2 or 3 or those in Table 4. In one embodiment, for each variant in Tables 1-3, all positions except for the indicated position(s) are identical to SEQ ID NO: 1, 2 or 3 or those in Table 4. Amino acid substitutions are indicated by a letter indicating the identity of the original amino acid, followed by a number indicating the position of the substituted amino acid in SEQ ID NO: 1, 2 or 3 or those in Table 4, followed by a letter indicating the identity of the substituted amino acid. For example, "D12A" indicates that the aspartic acid at position 12 in SEQ ID NO: 1 or 2 is replaced with an alanine. The single-letter code used to identify amino acids is the standard code known by those skilled in the art. Some variants in Tables 1-3 comprise two or more substitutions, which is indicated by a list of substitutions. The one or more amino acid substitutions can be selected from any one of the variants listed in Tables 1-3, or from any combination of two or more variants listed in Tables 1-3. When selecting from a single variant in Tables 1-3, the resulting variant can comprise one or more of the substitutions of the selected variant in any combination, including all of the indicated substitutions or less than all of the indicated substitutions. When substitutions are selected from those of two or more variants in Tables 1-3, the resulting variant can comprise one or more of the substitutions of the selected variants, including all of the indicated substitutions or less than all of the indicated substitutions from each of the two or more selected variants, in any combination. For example, the resulting variant can comprise 1, 2, 3, or 4 substitutions from a single variant in Tables 1-3. As a further example, the resulting variant can comprise 1, 2, 3, 4, 5, 6, 7, 8, 9, 10, 11, 12, 13, 14, 15, 16, 20, 25, or more substitutions selected from 1, 2, 3, 4, 5, or more selected variants of Tables 1-3. In some embodiments, the resulting variant comprises all of the indicated substitutions of a selected variant in Tables 1-3. In some embodiments, the resulting variant differs from SEQ ID NO: 1, 2 or 3 or those in Table 4 by at least one amino acid substitution, but less than 25, 20, 10, 5, 4, or 3 amino acid substitutions. In some embodiments, the resulting variant comprises, consists essentially of, or consists of a sequence as indicated by a variant selected from Tables 1-3, differing from SEQ ID NO: 1, 2 or 3 or those in Table 4 only at the indicated amino acid substitutions.

In some embodiments, the nucleic acid molecule is an isolated nucleic acid molecule encoding a variant of a reference polypeptide (the reference polypeptide having an amino acid sequence of SEQ ID NO: 1, 2 or 3 or those in Table 4), wherein the variant (i) comprises one or more amino acid substitutions of a corresponding variant selected from Table 1-3, and (ii) has at least 65%, 70%, 75%, 80%, 85%, 90%, 95%, 98% 99%, or 100% sequence identity to the corresponding variant. In cases where the second variant has 100% sequence identity to the corresponding variant, the second variant comprises a sequence as indicated by a variant selected from Table 1-3, and may or may not have one or more additional amino acids at either or both the amino- and carboxy-termini. In some embodiments, the resulting variant has at least 80%, 85%, 90%, or 95% sequence identity to a corresponding variant selected from Table 1-3; in some cases, identity is at least 90% or more. In cases where the resulting variant is less than 100% identical to a corresponding variant selected from Table 1-3, the position of one or more of the amino acid substitutions indicated for the corresponding variant may shift (e.g. in the case of insertion or deletion of one or more amino acids), but still be contained within the resulting variant. For example, the aspartic acid to alanine substitution corresponding to "D12A" (at position 12 relative to SEQ ID NO: 1 or 2) may be present, but at a different position in the resulting variant. Whether an amino acid corresponds to an indicated substitution, albeit at a different position, can be determined by sequence alignment, as is well known in the art. In general, an alignment showing identity or similarity of amino acids flanking the substituted amino acid, such that the flanking sequences are considered to be aligned with a homologous sequence of another polypeptide, will allow the substituted amino acid to be positioned locally with respect to the corresponding variant of Table 1-3 to determine a corresponding position to make the substitution, albeit at a shifted numerical position in a given polypeptide chain. In one embodiment, a region comprising at least three to fifteen amino acids, including the substituted position, will locally align with the corresponding variant sequence with a relatively high percent identity, including at the position of the substituted amino acid along the corresponding variant sequence (e.g. 90%, 95%, or 100% identity). In some embodiments, the one or more amino acid substitutions (e.g. all or less than all of the amino acid substitutions) indicated by a corresponding variant selected from Table 1-3 is considered to be present in a given variant, even if occurring at a different physical position along a polypeptide chain, if the sequence of the polypeptide being compared aligns with the corresponding variant with an identical match or similar amino acid at the indicated position along the corresponding variant sequence when using a BLASTP® alignment algorithm with default parameters, where a similar amino acid is one considered to have chemical properties sufficient for alignment with the variant position of interest using default parameters of the alignment algorithm.

In some embodiments, a nucleic acid molecule of the invention is complementary to a nucleic acid described in connection with any of the various embodiments herein.

It is understood that a nucleic acid of the invention or a polypeptide of the invention can exclude a wild type parental sequence, for example a parental sequence such as SEQ ID NOS: 1, 2 or 3 or sequences disclosed in Table 4. One skilled in the art will readily understand the meaning of a parental wild type sequence based on what is well known in the art. It is further understood that such a nucleic acid of the invention can exclude a nucleic acid sequence encoding a naturally occurring amino acid sequence as found in nature. Similarly, a polypeptide of the invention can exclude an amino acid sequence as found in nature. Thus, in a particular embodiment, the nucleic acid or polypeptide of the invention is as set forth herein, with the proviso that the encoded amino acid sequence is not the wild type parental sequence or a naturally occurring amino acid sequence and/or that the nucleic acid sequence is not a wild type or naturally occurring nucleic acid sequence. A naturally occurring amino acid or nucleic acid sequence is understood by those skilled in the art as relating to a sequence that is found in a naturally occurring organism as found in nature. Thus, a nucleic acid or amino acid sequence that is not found in the same state or having the same nucleotide or encoded amino acid sequence as in a naturally occurring organism is included within the meaning of a nucleic acid and/or amino acid sequence of the invention. For example, a nucleic acid or amino acid sequence that has been altered at one or more nucleotide or amino acid positions from a parent sequence, including variants as described herein, are included within the meaning of a nucleic acid or amino acid sequence of the invention that is not naturally occurring. An isolated nucleic acid molecule of the invention excludes a naturally occurring chromosome that contains the nucleic acid sequence, and can further exclude other molecules as found in a naturally occurring cell such as DNA binding proteins, for example, proteins such as histones that bind to chromosomes within a eukaryotic cell.

Thus, an isolated nucleic acid sequence of the invention has physical and chemical differences compared to a naturally occurring nucleic acid sequence. An isolated or non-naturally occurring nucleic acid of the invention does not contain or does not necessarily have some or all of the chemical bonds, either covalent or non-covalent bonds, of a naturally occurring nucleic acid sequence as found in nature. An isolated nucleic acid of the invention thus differs from a naturally occurring nucleic acid, for example, by having a different chemical structure than a naturally occurring nucleic acid sequence as found in a chromosome. A different chemical structure can occur, for example, by cleavage of phosphodiester bonds that release an isolated nucleic acid sequence from a naturally occurring chromosome. An isolated nucleic acid of the invention can also differ from a naturally occurring nucleic acid by isolating or separating the nucleic acid from proteins that bind to chromosomal DNA in either prokaryotic or eukaryotic cells, thereby differing from a naturally occurring nucleic acid by different non-covalent bonds. With respect to nucleic acids of prokaryotic origin, a non-naturally occurring nucleic acid of the invention does not necessarily have some or all of the naturally occurring chemical bonds of a chromosome, for example, binding to DNA binding proteins such as polymerases or chromosome structural proteins, or is not in a higher order structure such as being supercoiled. With respect to nucleic acids of eukaryotic origin, a non-naturally occurring nucleic acid of the invention also does not contain the same internal nucleic acid chemical bonds or chemical bonds with structural proteins as found in chromatin. For example, a non-naturally occurring nucleic acid of the invention is not chemically bonded to histones or scaffold proteins and is not contained in a centromere or telomere. Thus, the non-naturally occurring nucleic acids of the invention are chemically distinct from a naturally occurring nucleic acid because they either lack or contain different van der Waals interactions, hydrogen bonds, ionic or electrostatic bonds, and/or covalent bonds from a nucleic acid as found in nature. Such differences in bonds can occur either internally within separate regions of the nucleic acid (that is cis) or such difference in bonds can occur in trans, for example, interactions with chromosomal proteins. In the case of a nucleic acid of eukaryotic origin, a cDNA is considered to be an isolated or non-naturally occurring nucleic acid since the chemical bonds within a cDNA differ from the covalent bonds, that is the sequence, of a gene on chromosomal DNA. Thus, it is understood by those skilled in the art that an isolated or non-naturally occurring nucleic acid is distinct from a naturally occurring nucleic acid.

In one embodiment, the invention provides an isolated polypeptide comprising an amino acid sequence referenced as SEQ ID NO:1, 2 or 3 or in Table 4, wherein the amino acid sequence comprises an amino acid substitution corresponding to position I66. In some embodiments, the amino acid substitution at position I66 is an amino acid substitution as set forth in Table 1, 2 and/or 3. In some embodiments, the amino acid sequence, in addition to the substitution corresponding to amino acid position I66, comprises one or more amino acid substitutions at other amino acid variant positions set forth in Table 1, 2 and/or 3. In some embodiments, the amino acid sequence, in addition to the substitution at position I66, comprises one or more of the amino acid substitutions set forth in Table 1, 2 and/or 3.

In another embodiment, the invention provides an isolated polypeptide comprising an amino acid sequence referenced as SEQ ID NO:1, 2 or 3 or in Table 4, wherein said amino acid sequence comprises an amino acid substitution corresponding to position I66, wherein the amino acid sequence, other than the amino acid substitution corresponding to position I66, has at least 65%, 70%, 75%, 80%, 85%, 90%, 95%, 98% or 99% sequence identity, or is identical, to an amino acids sequence referenced as SEQ ID NO:1, 2 or 3 or in Table 4.

In some embodiments on of an isolated polypeptide of the invention, the amino acid substitution at position I66 is an amino acid substitution as set forth in Table 1, 2 and/or 3. In some embodiments, the amino acid sequence, in addition to the substitution corresponding to amino acid position I66, comprises one or more amino acid substitutions at other amino acid variant positions set forth in Table 1, 2 and/or 3. In some embodiments, the amino acid sequence, in addition to the substitution at position I66, comprises one or more of the amino acid substitutions set forth in Table 1, 2 and/or 3. In some embodiments, the amino acid sequence further comprises a conservative amino acid substitution in from 1 to 100 amino acid positions, wherein said positions are other than the one or more amino acid substitutions set forth in Table 1, 2 and/or 3.

In some embodiments of an isolated polypeptide of the invention, the amino acid sequence comprises no modification at from 2 to 300 amino acid positions compared to the parent sequence, other than the one or more amino acid substitutions set forth in Table 1, 2 and/or 3, wherein the positions are selected from those that are identical to between 2, 3, 4, or 5 of the amino acid sequences referenced as SEQ ID NO:1, 2 or 3 or in Table 4. In one embodiment, the amino acid sequence comprises at least 2, 3, 4, 5, 6, 7, 8, 9, 10, 11, 12, 13, 14, 15 or 16 of the amino acid substitutions set forth in Table 1, 2 and/or 3. In a particular embodiment, the amino acid sequence comprises the amino acid substitutions of a variant as set forth in Table 1, 2 and/or 3.

In one embodiment, an isolated polypeptide comprises an amino acid sequence referenced as SEQ ID NO:1, 2 or 3 or in Table 4, wherein the amino acid sequence comprises one or more of the amino acid substitutions set forth in Table 1, 2 and/or 3. In one embodiment, an isolated polypeptide comprises the consensus amino acid sequence of Loop A (SEQ ID NO:5) and/or Loop B (SEQ ID NO:6).

In another embodiment, an isolated polypeptide comprises an amino acid sequence referenced as SEQ ID NO:1, 2 or 3 or in Table 4, wherein the amino acid sequence comprises one or more of the amino acid substitutions set forth in Table 1, 2 and/or 3, wherein the amino acid sequence, other than the one or more amino acid substitutions, has at least 65%, 70%, 75%, 80%, 85%, 90%, 95%, 98% or 99% sequence identity, or is identical, to an amino acids sequence referenced as SEQ ID NO:1, 2 or 3 or in Table 4. In one embodiment, the amino acid sequence further comprises a conservative amino acid substitution in from 1 to 100 amino acid positions, wherein the positions are other than the one or more amino acid substitutions set forth in Table 1, 2 and/or 3. In another embodiment, the amino acid sequence comprises no modification at from 2 to 300 amino acid positions compared to the parent sequence, other than the one or more amino acid substitutions set forth in Table 1, 2 and/or 3, wherein the positions are selected from those that are identical to between 2, 3, 4, or 5 of the amino acid sequences referenced as SEQ ID NO:1, 2 or 3 or in Table 4. In one embodiment, the amino acid sequence comprises at least 2, 3, 4, 5, 6, 7, 8, 9, 10, 11, 12, 13, 14, 15 or 16, or more, of the amino acid substitutions set forth in Table 1, 2 and/or 3, for example, 17, 18, 19, 20, 21, 22, 23, 24, 25, 26, 27, 28, 29, 30, 31, 32, 33, 34, 35, 36, 37, 38, 39, 40, 41, 42 or 43, i.e., up to all of the amino acid positions having a substitution.

In one embodiment, the polypeptide of the invention encodes an aldehyde dehydrogenase. In one embodiment, the polypeptide can convert 3-hydroxybutyryl-CoA to 3-hydroxybutyraldehyde. In one embodiment, the polypeptide can convert 4-hydroxybutyryl-CoA to 4-hydroxybutyraldehyde. In one embodiment, the polypeptide has higher activity relative to the parental polypeptide. In one embodiment, the polypeptide has higher activity for 3-hydroxy-(R)-butyryl-CoA over 3-hydroxy-(S)-butyryl-CoA. In one embodiment, the polypeptide has higher specificity for 3-hydroxybutyryl-CoA over acetyl-CoA. In one embodiment, the polypeptide has higher specificity for 4-hydroxybutyryl-CoA over acetyl-CoA. In one embodiment, the polypeptide produces decreased byproducts in a cell or cell extract. In a particular embodiment, the byproduct is ethanol or 4-hydroxy-2-butanone. In one embodiment, the polypeptide has a higher kcat relative to the parental polypeptide.

In some embodiments, the invention provides an isolated polypeptide having an amino acid sequence disclosed herein, such SEQ ID NOS:1, 2 or 3 or those referenced in Table 4, wherein the amino acid sequence includes one or more variant amino acid positions as set forth in Tables 1, 2 and/or 3. In particular, such a polypeptide encodes an aldehyde dehydrogenase, which can convert an acyl-CoA to the corresponding aldehyde, for example, 3-hydroxybutyryl-CoA to 3-hydroxybutyraldehyde, or 4-hydroxybutyryl-CoA to 4-hydroxybutyraldehyde. In some aspects, the isolated polypeptide of the invention includes an amino acid sequence, other than the one or more variant amino acid positions as set forth in Tables 1, 2, and/or 3, with at least 65%, 70%, 75%, 80%, 85%, 90%, 91%, 92%, 93%, 94%, 95%, 96%, 97%, 98% or 99% sequence identity, or is identical, to an amino acids sequence referenced as SEQ ID NOS:1, 2 or 3 or in Table 4. It is understood that a variant amino acid position can include any one of the 20 naturally occurring amino acids, a conservative substitution of a wild type or parental sequence at the corresponding position of the variant amino acid position, or a specific amino acid at the variant amino acid position such as those disclosed herein in Tables 1, 2 and/or 3. It is further understood that any of the variant amino acid positions can be combined to generate further variants. Variants with combinations of two or more variant amino acid positions exhibited activities greater than wild type. Thus, as exemplified herein, generating enzyme variants by combining active variant amino acid positions resulted in enzyme variants with improved properties. One skilled in the art can readily generate polypeptides with single variant positions or combinations of variant positions using methods well known to those skilled in the art to generate polypeptides with desired properties, including increased activity, increased specificity for the R form of 3-hydroxybutyryl-CoA or 3-hydroxybutyraldehyde over the S form, increased specificity for 3-hydroxybutyryl-CoA and/or 4-hydroxybutyryl-CoA over acetyl-CoA, decreased byproduct formation, such as ethanol or 4-hydroxy-2-butanone, increased kcat, increased stability in vivo and/or in vitro and the like, as described herein.

"Homology" or "identity" or "similarity" refers to sequence similarity between two polypeptides or between two nucleic acid molecules. Homology can be determined by comparing a position in each sequence which may be aligned for purposes of comparison. When a position in the compared sequence is occupied by the same base or amino acid, then the molecules are identical at that position. A degree of homology between sequences is a function of the number of matching or homologous positions shared by the sequences. A polypeptide or polypeptide region (or a polynucleotide or polynucleotide region) has a certain percentage (for example, 65%, 70%, 75%, 80%, 85%, 90%, 95%, 98% or 99%) of "sequence identity" to another sequence means that, when aligned, that percentage of amino acids (or nucleotide bases) are the same in comparing the two sequences.

In certain embodiments, the invention provides an isolated polypeptide having an amino acid sequence that includes at least two, three, four, five, six, seven, eight, nine, ten, eleven, twelve, thirteen, fourteen, fifteen, sixteen, seventeen, eighteen, nineteen, twenty or more variants in any combination disclosed herein. The variants can include any combination of the variants set forth in Tables 1, 2, and/or 3. In some embodiments, the isolated polypeptide is a variant of a reference polypeptide, wherein the reference polypeptide has an amino acid sequence of SEQ ID NO: 1, 2 or 3 or those in Table 4, and the polypeptide variant is selected from Table 1-3 and has one or more amino acid substitutions relative to SEQ ID NO: 1, 2 or 3 or those in Table 4.

In some embodiments, the isolated polypeptide is a variant of a reference polypeptide, wherein the reference polypeptide has an amino acid sequence of SEQ ID NO: 1, 2 or 3 or those in Table 4, the polypeptide variant comprises one or more amino acid substitutions relative to SEQ ID NO: 1, 2 or 3 or those in Table 4, where the one or more amino acid substitutions are selected from Table 1-3, and the polypeptide variant has at least 65%, 70%, 75%, 80%, 85%, 90%, 95%, 98%, or 99% sequence identity to a corresponding variant selected from Table 1-3. The one or more amino acid substitutions can be selected from any one of the variants listed in Table 1-3, or from any combination of two or more variants listed in Table 1-3. When selecting from a single variant in Table 1-3, the resulting variant can comprise one or more of the substitutions of the selected variant in any combination, including all of the indicated substitutions or less than all of the indicated substitutions. When substitutions are selected from those of two or more variants in Table 1-3, the resulting variant can comprise one or more of the substitutions of the selected variants, including all of the indicated substitutions or less than all of the indicated substitutions from each of the two or more selected variants, in any combination. For example, the resulting variant can comprise 1, 2, 3, or 4 substitutions from a single variant in Table 1-3. As a further example, the resulting variant can comprise 1, 2, 3, 4, 5, 6, 7, 8, 9, 10, 11, 12, 13, 14, 15, 16, 20, 25, or more substitutions selected from 1, 2, 3, 4, 5, or more selected variants of Table 1-3, including up to all positions being substituted, as disclosed herein. In some embodiments, the resulting variant comprises all of the indicated substitutions of a selected variant in Table 1-3. In some embodiments, the resulting variant differs from SEQ ID NO: 1, 2 or 3 or those in Table 4 by at least one amino acid substitution, but less than 25, 20, 10, 5, 4, or 3 amino acid substitutions. In some embodiments, the resulting variant comprises, consists essentially of, or consists of a sequence as indicated by a variant selected from Table 1-3, differing from SEQ ID NO: 1, 2 or 3 or those in Table 4 only at the indicated amino acid substitution(s).

In some embodiments, the resulting variant has at least 80%, 85%, 90%, or 95% sequence identity to a corresponding variant selected from Table 1-3; in some cases, identity is at least 90% or more. In cases where the resulting variant is less than 100% identical to a corresponding variant selected from Table 1-3, the position of one or more of the amino acid substitutions indicated for the corresponding variant may shift (e.g. in the case of insertion or deletion of one or more amino acids), but still be contained within the resulting variant. For example, the glycine to glutamic acid substitution corresponding to "D12A" (at position 12 relative to SEQ ID NO: 1 or 2) may be present, but at a different position in the resulting variant.

Whether an amino acid corresponds to an indicated substitution, albeit at a different position, can be determined by sequence alignment, as described above and as well known in the art. In some embodiments, the one or more amino acid substitutions (e.g., all or less than all of the amino acid substitutions) indicated by a corresponding variant selected from Table 1-3 is considered to be present in a given variant, even if occurring at a different physical position along a polypeptide chain, if the sequence of the polypeptide being compared aligns with the corresponding variant with an identical match or similar amino acid at the indicated position along the corresponding variant sequence when using a BLASTP® alignment algorithm with default parameters, where a similar amino acid is one considered to have chemical properties sufficient for alignment with the variant position of interest using default parameters of the alignment algorithm.

The variants alone or in combination can produce an enzyme that retains or improves the activity relative to a reference polypeptide, for example, the wild-type (native) enzyme. In some aspects, the polypeptide of the invention can have any combination of variants set forth in Tables 1, 2, and/or 3. In some aspects, the polypeptide of the invention having any combination of variants set forth in Tables 1, 2, and/or 3 can convert an acyl-CoA to the corresponding aldehyde, for example, 3-hydroxybutyryl-CoA to 3-hydroxybutyraldehyde, or 4-hydroxybutyryl-CoA to 4-hydroxybutyraldehyde. Methods of generating and assaying such polypeptides are well known to one of skill in the art.

In some embodiments, the isolated polypeptide of the invention can further include a conservative amino acid substitution in from 1 to 100 amino acid positions, or alternatively from 2 to 100 amino acid positions, or alternatively from 3 to 100 amino acid positions, or alternatively from 4 to 100 amino acid positions, or alternatively from 5 to 100 amino acid positions, or alternatively from 6 to 100 amino acid positions, or alternatively from 7 to 100 amino acid positions, or alternatively from 8 to 100 amino acid positions, or alternatively from 9 to 100 amino acid positions, or alternatively from 10 to 100 amino acid positions, or alternatively from 15 to 100 amino acid positions, or alternatively from 20 to 100 amino acid positions, or alternatively from 30 to 100 amino acid positions, or alternatively from 40 to 100 amino acid positions, or alternatively from 50 to 100 amino acid positions, or any integer therein, wherein the positions are other than the variant amino acid positions set forth in Tables 1, 2, and/or 3. In some aspects, the conservative amino acid sequence is a chemically conservative or an evolutionary conservative amino acid substitution. Methods of identifying conservative amino acids are well known to one of skill in the art, any one of which can be used to generate the isolated polypeptides of the invention.

In some embodiments, the isolated polypeptide of the invention can include no modification at from 2 to 300 amino acid positions, or alternatively 3 to 300 amino acid positions, or alternatively 4 to 300 amino acid positions, or alternatively 5 to 300 amino acid positions, or alternatively 10 to 300 amino acid positions, or alternatively 20 to 300 amino acid positions, or alternatively 30 to 300 amino acid positions, or alternatively 40 to 300 amino acid positions, or alternatively 50 to 300 amino acid positions, or alternatively 60 to 300 amino acid positions, or alternatively 80 to 300 amino acid positions, or alternatively 100 to 300 amino acid positions, or alternatively 150 to 300 amino acid positions, or alternatively 200 to 300 amino acid positions, or alternatively 250 to 300 amino acid positions, or any integer therein, compared to the parent (wild-type) sequence, wherein the positions are selected from those that are identical to between 2, 3, 4, or 5 of the amino acid sequences referenced as SEQ ID NOS:1, 2 or 3 or in Table 4.

It is understood that the variant polypeptides such as polypeptide variants of aldehyde dehydrogenase, as disclosed herein, can carry out a similar enzymatic reaction as the parent polypeptide, for example, converting an acyl-CoA to its corresponding aldehyde, such as converting 3-hydroxybutyryl-CoA to 3-hydroxybutyraldehyde, or converting 4-hydroxybutyryl-CoA to 4-hydroxybutyraldehyde. It is further understood that the polypeptide variants of the aldehyde dehydrogenase enzyme can include variants that provide a beneficial characteristic to the polypeptide, including but not limited to, increased activity, increased specificity for the R form of 3-hydroxybutyryl-CoA or 3-hydroxybutyraldehyde over the S form, increased specificity for 3-hydroxybutyryl-CoA and/or 4-hydroxybutyryl-CoA over acetyl-CoA, decreased byproduct formation, such as ethanol or 4-hydroxy-2-butanone, increased kcat, increased stability in vivo and/or in vitro and the like (see Example). In a particular embodiment, the aldehyde dehydrogenase variant can exhibit an activity that is at least the same or higher than a wild type or parent polypeptide, that is, is higher than a parent polypeptide without the variant amino acid position(s). For example, the aldehyde dehydrogenase variants of the invention can have 1.2, 1.5, 2, 2.5, 3, 3.5, 4, 4.5, 5, 5.5, 6, 6.5, 7, 7.5, 8, 8.5, 9, 9.5, 10, or even higher fold activity of the variant polypeptide over a wild type or parent polypeptide (see Example). It is understood that activity refers to the ability of an aldehyde dehydrogenase of the invention to convert a substrate to a product relative to a wild type or parent polypeptide under the same assay conditions.

In another particular embodiment, the aldehyde dehydrogenase variant can exhibit increased specificity for the R form of 3-hydroxybutyryl-CoA or 3-hydroxybutyraldehyde over the S form, for example, about 2 to 40 fold higher, for example, 2 to 35, 2 to 30, 2 to 25, 2 to 20, 2 to 15, 2 to 10 or 2 to 5, for example, 2, 3, 4, 5, 6, 7, 8, 9, 10, 11, 12, 13, 14, 15, 20, 25, 30, 35, 40 or even higher fold activity. Such an increased specificity can be measured, for example, by the ratio of activity for the R over the S form of 3-hydroxybutyryl-CoA or 3-hydroxybutyraldehyde.

In another particular embodiment, the aldehyde dehydrogenase variant can exhibit increased specificity for 3-hydroxybutyryl-CoA and/or 4-hydroxybutyryl-CoA over acetyl-CoA, for example, 1.5 to 100, 1.5 to 95, 1.5 to 90, 1.5 to 85, 1.5 to 80, 1.5 to 75, 1.5 to 70, 1.5 to 65, 1.5 to 60, 1.5 to 55, 1.5 to 50, 1.5 to 45, 1.5 to 40, 1.5 to 35, 1.5 to 30, 1.5 to 25, 1.5 to 20, 1.5 to 15, 1.5 to 10, or 1.5 to 5, for example, 2, 3, 4, 5, 6, 7, 8, 9, 11, 12, 13, 14, 15, 20, 25, 30, 35, 40, 45, 50, 55, 60, 65, 70, 75, 80, 85, 90, 95, or 100-fold. Such an increased specificity can be measured, for example, by the ratio of activity for 3-hydroxybutyryl-CoA or 4-hydroxybutyryl-CoA over acetyl-CoA. Specificity is indicated by the activity on 3HB-CoA or 4HB-CoA divided by the activity on acetyl-CoA.

In another particular embodiment, the aldehyde dehydrogenase variant can exhibit decreased byproduct formation, such as ethanol and/or 4-hydroxy-2-butanone, for example, a decrease in byproduct formation of 10%, 15%, 20%, 25%, 30%, 35%, 40%, 45%, 50%, 60%, 65%, 70%, 75%, 80%, 85%, 90%, 95%, 96%, 97%, 98%, 99%. Such an aldehyde dehydrogenase variant can exhibit an activity that has decreased byproduct formation, as described above, relative to a wild type or a parent polypeptide, that is, a parent polypeptide without the variant amino acid position.

In another particular embodiment, the aldehyde dehydrogenase variant can exhibit increased kcat, for example, 1.25, 1.5, 1.75, 2, 2.5, 3, 3.5, 4, 4.5, 5, 5.5, 6, 6.5, 7, 7.5, 8, 8.5, 9, 9.5, 10-fold or higher, relative to a wild type or a parent polypeptide, that is, a parent polypeptide without the variant amino acid position(s). The kcat is understood to refer to its well known meaning in enzymology of the turnover number, where kcat=Vmax/[ET], where Vmax is the rate of enzyme reaction with saturating substrate, and [Er] is the total enzyme concentration (see Segel, *Enzyme Kinetics: Behavior and Analysis of RapidEquilibrium and Steady-State Enzyme Kinetics*, Wiley-Interscience, New York (1975)). Such an aldehyde dehydrogenase variant can exhibit an activity that has has increased kcat relative to a wild type or a parent polypeptide, that is, a parent polypeptide without the variant amino acid position(s).

In another particular embodiment, the aldehyde dehydrogenase variant can exhibit increased stability, either in vitro or in vivo, or both, relative to a wild type or a parent polypeptide, that is, a parent polypeptide without the variant amino acid position(s). For example, the aldehyde dehydrogenase variant can exhibit increased stability in vitro in a cell lysate.

It is understood that, in certain embodiments, an aldehyde dehydrogenase variant can exhibit two or more of the characteristics described above, for example, two or more of the characteristics of (1) increased activity, (2) increased specificity for the R form of 3-hydroxybutyryl-CoA or 3-hydroxybutyraldehyde over the S form, (3) increased specificity for 3-hydroxybutyryl-CoA and/or 4-hydroxybutyryl-CoA over acetyl-CoA, (4) decreased byproduct formation, such as ethanol and/or 4-hydroxy-2-butanone, (5) increased kcat, (6) increased stability in vivo and/or in vitro, and the like, in any combination. Such combinations include, for example, characteristics 1 and 2; 1 and 3; 1 and 4; 1 and 5; 1 and 6; 2 and 3; 2 and 4; 2 and 5; 2 and 6; 3 and 4; 3 and 5; 3 and 6; 4 and 5; 4 and 6; 5 and 6; 1, 2 and 3; 1, 2 and 4; 1, 2 and 5; 1, 2 and 6; 1, 3 and 4; 1, 3 and 5; 1, 3 and 6; 1, 4 and 5; 1, 4 and 6; 1, 5 and 6; 2, 3 and 4; 2, 3 and 5; 2, 3 and 6; 2, 4 and 5; 2, 4 and 6; 2, 5 and 6; 3, 4 and 5; 3, 4 and 6; 3, 5 and 6; 4, 5 and 6; 1, 2, 3 and 4; 1, 2, 3 and 5; 1, 2, 3 and 6; 1, 2, 4 and 5; 1, 2, 4 and 6; 1, 2, 5 and 6; 1, 3, 4 and 5; 1, 3, 4 and 6; 1, 3, 5 and 6; 1, 4, 5 and 6; 2, 3, 4 and 5; 2, 3, 4 and 6; 2, 3, 5 and 6; 3, 4, 5 and 6; 1, 2, 3, 4 and 5; 1, 3, 4, 5 and 6; 1, 2, 4, 5 and 6; 1, 2, 3, 5 and 6; 1, 2, 3, 4 and 6; 2, 3, 4, 5 and 6; 1, 2, 3, 4, 5 and 6.

The polypeptides of the invention can be isolated by a variety of methods well-known in the art, for example, recombinant expression systems, precipitation, gel filtration, ion-exchange, reverse-phase and affinity chromatography, and the like. Other well-known methods are described in Deutscher et al., *Guide to Protein Purification: Methods in Enzymology*, Vol. 182, (Academic Press, (1990)). Alternatively, the isolated polypeptides of the present invention can be obtained using well-known recombinant methods (see, for example, Sambrook et al., supra, 1989; Ausubel et al., supra, 1999). The methods and conditions for biochemical purification of a polypeptide of the invention can be chosen by those skilled in the art, and purification monitored, for example, by a functional assay.

One non-limiting example of a method for preparing the invention polypeptide is to express nucleic acids encoding the polypeptide in a suitable host cell, such as a bacterial cell, a yeast cell, or other suitable cell, using methods well known in the art, and recovering the expressed polypeptide, again using well-known purification methods, as described herein. Invention polypeptides can be isolated directly from cells that have been transformed with expression vectors as described herein. Recombinantly expressed polypeptides of the invention can also be expressed as fusion proteins with appropriate affinity tags, such as glutathione S transferase (GST), poly His, streptavidin, and the like, and affinity purified, if desired. A polypeptide of the invention can retain the affinity tag, if desired, or optionally the affinity tag can be removed from the polypeptide using well known methods to remove an affinity tag, for example, using appropriate enzymatic or chemical cleavage. Thus, the invention provides polypeptides of the invention without or optionally with an affinity tag. In some embodiments, the invention provides a host cell expressing a polypeptide of the invention disclosed herein. An invention polypeptide can also be produced by chemical synthesis using a method of polypeptide synthesis well know to one of skill in the art (Merrifield, *J. Am. Chem. Soc.* 85:2149 (1964); Bodansky, M., *Principles of Peptide Synthesis* (Springer-Verlag, 1984); Houghten, *Proc. Nati Acad Sci., USA* 82:5131(1985); Grant *Synthetic Peptides: A User Guide*. W.H. Freeman and Co., N.Y. (1992); Bodansky M and Trost B., Ed. *Principles of Peptide Synthesis*. Springer-Verlag Inc., NY (1993)).

In some embodiments, the invention provides using a polypeptide disclosed herein as a biocatalyst. A "biocatalyst," as used herein, refers to a biological substance that initiates or modifies the rate of a chemical reaction. A biocatalyst can be an enzyme. A polypeptide of the invention can be used to increase the rate of conversion of a substrate to a product as disclosed herein. In the context of an industrial reaction, a polypeptide of the invention can be used, absent a host cell expressing the polypeptide, to improve reactions generating 3-HBal, 1,3-BDO, 4-HBal or 1,4-BDO, or a downstream product related thereto such as an ester or amide thereof, for example, using in vitro methods. In one embodiment, the invention provides use of the polypeptide of the invention as a biocatalyst.

In some embodiments of the invention, the polypeptide encoding an aldehyde dehydrogenase of the invention is provided as a cell lysate of a cell expressing the aldehyde dehydrogenase. In such a case, the cell lysate serves as a source of the aldehyde dehydrogenase for carrying out the conversion of 3-hydroxybutyryl-CoA to 3-hydroxybutyraldehyde, or 4-hydroxybutyryl-CoA to 4-hydroxybutyraldehyde, or the reverse reaction, in an in vitro reaction. In another embodiment, the aldehyde dehydrogenase can be provided in a partially purified form, for example, partially purified from a cell lysate. In another embodiment, the aldehyde dehydrogenase can be provided in substantially purified form, in which the aldehyde dehydrogenase is substantially purified from other components, such as the components of a cell extract. Methods for partially purifying or substantially purifying a polypeptide encoding an aldehyde dehydrogenase are well known in the art, as described herein. In some embodiments, the aldehyde dehydrogenase is immobilized to a solid support, for example, a bead, plate or membrane. In a particular embodiment, the aldehyde dehydrogenase comprises an affinity tag, and the affinity tag is used to immobilize the aldehyde dehydrogenase to a solid support. Such an affinity tag can include, but is not limited to, glutathione S transferase (GST), poly His, streptavidin, and the like, as described herein.

In some embodiments, the invention provides a composition having a polypeptide disclosed herein and at least one substrate for the polypeptide. Substrate for each of the polypeptides disclosed herein are described herein and are exemplified in the Figures. The polypeptide within the composition of the invention can react with a substrate under in vitro or in vivo conditions. In this context, an in vitro condition refers to a reaction in the absence of or outside of a cell, including a cell of the invention.

In one embodiment, the invention provides a composition comprising a polypeptide of the invention and at least one substrate for the polypeptide. In one embodiment, the polypeptide can react with the substrate under in vitro conditions. In one embodiment, the substrate is 3-hydroxybutyryl-CoA. In one embodiment, the substrate is 3-hydroxy-(R)-butyryl-CoA. In one embodiment, the substrate is 4-hydroxybutyryl-CoA.

In some embodiments, the invention provides a method of constructing a host strain that can include, among other steps, introducing a vector disclosed herein into a host cell, for example, that is capable of expressing an amino acid sequence encoded by the vector and/or is capable of fermentation. Vectors of the invention can be introduced stably or transiently into a host cell using techniques well known in the art including, but not limited to, conjugation, electroporation, chemical transformation, transduction, transfection, and ultrasound transformation. Additional methods are disclosed herein, any one of which can be used in the method of the invention.

In an additional embodiment, the invention provides a cell that comprises a polypeptide of the invention, that is, an aldehyde dehydrogenase of the invention. Thus, the invention provides a non-naturally occurring cell comprising a polypeptide encoding an aldehyde dehydrogenase of the invention. Optionally, the cell can comprise a 3-HBal or 1,3-BDO pathway, or a 4-HBal or 1,4-BDO pathway, and additionally optionally include a pathway to produce a downstream product related thereto such as an ester or amide thereof. In some embodiments, the non-naturally occurring cell comprises at least one exogenous nucleic acid encoding an aldehyde dehydrogenase that converts an acyl-CoA to its corresponding aldehyde. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, in a particular embodiment, the invention provides a cell, in particular a non-naturally occurring cell, containing at least one exogenous nucleic acid encoding an aldehyde dehydrogenase, where the aldehyde dehydrogenase functions in a 3-HBal, 1,3-BDO, 4-HBal or 1,4-BDO pathway, such as that shown in FIGS. 1 and 2.

In one embodiment, the invention provides a cell comprising a vector of the invention comprising a nucleic acid of the invention. The invention also provides a cell comprising a nucleic acid of the invention. In one embodiment, the nucleic acid molecule is integrated into a chromosome of the cell. In a particular embodiment, the integration is site-specific. In an embodiment of the invention, the nucleic acid molecule is expressed. In one embodiment, the invention provides a cell comprising a polypeptide of the invention.

In one embodiment, the cell comprising a vector, nucleic acid or polypeptide is a microbial organism. In a particular embodiment, the microbial organism is a bacterium, yeast or fungus. In a particular embodiment, the cell is an isolated eukaryotic cell.

In one embodiment, the cell comprises a pathway that produces 3-hydroxybutyraldehyde (3-HBal) and/or 1,3-butanediol (1,3-BDO), or an ester or amide thereof. In another embodiment, the cell comprises a pathway that produces 4-hydroxybutyraldehyde (4-HBal) and/or 1,4-butanediol (1,4-BDO), or an ester or amide thereof. In one embodiment, the cell is capable of fermentation. In one embodiment, the cell further comprises at least one substrate for the polypeptide of the invention expressed in the cell. In a particular embodiment, the substrate is 3-hydroxybutyryl-CoA. In a particular embodiment, the substrate is 3-hydroxy-(R)-butyryl-CoA. In one embodiment, the cell has higher activity for 3-hydroxy-(R)-butyryl-CoA over 3-hydroxy-(S)-butyryl-CoA. In another particular embodiment, the substrate is 4-hydroxybutyryl-CoA. The invention also provides culture medium comprising a cell of the invention.

The aldehyde dehydrogenase of the invention can be utilized in a pathway that converts an acyl-CoA to its corresponding aldehyde. Exemplary pathways for 3-HBal and/or 1,3-BDO that comprise an aldehyde dehydrogenase have been described, for example, in WO 2010/127319, WO 2013/036764, U.S. Pat. No. 9,017,983, US 2013/0066035, each of which is incorporated herein by reference.

Exemplary 3-HBal and/or 1,3-BDO pathways are shown in FIG. 1 and described in WO 2010/127319, WO 2013/036764, U.S. Pat. No. 9,017,983 and US 2013/0066035. Such a 3-HBal and/or 1,3-BDO pathway that comprises an aldehyde dehydrogenase includes, for example, (G) acetoacetyl-CoA reductase (ketone reducing); (H) 3-hydroxybutyryl-CoA reductase (aldehyde forming), also referred to herein as 3-hydroxybutyraldehyde dehydrogenase, an aldehyde dehydrogenase (ALD); and (C) 3-hydroxybutyraldehyde reductase, also referred to herein as a 1,3-BDO dehydrogenase (see FIG. 1). Acetoacetyl-CoA can be formed by converting two molecules of acetyl-CoA into one molecule of acetoacetyl-CoA employing a thiolase. Acetoacetyl-CoA thiolase converts two molecules of acetyl-CoA into one molecule each of acetoacetyl-CoA and CoA (see WO 2013/036764 and US 2013/0066035).

Figure 2:
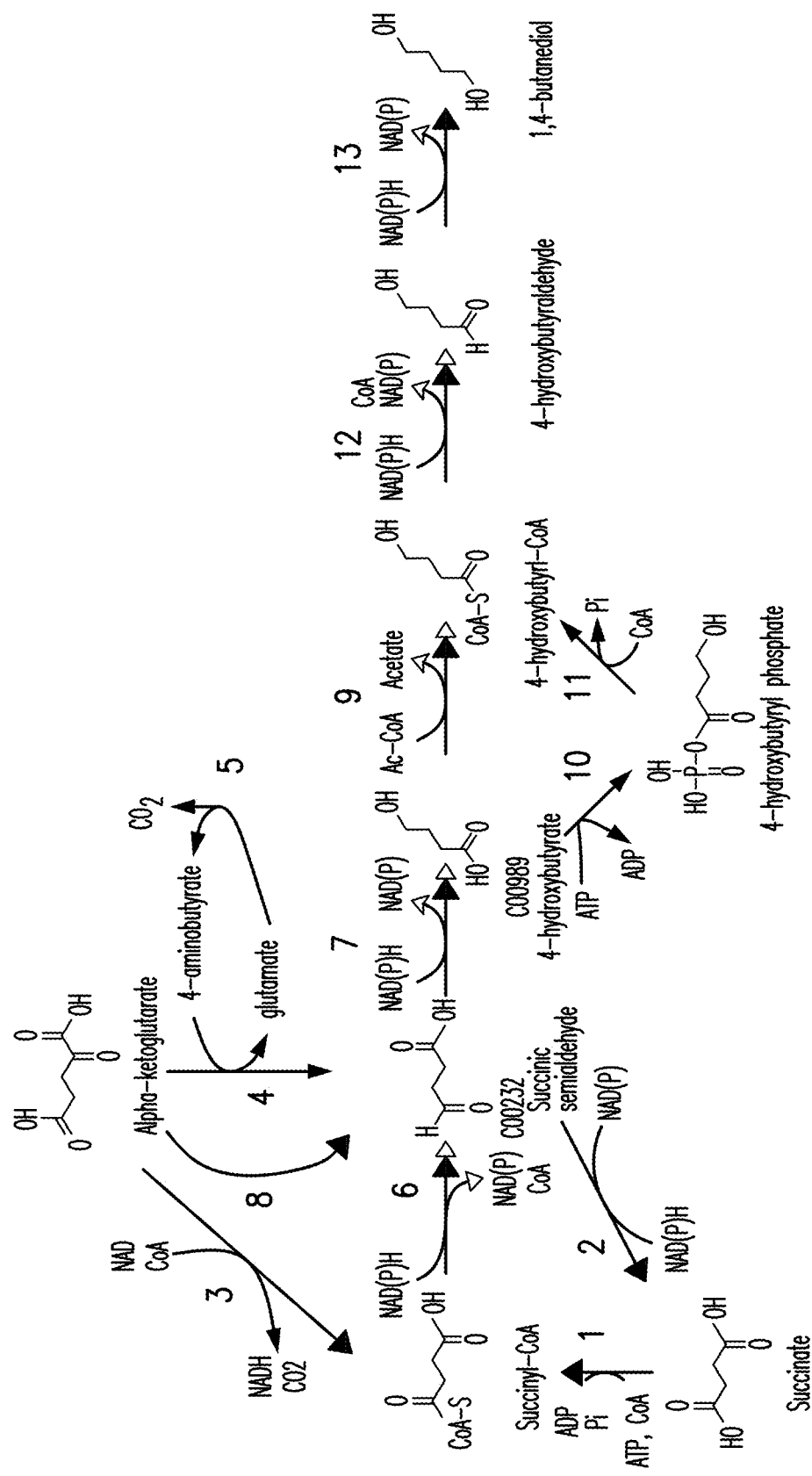
FIG. 2 shows an exemplary 1,4-butanediol (1,4-BDO) pathway that comprises an aldehyde dehydrogenase. Enzymes catalyzing the biosynthetic reactions are: (1) succinyl-CoA synthetase; (2) CoA-independent succinic semialdehyde dehydrogenase; (3) α-ketoglutarate dehydrogenase; (4) glutamate:succinate semialdehyde transaminase; (5) glutamate decarboxylase; (6) CoA-dependent succinic semialdehyde dehydrogenase; (7) 4-hydroxybutanoate dehydrogenase (also referred to as 4-hydroxybutyrate dehydrogenase); (8) α-ketoglutarate decarboxylase; (9) 4-hydroxybutyryl CoA:acetyl-CoA transferase; (10) butyrate kinase (also referred to as 4-hydroxybutyrate kinase); (11) phosphotransbutyrylase (also referred to as phospho-trans-4-hydroxybutyrylase); (12) aldehyde dehydrogenase (also referred to as 4-hydroxybutyryl-CoA reductase); (13) alcohol dehydrogenase (also referred to as 4-hydroxybutanal reductase or 4-hydroxybutyraldehyde reductase).

An exemplary 1,3-BDO pathway is shown in FIG. 2 of WO 2010/127319. Briefly, acetoacetyl-CoA can be converted to 3-hydroxybutyryl-CoA by acetoacetyl-CoA reductase (ketone reducing)(EC 1.1.1.a)(step G of FIG. 1). 3-Hydroxybutyryl-CoA can be converted to 3-hydroxybutyraldehyde by 3-hydroxybutyryl-CoA reductase (aldehyde forming)(EC 1.2.1.b), also referred to herein as 3-hydroxybutyraldehyde dehydrogenase, including an aldehyde dehydrogenase of the invention (step H of FIG. 1). 3-Hydroxybutyraldehyde can be converted to 1,3-butanediol by 3-hydroxybutyraldehyde reductase (EC 1.1.1.a), also referred to herein as 1,3-BDO dehydrogenase (step C of FIG. 1).

As disclosed herein, aldehyde dehydrogenases of the invention can function in a pathway to convert 3-hydroxybutyryl-CoA to 3-hydroxybutyraldehyde. In the pathway described above that comprises an aldehyde dehydrogenase that converts 3-hydroxybutyryl-CoA to 3-hydroxybutyraldehyde, the pathway converts acetoacetyl-CoA to 3-hydroxybutyryl-CoA (see FIG. 1). The aldehyde dehydrogenases of the invention can also be used in other 3-HBal and/or 1,3-BDO pathways that comprise 3-hydroxybutyryl-CoA as a substrate/product in the pathway. One skilled in the art can readily utilize an aldehyde dehydrogenase of the invention to convert 3-hydroxybutyryl-CoA to 3-hydroxybutyraldehyde in any desired pathway that comprises such a reaction.

Exemplary 4-HBal and/or 1,4-BDO pathways are shown in FIG. 2 and described in WO 2008/115840, WO 2010/030711, WO 2010/141920, WO 2011/047101, WO 2013/184602, WO 2014/176514, U.S. Pat. Nos. 8,067,214, 7,858,350, 8,129,169, 8,377,666, US 2013/0029381, US 2014/0030779, US 2015/0148513 and US 2014/0371417. Such a 4-HBal and/or 1,4-BDO pathway that comprises an aldehyde dehydrogenase includes, for example, (1) succinyl-CoA synthetase; (2) CoA-independent succinic semialdehyde dehydrogenase; (3) α-ketoglutarate dehydrogenase; (4) glutamate:succinate semialdehyde transaminase; (5) glutamate decarboxylase; (6) CoA-dependent succinic semialdehyde dehydrogenase; (7) 4-hydroxybutanoate dehydrogenase; (8) α-ketoglutarate decarboxylase; (9) 4-hydroxybutyryl CoA:acetyl-CoA transferase; (10) butyrate kinase (also referred to as 4-hydroxybutyrate kinase); (11) phosphotransbutyrylase (also referred to as phospho-trans-4-hydroxybutyrylase); (12) aldehyde dehydrogenase (also referred to as 4-hydroxybutyryl-CoA reductase); (13) alcohol dehydrogenase, such as 1,4-butanediol dehydrogenase (also referred to as 4-hydroxybutanal reductase or 4-hydroxybutyraldehyde reductase)(see FIG. 2).

Similar to FIG. 2, exemplary 1,4-BDO pathways are shown in FIG. 8A of WO 2010/141920. Briefly, succinyl-CoA can be converted to succinic semialdehyde by succinyl-CoA reductase (or succinate semialdehyde dehydrogenase) (EC 1.2.1.b). Succinate semialdehyde can be converted to 4-hydroxybutyrate by 4-hydroxybutyrate dehydrogenase (EC 1.1.1.a). Alternatively, succinyl-CoA can be converted to 4-hydroxybutyrate by succinyl-CoA reductase (alcohol forming) (EC 1.1.1.c). 4-Hydroxybutyrate can be converted to 4-hydroxybutyryl-CoA by 4-hydroxybutyryl-CoA transferase (EC 2.8.3.a), by 4-hydroxybutyryl-CoA hydrolase (EC 3.1.2.a) or by 4-hydroxybutyryl-CoA ligase (or 4-hydroxybutyryl-CoA synthetase) (EC 6.2.1.a). Alternatively, 4-hydroxybutyrate can be converted to 4-hydroxybutyryl-phosphate by 4-hydroxybutyrate kinase (EC 2.7.2.a). 4-Hydroxybutyryl-phosphate can be converted to 4-hydroxybutyryl-CoA by phosphotrans-4-hydroxybutyrylase (EC 2.3.1.a). Alternatively, 4-hydroxybutyryl-phosphate can be converted to 4-hydroxybutanal by 4-hydroxybutanal dehydrogenase (phosphorylating) (EC 1.2.1.d). 4-Hydroxybutyryl-CoA can be converted to 4-hydroxybutanal by 4-hydroxybutyryl-CoA reductase (or 4-hydroxybutanal dehydrogenase) (EC 1.2.1.b), including by an aldehyde dehydrogenase variant of the invention. Alternatively, 4-hydroxybutyryl-CoA can be converted to 1,4-butanediol by 4-hydroxybutyryl-CoA reductase (alcohol forming) (EC 1.1.1.c). 4-Hydroxybutanal can be converted to 1,4-butanediol by 1,4-butanediol dehydrogenase (EC 1.1.1.a).

Exemplary 1,4-BDO pathways are also shown in FIG. 8B of WO 2010/141920. Briefly, alpha-ketoglutarate can be converted to succinic semialdehyde by alpha-ketoglutarate decarboxylase (EC 4.1.1.a). Alternatively, alpha-ketoglutarate can be converted to glutamate by glutamate dehydrogenase (EC 1.4.1.a). 4-Aminobutyrate can be converted to succinic semialdehyde by 4-aminobutyrate oxidoreductase (deaminating) (EC 1.4.1.a) or 4-aminobutyrate transaminase (EC 2.6.1.a). Glutamate can be converted to 4-aminobutyrate by glutamate decarboxylase (EC 4.1.1.a). Succinate semialdehyde can be converted to 4-hydroxybutyrate by 4-hydroxybutyrate dehydrogenase (EC 1.1.1.a). 4-Hydroxybutyrate can be converted to 4-hydroxybutyryl-CoA by 4-hydroxybutyryl-CoA transferase (EC 2.8.3.a), by 4-hydroxybutyryl-CoA hydrolase (EC 3.1.2.a), or by 4-hydroxybutyryl-CoA ligase (or 4-hydroxybutyryl-CoA synthetase) (EC 6.2.1.a). 4-Hydroxybutyrate can be converted to 4-hydroxybutyryl-phosphate by 4-hydroxybutyrate kinase (EC 2.7.2.a). 4-Hydroxybutyryl-phosphate can be converted to 4-hydroxybutyryl-CoA by phosphotrans-4-hydroxybutyrylase (EC 2.3.1.a). Alternatively, 4-hydroxybutyryl-phosphate can be converted to 4-hydroxybutanal by 4-hydroxybutanal dehydrogenase (phosphorylating) (EC 1.2.1.d). 4-Hydroxybutyryl-CoA can be converted to 4-hydroxybutanal by 4-hydroxybutyryl-CoA reductase (or 4-hydroxybutanal dehydrogenase) (EC 1.2.1.b), including by an aldehyde dehydrogenase of the invention. 4-Hydroxybutyryl-CoA can be converted to 1,4-butanediol by 4-hydroxybutyryl-CoA reductase (alcohol forming) (EC 1.1.1.c). 4-Hydroxybutanal can be converted to 1,4-butanediol by 1,4-butanediol dehydrogenase (EC 1.1.1.a).

As disclosed herein, aldehyde dehydrogenases of the invention can function in a pathway to convert 4-hydroxybutyryl-CoA to 4-hydroxybutyraldehyde. In the pathways described above that comprise an aldehyde dehydrogenase that converts 4-hydroxybutyryl-CoA to 4-hydroxybutyraldehyde, the pathways convert 4-hydroxybutyrate to 4-hydroxybutyryl-CoA or 4-hydroxybutyryl phosphate to 4-hydroxybutyryl-CoA (see FIG. 2). The aldehyde dehydrogenases of the invention can also be used in other 4-HBal and/or 1,4-BDO pathways that comprise 4-hydroxybutyryl-CoA as a substrate/product in the pathway. One skilled in the art can readily utilize an aldehyde dehydrogenase of the invention to convert 4-hydroxybutyryl-CoA to 4-hydroxybutyraldehyde in any desired pathway that comprises such a reaction. For example, 4-oxobutyryl-CoA can be converted to 4-hydroxybutyryl-CoA as described and shown in WO 2010/141290, FIG. 9A. In addition, 5-hydroxy-2-oxopentanoic acid can be converted to 4-hydroxybutyryl-CoA as described and shown in WO 2010/141290, FIGS. 10 and 11. Also, acetoacetyl-CoA, 3-hydroxybutyryl-CoA, crotonyl-CoA and/or vinylacetyl-CoA can be converted to 4-hydroxybutyryl-CoA as described and shown in WO 2010/141290, FIG. 12. Additionally, 4-hydroxybut-2-enoyl-CoA can be converted to 4-hydroxybutyryl-CoA as described and shown in WO 2010/141290, FIG. 13. Thus, one skilled in the art will readily understand how to use an aldehyde dehydrogenase of the invention in a 4-HBal and/or 1,4-BDO pathway that comprises conversion of 4-hydroxybutyryl-CoA to 4-hydroxybutyraldehyde, as desired.

Enzyme types required to convert common central metabolic intermediates into 1,3-BDO or 1,4-BDO are indicated above with representative Enzyme Commission (EC) numbers (see also WO 2010/127319, WO 2013/036764, WO 2008/115840, WO 2010/030711, WO 2010/141920, WO 2011/047101, WO 2013/184602, WO 2014/176514, U.S. Pat. Nos. 9,017,983, 8,067,214, 7,858,350, 8,129,169, 8,377,666, US 2013/0066035, US 2013/0029381, US 2014/0030779, US 2015/0148513, and US 2014/0371417). The first three digits of each label correspond to the first three Enzyme Commission number digits which denote the general type of transformation independent of substrate specificity. Exemplary enzymes include: 1.1.1.a, Oxidoreductase (ketone to hydroxyl or aldehyde to alcohol); 1.1.1.c, Oxidoreductase (2 step, acyl-CoA to alcohol); 1.2.1.b, Oxidoreductase (acyl-CoA to aldehyde); 1.2.1.c, Oxidoreductase (2-oxo acid to acyl-CoA, decarboxylation); 1.2.1.d, Oxidoreductase (phosphorylating/dephosphorylating); 1.3.1.a, Oxidoreductase operating on CH—CH donors; 1.4.1.a, Oxidoreductase operating on amino acids (deaminating); 2.3.1.a, Acyltransferase (transferring phosphate group); 2.6.1.a, Aminotransferase; 2.7.2.a, Phosphotransferase, carboxyl group acceptor; 2.8.3.a, Coenzyme-A transferase; 3.1.2.a, Thioester hydrolase (CoA specific); 4.1.1.a, Carboxy-lyase; 4.2.1.a, Hydro-lyase; 4.3.1.a, Ammonia-lyase; 5.3.3.a, Isomerase; 5.4.3.a, Aminomutase; and 6.2.1.a, Acid-thiol ligase.

The aldehyde dehydrogenases of the invention can be utilized in a cell or in vitro to convert an acyl-CoA to its corresponding aldehyde. As disclosed herein, the aldehyde dehydrogenases of the invention have beneficial and useful properties, including but not limited to increased specificity for the R enantiomer of 3-hydroxybutyryl-CoA over the S enantiomer, increased specificity for 3-hydroxybutyryl-CoA and/or 4-hydroxybutyryl-CoA over acetyl-CoA, increased activity, decreased byproduct production, increased kcat, and the like. Aldehyde dehydrogenases of the invention can be used to produce the R-form of 1,3-butanediol (also referred to as (R)-1,3-butanediol), by enzymatically converting the product of an aldehyde dehydrogenase of the invention, 3-hydroxy-(R)-butyraldehyde, to (R)-1,3-butanediol using a 1,3-butanediol dehydrogenase.

The bio-derived R-form of 1,3-butanediol can be utilized for production of downstream products for which the R-form is preferred. In some embodiments, the R-form can be utilized as a pharmaceutical and/or nutraceutical (see WO 2014/190251). For example, (R)-1,3-butanediol can be used to produce (3R)-hydroxybutyl (3R)-hydroxybutyrate, which can have beneficial effects such as increasing the level of ketone bodies in the blood. Increasing the level of ketone bodies can lead to various clinical benefits, including an enhancement of physical and cognitive performance and treatment of cardiovascular conditions, diabetes and treatment of mitochondrial dysfunction disorders and in treating muscle fatigue and impairment (see WO 2014/190251). The bio-derived R-form of 1,3-butanediol can be utilized for production of downstream products in which a non-petroleum based product is desired, for example, by substituting petroleum-derived racemate 1,3-butanediol, its S-form or its R-form, with the bio-derived R-form.

In one embodiment, the invention provides 3-HBal or 1,3-BDO, or downstream products related thereto, such as an ester or amide thereof, enantiomerically enriched for the R form of the compound. In some embodiments, the 3-HBal or 1,3-BDO is a racemate enriched in R-enantiomer, that is, includes more R-enantiomer than S-enantiomer. For example, the 3-HBal or 1,3-BDO racemate can include 55% or more R-enantiomer and 45% or less S-enantiomer. For example, the 3-HBal or 1,3-BDO racemate can include 60% or more R-enantiomer and 40% or less S-enantiomer. For example, the 3-HBal or 1,3-BDO racemate can include 65% or more R-enantiomer and 35% or less S-enantiomer. For example, the 3-HBal or 1,3-BDO racemate can include 70% or more R-enantiomer and 30% or less S-enantiomer. For example, the 3-HBal or 1,3-BDO racemate can include 75% or more R-enantiomer and 25% or less S-enantiomer. For example, the 3-HBal or 1,3-BDO racemate can include 80% or more R-enantiomer and 20% or less S-enantiomer. For example, the 3-HBal or 1,3-BDO racemate can include 85% or more R-enantiomer and 15% or less S-enantiomer. For example, the 3-HBal or 1,3-BDO racemate can include 90% or more R-enantiomer and 10% or less S-enantiomer. For example, the 3-HBal or 1,3-BDO racemate can include 95% or more R-enantiomer and 5% or less S-enantiomer. In some embodiments, the 3-HBal or 1,3-BDO, or downstream products related thereto such as an ester or amide thereof, is greater than 90% R form, for example, greater than 95%, 96%, 97%, 98%, 99% or 99.9% R form. In one embodiment, the 3-HBal and/or 1,3-BDO, or downstream products related thereto, such as an ester or amide thereof, is ≥55% R-enantiomer, ≥60% R-enantiomer, ≥65% R-enantiomer, ≥70% R-enantiomer, ≥75% R-enantiomer, ≥80% R-enantiomer, ≥85% R-enantiomer, ≥90% R-enantiomer, or ≥95% R-enantiomer, and can be highly chemically pure, e.g., ≥99%, for example, ≥95%, ≥96%, ≥97%, ≥98%, ≥99%, ≥99.1%, ≥99.2%, ≥99.3%, ≥99.4%, ≥99.5%, ≥99.6%, ≥99.7%, ≥99.8% or ≥99.9% R-enantiomer.

In one embodiment, a petroleum-derived racemic mixture of a precursor of 3-HBal and/or 1,3-BDO, in particular a racemic mixture of 3-hydroxybutyryl-CoA, is used as a substrate for an aldehyde dehydrogenase of the invention, which exhibits increased specificity for the R form over the S form, to produce 3-HBal or 1,3-BDO, or a downstream product related thereto such as an ester or amide thereof, that is enantiomerically enriched for the R form. Such a reaction can be carried out by feeding a petroleum-derived precursor to a cell that expresses an aldehyde dehydrogenase of the invention, in particular a cell that can convert the precursor to 3-hydroxybutyryl-CoA, or can be carried out in vitro using one or more enzymes to convert the petroleum-derived precursor to 3-hydroxybutyryl-CoA, or a combination of in vivo and in vitro reactions. A reaction to produce 4-hydroxybutyryl-CoA with an aldehyde dehydrogenase of the invention can similarly be carried out by feeding a petroleum-derived precursor to a cell that expresses an aldehyde dehydrogenase of the invention, in particular a cell that can convert the precursor to 4-hydroxybutyryl-CoA, or can be carried out in vitro using one or more enzymes to convert the petroleum-derived precursor to 4-hydroxybutyryl-CoA, or a combination of in vivo and in vitro reactions.

While generally described herein as a cell that contains a 3-HBal, 1,3-BDO, 4-HBal or 1,4-BDO pathway comprising an aldehyde dehydrogenase of the invention, it is understood that the invention also provides a cell comprising at least one exogenous nucleic acid encoding an aldehyde dehydrogenase of the invention. The aldehyde dehydrogenase can be expressed in a sufficient amount to produce a desired product, such a product of a 3-HBal, 1,3-BDO, 4-HBal or 1,4-BDO pathway, or a downstream product related thereto such as an ester or amide thereof. Exemplary 3-HBal, 1,3-BDO, 4-HBal or 1,4-BDO pathways are shown in FIGS. 1 and 2 and are described herein.

It is understood that any of the pathways disclosed herein, as described in the Examples and exemplified in the Figures, including the pathways of FIGS. 1 and 2, can be utilized to generate a cell that produces any pathway intermediate or product, as desired, in particular a pathway that utilizes an aldehyde dehydrogenase of the invention. As disclosed herein, such a cell that produces an intermediate can be used in combination with another cell expressing one or more upstream or downstream pathway enzymes to produce a desired product. However, it is understood that a cell that produces a 3-HBal, 1,3-BDO, 4-HBal or 1,4-BDO pathway intermediate can be utilized to produce the intermediate as a desired product.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

As disclosed herein, a product or pathway intermediate that is a carboxylic acid can occur in various ionized forms, including fully protonated, partially protonated, and fully deprotonated forms. Accordingly, the suffix "-ate," or the acid form, can be used interchangeably to describe both the free acid form as well as any deprotonated form, in particular since the ionized form is known to depend on the pH in which the compound is found. It is understood that carboxylate products or intermediates includes ester forms of carboxylate products or pathway intermediates, such as O-carboxylate and 5-carboxylate esters. O- and S-carboxylates can include lower alkyl, that is C1 to C6, branched or straight chain carboxylates. Some such O- or S-carboxylates include, without limitation, methyl, ethyl, n-propyl, n-butyl, i-propyl, sec-butyl, and tert-butyl, pentyl, hexyl O- or S-carboxylates, any of which can further possess an unsaturation, providing for example, propenyl, butenyl, pentyl, and hexenyl S- or S-carboxylates. O-carboxylates can be the product of a biosynthetic pathway. Other biosynthetically accessible O-carboxylates can include medium to long chain groups, that is C7-C22, O-carboxylate esters derived from fatty alcohols, such as heptyl, octyl, nonyl, decyl, undecyl, lauryl, tridecyl, myristyl, pentadecyl, cetyl, palmitolyl, heptadecyl, stearyl, nonadecyl, arachidyl, heneicosyl, and behenyl alcohols, any one of which can be optionally branched and/or contain unsaturations. O-carboxylate esters can also be accessed via a biochemical or chemical process, such as esterification of a free carboxylic acid product or transesterification of an O- or S-carboxylate. S-carboxylates are exemplified by CoA S-esters, cysteinyl S-esters, alkylthioesters, and various aryl and heteroaryl thioesters.

The cells of the invention can be produced by introducing an expressible nucleic acid encoding an aldehyde dehydrogenase of the invention, and optionally expressible nucleic acids encoding one or more of the enzymes or proteins participating in one or more 3-HBal, 1,3-BDO, 4-HBal or 1,4-BDO biosynthetic pathways, and further optionally a nucleic acid encoding an enzyme that produces a downstream product related to 3-HBal, 1,3-BDO, 4-HBal or 1,4-BDO such as an ester or amide thereof. Depending on the host cell chosen, nucleic acids for some or all of a particular 3-HBal, 1,3-BDO, 4-HBal or 1,4-BDO biosynthetic pathway, or downstream product, can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is included for the deficient enzyme(s) or protein(s) to achieve 3-HBal, 1,3-BDO, 4-HBal or 1,4-BDO biosynthesis, or exogenous expression of endogenously expressed genes can be provided to increase expression of pathway enzymes, if desired. Thus, a cell of the invention can be produced by introducing an aldehyde dehydrogenase of the invention, and optionally exogenous enzyme or protein activities to obtain a desired biosynthetic pathway, or by introducing one or more exogenous enzyme or protein activities, including an aldehyde dehydrogenase of the invention that, together with one or more endogenous enzymes or proteins, produces a desired product such as 3-HBal, 1,3-BDO, 4-HBal or 1,4-BDO, or a downstream product related thereto such as an ester or amide thereof.

Host cells can be selected from, and the non-naturally cells expressing an aldehyde dehydrogenase of the invention generated in, for example, bacteria, yeast, fungus or any of a variety of microorganisms applicable or suitable to fermentation processes. Exemplary bacteria include any species selected from the order Enterobacteriales, family Enterobacteriaceae, including the genera *Escherichia* and *Klebsiella*; the order Aeromonadales, family Succinivibrionaceae, including the genus *Anaerobiospirilluin*; the order Pasteurellales, family Pasteurellaceae, including the genera *Actinobacillus* and *Mannheimia*; the order Rhizobiales, family Bradyrhizobiaceae, including the genus *Rhizobium*; the order Bacillales, family Bacillaceae, including the genus *Bacillus*; the order Actinomycetales, families Corynebacteriaceae and Streptomycetaceae, including the genus *Corynebacterium* and the genus *Streptomyces*, respectively; order Rhodospirillales, family Acetobacteraceae, including the genus *Gluconobacter*; the order Sphingomonadales, family Sphingomonadaceae, including the genus *Zymomonas*; the order Lactobacillales, families Lactobacillaceae and Streptococcaceae, including the genus *Lactobacillus* and the genus *Lactococcus*, respectively; the order Clostridiales, family Clostridiaceae, genus *Clostridium*; and the order P seudomonadales, family P seudomonadaceae, including the genus *Pseudomonas*. Non-limiting species of host bacteria include *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida. E. coli* is a particularly useful host organism since it is a well characterized microbial organism suitable for genetic engineering.

Similarly, exemplary species of yeast or fungi species include any species selected from the order Saccharomycetales, family Saccharomycetaceae, including the genera *Saccharomyces, Kluyveromyces* and *Pichia*; the order Saccharomycetales, family Dipodascaceae, including the genus *Yarrowia*; the order Schizosaccharomycetales, family Schizosaccaromycetaceae, including the genus *Schizosaccharomyces*; the order Eurotiales, family Trichocomaceae, including the genus *Aspergillus*; and the order Mucorales, family Mucoraceae, including the genus *Rhizopus*. Non-limiting species of host yeast or fungi include *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizopus oryzae, Yarrowia lipolytica*, and the like. A particularly useful host organism that is a yeast includes *Saccharomyces cerevisiae*.

Although generally described herein as utilizing a cell that is a microbial organism as a host cell, particularly for producing 3-HBal, 1,3-BDO, 4-HBal or 1,4-BDO, or a downstream product related thereto such as an ester or amide thereof, it is understood that a host cell can be a cell line of a higher eukaryote, such as a mammalian cell line or insect cell line. Thus, it is understood that reference herein to a host cell that is a microbial organism can alternatively utilize a higher eukaryotic cell line to produce a desired product. Exemplary higher eukaryotic cell lines include, but are not limited to, Chinese hamster ovary (CHO), human (Hela, Human Embryonic Kidney (HEK) 293, Jurkat), mouse (3T3), primate (Vero), insect (Sf9), and the like. Such cell lines are commercially available (see, for example, the American Type Culture Collection (ATCC; Manassas VA); Life Technologies, Carlsbad CA). It is understood that any suitable host cell can be used to introduce an aldehyde dehydrogenase of the invention, and optionally metabolic and/or genetic modifications to produce a desired product.

Depending on the 3-HBal, 1,3-BDO, 4-HBal or 1,4-BDO biosynthetic pathway constituents of a selected host cell, the non-naturally occurring cells of the invention will include at least one exogenously expressed 3-HBal, 1,3-BDO, 4-HBal or 1,4-BDO pathway-encoding nucleic acid and up to all encoding nucleic acids for one or more 3-HBal, 1,3-BDO, 4-HBal or 1,4-BDO biosynthetic pathways, or a downstream product related thereto such as an ester or amide thereof, including an aldehyde dehydrogenase of the invention. For example, 3-HBal, 1,3-BDO, 4-HBal or 1,4-BDO biosynthesis can be established in a host deficient in a pathway enzyme or protein through exogenous expression of the corresponding encoding nucleic acid, including an aldehyde dehydrogenase of the invention. In a host deficient in all enzymes or proteins of a 3-HBal, 1,3-BDO, 4-HBal or 1,4-BDO pathway, or a downstream product related thereto such as an ester or amide thereof, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of 3-HBal, 1,3-BDO, 4-HBal or 1,4-BDO pathway, or a downstream product related thereto such as an ester or amide thereof, can be included, including an aldehyde dehydrogenase of the invention.

Given the teachings and guidance provided herein, those skilled in the art will understand that the number of encoding nucleic acids to introduce in an expressible form will, at least, parallel the 3-HBal, 1,3-BDO, 4-HBal or 1,4-BDO pathway deficiencies of the selected host cell if a 3-HBal, 1,3-BDO, 4-HBal or 1,4-BDO pathway is to be included in the cell. Therefore, a non-naturally occurring cell of the invention can have one, two, three, four, five, six, seven, eight, and so forth, depending on the particular pathway, up to all nucleic acids encoding the enzymes or proteins constituting a 3-HBal, 1,3-BDO, 4-HBal or 1,4-BDO biosynthetic pathway disclosed herein. In some embodiments, the non-naturally occurring cells also can include other genetic modifications that facilitate or optimize 3-HBal, 1,3-BDO, 4-HBal or 1,4-BDO biosynthesis or that confer other useful functions onto the host cell. One such other functionality can include, for example, augmentation of the synthesis of one or more of the 3-HBal, 1,3-BDO, 4-HBal or 1,4-BDO pathway precursors such acetyl-CoA or acetoacetyl-CoA.

Generally, a host cell is selected such that it can express an aldehyde dehydrogenase of the invention, and optionally produces the precursor of a 3-HBal, 1,3-BDO, 4-HBal or 1,4-BDO pathway, in a cell containing such a pathway, either as a naturally produced molecule or as an engineered product that either provides de novo production of a desired precursor or increased production of a precursor naturally produced by the host cell. A host organism can be engineered to increase production of a precursor, as disclosed herein. In addition, a cell that has been engineered to produce a desired precursor can be used as a host organism and further engineered to express enzymes or proteins of a 3-HBal, 1,3-BDO, 4-HBal or 1,4-BDO pathway, or a downstream product related thereto such as an ester or amide thereof, if desired.

In some embodiments, a non-naturally occurring cell of the invention is generated from a host that contains the enzymatic capability to synthesize 3-HBal, 1,3-BDO, 4-HBal or 1,4-BDO, or a downstream product related thereto such as an ester or amide thereof. In this specific embodiment it can be useful to increase the synthesis or accumulation of a 3-HBal, 1,3-BDO, 4-HBal or 1,4-BDO pathway product to, for example, drive 3-HBal, 1,3-BDO, 4-HBal or 1,4-BDO pathway reactions toward 3-HBal, 1,3-BDO, 4-HBal or 1,4-BDO production, or a downstream product related thereto such as an ester or amide thereof. Increased synthesis or accumulation can be accomplished by, for example, overexpression of nucleic acids encoding one or more of the above-described 3-HBal, 1,3-BDO, 4-HBal or 1,4-BDO pathway enzymes or proteins, including an aldehyde dehydrogenase of the invention. Overexpression of the enzyme or enzymes and/or protein or proteins of the 3-HBal, 1,3-BDO, 4-HBal or 1,4-BDO pathway can occur, for example, through exogenous expression of the endogenous gene or genes, or through exogenous expression of the heterologous gene or genes, including exogenous expression of an aldehyde dehydrogenase of the invention.

Therefore, naturally occurring organisms can be readily converted to non-naturally occurring cells of the invention, for example, producing 3-HBal, 1,3-BDO, 4-HBal or 1,4-BDO or a downstream product related thereto such as an ester or amide thereof, through overexpression of one, two, three, four, five, six, seven, eight, or more, depending on the 3-HBal, 1,3-BDO, 4-HBal or 1,4-BDO pathway, that is, up to all nucleic acids encoding 3-HBal, 1,3-BDO, 4-HBal or 1,4-BDO biosynthetic pathway enzymes or proteins, or enzymes that produce a downstream product related thereto such as an ester or amide thereof. In addition, a non-naturally occurring organism can be generated by mutagenesis of an endogenous gene that results in an increase in activity of an enzyme in the 3-HBal, 1,3-BDO, 4-HBal or 1,4-BDO biosynthetic pathway, or a downstream product related thereto such as an ester or amide thereof.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring cell.

It is understood that any of the one or more exogenous nucleic acids can be introduced into a cell to produce a non-naturally occurring cell of the invention. The nucleic acids can be introduced so as to confer, for example, a 3-HBal, 1,3-BDO, 4-HBal or 1,4-BDO, or a downstream product related thereto such as an ester or amide thereof, biosynthetic pathway onto the cell, including introducing a nucleic acid encoding an aldehyde dehydrogenase of the invention. Alternatively, encoding nucleic acids can be introduced to produce a cell having the biosynthetic capability to catalyze some of the required reactions to confer 3-HBal, 1,3-BDO, 4-HBal or 1,4-BDO biosynthetic capability to produce an intermediate. For example, a non-naturally occurring cell having a 3-HBal, 1,3-BDO, 4-HBal or 1,4-BDO biosynthetic pathway can comprise at least two exogenous nucleic acids encoding desired enzymes or proteins, including an aldehyde dehydrogenase of the invention. Thus, it is understood that any combination of two or more enzymes or proteins of a biosynthetic pathway can be included in a non-naturally occurring cell of the invention, including an aldehyde dehydrogenase of the invention. Similarly, it is understood that any combination of three or more enzymes or proteins of a biosynthetic pathway can be included in a non-naturally occurring cell of the invention, as desired, so long as the combination of enzymes and/or proteins of the desired biosynthetic pathway results in production of the corresponding desired product. Similarly, any combination of four or more enzymes or proteins of a biosynthetic pathway as disclosed herein can be included in a non-naturally occurring cell of the invention, as desired, so long as the combination of enzymes and/or proteins of the desired biosynthetic pathway results in production of the corresponding desired product.

In addition to the biosynthesis of 3-HBal, 1,3-BDO, 4-HBal or 1,4-BDO, or a downstream product related thereto such as an ester or amide thereof, as described herein, the non-naturally occurring cells and methods of the invention also can be utilized in various combinations with each other and/or with other cells and methods well known in the art to achieve product biosynthesis by other routes. For example, one alternative to produce 3-HBal, 1,3-BDO, 4-HBal or 1,4-BDO other than use of the 3-HBal, 1,3-BDO, 4-HBal or 1,4-BDO producers is through addition of another cell capable of converting a 3-HBal, 1,3-BDO, 4-HBal or 1,4-BDO pathway intermediate to 3-HBal, 1,3-BDO, 4-HBal or 1,4-BDO. One such procedure includes, for example, the fermentation of a cell that produces a 3-HBal, 1,3-BDO, 4-HBal or 1,4-BDO pathway intermediate. The 3-HBal, 1,3-BDO, 4-HBal or 1,4-BDO pathway intermediate can then be used as a substrate for a second cell that converts the 3-HBal, 1,3-BDO, 4-HBal or 1,4-BDO pathway intermediate to 3-HBal, 1,3-BDO, 4-HBal or 1,4-BDO. The 3-HBal, 1,3-BDO, 4-HBal or 1,4-BDO pathway intermediate can be added directly to another culture of the second organism or the original culture of the 3-HBal, 1,3-BDO, 4-HBal or 1,4-BDO pathway intermediate producers can be depleted of these cells by, for example, cell separation, and then subsequent addition of the second organism to the fermentation broth can be utilized to produce the final product without intermediate purification steps. A cell that produces a downstream product related to 3-HBal, 1,3-BDO, 4-HBal or 1,4-BDO such as an ester or amide thereof, can optionally be included to produce such a downstream product.

Alternatively, such enzymatic conversions can be carried out in vitro, with a combination of enzymes or sequential exposure of substrates to enzymes that result in conversion of a substrate to a desired product. As another alternative, a combination of cell-based conversions and in vitro enzymatic conversions can be used, if desired.

In other embodiments, the non-naturally occurring cells and methods of the invention can be assembled in a wide variety of subpathways to achieve biosynthesis of, for example, 3-HBal, 1,3-BDO, 4-HBal or 1,4-BDO or a downstream product related thereto such as an ester or amide thereof. In these embodiments, biosynthetic pathways for a desired product of the invention can be segregated into different cells, and the different cells can be co-cultured to produce the final product. In such a biosynthetic scheme, the product of one cell is the substrate for a second cell until the final product is synthesized. For example, the biosynthesis of 3-HBal, 1,3-BDO, 4-HBal or 1,4-BDO, or a downstream product related thereto such as an ester or amide thereof, can be accomplished by constructing a cell that contains biosynthetic pathways for conversion of one pathway intermediate to another pathway intermediate or the product. Alternatively, 3-HBal, 1,3-BDO, 4-HBal or 1,4-BDO also can be biosynthetically produced from cells through co-culture or co-fermentation using two different cells in the same vessel, where the first cell produces a 3-HBal, 1,3-BDO, 4-HBal or 1,4-BDO intermediate and the second cell converts the intermediate to 3-HBal, 1,3-BDO, 4-HBal or 1,4-BDO, or a downstream product related thereto such as an ester or amide thereof.

Given the teachings and guidance provided herein, those skilled in the art will understand that a wide variety of combinations and permutations exist for the non-naturally occurring cells and methods of the invention together with other cells, with the co-culture of other non-naturally occurring cells having subpathways and with combinations of other chemical and/or biochemical procedures well known in the art to produce 3-HBal, 1,3-BDO, 4-HBal or 1,4-BDO, or a downstream product related thereto such as an ester or amide thereof.

Sources of encoding nucleic acids for a 3-HBal, 1,3-BDO, 4-HBal or 1,4-BDO pathway enzyme or protein, or a downstream product related thereto such as an ester or amide thereof, can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, Escherichia coli, Saccharomyces cerevisiae, Saccharomyces kluyveri, Clostridium kluyveri, Clostridium acetobutylicum, Clostridium beijerinckii, Clostridium saccharoperbutylacetonicuin, Clostridium perfringens, Clostridium difficile, Clostridium botulinum, Clostridium tyrxobutyricum, Clostridium tetanomorphum, Clostridium tetani, Clostridium propionicum, Clostridium aminobutyricum, Clostridium subterminale, Clostridium sticklandii, Ralstonia eutropha, Mycobacterium bovis, Mycobacterium tuberculosis, Porphyromonas gingivalis, Arabidopsis thaliana, Thermus thermophilus, Pseudomonas species, including Pseudomonas aeruginosa, Pseudomonas putida, Pseudomonas stutzeri, Pseudomonas fluorescens, Homo sapiens, Oryctolagus cuniculus, Rhodobacter spaeroides, Thermoanaerobacter brockii, Metallosphaera sedula, Leuconostoc mesenteroides, Chloroflexus aurantiacus, Roseiflexus castenholzii, Erythrobacter, Simmondsia chinensis, Acinetobacter species, including Acinetobacter calcoaceticus and Acinetobacter baylyi, Porphyromonas gingivalis, Sulfolobus tokodaii, Sulfolobus solfataricus, Sulfolobus acidocaldarius, Bacillus subtilis, Bacillus cereus, Bacillus megaterium, Bacillus brevis, Bacillus pumilus, Rattus norvegicus, Klebsiella pneumonia, Klebsiella oxytoca, Euglena gracilis, Treponema denticola, Moorella thermoacetica, Thermotoga maritima, Halobacterium salinarum, Geobacillus stearothermophilus, Aeropyrum pernix, Sus scrofa, Caenorhabditis elegans, Corynebacterium glutamicum, Acidaminococcus fermentans, Lactococcus lactis, Lactobacillus plantarum, Streptococcus thermophilus, Enterobacter aerogenes, Candida, Aspergillus terreus, Pedicoccus pentosaceus, Zymomonas mobilus, Acetobacter pasteurians, Kluyveromyces lactis, Eubacterium barkeri, Bacteroides capillosus, Anaerotruncus colihominis, Natranaerobius thermophilusm, Campylobacter jejuni, Haemophilus influenzae, Serratia marcescens, Citrobacter amalonaticus, Myxococcus xanthus, Fusobacterium nuleatum, Penicillium chrysogenum, marine gamma proteobacterium, butyrate-producing bacterium, Nocardia iowensis, Nocardia farcinica, Streptomyces griseus, Schizosaccharomyces pombe, Geobacillus thennoglucosidasius, Salmonella typhimurium, Vibrio cholera, Heliobacter pylori, Nicotiana tabacum, Oryza saliva, Haloferax meditefanei, Agrobacterium tumefaciens, Achromobacter denitrificans, Fusobacterium nucleatum, Streptomyces clavuli genus, Acinetobacter baumanii, Mus musculus, Lachancea kluyveri, Trichomonas vaginalis, Trypanosoma brucei, Pseudomonas stutzeri, Bradyrhizobium japonicum, Mesorhizobium loti, Bos taurus, Nicotiana glutinosa, Vibrio vulnificus, Selenomonas ruminantium, Vibrio parahaemolyticus, Archaeoglobus fulgidus, Haloarcula marismortui, Pyrobaculum aerophilum, Mycobacterium smegmatis MC2 155, Mycobacterium avium subsp. paratuberculosis K-10, Mycobacterium marinum M, Tsukamurella paurometabola DSM 20162, Cyanobium PCC7001, Dictyostelium discoideum AX4, Acidaminococcus fermentans, Acinetobacter baylyi, Acinetobacter calcoaceticus, Aquifex aeolicus, Arabidopsis thaliana, Archaeoglobus fulgidus, Aspergillus niger, Aspergillus terreus, Bacillus subtilis, Bos Taurus, Candida albicans, Candida tropicalis, Chlamydomonas reinhardtii, Chlorobium tepidum, Citrobacter koseri, Citrus junos, Clostridium acetobutylicum, Clostridium kluyveri, Clostridium saccharoperbutylacetonicum, Cyanobium PCC7001, Desulfatibacilluin alkenivorans, Dictyostelium discoideum, Fusobacterium nucleatum, Haloarcula marismortui, Homo sapiens, Hydrogenobacter thermophilus, Klebsiella pneumoniae, Kluyveromyces lactis, Lactobacillus brevis, Leuconostoc mesenteroides, Metallosphaera sedula, Methanothermobacter thermautotrophicus, Mus musculus, Mycobacterium avium, Mycobacterium bovis, Mycobacterium marinum, Mycobacterium smegmatis, Nicotiana tabacum, Nocardia iowensis, Oryctolagus cuniculus, Penicillium chrysogenum, Pichia pastoris, Porphyromonas gingivalis, Porphyromonas gingivalis, Pseudomonas aeruginos, Pseudomonas putida, Pyrobaculum aerophilum, Ralstonia eutropha, Rattus norvegicus, Rhodobacter sphaeroides, Saccharomyces cerevisiae, Salmonella enteric, Salmonella typhimurium, Schizosaccharomyces pombe, Sulfolobus acidocaldarius, Sulfolobus solfataricus, Sulfolobus tokodaii, Thermoanaerobacter tengcongensis, Thermus thermophilus, Trypanosoma brucei, Tsukamurella paurometabola, Yarrowia lipolytica, Zoogloea ramigera and Zymomonas mobilis, Clostridum species, including but no limited to Clostridium saccharoperbutylacetonicum, Clostridium beijerinckii, Clostridium saccharobutylicum, Clostridium botulinum, Clostridium methylpentosum, Clostridium sticklandii, Clostridium phytofermentans, Clostridium saccharolyticum, Clostridium asparagiforme, Clostridium celatum, Clostridium carboxidivorans, Clostridium clostridioforme, Clostridium bolteae, Caldalkalibacillus thermarum, Clostridium botulinum, Pelosinus fennentans, Thermoanaerobacterium thermosaccharolyticum, Desulfosporosinus speices, Thermoanaerobacterium species, including but not limited to Thermoanaerobacterium saccharolyticum, Thermoanaerobacterium xylanolyticum, Acetonema longum, Geobacillus species, including but not limited to Geobacillus thermoglucosidans, Bacillus azotoformans, Thermincola potens, Fusobacterium species, including but not limited to Fusobacterium nucleatum, Fusobacterium ulcerans, Fusobacterium varium, Ruminococcus species, including but not limited to Ruminococcus gnavus, Ruminococcus obeum, Lachnospiraceae bacterium, Flavonvctor plautii, Roseburia inulinivorans, Acetobacterium woodii, Eubacterium species, including but not limited to Eubacterium plexicaudatum, Eubacterium hallii, Eubacterium limosum, Eubacterium yurii, Eubacteriaceae bacterium, Thermosediminibacter oceani, Ilyobacter polytropus, Shuttleworthia satelles, Halanaerobium saccharolyticum, Thermoanaerobacter ethanolicus, Rhodospirillum rubrum, Vibrio, Propionibacterium propionicum as well as other exemplary species disclosed herein or available as source organisms for corresponding genes, including the source organisms of the aldehyde dehydrogenases described in Table 4. However, with the complete genome sequence available for now more than 550 species (with more than half of these available on public databases such as the NCBI), including 395 microorganism genomes and a variety of yeast, fungi, plant, and mammalian genomes, the identification of genes encoding the 3-HBal, 1,3-BDO, 4-HBal or 1,4-BDO biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of 3-HBal, 1,3-BDO, 4-HBal or 1,4-BDO, or a downstream product related thereto such as an ester or amide thereof, including expression of an aldehyde dehydrogenase of the invention, described herein with reference to a particular organism such as *E. coli* can be readily applied to other cells such as microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative 3-HBal, 1,3-BDO, 4-HBal or 1,4-BDO biosynthetic pathway exists in an unrelated species, 3-HBal, 1,3-BDO, 4-HBal or 1,4-BDO biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all cells using the cognate metabolic alterations to those exemplified herein to construct a cell in a species of interest that will synthesize 3-HBal, 1,3-BDO, 4-HBal or 1,4-BDO, or a downstream product related thereto such as an ester or amide thereof, if desired, including introducing an aldehyde dehydrogenase of the invention.

Methods for constructing and testing the expression levels of a non-naturally occurring host producing 3-HBal, 1,3-BDO, 4-HBal or 1,4-BDO, or a downstream product related thereto such as an ester or amide thereof, including an aldehyde dehydrogenase of the invention, can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, MD (1999).

An exogenous nucleic acid encoding an aldehyde dehydrogenase of the invention, and optionally exogenous nucleic acid sequences involved in a pathway for production of 3-HBal, 1,3-BDO, 4-HBal or 1,4-BDO, or a downstream product related thereto such as an ester or amide thereof, can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include a nucleic acid encoding an aldehyde dehydrogenase of the invention, and/or optionally one or more 3-HBal, 1,3-BDO, 4-HBal or 1,4-BDO biosynthetic pathway encoding nucleic acids, or nucleic acids encoding an enzyme that produces a downstream product related to 3-HBal, 1,3-BDO, 4-HBal or 1,4-BDO such as an ester or amide thereof, as exemplified herein operably linked to expression control sequences functional in the host organism. Expression vectors applicable for use in the host cells of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences encoding an aldehyde dehydrogenase of the invention or encoding polypeptides involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

A vector or expression vector can also be used to express an encoded nucleic acid to produce an encoded polypeptide by in vitro transcription and translation. Such a vector or expression vector will comprise at least a promoter, and includes the vectors described herein above. Such a vector for in vitro transcription and translation generally is double stranded DNA. Methods of in vitro transcription and translation are well known to those skilled in the art (see Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, MD (1999)). Kits for in vitro transcription and translation are also commercially available (see, for example, Promega, Madison, WI; New England Biolabs, Ipswich, MA; Thermo Fisher Scientific, Carlsbad, CA).

In one embodiment, the invention provides a method for producing 3-hydroxybutyraldehyde (3-HBal) and/or 1,3-butanediol (1,3-BDO), or an ester or amide thereof, comprising culturing a cell of the invention to produce 3-HBal and/or 1,3-BDO, or an ester or amide thereof. Such a cell expresses a polypeptide of the invention. In one embodiment, the invention provides a method for producing 4-hydroxybutyraldehyde (4-HBal) and/or 1,4-butanediol (1,4-BDO), or an ester or amide thereof, comprising culturing a cell of the invention to produce 4-HBal and/or 1,4-BDO, or an ester or amide thereof. In one embodiment, the cell is in a substantially anaerobic culture medium. In one embodiment, the method can further comprise isolating or purifying the 3-HBal and/or 1,3-BDO, or the 4-HBal and/or 1,4-BDO, or ester or amide thereof. In a particular embodiment, the isolating or purifying comprises distillation.

In one embodiment, the invention provides a process for producing a product of the invention, comprising chemically reacting the 3-HBal and/or 1,3-BDO, or the 4-HBal and/or 1,4-BDO, with itself or another compound in a reaction that produces the product.

In one embodiment, the invention provides a method for producing 3-hydroxybutyraldehyde (3-HBal) and/or 1,3-butanediol (1,3-BDO), or an ester or amide thereof, comprising providing a substrate to a polypeptide of the invention and converting the substrate to 3-HBal and/or 1,3-BDO, wherein the substrate is a racemic mixture of 1,3-hydroxybutyryl-CoA. In one embodiment, the 3-HBal and/or 1,3-BDO is enantiomerically enriched for the R form. In one embodiment, the invention provides a method for producing 4-hydroxybutyraldehyde (4-HBal) and/or 1,4-butanediol (1,4-BDO), or an ester or amide thereof, comprising providing a substrate to a polypeptide of the invention and converting the substrate to 4-HBal and/or 1,4-BDO, wherein the substrate is 1,4-hydroxybutyryl-CoA. In one embodiment, the polypeptide is present in a cell, in a cell lysate, or is isolated from a cell or cell lysate.

In one embodiment, the invention provides a method for producing 3-HBal and/or 1,3-BDO, or 4-HBal and/or 1,4-BDO, comprising incubating a lysate of a cell of the invention to produce 3-HBal and/or 1,3-BDO, or 4-HBal and/or 1,4-BDO. In one embodiment, the cell lysate is mixed with a second cell lysate, wherein the second cell lysate comprises an enzymatic activity to produce a substrate of a polypeptide of the invention, or a downstream product of 3-HBal and/or 1,3-BDO. or 4-HBal and/or 1,4-BDO.

The invention also provides a method for producing a polypeptide of the invention, comprising expressing the polypeptide in a cell. The invention additionally provides a method for producing a polypeptide of the invention, comprising in vitro transcribing and translating a nucleic acid of the invention or a vector of the invention to produce the polypeptide.

As described herein, a cell can be used to express an aldehyde dehydrogenase of the invention, and optionally the cell can include a metabolic pathway that utilizes an aldehyde dehydrogenase of the invention to produce a desired product, such as 3-HBal and/or 1,3-BDO, or 4-HBal and/or 1,4-BDO. Such methods for expressing a desired product are described herein. Alternatively, an aldehyde dehydrogenase of the invention can be expressed, and/or a desired product produced, in a cell lysate, for example, a cell lysate of a cell expressing an aldehyde dehydrogenase of the invention, or a cell expressing an aldehyde dehydrogenase of the invention and a metabolic pathway to produce a desired product, as described herein. In another embodiment, an aldehyde dehydrogenase of the invention can be expressed by in vitro transcription and translation, in which the aldehyde dehydrogenase is produced in a cell free system. The aldehyde dehydrogenase expressed by in vitro transcription and translation can be used to carry out a reaction in vitro. Optionally, other enzymes, or cell lysate(s) containing such enzymes, can be used to convert the product of the aldehyde dehydrogenase enzymatic reaction to a desired downstream product in vitro.

Suitable purification and/or assays to test for the expression of an aldehyde dehydrogenase, or for production of 3-HBal, 1,3-BDO, 4-HBal or 1,4-BDO, or a downstream product related thereto such as an ester or amide thereof, including assays to test for aldehyde dehydrogenase activity, can be performed using well known methods (see also Example). Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art (see also Example).

The 3-HBal, 1,3-BDO, 4-HBal or 1,4-BDO, or other desired product, such as a downstream product related thereto such as an ester or amide thereof, can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring cells expressing an aldehyde dehydrogenase of the invention described herein can be cultured to produce and/or secrete the biosynthetic products of the invention. For example, the cells that produce 3-HBal, 1,3-BDO, 4-HBal or 1,4-BDO, or a downstream product related thereto such as an ester or amide thereof, can be cultured for the biosynthetic production of 3-HBal, 1,3-BDO, 4-HBal or 1,4-BDO, or a downstream product related thereto such as an ester or amide thereof. Accordingly, in some embodiments, the invention provides culture medium containing the 3-HBal, 1,3-BDO, 4-HBal or 1,4-BDO, or a downstream product related thereto such as an ester or amide thereof, or 3-HBal, 1,3-BDO, 4-HBal or 1,4-BDO pathway intermediate described herein. In some aspects, the culture medium can also be separated from the non-naturally occurring cells of the invention that produced the 3-HBal, 1,3-BDO, 4-HBal or 1,4-BDO, or a downstream product related thereto such as an ester or amide thereof, or 3-HBal, 1,3-BDO, 4-HBal or 1,4-BDO pathway intermediate. Methods for separating a cell from culture medium are well known in the art. Exemplary methods include filtration, flocculation, precipitation, centrifugation, sedimentation, and the like.

For the production of an aldehyde dehydrogenase of the invention, or of 3-HBal, 1,3-BDO, 4-HBal or 1,4-BDO, or a downstream product related thereto such as an ester or amide thereof, in a cell expressing an aldehyde dehydrogenase of the invention, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United States publication 2009/0047719, filed Aug. 10, 2007. Fermentations can be performed in a batch, fed-batch or continuous manner, as disclosed herein. Fermentations can also be conducted in two phases, if desired. The first phase can be aerobic to allow for high growth and therefore high productivity, followed by an anaerobic phase of high yields of a desired product such as 3-HBal, 1,3-BDO, 4-HBal or 1,4-BDO, or a downstream product related thereto such as an ester or amide thereof.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring cell. Such sources include, for example: sugars such as glucose, xylose, arabinose, galactose, mannose, fructose, sucrose and starch; or glycerol, and it is understood that a carbon source can be used alone as the sole source of carbon or in combination with other carbon sources described herein or known in the art. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the cells of the invention for the expression of an aldehyde dehydrogenase of the invention, and optionally production of 3-HBal, 1,3-BDO, 4-HBal or 1,4-BDO, or a downstream product thereof, such as an ester or amide thereof.

In addition to renewable feedstocks such as those exemplified above, the cells of the invention that produce 3-HBal, 1,3-BDO, 4-HBal or 1,4-BDO or a downstream product thereof, such as an ester or amide thereof, also can be modified for growth on syngas as its source of carbon. In this specific embodiment, one or more proteins or enzymes are expressed in the 3-HBal, 1,3-BDO, 4-HBal or 1,4-BDO producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. H₂-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

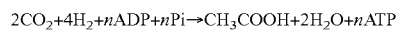

$$2CO_2 + 4H_2 + n\text{ADP} + n\text{Pi} \rightarrow CH_3COOH + 2H_2O + n\text{ATP}$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC) (see WO2009/094485). Following the teachings and guidance provided herein for introducing a sufficient number of encoding nucleic acids to generate a 3-HBal, 1,3-BDO, 4-HBal or 1,4-BDO pathway, or a downstream product related thereto such as an ester or amide thereof, including a nucleic acid encoding an aldehyde dehydrogenase of the invention, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the cells of the invention such that the modified organism contains the complete Wood-Ljungdahl pathway will confer syngas utilization ability.

Additionally, the reductive (reverse) tricarboxylic acid cycle coupled with carbon monoxide dehydrogenase and/or hydrogenase activities can also be used for the conversion of CO, $CO_2$ and/or $H_2$ to acetyl-CoA and other products such as acetate. Organisms capable of fixing carbon via the reductive TCA pathway can utilize one or more of the following enzymes: ATP citrate-lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, NAD(P)H:ferredoxin oxidoreductase, carbon monoxide dehydrogenase, and hydrogenase. Specifically, the reducing equivalents extracted from CO and/or $H_2$ by carbon monoxide dehydrogenase and hydrogenase are utilized to fix $CO_2$ via the reductive TCA cycle into acetyl-CoA or acetate. Acetate can be converted to acetyl-CoA by enzymes such as acetyl-CoA transferase, acetate kinase/phosphotransacetylase, and acetyl-CoA synthetase. Acetyl-CoA can be converted to glyceraldehyde-3-phosphate, phosphoenolpyruvate, and pyruvate, by pyruvateferredoxin oxidoreductase and the enzymes of gluconeogenesis. Acetyl-CoA can also be converted to acetoacetyl-CoA by, for example, acetoacetyl-CoA thiolase to funnel into a 1,3-BDO pathway, as disclosed herein (see FIG. 1). Following the teachings and guidance provided herein for introducing a sufficient number of encoding nucleic acids to generate a 3-HBal, 1,3-BDO, 4-HBal or 1,4-BDO pathway, or pathway to generate a downstream product related thereto such as an ester or amide thereof, those skilled in the art will understand that the same engineering design also can be performed with respect to introducing at least the nucleic acids encoding the reductive TCA pathway enzymes or proteins absent in the host organism. Therefore, introduction of one or more encoding nucleic acids into the cells of the invention can be performed such that the modified organism contains a reductive TCA pathway.

Accordingly, given the teachings and guidance provided herein, those skilled in the art will understand that a non-naturally occurring cell can be produced that produces and/or secretes the biosynthesized compounds of the invention when grown on a carbon source such as a carbohydrate. Such compounds include, for example, 3-HBal, 1,3-BDO, 4-HBal or 1,4-BDO, or a downstream product related thereto such as an ester or amide thereof, and any of the intermediate metabolites in the 3-HBal, 1,3-BDO, 4-HBal or 1,4-BDO pathway. All that is required is to engineer in one or more of the required enzyme or protein activities to achieve biosynthesis of the desired compound or intermediate including, for example, inclusion of some or all of the biosynthetic pathways for 3-HBal, 1,3-BDO, 4-HBal or 1,4-BDO, or a downstream product related thereto such as an ester or amide thereof, including an aldehyde dehydrogenase of the invention. Accordingly, the invention provides a non-naturally occurring cell that produces and/or secretes 3-HBal, 1,3-BDO, 4-HBal or 1,4-BDO, or a downstream product related thereto such as an ester or amide thereof, when grown on a carbohydrate or other carbon source and produces and/or secretes any of the intermediate metabolites shown in the 3-HBal, 1,3-BDO, 4-HBal or 1,4-BDO pathway when grown on a carbohydrate or other carbon source. The cells producing 3-HBal, 1,3-BDO, 4-HBal or 1,4-BDO, or a downstream product related thereto such as an ester or amide thereof, of the invention can initiate synthesis from an intermediate of a 3-HBal, 1,3-BDO, 4-HBal or 1,4-BDO pathway.

The non-naturally occurring cells of the invention are constructed using methods well known in the art as exemplified herein to exogenously express an aldehyde dehydrogenase of the invention, and optionally at least one nucleic acid encoding a 3-HBal, 1,3-BDO, 4-HBal or 1,4-BDO pathway enzyme or protein, or a downstream product related thereto such as an ester or amide thereof. The enzymes or proteins can be expressed in sufficient amounts to produce 3-HBal, 1,3-BDO, 4-HBal or 1,4-BDO, or a downstream product related thereto such as an ester or amide thereof. It is understood that the cells of the invention are cultured under conditions sufficient to express an aldehyde dehydrogenase of the invention or produce 3-HBal, 1,3-BDO, 4-HBal or 1,4-BDO, or a downstream product related thereto such as an ester or amide thereof. Following the teachings and guidance provided herein, the non-naturally occurring cells of the invention can achieve biosynthesis of 3-HBal, 1,3-BDO, 4-HBal or 1,4-BDO, or a downstream product related thereto such as an ester or amide thereof, resulting in intracellular concentrations between about 0.1-300 mM or more, for example, 0.1-1.3 M or higher. Generally, the intracellular concentration of 3-HBal, 1,3-BDO, 4-HBal or 1,4-BDO, or a downstream product related thereto such as an ester or amide thereof, is between about 3-150 mM, particularly between about 5-125 mM and more particularly between about 8-100 mM, including about 10 mM, mM, 50 mM, 80 mM, or more. Intracellular concentrations between and above each of these exemplary ranges also can be achieved from the non-naturally occurring cells of the invention. For example, the intracellular concentration of 3-HBal, 1,3-BDO, 4-HBal or 1,4-BDO, or a downstream product related thereto such as an ester or amide thereof, can be between about 100 mM to 1.3 M, including about 100 mM, 200 mM, 500 mM, 800 mM, 1 M, 1.1 M, 1.2 M, 1.3 M, or higher.

A cell of the invention is cultured using well known methods. The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring cells as well as other anaerobic conditions well known in the art. Under such anaerobic or substantially anaerobic conditions, the 3-HBal, 1,3-BDO, 4-HBal or 1,4-BDO producers can synthesize 3-HBal, 1,3-BDO, 4-HBal or 1,4-BDO, or a downstream product related thereto such as an ester or amide thereof, at intracellular concentrations of 5-10 mM or more as well as all other concentrations exemplified herein. It is understood that, even though the above description refers to intracellular concentrations, 3-HBal, 1,3-BDO, 4-HBal or 1,4-BDO producing cells can produce 3-HBal, 1,3-BDO, 4-HBal or 1,4-BDO, or a downstream product related thereto such as an ester or amide thereof, intracellularly and/or secrete the product into the culture medium.

As described herein, one exemplary growth condition for achieving biosynthesis of 3-HBal, 1,3-BDO, 4-HBal or 1,4-BDO, or a downstream product related thereto such as an ester or amide thereof, includes anaerobic culture or fermentation conditions. In certain embodiments, the non-naturally occurring cells of the invention can be sustained, cultured or fermented under anaerobic or substantially anaerobic conditions. Briefly, an anaerobic condition refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of 3-HBal, 1,3-BDO, 4-HBal or 1,4-BDO, or a downstream product related thereto such as an ester or amide thereof, by a cell of the invention. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of 3-HBal, 1,3-BDO, 4-HBal or 1,4-BDO, or a downstream product related thereto such as an ester or amide thereof. Generally, and as with non-continuous culture procedures, the continuous and/or near-continuous production of 3-HBal, 1,3-BDO, 4-HBal or 1,4-BDO, or a downstream product related thereto such as an ester or amide thereof, will include culturing a non-naturally occurring cell producing 3-HBal, 1,3-BDO, 4-HBal or 1,4-BDO, or a downstream product related thereto such as an ester or amide thereof, of the invention in sufficient nutrients and medium to sustain and/or nearly sustain growth in an exponential phase. Continuous culture under such conditions can include, for example, growth or culturing for 1 day, 2, 3, 4, 5, 6 or 7 days or more. Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the cell of the invention is for a sufficient period of time to produce a sufficient amount of product for a desired purpose.

Exemplary fermentation processes include, but are not limited to, fed-batch fermentation and batch separation; fed-batch fermentation and continuous separation; and continuous fermentation and continuous separation. In an exemplary batch fermentation protocol, the production organism is grown in a suitably sized bioreactor sparged with an appropriate gas. Under anaerobic conditions, the culture is sparged with an inert gas or combination of gases, for example, nitrogen, $N_2/CO_2$ mixture, argon, helium, and the like. As the cells grow and utilize the carbon source, additional carbon source(s) and/or other nutrients are fed into the bioreactor at a rate approximately balancing consumption of the carbon source and/or nutrients. The temperature of the bioreactor is maintained at a desired temperature, generally in the range of 22-37 degrees C., but the temperature can be maintained at a higher or lower temperature depending on the the growth characteristics of the production organism and/or desired conditions for the fermentation process. Growth continues for a desired period of time to achieve desired characteristics of the culture in the fermenter, for example, cell density, product concentration, and the like. In a batch fermentation process, the time period for the fermentation is generally in the range of several hours to several days, for example, 8 to 24 hours, or 1, 2, 3, 4 or 5 days, or up to a week, depending on the desired culture conditions. The pH can be controlled or not, as desired, in which case a culture in which pH is not controlled will typically decrease to pH 3-6 by the end of the run. Upon completion of the cultivation period, the fermenter contents can be passed through a cell separation unit, for example, a centrifuge, filtration unit, and the like, to remove cells and cell debris. In the case where the desired product is expressed intracellularly, the cells can be lysed or disrupted enzymatically or chemically prior to or after separation of cells from the fermentation broth, as desired, in order to release additional product. The fermentation broth can be transferred to a product separations unit. Isolation of product occurs by standard separations procedures employed in the art to separate a desired product from dilute aqueous solutions. Such methods include, but are not limited to, liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like) to provide an organic solution of the product, if appropriate, standard distillation methods, and the like, depending on the chemical characteristics of the product of the fermentation process.

In an exemplary fully continuous fermentation protocol, the production organism is generally first grown up in batch mode in order to achieve a desired cell density. When the carbon source and/or other nutrients are exhausted, feed medium of the same composition is supplied continuously at a desired rate, and fermentation liquid is withdrawn at the same rate. Under such conditions, the product concentration in the bioreactor generally remains constant, as well as the cell density. The temperature of the fermenter is maintained at a desired temperature, as discussed above. During the continuous fermentation phase, it is generally desirable to maintain a suitable pH range for optimized production. The pH can be monitored and maintained using routine methods, including the addition of suitable acids or bases to maintain a desired pH range. The bioreactor is operated continuously for extended periods of time, generally at least one week to several weeks and up to one month, or longer, as appropriate and desired. The fermentation liquid and/or culture is monitored periodically, including sampling up to every day, as desired, to assure consistency of product concentration and/or cell density. In continuous mode, fermenter contents are constantly removed as new feed medium is supplied. The exit stream, containing cells, medium, and product, are generally subjected to a continuous product separations procedure, with or without removing cells and cell debris, as desired. Continuous separations methods employed in the art can be used to separate the product from dilute aqueous solutions, including but not limited to continuous liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like), standard continuous distillation methods, and the like, or other methods well known in the art.

Fermentation procedures are well known in the art. Briefly, fermentation for the biosynthetic production of 3-HBal, 1,3-BDO, 4-HBal or 1,4-BDO, or a downstream product related thereto such as an ester or amide thereof, can be utilized in, for example, fed-batch fermentation and batch separation; fed-batch fermentation and continuous separation, or continuous fermentation and continuous separation. Examples of batch and continuous fermentation procedures are well known in the art and described herein.

In addition to the fermentation procedures described herein using the producers of 3-HBal, 1,3-BDO, 4-HBal or 1,4-BDO, or a downstream product related thereto such as an ester or amide thereof, of the invention for continuous production of substantial quantities of 3-HBal, 1,3-BDO, 4-HBal or 1,4-BDO, or a downstream product related thereto such as an ester or amide thereof, the 3-HBal, 1,3-BDO, 4-HBal or 1,4-BDO, or a downstream product related thereto such as an ester or amide, producers also can be, for example, simultaneously subjected to chemical synthesis and/or enzymatic procedures to convert the product to other compounds, or the product can be separated from the fermentation culture and sequentially subjected to chemical and/or enzymatic conversion to convert the product to other compounds, if desired.

In addition to the culturing and fermentation conditions disclosed herein, growth condition for achieving expression of an aldehyde dehydrogenase of the invention or biosynthesis of 3-HBal, 1,3-BDO, 4-HBal or 1,4-BDO, or a downstream product related thereto such as an ester or amide thereof, can include the addition of an osmoprotectant to the culturing conditions. In certain embodiments, the non-naturally occurring cells of the invention can be sustained, cultured or fermented as described herein in the presence of an osmoprotectant. Briefly, an osmoprotectant refers to a compound that acts as an osmolyte and helps a cell as described herein survive osmotic stress. Osmoprotectants include, but are not limited to, betaines, amino acids, and the sugar trehalose. Non-limiting examples of such are glycine betaine, praline betaine, dimethylthetin, dimethylsulfoniopropionate, 3-dimethylsulfonio-2-methylpropionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a cell described herein from osmotic stress will depend on the cell used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about no more than about 100 mM or no more than about 500 mM.

In some embodiments, the carbon feedstock and other cellular uptake sources such as phosphate, ammonia, sulfate, chloride and other halogens can be chosen to alter the isotopic distribution of the atoms present in 3-HBal, 1,3-BDO, 4-HBal or 1,4-BDO, or a downstream product related thereto such as an ester or amide thereof, or any 3-HBal, 1,3-BDO, 4-HBal or 1,4-BDO pathway intermediate. The various carbon feedstock and other uptake sources enumerated above will be referred to herein, collectively, as "uptake sources." Uptake sources can provide isotopic enrichment for any atom present in the product 3-HBal, 1,3-BDO, 4-HBal or 1,4-BDO, or a downstream product related thereto such as an ester or amide thereof, or 3-HBal, 1,3-BDO, 4-HBal or 1,4-BDO pathway intermediate, or for side products generated in reactions diverging away from a 3-HBal, 1,3-BDO, 4-HBal or 1,4-BDO pathway. Isotopic enrichment can be achieved for any target atom including, for example, carbon, hydrogen, oxygen, nitrogen, sulfur, phosphorus, chloride or other halogens.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can be selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target atom isotopic ratio of an uptake source can be achieved by selecting a desired origin of the uptake source as found in nature. For example, as discussed herein, a natural source can be a biobased source derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

The unstable carbon isotope carbon-14 or radiocarbon makes up for roughly 1 in $10^{12}$ carbon atoms in the earth's atmosphere and has a half-life of about 5700 years. The stock of carbon is replenished in the upper atmosphere by a nuclear reaction involving cosmic rays and ordinary nitrogen ($^{14}N$). Fossil fuels contain no carbon-14, as it decayed long ago. Burning of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the biobased content of solid, liquid, and gaseous samples using radiocarbon dating by the American Society for Testing and Materials (ASTM) International. The standard is based on the use of radiocarbon dating for the determination of a product's biobased content. ASTM D6866 was first published in 2004, and the current active version of the standard is ASTM D6866-11 (effective Apr. 1, 2011). Radiocarbon dating techniques are well known to those skilled in the art, including those described herein.

The biobased content of a compound is estimated by the ratio of carbon-14 ($^{14}C$) to carbon-12 ($^{12}C$). Specifically, the Fraction Modern (Fm) is computed from the expression: Fm=(S−B)/(M−B), where B, S and M represent the $^{14}C/^{12}C$ ratios of the blank, the sample and the modern reference, respectively. Fraction Modern is a measurement of the deviation of the $^{14}C/^{12}C$ ratio of a sample from "Modern." Modern is defined as 95% of the radiocarbon concentration (in AD 1950) of National Bureau of Standards (NB S) Oxalic Acid I (i.e., standard reference materials (SRM) 4990b) normalized to $\delta^{13}C_{VPDB}$=−19 per mil (Olsson, *The use of Oxalic acid as a Standard*. in, *Radiocarbon Variations and Absolute Chronology*, Nobel Symposium, 12th Proc., John Wiley & Sons, New York (1970)). Mass spectrometry results, for example, measured by ASM, are calculated using the internationally agreed upon definition of 0.95 times the specific activity of NB S Oxalic Acid I (SRM 4990b) normalized to $\delta^{13}C^{VPDB}$=−19 per mil. This is equivalent to an absolute (AD 1950) $^{14}C/^{12}C$ ratio of 1.176±0.010×10$^{-12}$ (Karlen et al., *Arkiv Geofysik*, 4:465-471 (1968)). The standard calculations take into account the differential uptake of one isotope with respect to another, for example, the preferential uptake in biological systems of $C^{12}$ over $C^{13}$ over $C^{14}$, and these corrections are reflected as a Fm corrected for $\delta^{13}$.

An oxalic acid standard (SRM 4990b or HOx 1) was made from a crop of 1955 sugar beet. Although there were 1000 lbs made, this oxalic acid standard is no longer commercially available. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is 1.2933±0.001 (the weighted mean). The isotopic ratio of HOx II is −17.8 per mil. ASTM D6866-11 suggests use of the available Oxalic Acid II standard SRM 4990 C (Hox2) for the modern standard (see discussion of original vs. currently available oxalic acid standards in Mann, *Radiocarbon*, (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes biobased sources.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample. A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. For example, a product that is 50% starch-based material and 50% water would be considered to have a Biobased Content=100% (50% organic content that is 100% biobased) based on ASTM D6866. In another example, a product that is 50% starch-based material, 25% petroleum-based, and 25% water would have a Biobased Content=66.7% (75% organic content but only 50% of the product is biobased). In another example, a product that is 50% organic carbon and is a petroleum-based product would be considered to have a Biobased Content=0% (50% organic carbon but from fossil sources). Thus, based on the well known methods and known standards for determining the biobased content of a compound or material, one skilled in the art can readily determine the biobased content of a compound or material and/or prepared downstream products that utilize a compound or material of the invention having a desired biobased content.

Applications of carbon-14 dating techniques to quantify bio-based content of materials are known in the art (Currie et al., *Nuclear Instruments and Methods in Physics Research B*, 172:281-287 (2000)). For example, carbon-14 dating has been used to quantify bio-based content in terephthalate-containing materials (Colonna et al., *Green Chemistry*, 13:2543-2548 (2011)). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid) (Currie et al., supra, 2000). In contrast, polybutylene terephthalate polymer derived from both renewable 1,4-butanediol and renewable terephthalic acid resulted in bio-based content exceeding 90% (Colonna et al., supra, 2011).

Accordingly, in some embodiments, the present invention provides 3-HBal, 1,3-BDO, 4-HBal or 1,4-BDO or a downstream product related thereto such as an ester or amide thereof, or a 3-HBal, 1,3-BDO, 4-HBal or 1,4-BDO pathway intermediate, produced by a cell of the invention, that has a carbon-12, carbon-13, and carbon-14 ratio that reflects an atmospheric carbon, also referred to as environmental carbon, uptake source. For example, in some aspects the 3-HBal, 1,3-BDO, 4-HBal or 1,4-BDO, or a downstream product related thereto such as an ester or amide thereof, or a 3-HBal, 1,3-BDO, 4-HBal or 1,4-BDO pathway intermediate can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some such embodiments, the uptake source is $CO_2$. In some embodiments, the present invention provides 3-HBal, 1,3-BDO, 4-HBal or 1,4-BDO, or a downstream product related thereto such as an ester or amide thereof, or a 3-HBal, 1,3-BDO, 4-HBal or 1,4-BDO pathway intermediate that has a carbon-12, carbon-13, and carbon-14 ratio that reflects petroleum-based carbon uptake source. In this aspect, the 3-HBal, 1,3-BDO, 4-HBal or 1,4-BDO, or a downstream product related thereto such as an ester or amide thereof, or a 3-HBal, 1,3-BDO, 4-HBal or 1,4-BDO pathway intermediate can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, the present invention provides 3-HBal, 1,3-BDO, 4-HBal or 1,4-BDO, or a downstream product related thereto such as an ester or amide thereof, or a 3-HBal, 1,3-BDO, 4-HBal or 1,4-BDO pathway intermediate that has a carbon-12, carbon-13, and carbon-14 ratio that is obtained by a combination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, the present invention relates to the biologically produced 3-HBal, 1,3-BDO, 4-HBal or 1,4-BDO, or a downstream product related thereto such as an ester or amide thereof, or 3-HBal, 1,3-BDO, 4-HBal or 1,4-BDO pathway intermediate as disclosed herein, and to the products derived therefrom, wherein the 3-HBal, 1,3-BDO, 4-HBal or 1,4-BDO, or a downstream product related thereto such as an ester or amide thereof, or a 3-HBal, 1,3-BDO, 4-HBal or 1,4-BDO pathway intermediate has a carbon-12, carbon-13, and carbon-14 isotope ratio of about the same value as the $CO_2$ that occurs in the environment. For example, in some aspects the invention provides bioderived 3-HBal, 1,3-BDO, 4-HBal or 1,4-BDO, or a downstream product related thereto such as an ester or amide thereof, or a bioderived 3-HBal, 1,3-BDO, 4-HBal of 1,4-BDO intermediate having a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from bioderived 3-HBal, 1,3-BDO, 4-HBal or 1,4-BDO, or a downstream product related thereto such as an ester or amide thereof, or a bioderived 3-HBal, 1,3-BDO, 4-HBal or 1,4-BDO pathway intermediate as disclosed herein, wherein the bioderived product is chemically modified to generate a final product. Methods of chemically modifying a bioderived product of 3-HBal, 1,3-BDO, 4-HBal or 1,4-BDO, or a downstream product related thereto such as an ester or amide thereof, or an intermediate of a 3-HBal, 1,3-BDO, 4-HBal or 1,4-BDO, to generate a desired product are well known to those skilled in the art, as described herein. The invention further provides plastics, elastic fibers, polyurethanes, polyesters, including polyhydroxyalkanoates, nylons, organic solvents, polyurethane resins, polyester resins, hypoglycaemic agents, butadiene and/or butadiene-based products, which can be based on 3-HBal and/or 1,3-BDO, or a downstream product related thereto such as an ester or amide thereof, and plastics, elastic fibers, polyurethanes, polyesters, including polyhydroxyalkanoates such as poly-4-hydroxybutyrate (P4HB) or co-polymers thereof, poly(tetramethylene ether) glycol (PTMEG) (also referred to as PTMO, polytetramethylene oxide), polybutylene terephthalate (PBT), and polyurethane-polyurea copolymers, referred to as spandex, elastane or Lycra™, nylons, and the like, which can be based on 4-HBal and/or 1,4-BDO, or a downstream product related thereto such as an ester or amide thereof, having a carbon-12 versus carbon-13 versus carbon-14 isotope ratio of about the same value as the $CO_2$ that occurs in the environment, wherein the plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra™, nylons, organic solvents, polyurethane resins, polyester resins, hypoglycaemic agents, butadiene, and/or butadiene-based products are generated directly from or in combination with bioderived 3-HBal, 1,3-BDO, 4-HBal or 1,4-BDO, or a downstream product related thereto such as an ester or amide thereof, or a bioderived 3-HBal, 1,3-BDO, 4-HBal or 1,4-BDO pathway intermediate as disclosed herein. Methods for producing butadiene and/or butadiene-based products have been described previously (see, for example, WO 2010/127319, WO 2013/036764, U.S. Pat. No. 9,017,983, US 2013/0066035, WO/2012/018624, US 2012/0021478, each of which is incorporated herein by reference). 1,3-BDO can be reacted with an acid, either in vivo or in vitro, to convert to an ester using, for example, a lipase. Such esters can have nutraceutical, pharmaceutical and food uses, and are advantaged when R-form of 1,3-BDO is used since that is the form (compared to S-form or the racemic mixture) best utilized by both animals and humans as an energy source (e.g., a ketone ester, such as (R)-3-hydroxybutyl-R-1,3-butanediol monoester (which has Generally Recognized As Safe (GRAS) approval in the United States) and (R)-3-hydroxybutyrate glycerol monoester or diester). The ketone esters can be delivered orally, and the ester releases R-1,3-butanediol that is used by the body (see, for example, WO2013150153). Methods of producing amides are well known in the art (see, for example, Goswami and Van Lanen, *Mol. Biosyst.* 11(2):338-353 (2015)).

Thus the present invention is particularly useful to provide an improved enzymatic route and microorganism to provide an improved composition of 1,3-BDO, namely R-1,3-butanediol, highly enriched or essentially enantiomerically pure, and further having improved purity qualities with respect to by-products. 1,3-BDO has further food related uses including use directly as a food source, a food ingredient, a flavoring agent, a solvent or solubilizer for flavoring agents, a stabilizer, an emulsifier, and an anti-microbial agent and preservative. 1,3-BDO is used in the pharmaceutical industry as a parenteral drug solvent. 1,3-BDO finds use in cosmetics as an ingredient that is an emollient, a humectant, that prevents crystallization of insoluble ingredients, a solubilizer for less-water-soluble ingredients such as fragrances, and as an anti-microbial agent and preservative. For example, it can be used as a humectant, especially in hair sprays and setting lotions; it reduces loss of aromas from essential oils, preserves against spoilage by microorganisms, and is used as a solvent for benzoates. 1,3-BDO can be used at concentrations from 0.1% to 50%, and even less than 0.1% and even more than 50%. It is used in hair and bath products, eye and facial makeup, fragrances, personal cleanliness products, and shaving and skin care preparations (see, for example, the Cosmetic Ingredient Review board's report: "Final Report on the Safety Assessment of Butylene Glycol, Hexylene Glycol, Ethoxydiglycol, and Dipropylene Glycol", *Journal of the American College of Toxicology*, Volume 4, Number 5, 1985, which is incorporated herein by reference). This report provides specific uses and concentrations of 1,3-BDO in cosmetics; see for examples the report's Table 2 therein entitled "Product Formulation Data".

In one embodiment, the invention provides culture medium comprising bioderived 3-HBal and/or 1,3-BDO, or 4-HBal and/or 1,4-BDO, wherein the bioderived 3-HBal and/or 1,3-BDO, or 4-HBal and/or 1,4-BDO, has a carbon-12, carbon-13 and carbon-14 isotope ratio that reflects an atmospheric carbon dioxide uptake source, and wherein the bioderived 3-HBal and/or 1,3-BDO, or 4-HBal and/or 1,4-BDO is produced by a cell, or in a cell lysate, of the invention or a method of the invention. In one embodiment, the culture medium is separated from the cell.

In one embodiment, the invention provides 3-hydroxybutyraldeyde (3-HBal) and/or 1,3-butanediol (1,3-BDO), or 4-hydroxybutyraldeyde (4-HBal) and/or 1,4-butanediol (1,4-BDO), having a carbon-12, carbon-13 and carbon-14 isotope ratio that reflects an atmospheric carbon dioxide uptake source, wherein the 3-HBal and/or 1,3-BDO, or the 4-HBal and/or 1,4-BDO, is produced by a cell, or in a cell lysate, of the invention or a method of the invention. In one embodiment, the 3-HBal and/or 1,3-BDO, or the 4-HBal and/or 1,4-BDO, has an Fm value of at least 80%, at least 85%, at least 90%, at least 95% or at least 98%.

In one embodiment, the invention provides 3-hydroxybutyraldeyde (3-HBal) and/or 1,3-butanediol (1,3-BDO), or 4-hydroxybutyraldeyde (4-HBal) and/or 1,4-butanediol (1,4-BDO), produced by a cell, or in a cell lysate of the invention or a method of the invention. In one embodiment, the invention provides 3-hydroxybutyraldeyde (3-HBal) and/or 1,3-butanediol (1,3-BDO) having a carbon-12, carbon-13 and carbon-14 isotope ratio that reflects an atmospheric carbon dioxide uptake source, wherein the 3-HBal and/or 1,3-BDO is produced by a cell, or in a cell lysate, of the invention or a method of the invention, wherein the 3-HBal and/or 1,3-BDO is enantiomerically enriched for the R form. In one embodiment, the 3-HBal and/or 1,3-BDO has an Fm value of at least 80%, at least 85%, at least 90%, at least 95% or at least 98%.

In one embodiment, the invention provides 3-hydroxybutyraldehyde (3-HBal) and/or 1,3-butanediol (1,3-BDO) produced by a cell, or in a cell lysate, of the invention or a method of the invention, wherein the 3-HBal and/or 1,3-BDO is enantiomerically enriched for the R form. In one embodiment, the R form is greater than 95%, 96%, 97%, 98%, 99%, 99.1%, 99.2%, 99.3%, 99.4%, 99.5%, 99.6%, 99.7%, 99.8% or 99.9% of the 3-HBal and/or 1,3-BDO. In one embodiment, the 3-HBal and/or 1,3-BDO is ≥55% R-enantiomer, ≥60% R-enantiomer, ≥65% R-enantiomer, ≥70% R-enantiomer, ≥75% R-enantiomer, ≥80% R-enantiomer, ≥85% R-enantiomer, ≥90% R-enantiomer, or ≥95% R-enantiomer, and can be highly chemically pure, e.g., ≥99%, for example, ≥95%, ≥96%, ≥97%, ≥98%, ≥99%, ≥99.1%, ≥99.2%, ≥99.3%, ≥99.4%, ≥99.5%, ≥99.6%, ≥99.7%, ≥99.8% or ≥99.9% R-enantiomer.

In one embodiment, the invention provides a composition comprising 3-HBal and/or 1,3-BDO, or the 4-HBal and/or 1,4-BDO, produced by a cell, or in a cell lysate, of the invention or a method of the invention and a compound other than the 3-HBal and/or 1,3-BDO, or 4-HBal or 1,4-BDO, respectively. In one embodiment, the compound other than the 3-HBal and/or 1,3-BDO, or the 4-HBal and/or 1,4-BDO, is a portion of a cell that produces the 3-HBal and/or 1,3-BDO, or the 4-HBal and/or 1,4-BDO, respectively, or that expresses a polypeptide of the invention.

In one embodiment, the invention provides a composition comprising 3-HBal and/or 1,3-BDO, or the 4-HBal and/or 1,4-BDO, produced by a cell, or in a cell lysate, of the invention or a method of the invention, or a cell lysate or culture supernatant of a cell producing the 3-HBal and/or 1,3-BDO, or the 4-HBal and/or 1,4-BDO.

In one embodiment, the invention provides a product comprising 3-HBal and/or 1,3-BDO, or the 4-HBal and/or 1,4-BDO, produced by a cell, or in a cell lysate of the invention or a method of the invention, wherein the product is a plastic, elastic fiber, polyurethane, polyester, polyhydroxyalkanoate, poly-4-hydroxybutyrate (P4HB) or a co-polymer thereof, poly(tetramethylene ether) glycol (PTMEG), polybutylene terephthalate (PBT), polyurethane-polyurea copolymer, nylon, organic solvent, polyurethane resin, polyester resin, hypoglycaemic agent, butadiene or butadiene-based product. In one embodiment, the product is a cosmetic product or a food additive. In one embodiment, the product comprises at least 0.1%, at least 0.5%, at least 1%, at least 5%, at least 10%, at least 20%, at least 30%, at least 40% or at least 50% bioderived 3-HBal and/or 1,3-BDO, or bioderived 4-HBal and/or 1,4-BDO. In one embodiment, the product comprises a portion of the produced 3-HBal and/or 1,3-BDO, or the produced 4-HBal and/or 1,4-BDO, as a repeating unit. In one embodiment, the invention provides a molded product obtained by molding a product made with or derived from 3-HBal and/or 1,3-BDO, or 4-HBal and/or 1,4-BDO produced by a cell, or in a cell lysate of the invention or a method of the invention.

The invention further provides a composition comprising bioderived 3-HBal, 1,3-BDO, 4-HBal or 1,4-BDO, or a downstream product related thereto such as an ester or amide thereof, and a compound other than the bioderived 3-HBal, 1,3-BDO, 4-HBal or 1,4-BDO, or a downstream product related thereto such as an ester or amide thereof. The compound other than the bioderived product can be a cellular portion, for example, a trace amount of a cellular portion of, or can be fermentation broth or culture medium or a purified or partially purified fraction thereof produced in the presence of, a non-naturally occurring cell of the invention having a pathway that produces 3-HBal, 1,3-BDO, 4-HBal or 1,4-BDO, or a downstream product related thereto such as an ester or amide thereof. The composition can comprise, for example, a reduced level of a byproduct when produced by an organism having reduced byproduct formation, as disclosed herein. The composition can comprise, for example, bioderived 3-HBal, 1,3-BDO, 4-HBal or 1,4-BDO, or a downstream product related thereto such as an ester or amide thereof, or a cell lysate or culture supernatant of a cell of the invention.

3-HBal, 1,3-BDO, 4-HBal or 1,4-BDO, or a downstream product related thereto such as an ester or amide thereof, is a chemical used in commercial and industrial applications. Non-limiting examples of such applications include production of plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra™, nylons, organic solvents, polyurethane resins, polyester resins, hypoglycaemic agents, butadiene and/or butadiene-based products. Moreover, 3-HBal, 1,3-BDO, 4-HBal or 1,4-BDO is also used as a raw material in the production of a wide range of products including plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra™, nylons, organic solvents, polyurethane resins, polyester resins, hypoglycaemic agents, butadiene and/or butadiene-based products. Accordingly, in some embodiments, the invention provides biobased plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra™, nylons, organic solvents, polyurethane resins, polyester resins, hypoglycaemic agents, butadiene and/or butadiene-based products comprising one or more bioderived 3-HBal, 1,3-BDO, 4-HBal or 1,4-BDO, or a downstream product related thereto such as an ester or amide thereof, or bioderived 3-HBal, 1,3-BDO, 4-HBal or 1,4-BDO pathway intermediate produced by a non-naturally occurring cell of the invention, for example, expressing an aldehyde dehydrogenase of the invention, or produced using a method disclosed herein.

As used herein, the term "bioderived" means derived from or synthesized by a biological organism and can be considered a renewable resource since it can be generated by a biological organism. Such a biological organism, in particular the cells of the invention disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound of the invention. A biobased or bioderived product is in contrast to a petroleum derived product, wherein such a product is derived from or synthesized from petroleum or a petrochemical feedstock.

In some embodiments, the invention provides plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra", nylons, organic solvents, polyurethane resins, polyester resins, hypoglycaemic agents, butadiene and/or butadiene-based products comprising bioderived 3-HBal, 1,3-BDO, 4-HBal or 1,4-BDO, or a downstream product related thereto such as an ester or amide thereof, or bioderived 3-HBal, 1,3-BDO, 4-HBal or 1,4-BDO pathway intermediate, wherein the bioderived 3-HBal, 1,3-BDO, 4-HBal or 1,4-BDO, or a downstream product related thereto such as an ester or amide thereof, or bioderived 3-HBal, 1,3-BDO, 4-HBal or 1,4-BDO pathway intermediate includes all or part of the 3-HBal, 1,3-BDO, 4-HBal or 1,4-BDO, or a downstream product related thereto such as an ester or amide thereof, or 3-HBal, 1,3-BDO, 4-HBal or 1,4-BDO pathway intermediate used in the production of plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra™, nylons, organic solvents, polyurethane resins, polyester resins, hypoglycaemic agents, butadiene and/or butadiene-based products. For example, the final plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra", nylons, organic solvents, polyurethane resins, polyester resins, hypoglycaemic agents, butadiene and/or butadiene-based products can contain the bioderived 3-HBal, 1,3-BDO, 4-HBal or 1,4-BDO, or a downstream product related thereto such as an ester or amide thereof, or 3-HBal, 1,3-BDO, 4-HBal or 1,4-BDO pathway intermediate, or a portion thereof that is the result of the manufacturing of plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra", nylons, organic solvents, polyurethane resins, polyester resins, hypoglycaemic agents, butadiene and/or butadiene-based products. Such manufacturing can include chemically reacting the bioderived 3-HBal, 1,3-BDO, 4-HBal or 1,4-BDO, or a downstream product related thereto such as an ester or amide thereof, or bioderived 3-HBal, 1,3-BDO, 4-HBal or 1,4-BDO pathway intermediate (e.g. chemical conversion, chemical functionalization, chemical coupling, oxidation, reduction, polymerization, copolymerization and the like) into the final plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra", nylons, organic solvents, polyurethane resins, polyester resins, hypoglycaemic agents, butadiene and/or butadiene-based products. Thus, in some aspects, the invention provides a biobased plastic, elastic fiber, polyurethane, polyester, including polyhydroxyalkanoate such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymer, referred to as spandex, elastane or Lycra", nylon, polyurethane resin, polyester resin, hypoglycaemic agent, butadiene and/or butadiene-based product comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived 3-HBal, 1,3-BDO, 4-HBal or 1,4-BDO, or a downstream product related thereto such as an ester or amide thereof, or bioderived 3-HBal, 1,3-BDO, 4-HBal or 1,4-BDO pathway intermediate as disclosed herein.

Additionally, in some embodiments, the invention provides a composition having a bioderived 3-HBal, 1,3-BDO, 4-HBal or 1,4-BDO, or a downstream product related thereto such as an ester or amide thereof, or 3-HBal, 1,3-BDO, 4-HBal or 1,4-BDO pathway intermediate disclosed herein and a compound other than the bioderived 3-HBal, 1,3-BDO, 4-HBal or 1,4-BDO, or a downstream product related thereto such as an ester or amide thereof, or 3-HBal, 1,3-BDO, 4-HBal or 1,4-BDO pathway intermediate. For example, in some aspects, the invention provides biobased plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra™, nylons, organic solvents, polyurethane resins, polyester resins, hypoglycaemic agents, butadiene and/or butadiene-based products wherein the 3-HBal, 1,3-BDO, 4-HBal or 1,4-BDO, or a downstream product related thereto such as an ester or amide thereof, or 3-HBal, 1,3-BDO, 4-HBal or 1,4-BDO pathway intermediate used in its production is a combination of bioderived and petroleum derived 3-HBal, 1,3-BDO, 4-HBal or 1,4-BDO, or a downstream product related thereto such as an ester or amide thereof, or 3-HBal, 1,3-BDO, 4-HBal or 1,4-BDO pathway intermediate. For example, biobased plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra™, nylons, organic solvents, polyurethane resins, polyester resins, hypoglycaemic agents, butadiene and/or butadiene-based products can be produced using 50% bio-derived 3-HBal, 1,3-BDO, 4-HBal or 1,4-BDO, or a downstream product related thereto such as an ester or amide thereof, and 50% petroleum derived 3-HBal, 1,3-BDO, 4-HBal or 1,4-BDO, or a downstream product related thereto such as an ester or amide thereof, or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the cells disclosed herein. It is understood that methods for producing plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra™, nylons, organic solvents, polyurethane resins, polyester resins, hypoglycaemic agents, butadiene and/or butadiene-based products using the bioderived 3-HBal, 1,3-BDO, 4-HBal or 1,4-BDO, or a downstream product related thereto such as an ester or amide thereof, or bioderived 3-HBal, 1,3-BDO, 4-HBal or 1,4-BDO pathway intermediate of the invention are well known in the art.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of 3-HBal, 1,3-BDO, 4-HBal or 1,4-BDO, or a downstream product related thereto such as an ester or amide thereof.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring cells for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. publication 2009/0047719, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host cells. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

As disclosed herein, the invention relates to aldehyde dehydrogenase variants (see Example). The generation of such variants is described in the Example. Any of a variety of methods can be used to generate an aldehyde dehydrogenase variant such as the aldehyde dehydrogenase variants disclosed herein. Such methods include, but are not limited to, site-directed mutagenesis, random mutagenesis, combinatorial libraries, and other mutagenesis methods described below (see Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, M D (1999); Gillman et al., *Directed Evolution Library Creation: Methods and Protocols (Methods in Molecular Biology)* Springer, 2nd ed (2014).

As disclosed herein, a nucleic acid encoding a desired activity of a pathway for 3-HBal, 1,3-BDO, 4-HBal or 1,4-BDO, or a downstream product related thereto such as an ester or amide thereof, can be introduced into a host organism. In some cases, it can be desirable to modify an activity of a 3-HBal, 1,3-BDO, 4-HBal or 1,4-BDO, or a downstream product related thereto such as an ester or amide thereof, pathway enzyme or protein to increase production of 3-HBal, 1,3-BDO, 4-HBal or 1,4-BDO, or a downstream product related thereto such as an ester or amide thereof. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, >$10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng* 22:1-9 (2005).; and Sen et al., *Appl. Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

A number of exemplary methods have been developed for the mutagenesis and diversification of genes to target desired properties of specific enzymes. Such methods are well known to those skilled in the art. Any of these can be used to alter and/or optimize the activity of a pathway enzyme or protein for producing 3-HBal, 1,3-BDO, 4-HBal or 1,4-BDO, or a downstream product thereof such as an ester or amide thereof, or an aldehyde dehydrogenase of the invention. Such methods include, but are not limited to EpPCR, which introduces random point mutations by reducing the fidelity of DNA polymerase in PCR reactions (Pritchard et al., *J Theor. Biol.* 234:497-509 (2005)); Error-prone Rolling Circle Amplification (epRCA), which is similar to epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats (Fujii et al., *Nucleic Acids Res.* 32:e145 (2004); and Fujii et al., *Nat. Protoc.* 1:2493-2497 (2006)); DNA or Family Shuffling, which typically involves digestion of two or more variant genes with nucleases such as Dnase I or EndoV to generate a pool of random fragments that are reassembled by cycles of annealing and extension in the presence of DNA polymerase to create a library of chimeric genes (Stemmer, *Proc Natl Acad Sci USA* 91:10747-10751 (1994); and Stemmer, *Nature* 370:389-391 (1994)); Staggered Extension (StEP), which entails template priming followed by repeated cycles of 2 step PCR with denaturation and very short duration of annealing/extension (as short as 5 sec) (Zhao et al., *Nat. Biotechnol.* 16:258-261 (1998)); Random Priming Recombination (RPR), in which random sequence primers are used to generate many short DNA fragments complementary to different segments of the template (Shao et al., *Nucleic Acids Res* 26:681-683 (1998)).

Additional methods include Heteroduplex Recombination, in which linearized plasmid DNA is used to form heteroduplexes that are repaired by mismatch repair (Volkov et al, *Nucleic Acids Res.* 27:e18 (1999); and Volkov et al., *Methods Enzymol* 328:456-463 (2000)); Random Chimeragenesis on Transient Templates (RACHITT), which employs Dnase I fragmentation and size fractionation of single stranded DNA (ssDNA) (Coco et al., *Nat. Biotechnol.* 19:354-359 (2001)); Recombined Extension on Truncated templates (RETT), which entails template switching of unidirectionally growing strands from primers in the presence of unidirectional ssDNA fragments used as a pool of templates (Lee et al., *J. Molec. Catalysis* 26:119-129 (2003)); Degenerate Oligonucleotide Gene Shuffling (DOGS), in which degenerate primers are used to control recombination between molecules; (Bergquist and Gibbs, *Methods Mol. Biol* 352:191-204 (2007); Bergquist et al., *Biomol. Eng* 22:63-72 (2005); Gibbs et al., *Gene* 271:13-20 (2001)); Incremental Truncation for the Creation of Hybrid Enzymes (ITCHY), which creates a combinatorial library with 1 base pair deletions of a gene or gene fragment of interest (Ostermeier et al., *Proc. Natl. Acad Sci. USA* 96:3562-3567 (1999); and Ostermeier et al., *Nat. Biotechnol.* 17:1205-1209 (1999)); Thio-Incremental Truncation for the Creation of Hybrid Enzymes (THIO-ITCHY), which is similar to ITCHY except that phosphothioate dNTPs are used to generate truncations (Lutz et al., *Nucleic Acids Res* 29:E16 (2001)); SCRATCHY, which combines two methods for recombining genes, ITCHY and DNA shuffling (Lutz et al., *Proc. Natl. Acad Sci. USA* 98:11248-11253 (2001)); Random Drift Mutagenesis (RNDM), in which mutations made via epPCR are followed by screening/selection for those retaining usable activity (Bergquist et al., *Biomol. Eng* 22:63-72 (2005)); Sequence Saturation Mutagenesis (SeSaM), a random mutagenesis method that generates a pool of random length fragments using random incorporation of a phosphothioate nucleotide and cleavage, which is used as a template to extend in the presence of "universal" bases such as inosine, and replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)); Synthetic Shuffling, which uses overlapping oligonucleotides designed to encode "all genetic diversity in targets" and allows a very high diversity for the shuffled progeny (Ness et al., *Nat. Biotechnol.* 20:1251-1255 (2002)); Nucleotide Exchange and Excision Technology NexT, which exploits a combination of dUTP incorporation followed by treatment with uracil DNA glycosylase and then piperidine to perform endpoint DNA fragmentation (Muller et al., *Nucleic Acids Res.* 33:e117 (2005)).

Further methods include Sequence Homology-Independent Protein Recombination (SHIPREC), in which a linker is used to facilitate fusion between two distantly related or unrelated genes, and a range of chimeras is generated between the two genes, resulting in libraries of single-crossover hybrids (Sieber et al., *Nat. Biotechnol.* 19:456-460 (2001)); Gene Site Saturation Mutagenesis™ (GSSM™), in which the starting materials include a supercoiled double stranded DNA (dsDNA) plasmid containing an insert and two primers which are degenerate at the desired site of mutations (Kretz et al., *Methods Enzymol.* 388:3-11(2004)); Combinatorial Cassette Mutagenesis (CCM), which involves the use of short oligonucleotide cassettes to replace limited regions with a large number of possible amino acid sequence alterations (Reidhaar-Olson et al. *Methods Enzymol.* 208:564-586 (1991); and Reidhaar-Olson et al. *Science* 241:53-57 (1988)); Combinatorial Multiple Cassette Mutagenesis (CMCM), which is essentially similar to CCM and uses epPCR at high mutation rate to identify hot spots and hot regions and then extension by CMCM to cover a defined region of protein sequence space (Reetz et al., *Angew. Chem. Int. Ed Engl.* 40:3589-3591 (2001)); the Mutator Strains technique, in which conditional is mutator plasmids, utilizing the mutD5 gene, which encodes a mutant subunit of DNA polymerase III, to allow increases of 20 to 4000-× in random and natural mutation frequency during selection and block accumulation of deleterious mutations when selection is not required (Selifonova et al., *Appl. Environ. Microbiol.* 67:3645-3649 (2001)); Low et al., *J. Mol. Biol.* 260:359-3680 (1996)).

Additional exemplary methods include Look-Through Mutagenesis (LTM), which is a multidimensional mutagenesis method that assesses and optimizes combinatorial mutations of selected amino acids (Rajpal et al., *Proc. Natl. Acad Sci. USA* 102:8466-8471 (2005)); Gene Reassembly, which is a DNA shuffling method that can be applied to multiple genes at one time or to create a large library of chimeras (multiple mutations) of a single gene (Tunable GeneReassembly™ (TGR™) Technology supplied by Verenium Corporation), in Silico Protein Design Automation (PDA), which is an optimization algorithm that anchors the structurally defined protein backbone possessing a particular fold, and searches sequence space for amino acid substitutions that can stabilize the fold and overall protein energetics, and generally works most effectively on proteins with known three-dimensional structures (Hayes et al., *Proc. Natl. Acad Sci. USA* 99:15926-15931 (2002)); and Iterative Saturation Mutagenesis (ISM), which involves using knowledge of structure/function to choose a likely site for enzyme improvement, performing saturation mutagenesis at chosen site using a mutagenesis method such as Stratagene QuikChange (Stratagene; San Diego CA), screening/selecting for desired properties, and, using improved clone(s), starting over at another site and continue repeating until a desired activity is achieved (Reetz et al., *Nat. Protoc.* 2:891-903 (2007); and Reetz et al., *Angew. Chem. Int. Ed Engl.* 45:7745-7751(2006)).

Any of the aforementioned methods for mutagenesis can be used alone or in any combination. Additionally, any one or combination of the directed evolution methods can be used in conjunction with adaptive evolution techniques, as described herein.

It is understood that modifications which do not substantially affect the activity of the various embodiments of this invention are also provided within the definition of the invention provided herein. Accordingly, the following examples are intended to illustrate but not limit the present invention.

EXAMPLE

Aldehyde Dehydrogenase Variants

This example describes generation of aldehyde dehydrogenase variants with desirable properties.

Mutagenesis techniques were used to generate variant aldehyde dehydrogenases based on template ALD-1. Variants were generated using error prone PCR, site directed mutagenesis, and by spontaneous mutations during genetic selection. Template ALD-1 corresponds to the aldehyde dehydrogenase provided below:

```
                                              (SEQ ID NO: 1)
MIKDTLVSITKDLKLKTNVENANLKNYKDDSSCFGVFENV

ENAISNAVHAQKILSLHYTKEQREKIITEIRKAALENKEI

LATMILEETHMGRYEDKILKHELVAKYTPGTEDLTTTAWS

GDNGLTVVEMSPYGVIGAITPSTNPTETVICNSIGMIAAG

NTVVFNGHPGAKKCVAFAVEMINKAIISCGGPENLVTTIK

NPTMDSLDAIIKHPSIKLLCGTGGPGMVKTLLNSGKKAIG

AGAGNPPVIVDDTADIEKAGKSIIEGCSFDNNLPCIAEKE

VFVFENVADDLISNMLKNNAVIINEDQVSKLIDLVLQKNN

ETQEYSINKKWVGKDAKLFLDEIDVESPSSVKCIICEVSA

SHPFVMTELMMPILPIVRVKDIDEAIEYAKIAEQNRKHSA

YIYSKNIDNLNRFEREIDTTIFVKNAKSFAGVGYEAEGFT

TFTIAGSTGEGITSARNFTRQRRCVLAG.
```

Additional ALD sequences for ALD-2 and ALD-3 are provided below:

```
ALD-2
                                              (SEQ ID NO: 2)
MNTENIEQAIRKILSEELSNPQSSTATNTTVPGKNGIFKT

VNEAIAATKAAQENYADQPISVRNKVIDAIREGFRPYIED

MAKRIHDETGMGTVSAKIAKLNNALYNTPGPEILQPEAET

GDGGLVMYEYAPFGVIGAVGPSTNPSETVIANAIMMLAGG

NTLFFGAHPGAKNITRWTIEKLNELVADATGLHNLVVSLE

TPSIESVQEVMQHPDVAMLSITGGPAVVHQALISGKKAVG

AGAGNPPAMVDATANIALAAHNIVDSAAFDNNILCTAEKE

VVVEAAVKDELIMRMQQEGAFLVTDSADIEKLAQMTIGPK

GAPDRKFVGKDATYILDQAGISYTGTPTLIILEAAKDHPL
```

-continued
```
VTTEMLMPILPVVCCPDFDSVLATATEVEGGLHHTASIHS

ENLPHINKAAHRLNTSIFVVNGPTYCGTGVATNGAHSGAS

ALTIATPTGEGTATSKTYTRRRRLNSPEGFSLRTWEA

ALD-3
                                  (SEQ ID NO: 3)
MTVNEQLVQDIIKNVVASMQLTQTNKTELGVFDDMNQAIE

AAKEAQLVVKKMSMDQREKIISAIRKKTIEHAETLARMAV

EETGMGNVGHKILKHQLVAEKTPGTEDITTTAWSGDRGLT

L VEMGPFGVIGAITPCTNPSETIICNTIGMLAGGNTVVF

NPHPAAIKTSNFAVQLINEASLSAGGPVNIACSVRKPTLD

SSKIMMSHQDIPLIAATGGPGVVTAVLQSGKRGIGAGAGN

PPVLVDETADIRKAAEDIINGCTFDNNLPCIAEKEVVAID

AIANELMNYMVKEQGCYAITKEQQEKLTNLVITPKGLNRN

CVGKDARTLLGMIGIDVPSNIRCIIFEGEKEHPLISEELM

MPILGIVRAKSFDDAVEKAVWLEHGNRHSAHIHSKNVDRI

TTYAKAIDTAILVKNAPSYAAIGFGGEGFCTFTIASRTGE

GLTSASTFTKRRRCVMSDSLCIR
```

ALD-1 is slightly more specific for the R enantiomer of 3-hydroxybutyryl-CoA compared to the S enantiomer. A sequence alignment of ALD-1 to ALD-2 and ALD-3 is shown in FIG. 3. The sequences correspond to SEQ ID NOS:1, 2 and 3, respectively. A crystal structure also exists for ALD-3 (PDBID 4C3S), and ALD-2 is more closely related to ALD-3 than ALD-1. Therefore ALD-3 was used as the template. Underlined in FIG. 3 are 2 loop regions, the first designated A, the second B, both involved in substrate specificity and enantiomer specificity as determined herein. Loop A in ALD-1 is sequence LQKNNETQEYSINKKWVGKD (SEQ ID NO:124), in ALD-2 is sequence IGPKGAPDRKFVGKD (SEQ ID NO:125) and in ALD-3 is sequence IIPKGLNRNCVGKD (SEQ ID NO:126). Loop B in ALD-1 is sequence SFAGVGYEAEGFTTFTIA (SEQ ID NO:127), in ALD-2 is sequence TYCGTGVATNGAHSGASALTIA (SEQ ID NO:128), and in ALD-3 is sequence SYAAIGFGGEGFCTFTIA (SEQ ID NO:129). The sequence and the length of the substrate specificity loop A and B from ALD-2 differs from those of ALD-1 and ALD-3; nevertheless the alignment shows sufficient conservation to facilitate identification of corresponding positions for substitution as described herein, and especially so if combined with 3D modeling as shown in FIG. 6, which shows the two loop regions interacting to affect substrate specificity and enantiomer specificity, especially when modified with exemplary substitutions as described herein. ALD-1 and ALD-3 are 51.9% identical. ALD-1 and ALD-2 are 35.9% identical. ALD-3 and ALD-2 are 40% identical. A consensus ALD sequence based on the alignment of FIG. 3 was generated. A consensus for Loop A based on alignment of ALD-1, ALD-2 and ALD-3 is IXPKG-----XXNRKXVGKD (SEQ ID NO:5). A consensus for Loop B based on alignment of ALD-1, ALD-2 and ALD-3 is SYAGXWOOCE----GFXTFTIA (SEQ ID NO:6).

Additional alignments were performed (FIG. 4). FIG. 4A shows an alignment with a 40-55% cutoff compared to ALD-1. FIG. 4B shows an alignment with a 75-90% cutoff compared to ALD-1. FIG. 4C shows an alignment with a 90% cutoff compared to ALD-1. The alignments of exemplary aldehyde deydrogenases (ALD) shown in FIGS. 4A-4C demonstrate identifying positions in ALDs that correspond to positions in the representative template ALD sequence where substitutions of the invention can be made. Underlined are two key loop regions, the first designated A, the second B, both involved in substrate specificity and enantiomer specificity as determined herein. FIGS. 4A-4C demonstrate that corresponding positions for substitutions taught herein can be identified in ALDs that are at least 40% identical with ALD-1, especially the Loop A and B regions, and especially the very conserved Loop B region.

Mutagenesis to increase the specificity of variant 45 for 3HB-CoA relative to acetyl-CoA led to several variants with increased 1,3 BDO production and decreased ethanol. Mutations that increase specificity of 3-hydroxybutyryl-CoA over acetyl-CoA provide a decrease in ethanol, since the acetaldehyde generated from acetyl-CoA can be converted to ethanol by enzymes natively in the host cell or by a pathway enzyme that converts 3-hydroxybutyraldehyde to 1,3-butanediol. Variants that increase enzymatic activity of aldehyde dehydrogenase or increase its specificity for 3-hydroxybutyryl-CoA decrease 4-hydroxy-2-butanone by increasing flux through an enzymatic pathway to 1,3-butanediol which pulls acetoacetyl-CoA towards 1,3-butanediol formation, decreasing its availability for two-step conversion to 4-hydroxy-2-butanone by native enzymes or less-specific pathway enzymes. The sequence of variant 45 is provided below:

```
                                  (SEQ ID NO: 4)
MIKDTLVSITKDLKLKTNVENANLKNYKDDSSCFGVFENV

ENAISNAVHAQKILSLHYTKEQREKIITEIRKAALENKEI

LATMILEETHMGRYEDKILKHELVAKYTPGTEDLTTTAWS

GDNGLTVVEMSPYGVIGAITPSTNPTETVICNSIGMIAAG

NTVVFNGHPGAKKSVAFAVEMINKAIISCGGPENLVTTIK

NPTRDSLDAIIKHPSIKLLVGTGGPGMVKTLLNSGKKAIG

AGAGNPPVIVDDTADIEKAGKSIIEGASFDNNLPCIAEKE

VFVFENVADDLISNMLKNNAVIINEDQVSKLIDLVLQKNN

ETQEYSINKKWVGKDAKLFLDEIDVESPSSVKCIITEVSA

SHPFVMTELMMPILPIVRVKDIDEAIEYAKIAEQNHKHSA

YIYSKNIDNLNRFEREIDTTIFVKNAKSFAGVGYEAPGFT

TFTIAGSTGEGITSARNFTRQRRIVLVG
```

The assay performed is an in vitro assay to examine the activity on 3HB-CoA by monitoring a decrease in absorbance as NADH is converted to NAD. Assays were also performed with acetyl-CoA (AcCoA) as a substrate, and improved enzymes were identified as an improvement in the ratio of activity for 3HB-CoA vs. AcCoA. Mutations that increase specificity of 3-hydroxybutyryl-CoA over acetyl-CoA provide a decrease in ethanol, since the acetaldehyde generated from acetyl-CoA can be converted to ethanol by enzymes natively in the host cell or by a pathway enzyme that converts 3-hydroxybutyraldehyde to 1,3-butanediol.

Figure 5A:
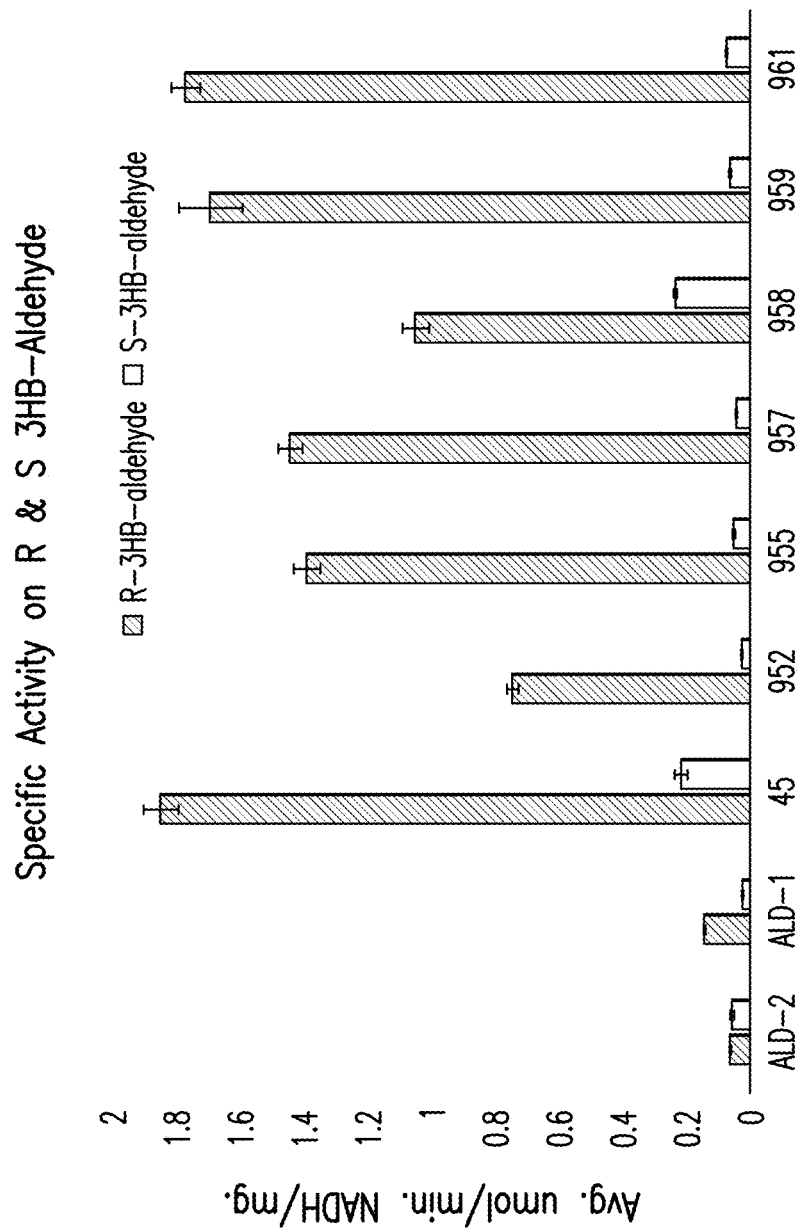
FIGS. 5A and 5B show enzyme activities of various exemplary aldehyde dehydrogenases. Figure shows the specific activity of ALD-2, ALD-1 and ALD-1 variants on 3 hydroxy-(R)-butyraldehyde (left bar in sets of bars) and 3 hydroxy-(S)-butyraldehyde (right bar in sets of bars).
Figure 5B:
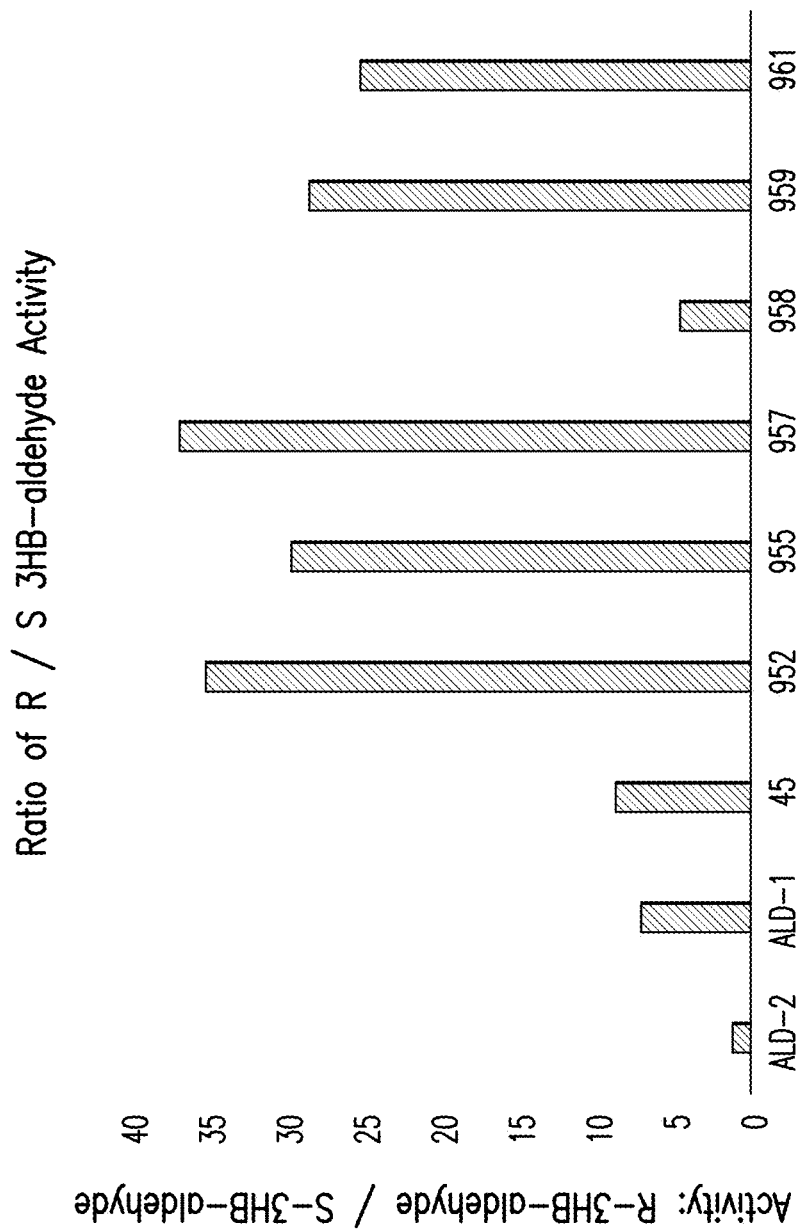

Further investigation of a subset of these variants with (R) and (S) 3-hydroxybutyraldehyde showed that five of the tested variants (952, 955, 957, 959, 961) had improved selectivity for the R enantiomer compared to the parent enzyme (variant 45) and wildtype ALD-1 (FIG. 5). FIG. 5A shows the specific activity of ALD-2, ALD-1 and ALD-1 variants on 3 hydroxy-(R)-butyraldehyde (left bars in sets of bars) and 3 hydroxy-(S)-butyraldehyde (right bars in sets of bars). Purified streptavidin-tagged proteins were assayed at 35° C. in WI buffer pH 7.5, 0.5 mM NAD+, 2 mM CoA in the presence of either 10 mM R or S 3-hydroxybutyraldehyde, and activity was monitored by change in NADH absorbance at 340 nm. WI buffer contains 5 mM potassium phosphate monobasic, 20 mM potassium phosphate dibasic, 10 mM sodium glutamate, monohydrate, and 150 mM potassium chloride, pH 7.5. Thus, the enzyme reaction in the assay was carried out in the reverse direction from that shown in FIG. 1, that is, the reaction measured the conversion of 3-hydroxybutyraldehyde to 3-hydroxybutyryl-CoA. As shown in FIG. 5B, certain aldehyde dehydrogenase variants exhibited selectivity for R-3-hydroxybutyraldehyde (R-3HB-aldehyde) over S-3-hydroxybutyraldehyde (S-3HB-aldehyde).

Figure 6C:
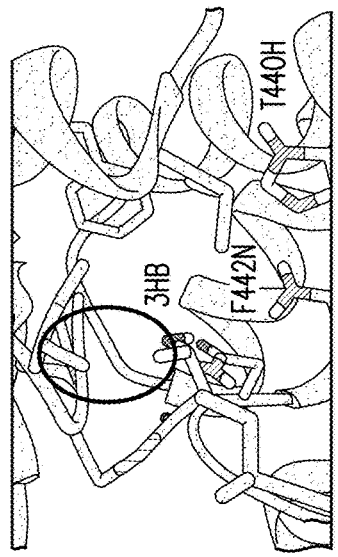
FIGS. 6A-6C show ribbon diagrams of the structure of the aldehyde dehydrogenase 959. The diagrams show docking of 3-hydroxy-(R)-butyraldehyde (FIG. 6A) or 3-hydroxy-(S)-butyraldehyde (FIG. 6B) into the structure of 959.
Figure 6B:
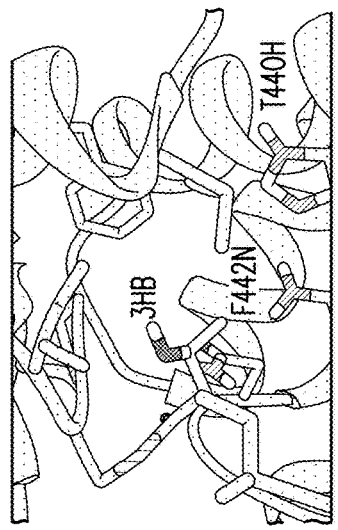
Figure 6A:
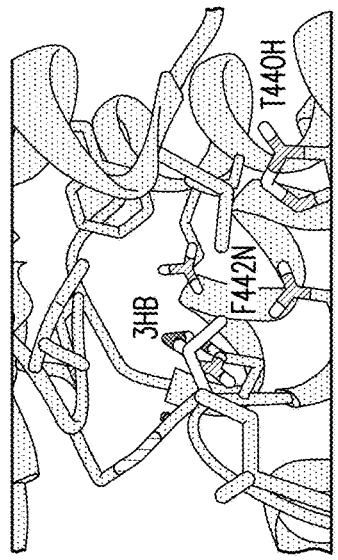

Computational modeling of the mutant 959 using an ALD-1 crystal structure suggests that the amino acid substitution F442N allows a hydrogen bond network to be formed with the hydroxyl on carbon 3 of the R isomer but not the (S) isomer (FIG. 6). FIGS. 6A-6C show ribbon diagrams of the structure of the aldehyde dehydrogenase 959. The diagrams show docking of 3-hydroxy-(R)-butyraldehyde (FIG. 6A) or 3-hydroxy-(S)-butyraldehyde (FIG. 6B) into the structure of 959. FIG. 6C shows that when the 3-hydroxy-(S)-butyraldehyde is docked in the same orientation most energetically favored for docking of 3-hydroxy-(R)-butyraldehyde as shown in FIG. 6A an unfavorable interaction (circled) is created with an isoleucine located in the active site. The model indicates that mutation F442N creates a hydrogen bond between the protein and a hydroxyl of 3-hydroxy-(R)-butyraldehyde that is not possible with the S enantiomer.

Exemplary aldehyde dehydrogenase variants are shown in Tables 1A-1D.

TABLE 1A

Exemplary ALD Variants

| Variant | 12 | 19 | 33 | 44 | 65 | 66 | 72 | 73 | 107 | 122 | 129 | 139 | 143 |
|---|---|---|---|---|---|---|---|---|---|---|---|---|---|
| 12 | D12A | | | | | | | | | | | I139S | |
| 16 | D12A | | C33R | | | | | | | | | I139S | |
| 17 | D12A | | | | | | | | | | | I139V | T143N |
| 30 | | | | | | | | | | | E129I | | |
| 34 | D12A | | | | | | | | | | | I139S | |
| 56 | D12A | | | | | | | | | | | I139S | |
| 71 | | | | | | | | | Y107K | | | | |
| 80 | | | | | | | | | Y107K | | | | |
| 93 | D12A | | | | | | | | | | | I139S | |
| 156 | D12A | | | | | | | | Y107K | | | | |
| 166 | D12A | | | | | | | | Y107K | | | | |
| 180 | D12A | | | | | | | | | | | I139S | |
| 182 | | | | | | | | | | | | | |
| 184 | D12A | | | | | | | | | | | I139S | |
| 194 | | | | | | | | | | | | I139S | |
| 199 | | | | | | | | | | | | | |
| 203 | | | | | | | | | | | | | |
| 205 | D12A | | | | | | | | | | | I139S | |
| 208 | | | | | | | | | | | | | |
| 213 | | | | | | | | | | | | | T143S |
| 235 | D12A | | | | | | | | | | | I139S | |
| 240 | D12A | | | | | | | | | | | I139V | |
| 321 | D12V | | | | | | | | | | | I139S | |
| 331 | | | | | K65A | I66M | | | | | | | |
| 598 | D12A | | | | | | | | | | | I139S | |
| 601 | | | | | K65A | I66Q | | | | | | | |
| 602 | | | | | K65A | I66N | | | | | | | |
| 603 | | | | | K65A | I66H | | | | | | | |
| 604 | | | | | K65A | I66T | | | | | | | |
| 605 | | | | | K65A | I66S | | | | | | | |
| 45 | | | | | | | | | | | | | |
| 681 | | | | | K65A | I66M | | A73S | | | | | |
| 682 | | | | | K65A | I66Q | | A73S | | | | | |
| 683 | | | | | K65A | I66N | | A73S | | | | | |
| 684 | | | | | K65A | I66H | | A73S | | | | | |
| 685 | | | | | K65A | I66T | | A73S | | | | | |
| 686 | | | | | K65A | I66S | | A73S | | | | | |
| 687 | | | | | | | | | | | | | |
| 688 | | | | | K65A | | | | | | | | |
| 721 | | | | | | I66M | | | | | | | |
| 722 | | | | | | I66Q | | | | | | | |
| 723 | | | | | | I66N | | | | | | | |
| 724 | | | | | | I66H | | | | | | | |
| 725 | | | | | | I66T | | | | | | | |
| 726 | | | | | | I66S | | | | | | | |
| 775 | | | | | | I66Q | | | | | | | |
| 776 | | | | | | I66N | | | | | | | |
| 777 | | | | | | I66H | | | | | | | |
| 778 | | | | | | I66T | | | | | | | |
| 779 | | | | | | I66S | | | | | | | |

TABLE 1A-continued

Exemplary ALD Variants

| Variant | 12 | 19 | 33 | 44 | 65 | 66 | 72 | 73 | 107 | 122 | 129 | 139 | 143 |
|---|---|---|---|---|---|---|---|---|---|---|---|---|---|
| 780 | | | | | | I66M | | | | | | | |
| 781 | | | | | K65A | | | | | | | | |
| 782 | | | | | K65A | I66M | | | | | | | |
| 783 | D12A | | | | | I66M | | | | | | I139V | |
| 784 | D12A | | | | K65A | | | | | | | I139V | |
| 785 | D12A | | | | K65A | I66M | | | | | | I139V | |
| 921 | | | | | K65A | I66Q | | | | | | | |
| 922 | | | | | K65A | I66N | | | | | | | |
| 923 | | | | | K65A | I66H | | | | | | | |
| 924 | | | | | K65A | I66T | | | | | | | |
| 925 | | | | | K65A | I66S | | | | | | | |
| 951 | | | | | | | | | | | | | |
| 952 | | | | | | | | | | | | | |
| 953 | | | | | | | | | | | | | |
| 954 | | | | | | | | | | | | | |
| 955 | | | | | | | | | | | | | |
| 956 | | | | | | | | | | | | | |
| 957 | | | | | | | | | | | | | |
| 958 | | | | | | | | | | | | | |
| 959 | | | | | | | | | | | | | |
| 960 | | V19I | | | | | | | | D122N | | | |
| 961 | | | | | | | | | | | | | |
| 975 | D12A | | | | | | | | | | | I139V | |
| 991 | D12A | | | | | | | | | | | I139L | T143N |
| 992 | | | | | | | | A73S | | | | | |
| 993 | | | | | | | | | | | | | |
| 994 | | | | | | | | | | | | | |
| 995 | | | | | | | | | | | | | |
| 996 | | | | | | | | | | | | | |
| 997 | | | | I44L | | | | | | | | | |
| 998 | | | | | | | | | | | | | |
| 999 | | | | | K65A | | | | | | | | |
| 1000 | | | | | | | | | | | | | |
| 1001 | | | | | | | | | | | | | |
| 1002 | | | | | | | | | | | | | |
| 1003 | | | | | | | | | | | | | |
| 1004 | | | | | | | | | | | | | |
| 1005 | | | | | | | | | | | | | |
| 1006 | | | | | | | | | | | | | |
| 1007 | | | | | | I66M | | | | | | | |
| 1008 | | | | | K65A | | | | | | | | |
| 1009 | | | | | K65A | I66M | | | | | | | |
| 1011 | | | | | | | | | | | | | |
| 1012 | | | | | | I66M | | | | | | | |
| 1013 | | | | | K65A | | | | | | | | |
| 1014 | | | | | K65A | I66M | | | | | | | |
| 1015 | | | | | | | | | | | | | |
| 1016 | | | | | | | | | | | | | |
| 1017 | | | | | | | | | | | | | |
| 1018 | | | | | | | | | | | | | |
| 1019 | | | | | | | | | | | | | |
| 1020 | | | | | | | | | | | | | |
| 1021 | | | | | | | | | | | | | |
| 1022 | | | | | | | | | | | | | |
| 1023 | | | | | | | | | | | | | |
| 1024 | | | | | | | | | | | | | |
| 1025 | | | | | | | | | | | | | |
| 1026 | | | | | | | | | | | | | |
| 1027 | | | | | | | | | | | | | |
| 1028 | | | | | | | | | | | | | |
| 1029 | | | | | | | | | | | | | |
| 1030 | | | | | | | | | | | | | |
| 1031 | | | | | | | | | | | | | |
| 1032 | | | | | | | | | | | | | |
| 1033 | | | | | | | | | | | | | |
| 1034 | | | | | | | | | | | | | |
| 1035 | | | | | | | | | | | | | |
| 1036 | | | | | | | | | | | | | |
| 1037 | | | | | | | K72N | | | | | | |
| 1038 | | | | | | | | | | | | | |
| 1039 | | | | | | | | | | | | | |
| 1040 | | | | | | | | | | | | | |
| 1041 | | | | | | | | | | | | | |
| 1042 | | | | | | | | | | | | | |

TABLE 1A-continued

Exemplary ALD Variants

| Variant | \multicolumn{13}{c}{Position} |
|---|---|---|---|---|---|---|---|---|---|---|---|---|---|
| | 12 | 19 | 33 | 44 | 65 | 66 | 72 | 73 | 107 | 122 | 129 | 139 | 143 |
| 1043 | | | | | | | | | | | | | |
| 1044 | | | | | | | | | | | | | |
| 1045 | | | | | | | | | | | | | |
| 1046 | | | | | | | | | | | | | |
| 1047 | | | | | | | | | | | | | |
| 1048 | | | | | | | | | | | | | |
| 1049 | | | | | | | | | | | | | |
| 1050 | | | | | | | | | | | | | |
| 1051 | | | | | | | | | | | | | |
| 1052 | | | | | | | | | | | | | |
| 1053 | | | | | | | | | | | | | |
| 1054 | | | | | | | | | | | | | |
| 1055 | | | | | | | | | | | | | |
| 1056 | | | | | | | | | | | | | |
| 1057 | | | | | | | | | | | | | |
| 1058 | | | | | | | | | | | | | |
| 1059 | | | | | | | | | | | | | |
| 1060 | | | | | | | | | | | | | |
| 1061 | | | | | | | | | | | | | |
| 1062 | | | | | | | | | | | | | |
| 1063 | | | | | | | | | | | | | |
| 1064 | | | | | | | | | | | | | |
| 1065 | | | | | | | | | | | | | |
| 1066 | | | | | | | | | | | | | |
| 1067 | | | | | | | | | | | | | |
| 1068 | | | | | | | | | | | | | |
| 1069 | | | | | | | | | | | | | |
| 1070 | | | | | | | | | | | | | |
| 1071 | | | | | | | | | | | | | |
| 1072 | | | | | | | | | | | | | |
| 1073 | | | | | | | | | | | | | |
| 1074 | | | | | | | | | | | | | |
| 1075 | | | | | | | | | | | | | |
| 1076 | | | | | | | | | | | | | |
| 1077 | | | | | | | | | | | | | |
| 1078 | | | | | | | | | | | | | |
| 1079 | | | | | | | | | A73D | | | | |
| 1080 | | | | | | | | | A73G | | | | |
| 1081 | | | | | | | | | A73L | | | | |
| 1082 | | | | | | | | | A73Q | | | | |
| 1083 | | | | | | | | | A73F | | | | |
| 1084 | | | | | | | | | A73G | | | | |
| 1085 | | | | | | | | | A73E | | | | |
| 1086 | | | | | | | | | A73W | | | | |
| 1087 | | | | | | | | | | | | | |
| 1088 | | | | | | | | | | | | | |
| 1089 | | | | | | | | | | | | | |
| 1090 | | | | | | | | | | | | | |
| 1091 | | | | | | | | | | | | | |
| 1092 | | | | | | | | | | | | | |
| 1093 | | | | | | | | | A73L | | | | |
| 1094 | | | | | | | | | A73R | | | | |
| 1095 | | | | | | | | | A73C | | | | |
| 1096 | | | | | | | | | | | | | |
| 1097 | | | | | | | | | A73W | | | | |
| 1098 | | | | | | | | | A73M | | | | |
| 1099 | | | | | | | | | | | | | |
| 1100 | | | | | | | | | A73F | | | | |
| 1101 | | | | | | | | | | | | | |

TABLE 1B

Exemplary ALD Variants

| Variant | \multicolumn{10}{c}{Position} |
|---|---|---|---|---|---|---|---|---|---|---|
| | 145 | 155 | 163 | 167 | 174 | 189 | 204 | 220 | 227 | 229 |
| 12 | | | | | | | M204R | | | |
| 16 | | | | | C174S | C189A | M204R | C220V | | |
| 17 | | | | G167S | C174S | | M204R | C220V | | |

TABLE 1B-continued

Exemplary ALD Variants

| Variant | 145 | 155 | 163 | 167 | 174 | 189 | 204 | 220 | 227 | 229 |
|---|---|---|---|---|---|---|---|---|---|---|
| 30 | | | | | C174S | | | C220V | | |
| 34 | | | | | C174S | | M204R | C220V | | |
| 56 | | | | | C174S | | M204R | C220V | | |
| 71 | | | | | C174S | | M204R | C220V | | |
| 80 | | | | | C174S | | | C220V | | |
| 93 | | | | | C174S | | M204R | C220V | | |
| 156 | | | | | C174S | | M204R | C220V | | |
| 166 | | | | | C174S | | | C220V | | |
| 180 | | | | | C174S | | M204R | C220V | | |
| 182 | | | | | C174S | | M204R | C220V | | |
| 184 | | | | | C174S | | M204R | C220V | | |
| 194 | | | | | C174S | | M204R | C220V | | |
| 199 | | | | | C174S | | M204R | C220V | | |
| 203 | | | | | C174S | | M204R | C220V | | |
| 205 | | | | | C174S | | M204R | C220V | | |
| 208 | | | | | C174S | | M204R | C220V | | |
| 213 | | | | | C174S | | M204R | C220V | | |
| 235 | | | | | C174S | | M204R | C220V | | |
| 240 | | | | | C174S | | M204R | C220V | M227K | |
| 321 | | | | | | | M204R | | | |
| 331 | | | | | C174S | | M204R | C220V | | |
| 598 | | | | | C174S | | M204R | C220V | M227Q | |
| 601 | | | | | C174S | | M204R | C220V | | |
| 602 | | | | | C174S | | M204R | C220V | | |
| 603 | | | | | C174S | | M204R | C220V | | |
| 604 | | | | | C174S | | M204R | C220V | | |
| 605 | | | | | C174S | | M204R | C220V | | |
| 45 | | | | | C174S | | M204R | C220V | | |
| 681 | | | | | C174S | | M204R | C220V | M227I | |
| 682 | | | | | C174S | | M204R | C220V | M227I | |
| 683 | | | | | C174S | | M204R | C220V | M227I | |
| 684 | | | | | C174S | | M204R | C220V | M227I | |
| 685 | | | | | C174S | | M204R | C220V | M227I | |
| 686 | | | | | C174S | | M204R | C220V | M227I | |
| 687 | | | | | C174S | | M204R | C220V | | |
| 688 | | | | | C174S | | M204R | C220V | | |
| 721 | | | | | C174S | | M204R | C220V | | |
| 722 | | | | | C174S | | M204R | C220V | | |
| 723 | | | | | C174S | | M204R | C220V | | |
| 724 | | | | | C174S | | M204R | C220V | | |
| 725 | | | | | C174S | | M204R | C220V | | |
| 726 | | | | | C174S | | M204R | C220V | | |
| 775 | | | | | C174S | | M204R | C220V | | |
| 776 | | | | | C174S | | M204R | C220V | | |
| 777 | | | | | C174S | | M204R | C220V | | |
| 778 | | | | | C174S | | M204R | C220V | | |
| 779 | | | | | C174S | | M204R | C220V | | |
| 780 | | | | | C174S | | M204R | C220V | | |
| 781 | | | | | C174S | | M204R | C220V | | |
| 782 | | | | | C174S | | M204R | C220V | | |
| 783 | | | | | C174S | | M204R | C220V | M227Q | |
| 784 | | | | | C174S | | M204R | C220V | M227Q | |
| 785 | | | | | C174S | | M204R | C220V | M227Q | |
| 921 | | | | | C174S | | M204R | C220V | | |
| 922 | | | | | C174S | | M204R | C220V | | |
| 923 | | | | | C174S | | M204R | C220V | | |
| 924 | | | | | C174S | | M204R | C220V | | |
| 925 | | | | | C174S | | M204R | C220V | | |
| 951 | | | | | C174S | | M204R | C220V | | |
| 952 | | | | | C174S | | M204R | C220V | | |
| 953 | | | | | C174S | | M204R | C220V | | |
| 954 | | | | | C174S | | M204R | C220V | | |
| 955 | | | | | C174S | | M204R | C220V | | |
| 956 | | | | | C174S | | M204R | C220V | | |
| 957 | | | | | C174S | | M204R | C220V | | |
| 958 | | | | | C174S | | M204R | C220V | | |
| 959 | | | | | C174S | | M204R | C220V | | |
| 960 | | | | | C174S | | M204R | C220V | | |
| 961 | | | | | C174S | | M204R | C220V | | |
| 975 | | | | | C174S | | M204R | C220V | M227Q | |
| 991 | | | | | C174S | | M204R | C220V | | |
| 992 | | | | | C174S | | M204R | C220V | | |
| 993 | | | | | C174S | | M204R | C220V | | |
| 994 | | | V163C | | C174S | | M204R | C220V | | |

TABLE 1B-continued

Exemplary ALD Variants

| Variant | Position | | | | | | | | | |
|---|---|---|---|---|---|---|---|---|---|---|
| | 145 | 155 | 163 | 167 | 174 | 189 | 204 | 220 | 227 | 229 |
| 995 | | | | | C174S | | M204R | C220V | | K 229S |
| 996 | | | | | C174S | | M204R | C220V | | |
| 997 | | | | | C174S | | M204R | C220V | | |
| 998 | | | | | C174S | | M204R | C220V | | |
| 999 | | | | | C174S | | M204R | C220V | | |
| 1000 | | | V163C | | C174S | | M204R | C220V | | |
| 1001 | | | | | C174S | | M204R | C220V | | |
| 1002 | | | | | C174S | | M204R | C220V | | |
| 1003 | | G155G | | | C174S | | M204R | C220V | | |
| 1004 | P145P | | | | C174S | | M204R | C220V | | |
| 1005 | | | | | C174S | | M204R | C220V | | |
| 1006 | | | | | C174S | | M204R | C220V | | |
| 1007 | | | | | C174S | | M204R | C220V | | |
| 1008 | | | | | C174S | | M204R | C220V | | |
| 1009 | | | | | C174S | | M204R | C220V | | |
| 1011 | | | | | C174S | | M204R | C220V | | |
| 1012 | | | | | C174S | | M204R | C220V | | |
| 1013 | | | | | C174S | | M204R | C220V | | |
| 1014 | | | | | C174S | | M204R | C220V | | |
| 1015 | | | | | C174S | | M204R | C220V | M227I | |
| 1016 | | | | | C174S | | M204R | C220V | | |
| 1017 | | | | | C174S | | M204R | C220V | | |
| 1018 | | | | | C174S | | M204R | C220V | | |
| 1019 | | | | | C174S | | M204R | C220V | | |
| 1020 | | | | | C174S | | M204R | C220V | | |
| 1021 | | | | | C174S | | M204R | C220V | M227V | |
| 1022 | | | | | C174S | | M204R | C220V | M227V | |
| 1023 | | | | | C174S | | M204R | C220V | M227I | |
| 1024 | | | | | C174S | | M204R | C220V | M227I | |
| 1025 | | | | | C174S | | M204R | C220V | | |
| 1026 | | | | | C174S | | M204R | C220V | | |
| 1027 | | | | | C174S | | M204R | C220V | M227I | |
| 1028 | | | | | C174S | | M204R | C220V | | |
| 1029 | | | | | C174S | | M204R | C220V | | |
| 1030 | | | | | C174S | | M204R | C220V | | |
| 1031 | | | | | C174S | | M204R | C220V | | |
| 1032 | | | | | C174S | | M204R | C220V | | |
| 1033 | | | | | C174S | | M204R | C220V | | |
| 1034 | | | | | C174S | | M204R | C220V | M227I | |
| 1035 | | | | | C174S | | M204R | C220V | | |
| 1036 | | | | | C174S | | M204R | C220V | | |
| 1037 | | | | | C174S | | M204R | C220V | | |
| 1038 | | | | | C174S | | M204R | C220V | | |
| 1039 | | | | | C174S | | M204R | C220V | | |
| 1040 | | | | | C174S | | M204R | C220V | | |
| 1041 | | | | | C174S | | M204R | C220V | | |
| 1042 | | | | | C174S | | M204R | C220V | | |
| 1043 | | | | | C174S | | M204R | C220V | M227V | |
| 1044 | | | | | C174S | | M204R | C220V | | |
| 1045 | | | | | C174S | | M204R | C220V | | |
| 1046 | | | | | C174S | | M204R | C220V | | |
| 1047 | | | | | C174S | | M204R | C220V | M227C | |
| 1048 | | | | | C174S | | M204R | C220V | M227L | |
| 1049 | | | | | C174S | | M204R | C220V | | |
| 1050 | | | | | C174S | | M204R | C220V | M227C | |
| 1051 | | | | | C174S | | M204R | C220V | | |
| 1052 | | | | | C174S | | M204R | C220V | | |
| 1053 | | | | | C174S | | M204R | C220V | M227C | |
| 1054 | | | | | C174S | | M204R | C220V | M227C | |
| 1055 | | | | | C174S | | M204R | C220V | | |
| 1056 | | | | | C174S | | M204R | C220V | | |
| 1057 | | | | | C174S | | M204R | C220V | | |
| 1058 | | | | | C174S | | M204R | C220V | | |
| 1059 | | | | | C174S | | M204R | C220V | | |
| 1060 | | | | | C174S | | M204R | C220V | M227L | |
| 1061 | | | | | C174S | | M204R | C220V | M227A | |
| 1062 | | | | | C174S | | M204R | C220V | | |
| 1063 | | | | | C174S | | M204R | C220V | | |
| 1064 | | | | | C174S | | M204R | C220V | | |
| 1065 | | | | | C174S | | M204R | C220V | | |
| 1066 | | | | | C174S | | M204R | C220V | M227I | |
| 1067 | | | | | C174S | | M204R | C220V | M227I | |
| 1068 | | | | | C174S | | M204R | C220V | M227I | |
| 1069 | | | | | C174S | | M204R | C220V | | |

TABLE 1B-continued

Exemplary ALD Variants

| Variant | 145 | 155 | 163 | 167 | 174 | 189 | 204 | 220 | 227 | 229 |
|---|---|---|---|---|---|---|---|---|---|---|
| 1070 | | | | | C174S | | M204R | C220V | M227V | |
| 1071 | | | | | C174S | | M204R | C220V | M227C | |
| 1072 | | | | | C174S | | M204R | C220V | | |
| 1073 | | | | | C174S | | M204R | C220V | | |
| 1074 | | | | | C174S | | M204R | C220V | | |
| 1075 | | | | | C174S | | M204R | C220V | | |
| 1076 | | | | | C174S | | M204R | C220V | M227L | |
| 1077 | | | | | C174S | | M204R | C220V | | |
| 1078 | | | | | C174S | | M204R | C220V | M227V | |
| 1079 | | | | | C174S | | M204R | C220V | M227I | |
| 1080 | | | | | C174S | | M204R | C220V | M227I | |
| 1081 | | | | | C174S | | M204R | C220V | M227I | |
| 1082 | | | | | C174S | | M204R | C220V | M227I | |
| 1083 | | | | | C174S | | M204R | C220V | M227I | |
| 1084 | | | | | C174S | | M204R | C220V | M227I | |
| 1085 | | | | | C174S | | M204R | C220V | M227I | |
| 1086 | | | | | C174S | | M204R | C220V | M227I | |
| 1087 | | | V163G | | C174S | | M204R | C220V | M227I | |
| 1088 | | | V163T | | C174S | | M204R | C220V | M227I | |
| 1089 | | | | | C174S | | M204R | C220V | M227L | |
| 1090 | | | | | C174S | | M204R | C220V | | |
| 1091 | | | | | C174S | | M204R | C220V | | |
| 1092 | | | | | C174S | | M204R | C220V | | |
| 1093 | | | | | C174S | | M204R | C220V | M227I | |
| 1094 | | | | | C174S | | M204R | C220V | M227I | |
| 1095 | | | V163C | | C174S | | M204R | C220V | M227I | |
| 1096 | | | V163C | | C174S | | M204R | C220V | M227I | |
| 1097 | | | V163C | | C174S | | M204R | C220V | M227I | |
| 1098 | | | V163C | | C174S | | M204R | C220V | M227I | |
| 1099 | | | V163C | | C174S | | M204R | C220V | M227I | |
| 1100 | | | V163C | | C174S | | M204R | C220V | M227I | |
| 1101 | | | V163C | | C174S | | M204R | C220V | M227I | |

TABLE 1C

Exemplary ALD Variants

| Variant | 230 | 243 | 244 | 254 | 267 | 315 | 353 | 356 | 396 | 429 |
|---|---|---|---|---|---|---|---|---|---|---|
| 12 | | | | | | | | | R396H | |
| 16 | | | | | C267A | | C353A | C356T | R396H | |
| 17 | T230R | | | | C267A | | | C356T | R396H | F429Y |
| 30 | | | | | C267A | | | C356T | R396H | |
| 34 | | | | | C267A | | | C356T | R396H | |
| 56 | | | | | C267A | | | C356T | R396H | F429Y |
| 71 | | | | | C267A | | | C356T | | |
| 80 | | | | | C267A | | | C356T | | |
| 93 | T230R | | | | C267A | | | C356T | R396H | F429Y |
| 156 | | | | | C267A | | | C356T | | |
| 166 | | | | | C267A | | | C356T | | |
| 180 | | | | | C267A | | | C356T | R396H | |
| 182 | | A243P | | | C267A | | | C356T | R396H | |
| 184 | | | | | C267A | | | C356T | R396H | |
| 194 | | | | | C267A | | | C356T | R396H | |
| 199 | | | | | C267A | | | C356T | R396H | F429Q |
| 203 | | | | | C267A | | | C356T | R396H | F429Y |
| 205 | | A243P | | | C267A | | | C356T | R396H | F429Y |
| 208 | | | | | C267A | | | C356T | R396H | |
| 213 | | | | | C267A | | | C356T | R396H | |
| 235 | | A243P | | | C267A | | | C356T | R396H | |
| 240 | | | | | C267A | | | C356T | R396H | F429Y |
| 321 | | | | | | | | | R396H | |
| 331 | | A243Q | | | C267A | | | C356T | R396H | |
| 598 | T230R | A243P | | | C267A | | | C356T | R396H | F429Y |
| 601 | | A243Q | | | C267A | | | C356T | R396H | |
| 602 | | A243Q | | | C267A | | | C356T | R396H | |
| 603 | | A243Q | | | C267A | | | C356T | R396H | |
| 604 | | A243Q | | | C267A | | | C356T | R396H | |
| 605 | | A243Q | | | C267A | | | C356T | R396H | |

TABLE 1C-continued

Exemplary ALD Variants

| | Position | | | | | | | | | |
|---|---|---|---|---|---|---|---|---|---|---|
| Variant | 230 | 243 | 244 | 254 | 267 | 315 | 353 | 356 | 396 | 429 |
| 45 | | | | | C267A | | | C356T | R396H | |
| 681 | T230C | A243P | | | C267A | | | C356T | R396H | |
| 682 | T230C | A243P | | | C267A | | | C356T | R396H | |
| 683 | T230C | A243P | | | C267A | | | C356T | R396H | |
| 684 | T230C | A243P | | | C267A | | | C356T | R396H | |
| 685 | T230C | A243P | | | C267A | | | C356T | R396H | |
| 686 | T230C | A243P | | | C267A | | | C356T | R396H | |
| 687 | | | | | C267A | | | C356T | R396H | |
| 688 | | A243Q | | | C267A | | | C356T | R396H | |
| 721 | | A243Q | | | C267A | | | C356T | R396H | |
| 722 | | A243Q | | | C267A | | | C356T | R396H | |
| 723 | | A243Q | | | C267A | | | C356T | R396H | |
| 724 | | A243Q | | | C267A | | | C356T | R396H | |
| 725 | | A243Q | | | C267A | | | C356T | R396H | |
| 726 | | A243Q | | | C267A | | | C356T | R396H | |
| 775 | | A243P | | | C267A | | | C356T | R396H | |
| 776 | | A243P | | | C267A | | | C356T | R396H | |
| 777 | | A243P | | | C267A | | | C356T | R396H | |
| 778 | | A243P | | | C267A | | | C356T | R396H | |
| 779 | | A243P | | | C267A | | | C356T | R396H | |
| 780 | | | | | C267A | | | C356T | R396H | F429H |
| 781 | | | | | C267A | | | C356T | R396H | F429H |
| 782 | | | | | C267A | | | C356T | R396H | F429H |
| 783 | T230R | A243P | | | C267A | | | C356T | R396H | F429Y |
| 784 | T230R | A243P | | | C267A | | | C356T | R396H | F429Y |
| 785 | T230R | A243P | | | C267A | | | C356T | R396H | F429Y |
| 921 | | A243P | | | C267A | | | C356T | R396H | |
| 922 | | A243P | | | C267A | | | C356T | R396H | |
| 923 | | A243P | | | C267A | | | C356T | R396H | |
| 924 | | A243P | | | C267A | | | C356T | R396H | |
| 925 | | A243P | | | C267A | | | C356T | R396H | |
| 951 | | | | | C267A | | | C356T | R396H | F429H |
| 952 | | | | | C267A | | | C356T | R396H | F429M |
| 953 | | | | | C267A | | | C356T | R396H | F429M |
| 954 | | | | | C267A | | | C356T | R396H | F429Q |
| 955 | | | | | C267A | | | C356T | R396H | |
| 956 | | | | | C267A | | | C356T | R396H | |
| 957 | | | | | C267A | | | C356T | R396H | |
| 958 | | | | | C267A | | | C356T | R396H | |
| 959 | | | | | C267A | | | C356T | R396H | |
| 960 | | | | | C267A | | | C356T | R396H | F429D |
| 961 | | | | | C267A | V315A | | C356T | R396H | |
| 975 | T230R | A243P | | | C267A | | | C356T | R396H | F429Y |
| 991 | T230R | A243P | | | C267A | | | C356T | R396H | F429Y |
| 992 | | | | | C267A | | | C356T | R396H | |
| 993 | | | | A254T | C267A | | | C356T | R396H | |
| 994 | | | | | C267A | | | C356T | R396H | |
| 995 | | | | | C267A | | | C356T | R396H | |
| 996 | | | | | C267A | | | C356L | R396H | |
| 997 | | | | | C267A | | | C356T | R396H | |
| 998 | | | | | C267A | | | C356T | R396H | |
| 999 | | | | | C267A | | | C356T | R396H | |
| 1000 | | | | | C267A | | | C356T | R396H | |
| 1001 | | | | | C267A | | | C356T | R396H | |
| 1002 | | | | | C267A | | | C356T | R396H | |
| 1003 | | | | | C267A | | | C356T | R396H | |
| 1004 | | | | | C267A | | | C356T | R396H | |
| 1005 | | | G244G | | C267A | | | C356T | R396H | |
| 1006 | | | | | C267A | | | C356T | R396H | |
| 1007 | | | | | C267A | | | C356T | R396H | |
| 1008 | | | | | C267A | | | C356T | R396H | |
| 1009 | | | | | C267A | | | C356T | R396H | |
| 1011 | | A243P | | | C267A | | | C356T | R396H | |
| 1012 | | A243P | | | C267A | | | C356T | R396H | |
| 1013 | | A243P | | | C267A | | | C356T | R396H | |
| 1014 | | A243P | | | C267A | | | C356T | R396H | |
| 1015 | T230K | | | | C267A | | | C356T | R396H | |
| 1016 | T230R | A243Q | | | C267A | | | C356T | R396H | |
| 1017 | T230H | A243Q | | | C267A | | | C356T | R396H | |
| 1018 | T230A | A243E | | | C267A | | | C356T | R396H | |
| 1019 | T230M | A243S | | | C267A | | | C356T | R396H | |
| 1020 | T230H | A243N | | | C267A | | | C356T | R396H | |
| 1021 | T230C | | | | C267A | | | C356T | R396H | |
| 1022 | T230H | | | | C267A | | | C356T | R396H | |

TABLE 1C-continued

Exemplary ALD Variants

| Variant | 230 | 243 | 244 | 254 | 267 | 315 | 353 | 356 | 396 | 429 |
|---|---|---|---|---|---|---|---|---|---|---|
| 1023 | T230L | | | | C267A | | | C356T | R396H | |
| 1024 | T230C | | | | C267A | | | C356T | R396H | |
| 1025 | T230M | A243E | | | C267A | | | C356T | R396H | |
| 1026 | T230S | A243Q | | | C267A | | | C356T | R396H | |
| 1027 | T230A | | | | C267A | | | C356T | R396H | |
| 1028 | T230K | | | | C267A | | | C356T | R396H | |
| 1029 | T230Y | A243Q | | | C267A | | | C356T | R396H | |
| 1030 | T230G | A243Q | | | C267A | | | C356T | R396H | |
| 1031 | T230M | A243K | | | C267A | | | C356T | R396H | |
| 1032 | T230T | A243L | | | C267A | | | C356T | R396H | |
| 1033 | T230I | | | | C267A | | | C356T | R396H | |
| 1034 | T230K | | | | C267A | | | C356T | R396H | F429L |
| 1035 | T230H | | | | C267A | | | C356T | R396H | |
| 1036 | T230Y | A243E | | | C267A | | | C356T | R396H | |
| 1037 | | A243S | | | C267A | | | C356T | R396H | |
| 1038 | T230C | A243K | | | C267A | | | C356T | R396H | |
| 1039 | T230H | A243K | | | C267A | | | C356T | R396H | |
| 1040 | T230H | A243C | | | C267A | | | C356T | R396H | |
| 1041 | T230A | A243Q | | | C267A | | | C356T | R396H | |
| 1042 | T230S | A243C | | | C267A | | | C356T | R396H | |
| 1043 | T230S | | | | C267A | | | C356T | R396H | |
| 1044 | T230H | A243M | | | C267A | | | C356T | R396H | |
| 1045 | T230A | A243K | | | C267A | | | C356T | R396H | |
| 1046 | T230W | | | | C267A | | | C356T | R396H | |
| 1047 | T230R | | | | C267A | | | C356T | R396H | |
| 1048 | T230N | | | | C267A | | | C356T | R396H | |
| 1049 | T230N | | | | C267A | | | C356T | R396H | |
| 1050 | T230L | | | | C267A | | | C356T | R396H | |
| 1051 | T230V | | | | C267A | | | C356T | R396H | |
| 1052 | T230L | | | | C267A | | | C356T | R396H | |
| 1053 | T230K | | | | C267A | | | C356T | R396H | |
| 1054 | T230V | | | | C267A | | | C356T | R396H | |
| 1055 | T230T | A243N | | | C267A | | | C356T | R396H | |
| 1056 | T230T | A243I | | | C267A | | | C356T | R396H | |
| 1057 | T230T | A243C | | | C267A | | | C356T | R396H | |
| 1058 | T230G | A243K | | | C267A | | | C356T | R396H | |
| 1059 | T230R | A243K | | | C267A | | | C356T | R396H | |
| 1060 | | A243P | | | C267A | | | C356T | R396H | |
| 1061 | | A243P | | | C267A | | | C356T | R396H | |
| 1062 | | A243Q | | | C267A | | | C356T | R396H | |
| 1063 | T230Q | | | | C267A | | | C356T | R396H | |
| 1064 | T230N | A243I | | | C267A | | | C356T | R396H | |
| 1065 | T230C | A243C | | | C267A | | | C356T | R396H | |
| 1066 | T230R | | | | C267A | | | C356T | R396H | |
| 1067 | | A243L | | | C267A | | | C356T | R396H | |
| 1068 | | A243M | | | C267A | | | C356T | R396H | |
| 1069 | | A243M | | | C267A | | | C356T | R396H | |
| 1070 | | | | | C267A | | | C356T | R396H | |
| 1071 | | A243Q | | | C267A | | | C356T | R396H | |
| 1072 | T230R | A243C | | | C267A | | | C356T | R396H | |
| 1073 | T230L | A243M | | | C267A | | | C356T | R396H | |
| 1074 | T230I | A243M | | | C267A | | | C356T | R396H | |
| 1075 | T230M | A243Q | | | C267A | | | C356T | R396H | |
| 1076 | T230W | | | | C267A | | | C356T | R396H | |
| 1077 | T230V | A243M | | | C267A | | | C356T | R396H | |
| 1078 | T230I | | | | C267A | | | C356T | R396H | |
| 1079 | T230K | | | | C267A | | | C356T | R396H | |
| 1080 | T230K | | | | C267A | | | C356T | R396H | |
| 1081 | T230K | | | | C267A | | | C356T | R396H | |
| 1082 | T230K | | | | C267A | | | C356T | R396H | |
| 1083 | T230K | | | | C267A | | | C356T | R396H | |
| 1084 | T230K | | | | C267A | | | C356T | R396H | |
| 1085 | T230K | | | | C267A | | | C356T | R396H | |
| 1086 | T230K | | | | C267A | | | C356T | R396H | |
| 1087 | T230K | | | | C267A | | | C356T | R396H | |
| 1088 | T230K | | | | C267A | | | C356T | R396H | |
| 1089 | T230S | | | | C267A | | | C356T | R396H | |
| 1090 | | A243E | | | C267A | | | C356T | R396H | |
| 1091 | T230T | A243E | | | C267A | | | C356T | R396H | |
| 1092 | | A243K | | | C267A | | | C356T | R396H | |
| 1093 | T230K | | | | C267A | | | C356T | R396H | |
| 1094 | T230K | | | | C267A | | | C356T | R396H | |
| 1095 | T230K | | | | C267A | | | C356T | R396H | |
| 1096 | T230K | | | | C267A | | | C356T | R396H | |

TABLE 1C-continued

Exemplary ALD Variants

| Variant | Position | | | | | | | | | |
|---|---|---|---|---|---|---|---|---|---|---|
| | 230 | 243 | 244 | 254 | 267 | 315 | 353 | 356 | 396 | 429 |
| 1097 | T230K | | | | C267A | | | C356T | R396H | |
| 1098 | T230K | | | | C267A | | | C356T | R396H | |
| 1099 | T230K | | | | C267A | | | C356T | R396H | |
| 1100 | T230K | | | | C267A | | | C356T | R396H | |
| 1101 | T230K | | | | C267A | | | C356T | R396H | |

TABLE 1D

Exemplary ALD Variants

| Variant | Position | | | | | | | | | | |
|---|---|---|---|---|---|---|---|---|---|---|---|
| | 432 | 437 | 440 | 441 | 442 | 444 | 447 | 450 | 460 | 464 | 467 |
| 12 | | | | | | | | | | | |
| 16 | | | | | | | | | | C464V | |
| 17 | | E437P | | | F442T | | | | | C464I | A467V |
| 30 | | | | | | | | | | C464I | A467V |
| 34 | | | | | | | | | | C464I | |
| 56 | | E437P | | | F442T | | | | | C464I | A467V |
| 71 | | | | | | | | | | C464I | A467V |
| 80 | | | | | | | | | | C464I | |
| 93 | | E437P | | | F442T | | | | | C464I | A467V |
| 156 | | | | | | | | | | C464I | A467V |
| 166 | | | | | | | | | | C464I | |
| 180 | | | | | | | | | | C464I | A467V |
| 182 | | E437P | | | | | | | | C464I | A467V |
| 184 | | E437P | | | | | | | | C464I | A467V |
| 194 | | E437P | | | | | | | | C464I | A467V |
| 199 | | E437P | | | | | | | | C464I | A467V |
| 203 | | E437P | | | F442T | | | | | C464I | A467V |
| 205 | | E437P | | | F442T | | | | | C464I | A467V |
| 208 | | E437P | | | F442Y | | | | | C464I | A467V |
| 213 | | E437P | | | | | | | | C464I | A467V |
| 235 | | E437P | | | | | | | | C464I | A467V |
| 240 | | E437P | | | F442T | | | | | C464I | A467V |
| 321 | | | | | | | | | | | |
| 331 | | E437P | | | F442N | | | | | C464I | A467V |
| 598 | | E437P | | | F442T | | | | | C464I | A467V |
| 601 | | E437P | | | F442N | | | | | C464I | A467V |
| 602 | | E437P | | | F442N | | | | | C464I | A467V |
| 603 | | E437P | | | F442N | | | | | C464I | A467V |
| 604 | | E437P | | | F442N | | | | | C464I | A467V |
| 605 | | E437P | | | F442N | | | | | C464I | A467V |
| 45 | | E437P | | | | | | | | C464I | A467V |
| 681 | | E437P | | | F442N | | S447P | | | C464I | A467V |
| 682 | | E437P | | | F442N | | S447P | | | C464I | A467V |
| 683 | | E437P | | | F442N | | S447P | | | C464I | A467V |
| 684 | | E437P | | | F442N | | S447P | | | C464I | A467V |
| 685 | | E437P | | | F442N | | S447P | | | C464I | A467V |
| 686 | | E437P | | | F442N | | S447P | | | C464I | A467V |
| 687 | | E437P | | | F442M | | | | | C464I | A467V |
| 688 | | E437P | | | F442N | | | | | C464I | A467V |
| 721 | | E437P | | | F442N | | | | | C464I | A467V |
| 722 | | E437P | | | F442N | | | | | C464I | A467V |
| 723 | | E437P | | | F442N | | | | | C464I | A467V |
| 724 | | E437P | | | F442N | | | | | C464I | A467V |
| 725 | | E437P | | | F442N | | | | | C464I | A467V |
| 726 | | E437P | | | F442N | | | | | C464I | A467V |
| 775 | | E437P | | | F442N | | | | | C464I | A467V |
| 776 | | E437P | | | F442N | | | | | C464I | A467V |
| 777 | | E437P | | | F442N | | | | | C464I | A467V |
| 778 | | E437P | | | F442N | | | | | C464I | A467V |
| 779 | | E437P | | | F442N | | | | | C464I | A467V |
| 780 | | E437P | | | F442H | | | | | C464I | A467V |
| 781 | | E437P | | | F442H | | | | | C464I | A467V |
| 782 | | E437P | | | F442H | | | | | C464I | A467V |
| 783 | | E437P | | | F442T | | | | | C464I | A467V |
| 784 | | E437P | | | F442T | | | | | C464I | A467V |
| 785 | | E437P | | | F442T | | | | | C464I | A467V |
| 921 | | E437P | | | F442N | | | | | C464I | A467V |

TABLE 1D-continued

Exemplary ALD Variants

| Variant | 432 | 437 | 440 | 441 | 442 | 444 | 447 | 450 | 460 | 464 | 467 |
|---|---|---|---|---|---|---|---|---|---|---|---|
| 922 |  | E437P |  |  | F442N |  |  |  |  | C464I | A467V |
| 923 |  | E437P |  |  | F442N |  |  |  |  | C464I | A467V |
| 924 |  | E437P |  |  | F442N |  |  |  |  | C464I | A467V |
| 925 |  | E437P |  |  | F442N |  |  |  |  | C464I | A467V |
| 951 |  | E437P |  |  | F442H |  |  |  |  | C464I | A467V |
| 952 |  | E437P |  |  | F442H |  |  |  |  | C464I | A467V |
| 953 |  | E437P |  |  | F442N |  |  |  |  | C464I | A467V |
| 954 |  | E437P |  |  |  |  |  |  |  | C464I | A467V |
| 955 |  | E437P |  |  | F442N |  |  |  |  | C464I | A467V |
| 956 |  | E437P |  |  | F442N |  |  |  |  | C464I | A467V |
| 957 |  | E437P |  |  | F442Q |  |  |  |  | C464I | A467V |
| 958 |  | E437P |  |  |  | I444V |  |  |  | C464I | A467V |
| 959 |  | E437P | T440H |  | F442N |  |  |  |  | C464I | A467V |
| 960 |  | E437P |  |  | F442Q |  |  | E450E |  | C464I | A467V |
| 961 |  | E437P | T440H |  | F442N |  |  |  |  | C464I | A467V |
| 975 |  | E437P |  |  | F442T |  |  |  |  | C464I | A467V |
| 991 |  | E437P |  |  | F442T |  |  |  |  | C464I | A467V |
| 992 |  | E437P |  |  | F442M |  | S447M |  |  | C464I | A467V |
| 993 |  | E437P |  |  | F442M |  |  |  |  | C464I | A467V |
| 994 |  | E437P |  |  | F442M |  |  |  |  | C464I | A467V |
| 995 |  | E437P |  |  | F442N |  |  |  |  | C464I | A467V |
| 996 |  | E437P |  |  | F442N |  |  |  |  | C464I | A467V |
| 997 |  | E437P |  | T441G |  |  |  |  |  | C464I | A467V |
| 998 |  | E437P |  |  | F442M |  |  |  |  | C464I | A467V |
| 999 |  | E437P |  |  | F442N |  |  |  |  | C464I | A467V |
| 1000 |  | E437P |  |  | F442N |  |  |  |  | C464I | A467V |
| 1001 |  | E437P |  |  | F442M |  |  |  | R460K | C464I | A467V |
| 1002 |  | E437P |  |  | F442M |  | S447M |  |  | C464I | A467V |
| 1003 |  | E437P |  |  | F442F |  |  |  |  | C464I | A467V |
| 1004 |  | E437P |  |  |  |  |  |  |  | C464I | A467V |
| 1005 |  | E437P |  |  |  |  |  |  |  | C464I | A467V |
| 1006 | V432V | E437P |  |  |  |  |  |  |  | C464I | A467V |
| 1007 | V432V | E437P |  |  |  |  |  |  |  | C464I | A467V |
| 1008 | V432V | E437P |  |  |  |  |  |  |  | C464I | A467V |
| 1009 | V432V | E437P |  |  |  |  |  |  |  | C464I | A467V |
| 1011 |  | E437P |  |  | F442N |  |  |  |  | C464I | A467V |
| 1012 |  | E437P |  |  | F442N |  |  |  |  | C464I | A467V |
| 1013 |  | E437P |  |  | F442N |  |  |  |  | C464I | A467V |
| 1014 |  | E437P |  |  | F442N |  |  |  |  | C464I | A467V |
| 1015 |  | E437P |  |  | F442N |  |  |  |  | C464I | A467V |
| 1016 |  | E437P |  |  | F442N |  |  |  |  | C464I | A467V |
| 1017 |  | E437P |  |  | F442N |  |  |  |  | C464I | A467V |
| 1018 |  | E437P |  |  | F442N |  |  |  |  | C464I | A467V |
| 1019 |  | E437P |  |  | F442N |  |  |  |  | C464I | A467V |
| 1020 |  | E437P |  |  | F442N |  |  |  |  | C464I | A467V |
| 1021 |  | E437P |  |  | F442N |  |  |  |  | C464I | A467V |
| 1022 |  | E437P |  |  | F442N |  |  |  |  | C464I | A467V |
| 1023 |  | E437P |  |  | F442N |  |  |  |  | C464I | A467V |
| 1024 |  | E437P |  |  | F442N |  |  |  |  | C464I | A467V |
| 1025 |  | E437P |  |  | F442N |  |  |  |  | C464I | A467V |
| 1026 |  | E437P |  |  | F442N |  |  |  |  | C464I | A467V |
| 1027 |  | E437P |  |  | F442N |  |  |  |  | C464I | A467V |
| 1028 |  | E437P |  |  | F442N |  |  |  |  | C464I | A467V |
| 1029 |  | E437P |  |  | F442N |  |  |  |  | C464I | A467V |
| 1030 |  | E437P |  |  | F442N |  |  |  |  | C464I | A467V |
| 1031 |  | E437P |  |  | F442N |  |  |  |  | C464I | A467V |
| 1032 |  | E437P |  |  | F442N |  |  |  |  | C464I | A467V |
| 1033 |  | E437P |  |  | F442N |  |  |  |  | C464I | A467V |
| 1034 | V432N | E437P |  |  | F442N |  |  |  |  | C464I | A467V |
| 1035 |  | E437P |  |  | F442N |  |  |  |  | C464I | A467V |
| 1036 |  | E437P |  |  | F442N |  |  |  |  | C464I | A467V |
| 1037 |  | E437P |  |  | F442N |  |  |  |  | C464I | A467V |
| 1038 |  | E437P |  |  | F442N |  |  |  |  | C464I | A467V |
| 1039 |  | E437P |  |  | F442N |  |  |  |  | C464I | A467V |
| 1040 |  | E437P |  |  | F442N |  |  |  |  | C464I | A467V |
| 1041 |  | E437P |  |  | F442N |  |  |  |  | C464I | A467V |
| 1042 |  | E437P |  |  | F442N |  |  |  |  | C464I | A467V |
| 1043 |  | E437P |  |  | F442N |  |  |  |  | C464I | A467V |
| 1044 |  | E437P |  |  | F442N |  |  |  |  | C464I | A467V |
| 1045 |  | E437P |  |  | F442N |  |  |  |  | C464I | A467V |
| 1046 |  | E437P |  |  | F442N |  |  |  |  | C464I | A467V |
| 1047 |  | E437P |  |  | F442N |  |  |  |  | C464I | A467V |
| 1048 |  | E437P |  |  | F442N |  |  |  |  | C464I | A467V |
| 1049 |  | E437P |  |  | F442N |  |  |  |  | C464I | A467V |

TABLE 1D-continued

Exemplary ALD Variants

| Variant | 432 | 437 | 440 | 441 | 442 | 444 | 447 | 450 | 460 | 464 | 467 |
|---|---|---|---|---|---|---|---|---|---|---|---|
| 1050 |  | E437P |  |  | F442N |  |  |  |  | C464I | A467V |
| 1051 |  | E437P |  |  | F442N |  |  |  |  | C464I | A467V |
| 1052 |  | E437P |  |  | F442N |  |  |  |  | C464I | A467V |
| 1053 |  | E437P |  |  | F442N |  |  |  |  | C464I | A467V |
| 1054 |  | E437P |  |  | F442N |  |  |  |  | C464I | A467V |
| 1055 |  | E437P |  |  | F442N |  |  |  |  | C464I | A467V |
| 1056 |  | E437P |  |  | F442N |  |  |  |  | C464I | A467V |
| 1057 |  | E437P |  |  | F442N |  |  |  |  | C464I | A467V |
| 1058 |  | E437P |  |  | F442N |  |  |  |  | C464I | A467V |
| 1059 |  | E437P |  |  | F442N |  |  |  |  | C464I | A467V |
| 1060 |  | E437P |  |  | F442N |  |  |  |  | C464I | A467V |
| 1061 |  | E437P |  |  | F442N |  |  |  |  | C464I | A467V |
| 1062 |  | E437P |  |  | F442N |  |  |  |  | C464I | A467V |
| 1063 |  | E437P |  |  | F442N |  |  |  |  | C464I | A467V |
| 1064 |  | E437P |  |  | F442N |  |  |  |  | C464I | A467V |
| 1065 |  | E437P |  |  | F442N |  |  |  |  | C464I | A467V |
| 1066 |  | E437P |  |  | F442N |  |  |  |  | C464I | A467V |
| 1067 |  | E437P |  |  | F442N |  |  |  |  | C464I | A467V |
| 1068 |  | E437P |  |  | F442N |  |  |  |  | C464I | A467V |
| 1069 |  | E437P |  |  | F442N |  |  |  |  | C464I | A467V |
| 1070 |  | E437P |  |  | F442N |  |  |  |  | C464I | A467V |
| 1071 |  | E437P |  |  | F442N |  |  |  |  | C464I | A467V |
| 1072 |  | E437P |  |  | F442N |  |  |  |  | C464I | A467V |
| 1073 |  | E437P |  |  | F442N |  |  |  |  | C464I | A467V |
| 1074 |  | E437P |  |  | F442N |  |  |  |  | C464I | A467V |
| 1075 |  | E437P |  |  | F442N |  |  |  |  | C464I | A467V |
| 1076 |  | E437P |  |  | F442N |  |  |  |  | C464I | A467V |
| 1077 |  | E437P |  |  | F442N |  |  |  |  | C464I | A467V |
| 1078 |  | E437P |  |  | F442N |  |  |  |  | C464I | A467V |
| 1079 |  | E437P |  |  | F442N |  | S447P |  |  | C464I | A467V |
| 1080 |  | E437P |  |  | F442N |  | S447H |  |  | C464I | A467V |
| 1081 |  | E437P |  |  | F442N |  | S447K |  |  | C464I | A467V |
| 1082 |  | E437P |  |  | F442N |  | S447R |  |  | C464I | A467V |
| 1083 |  | E437P |  |  | F442N |  | S447K |  |  | C464I | A467V |
| 1084 |  | E437P |  |  | F442N |  | S447K |  |  | C464I | A467V |
| 1085 |  | E437P |  |  | F442N |  | S447K |  |  | C464I | A467V |
| 1086 |  | E437P |  |  | F442N |  | S447R |  |  | C464I | A467V |
| 1087 |  | E437P |  |  | F442N |  | S447P |  |  | C464I | A467V |
| 1088 |  | E437P |  |  | F442N |  | S447P |  |  | C464I | A467V |
| 1089 |  | E437P |  |  | F442N |  |  |  |  | C464I | A467V |
| 1090 |  | E437P |  |  | F442N |  |  |  |  | C464I | A467V |
| 1091 |  | E437P |  |  | F442N |  |  |  |  | C464I | A467V |
| 1092 |  | E437P |  |  | F442N |  |  |  |  | C464I | A467V |
| 1093 |  | E437P |  |  | F442N |  | S447P |  |  | C464I | A467V |
| 1094 |  | E437P |  |  | F442N |  | S447T |  |  | C464I | A467V |
| 1095 |  | E437P |  |  | F442N |  |  |  |  | C464I | A467V |
| 1096 |  | E437P |  |  | F442N |  | S447E |  |  | C464I | A467V |
| 1097 |  | E437P |  |  | F442N |  | S447K |  |  | C464I | A467V |
| 1098 |  | E437P |  |  | F442N |  | S447R |  |  | C464I | A467V |
| 1099 |  | E437P |  |  | F442N |  | S447P |  |  | C464I | A467V |
| 1100 |  | E437P |  |  | F442N |  | S447P |  |  | C464I | A467V |
| 1101 |  | E437P |  |  | F442N |  | S447S |  |  | C464I | A467V |

Various activities of the ALD variants were determined and are shown in Table 2.

TABLE 2

| Activities of Exemplary ALD Variants. | | | | | |
|---|---|---|---|---|---|
| Variant | Mutations Relative to Wild-Type Ald | Small Scale In Vivo 1,3 BDO Production[1] | 3HBCoA/ AcCoA Specificity[2] | R-3HB Aldehyde/ S-3HB Aldehyde | Specific activity[3] |
| 12 | D12A, I139S, M204R, R396H | yes |  |  |  |
| 16 | D12A, C33R, I139S, C174S, C189A, M204R, C220V, C267A, C353A, C356T, R396H, C464V |  |  |  |  |
| 17 | D12A, I139V, T143N, G167S, C174S, M204R, C220V, T230R, C267A, C356T, R396H, F429Y, F442T, E437P, C464I, A467V |  |  |  |  |

TABLE 2-continued

Activities of Exemplary ALD Variants.

| Variant | Mutations Relative to Wild-Type Ald | Small Scale In Vivo 1,3 BDO Production[1] | 3HBCoA/ AcCoA Specificity[2] | R-3HB Aldehyde/ S-3HB Aldehyde | Specific activity[3] |
|---|---|---|---|---|---|
| 30 | E129I, C174S, C220V, C267A, C356T, R396H, C464I, A467V | * | | | |
| 34 | D12A, I139S, C174S, M204R, C220V, C267A, C356T, R396H, C464I | Yes | | | |
| 56 | D12A, I139S, C174S, M204R, C220V, C267A, C356T, R396H, F429Y, , E437P, F442T, C464I, A467V | yes | | | |
| 71 | Y107K, C174S, M204R, C220V, C267A, C356T, C464I, A467V | | | | |
| 80 | Y107K, C174S, C220V, C267A, C356T, C464I | * | | | |
| 93 | D12A, I139S, C174S, M204R, T230R, C220V, C267A, C356T, R396H, F429Y, F442T, E437P, C464I, A467V | * | | | |
| 156 | D12A, Y107K, C174S, M204R, C220V, C267A, C356T, C464I, A467V | * | | | |
| 166 | D12A, Y107K, C174S, C220V, C267A, C356T, C464I | * | | | |
| 180 | D12A, I139S, C174S, M204R, C220V, C267A, C356T, R396H, C464I, A467V | * | | | |
| 182 | C174S, M204R, C220V, A243P, C267A, C356T, R396H, E437P, C464I, A467V | * | | | |
| 184 | D12A, I139S, C174S, M204R, C220V, C267A, C356T, R396H, E437P, C464I, A467V | * | | | |
| 194 | I139S, C174S, M204R, C220V, C267A, C356T, R396H, E437P, C464I, A467V | * | | | |
| 199 | C174S, M204R, C220V, C267A, C356T, R396H, F429Q, E437P, C464I, A467V | * | | | |
| 203 | C174S, M204R, C220V, C267A, C356T, R396H, F429Y, E437P, F442T, C464I, A467V | * | | | |
| 205 | D12A, I139S, C174S, M204R, C220V, A243P, C267A, C356T, R396H, F429Y, F442T, E437P, C464I, A467V | * | | | |
| 208 | C174S, M204R, C220V, C267A, C356T, R396H, E437P, F442Y, C464I, A467V | * | | | |
| 213 | T143S, C174S, M204R, C220V, C267A, C356T, R396H, E437P, C464I, A467V | * | | | |
| 235 | D12A, I139S, C174S, M204R, C220V, A243P, C267A, C356T, R396H, E437P, C464I, A467V | * | | | |
| 240 | D12A, I139V, C174S, M204R, M227K, C220V, C267A, C356T, R396H, F429Y, F442T, E437P, C464I, A467V | * | | | |
| 321 | D12V, I139S, M204R, R396H | * | | | |
| 598 | D12A, I139S, C174S, M204R, M227Q, T230R, A243P, C220V, C267A, C356T, R396H, F429Y, F442T, E437P, C464I, A467V | Yes | + | | |
| 45 | C174S, M204R, C220V, C267A, C356T, R396H, E437P, C464I, A467V | Yes | +++ | + | |
| 951 | C174S, M204R, C220V, C267A, C356T, R396H, F429H, E437P, F442H, C464I, A467V | | + | + | |
| 952 | C174S, M204R, C220V, C267A, C356T, R396H, F429M, E437P, F442H, C464I, A467V | | + | | |
| 953 | C174S, M204R, C220V, C267A, C356T, R396H, F429M, E437P, F442N, C464I, A467V | | + | | |
| 954 | C174S, M204R, C220V, C267A, C356T, R396H, F429Q, E437P, C464I, A467V | | + | | |
| 955 | C174S, M204R, C220V, C267A, C356T, R396H, E437P, F442N, C464I, A467V | Yes | +++ | + | |
| 957 | C174S, M204R, C220V, C267A, C356T, R396H, E437P, F442Q, C464I, A467V | | + | + | |
| 958 | C174S, M204R, C220V, C267A, C356T, R396H, E437P, I444V, C464I, A467V | | + | + | |
| 959 | C174S, M204R, C220V, C267A, C356T, R396H, E437P, T440H, F442N, C464I, A467V | | + | + | |
| 960 | V19I, D122N, C174S, M204R, C220V, C267A, C356T, R396H, F429D, E437P, F442Q, E450E, C464I, A467V | | + | | |
| 961 | C174S, M204R, C220V, C267A, V315A, C356T, R396H, E437P, T440H, F442N, C464I, A467V | | + | + | |
| 975 | D12A, I139V, C174S, M204R, C220V, M227Q, T230R, A243P, C267A, C356T, R396H, F429Y, F442T, E437P, C464I, A467V | Yes | | | |

TABLE 2-continued

Activities of Exemplary ALD Variants.

| Variant | Mutations Relative to Wild-Type Ald | Small Scale In Vivo 1,3 BDO Production[1] | 3HBCoA/ AcCoA Specificity[2] | R-3HB Aldehyde/ S-3HB Aldehyde | Specific activity[3] |
|---|---|---|---|---|---|
| 991 | D12A, I139L, T143N, C174S, M204R, C220V, T230R, A243P, C267A, C356T, R396H, F429Y, F442T, E437P, C464I, A467V | | | | |
| 992 | A73S, C174S, M204R, C220V, C267A, C356T, R396H, E437P, F442M, S447M, C464I, A467V | | + | '+ | |
| 993 | C174S, M204R, C220V, A254T, C267A, C356T, R396H, E437P, F442M, C464I, A467V | | + | | |
| 994 | V163C, C174S, M204R, C220V, C267A, C356T, R396H, E437P, F442M, C464I, A467V | | + | | |
| 995 | C174S, M204R, C220V, K 229S, C267A, C356T, R396H, E437P, F442N, C464I, A467V | | + | | |
| 996 | C174S, M204R, C220V, C267A, C356L, R396H, E437P, F442N, C464I, A467V | | + | | |
| 997 | C174S, M204R, C220V, C267A, C356T, R396H, E437P, T441G, I44L, C464I, A467V | | + | | |
| 998 | C174S, M204R, C220V, C267A, C356T, R396H, E437P, F442M, C464I, A467V | | + | '+ | |
| 999 | K65A, C174S, M204R, C220V, C267A, C356T, R396H, E437P, F442N, C464I, A467V | | + | | |
| 1000 | V163C, C174S, M204R, C220V, C267A, C356T, R396H, E437P, F442N, C464I, A467V | | + | '+ | |
| 1001 | C174S, M204R, C220V, C267A, C356T, R396H, E437P, F442M, R460K, C464I, A467V | | + | | |
| 1002 | C174S, M204R, C220V, C267A, C356T, R396H, E437P, F442M, S447M, C464I, A467V | Yes | + | '+ | |
| 1003 | G155G, C174S, M204R, C220V, C267A, C356T, R396H, E437P, F442F, C464I, A467V | | | | |
| 1004 | P145P, C174S, M204R, C220V, C267A, C356T, R396H, E437P, C464I, A467V | | | | |
| 1005 | G244G, C174S, M204R, C220V, C267A, C356T, R396H, E437P, C464I, A467V | | | | |
| 1006 | C174S, M204R, C220V, C267A, C356T, R396H, V432V, E437P, C464I, A467V | | | | |
| 1015 | C174S, M204R, C220V, M227I, T230K, C267A, C356T, R396H, E437P, F442N, C464I, A467V | yes | '+++ | '- | |
| 1016 | C174S, M204R, C220V, T230R, A243Q, C267A, C356T, R396H, E437P, F442N, C464I, A467V | yes | '+++ | '- | |
| 1017 | C174S, M204R, C220V, T230H, A243Q, C267A, C356T, R396H, E437P, F442N, C464I, A467V | yes | '++ | '- | |
| 1018 | C174S, M204R, C220V, T230A, A243E, C267A, C356T, R396H, E437P, F442N, C464I, A467V | yes | '++ | '- | |
| 1019 | C174S, M204R, C220V, T230M, A243S, C267A, C356T, R396H, E437P, F442N, C464I, A467V | yes | '+++ | '- | |
| 1020 | C174S, M204R, C220V, T230H, A243N, C267A, C356T, R396H, E437P, F442N, C464I, A467V | yes | '++ | '- | |
| 1021 | C174S, M204R, C220V, M227V, T230C, C267A, C356T, R396H, E437P, F442N, C464I, A467V | yes | '++ | '- | |
| 1022 | C174S, M204R, C220V, M227V, T230H, C267A, C356T, R396H, E437P, F442N, C464I, A467V | yes | '++ | '- | |
| 1023 | C174S, M204R, C220V, M227I, T230L, C267A, C356T, R396H, E437P, F442N, C464I, A467V | yes | '++ | '- | |
| 1024 | C174S, M204R, C220V, M227I, T230C, C267A, C356T, R396H, E437P, F442N, C464I, A467V | yes | '++ | '- | |
| 1025 | C174S, M204R, C220V, T230M, A243E, C267A, C356T, R396H, E437P, F442N, C464I, A467V | yes | '++ | '- | |
| 1026 | C174S, M204R, C220V, T230S, A243Q, C267A, C356T, R396H, E437P, F442N, C464I, A467V | yes | '+++ | '- | |
| 1027 | C174S, M204R, C220V, M227I, T230A, C267A, C356T, R396H, E437P, F442N, C464I, A467V | yes | '+++ | '- | |

TABLE 2-continued

Activities of Exemplary ALD Variants.

| Variant | Mutations Relative to Wild-Type Ald | Small Scale In Vivo 1,3 BDO Production[1] | 3HBCoA/ AcCoA Specificity[2] | R-3HB Aldehyde/ S-3HB Aldehyde | Specific activity[3] |
|---|---|---|---|---|---|
| 1028 | C174S, M204R, C220V, T230K, C267A, C356T, R396H, E437P, F442N, C464I, A467V | yes | '− | | '− |
| 1029 | C174S, M204R, C220V, T230Y, A243Q, C267A, C356T, R396H, E437P, F442N, C464I, A467V | yes | '++ | | '− |
| 1030 | C174S, M204R, C220V, T230G, A243Q, C267A, C356T, R396H, E437P, F442N, C464I, A467V | yes | '++ | | '− |
| 1031 | C174S, M204R, C220V, T230M, A243K, C267A, C356T, R396H, E437P, F442N, C464I, A467V | yes | '+++ | | '− |
| 1032 | C174S, M204R, C220V, T230T, A243L, C267A, C356T, R396H, E437P, F442N, C464I, A467V | yes | '++ | | '− |
| 1033 | C174S, M204R, C220V, T230I, C267A, C356T, R396H, E437P, F442N, C464I, A467V | yes | '++ | | '− |
| 1034 | C174S, M204R, C220V, M227I, T230K, C267A, C356T, R396H, F429L, V432N, E437P, F442N, C464I, A467V | yes | '++ | | '− |
| 1035 | C174S, M204R, C220V, T230H, C267A, C356T, R396H, E437P, F442N, C464I, A467V | yes | '+++ | | '− |
| 1036 | C174S, M204R, C220V, T230Y, A243E, C267A, C356T, R396H, E437P, F442N, C464I, A467V | yes | '++ | | '− |
| 1037 | K72N, C174S, M204R, C220V, A243S, C267A, C356T, R396H, E437P, F442N, C464I, A467V | yes | '++ | | '− |
| 1038 | C174S, M204R, C220V, T230C, A243K, C267A, C356T, R396H, E437P, F442N, C464I, A467V | yes | '+++ | | '− |
| 1039 | C174S, M204R, C220V, T230H, A243K, C267A, C356T, R396H, E437P, F442N, C464I, A467V | yes | '+++ | | '− |
| 1040 | C174S, M204R, C220V, T230H, A243C, C267A, C356T, R396H, E437P, F442N, C464I, A467V | yes | '+++ | | '− |
| 1041 | C174S, M204R, C220V, T230A, A243Q, C267A, C356T, R396H, E437P, F442N, C464I, A467V | yes | '+++ | | '− |
| 1042 | C174S, M204R, C220V, T230S, A243C, C267A, C356T, R396H, E437P, F442N, C464I, A467V | yes | '+++ | | '− |
| 1043 | C174S, M204R, C220V, M227V, T230S, C267A, C356T, R396H, E437P, F442N, C464I, A467V | yes | '++ | | '− |
| 1044 | C174S, M204R, C220V, T230H, A243M, C267A, C356T, R396H, E437P, F442N, C464I, A467V | yes | '+++ | | '− |
| 1045 | C174S, M204R, C220V, T230A, A243K, C267A, C356T, R396H, E437P, F442N, C464I, A467V | yes | '+++ | | '− |
| 1046 | C174S, M204R, C220V, T230W, C267A, C356T, R396H, E437P, F442N, C464I, A467V | yes | '++ | | '− |
| 1047 | C174S, M204R, C220V, M227C, T230R, C267A, C356T, R396H, E437P, F442N, C464I, A467V | yes | '++ | | '− |
| 1048 | C174S, M204R, C220V, M227L, T230N, C267A, C356T, R396H, E437P, F442N, C464I, A467V | yes | '++ | | '− |
| 1049 | C174S, M204R, C220V, T230N, C267A, C356T, R396H, E437P, F442N, C464I, A467V | yes | '++ | | '− |
| 1050 | C174S, M204R, C220V, M227C, T230L, C267A, C356T, R396H, E437P, F442N, C464I, A467V | yes | '++ | | '− |
| 1051 | C174S, M204R, C220V, T230V, C267A, C356T, R396H, E437P, F442N, C464I, A467V | yes | '++ | | '− |
| 1052 | C174S, M204R, C220V, T230L, C267A, C356T, R396H, E437P, F442N, C464I, A467V | yes | '++ | | '− |
| 1053 | C174S, M204R, C220V, M227C, T230K, C267A, C356T, R396H, E437P, F442N, C464I, A467V | yes | '+ | | '− |
| 1054 | C174S, M204R, C220V, M227C, T230V, C267A, C356T, R396H, E437P, F442N, C464I, A467V | yes | '+++ | | '− |
| 1055 | C174S, M204R, C220V, T230T, A243N, C267A, C356T, R396H, E437P, F442N, C464I, A467V | yes | '+++ | | '− |

TABLE 2-continued

Activities of Exemplary ALD Variants.

| Variant | Mutations Relative to Wild-Type Ald | Small Scale In Vivo 1,3 BDO Production[1] | 3HBCoA/ AcCoA Specificity[2] | R-3HB Aldehyde/ S-3HB Aldehyde | Specific activity[3] |
|---|---|---|---|---|---|
| 1056 | C174S, M204R, C220V, T230T, A243I, C267A, C356T, R396H, E437P, F442N, C464I, A467V | yes | '+++ | | '- |
| 1057 | C174S, M204R, C220V, T230T, A243C, C267A, C356T, R396H, E437P, F442N, C464I, A467V | yes | '+ | | '- |
| 1058 | C174S, M204R, C220V, T230G, A243K, C267A, C356T, R396H, E437P, F442N, C464I, A467V | yes | '++ | | '- |
| 1059 | C174S, M204R, C220V, T230R, A243K, C267A, C356T, R396H, E437P, F442N, C464I, A467V | yes | '++ | | '- |
| 1060 | C174S, M204R, C220V, M227L, A243P, C267A, C356T, R396H, E437P, F442N, C464I, A467V | yes | '+ | | '- |
| 1061 | C174S, M204R, C220V, M227A, A243P, C267A, C356T, R396H, E437P, F442N, C464I, A467V | yes | '+++ | | '- |
| 1062 | C174S, M204R, C220V, A243Q, C267A, C356T, R396H, E437P, F442N, C464I, A467V | yes | '+ | | '- |
| 1063 | C174S, M204R, C220V, T230Q, C267A, C356T, R396H, E437P, F442N, C464I, A467V | yes | '++ | | '- |
| 1064 | C174S, M204R, C220V, T230N, A243I, C267A, C356T, R396H, E437P, F442N, C464I, A467V | yes | '++ | | '- |
| 1065 | C174S, M204R, C220V, T230C, A243C, C267A, C356T, R396H, E437P, F442N, C464I, A467V | yes | '+++ | | '- |
| 1066 | C174S, M204R, C220V, M227I, T230R, C267A, C356T, R396H, E437P, F442N, C464I, A467V | yes | '++ | | '- |
| 1067 | C174S, M204R, C220V, M227I, A243L, C267A, C356T, R396H, E437P, F442N, C464I, A467V | yes | '+++ | | '- |
| 1068 | C174S, M204R, C220V, M227I, A243M, C267A, C356T, R396H, E437P, F442N, C464I, A467V | yes | '++ | | '- |
| 1069 | C174S, M204R, C220V, A243M, C267A, C356T, R396H, E437P, F442N, C464I, A467V | yes | '++ | | '- |
| 1070 | C174S, M204R, C220V, M227V, C267A, C356T, R396H, E437P, F442N, C464I, A467V | yes | '++ | | '- |
| 1071 | C174S, M204R, C220V, M227C, A243Q, C267A, C356T, R396H, E437P, F442N, C464I, A467V | yes | '+++ | | '- |
| 1072 | C174S, M204R, C220V, T230R, A243C, C267A, C356T, R396H, E437P, F442N, C464I, A467V | yes | '++ | | '- |
| 1073 | C174S, M204R, C220V, T230L, A243M, C267A, C356T, R396H, E437P, F442N, C464I, A467V | yes | '++ | | '- |
| 1074 | C174S, M204R, C220V, T230I, A243M, C267A, C356T, R396H, E437P, F442N, C464I, A467V | yes | '+++ | | '- |
| 1075 | C174S, M204R, C220V, T230M, A243Q, C267A, C356T, R396H, E437P, F442N, C464I, A467V | yes | '++ | | '- |
| 1076 | C174S, M204R, C220V, M227L, T230W, C267A, C356T, R396H, E437P, F442N, C464I, A467V | yes | '++ | | '- |
| 1077 | C174S, M204R, C220V, T230V, A243M, C267A, C356T, R396H, E437P, F442N, C464I, A467V | yes | '++ | | '- |
| 1078 | C174S, M204R, C220V, M227V, T230I, C267A, C356T, R396H, E437P, F442N, C464I, A467V | yes | '++ | | '- |
| 1079 | A73D, C174S, M204R, C220V, M227I, T230K, C267A, C356T, R396H, E437P, F442N, S447P, C464I, A467V | yes | '++ | | '+ |
| 1080 | A73G, C174S, M204R, C220V, M227I, T230K, C267A, C356T, R396H, E437P, F442N, S447H, C464I, A467V | yes | '+ | | '- |
| 1081 | A73L, C174S, M204R, C220V, M227I, T230K, C267A, C356T, R396H, E437P, F442N, S447K, C464I, A467V | yes | '+ | | '- |

TABLE 2-continued

Activities of Exemplary ALD Variants.

| Variant | Mutations Relative to Wild-Type Ald | Small Scale In Vivo 1,3 BDO Production[1] | 3HBCoA/ AcCoA Specificity[2] | R-3HB Aldehyde/ S-3HB Aldehyde | Specific activity[3] |
|---|---|---|---|---|---|
| 1082 | A73Q, C174S, M204R, C220V, M227I, T230K, C267A, C356T, R396H, E437P, F442N, S447R, C464I, A467V | yes | '++ | | '− |
| 1083 | A73F, C174S, M204R, C220V, M227I, T230K, C267A, C356T, R396H, E437P, F442N, S447K, C464I, A467V | yes | '+ | | '− |
| 1084 | A73G, C174S, M204R, C220V, M227I, T230K, C267A, C356T, R396H, E437P, F442N, S447K, C464I, A467V | yes | '+ | | '− |
| 1085 | A73E, C174S, M204R, C220V, M227I, T230K, C267A, C356T, R396H, E437P, F442N, S447K, C464I, A467V | yes | '+ | | '− |
| 1086 | A73W, C174S, M204R, C220V, M227I, T230K, C267A, C356T, R396H, E437P, F442N, S447R, C464I, A467V | yes | '++ | | '− |
| 1087 | V163G, C174S, M204R, C220V, M227I, T230K, C267A, C356T, R396H, E437P, F442N, S447P, C464I, A467V | yes | '+ | | '− |
| 1088 | V163T, C174S, M204R, C220V, M227I, T230K, C267A, C356T, R396H, E437P, F442N, S447P, C464I, A467V | yes | '+ | | '− |
| 1089 | C174S, M204R, C220V, M227L, T230S, C267A, C356T, R396H, E437P, F442N, C464I, A467V | yes | '+ | | '− |
| 1090 | C174S, M204R, C220V, A243E, C267A, C356T, R396H, E437P, F442N, C464I, A467V | yes | '+ | | '+ |
| 1091 | C174S, M204R, C220V, T230T, A243E, C267A, C356T, R396H, E437P, F442N, C464I, A467V | yes | '+ | | '− |
| 1092 | C174S, M204R, C220V, A243K, C267A, C356T, R396H, E437P, F442N, C464I, A467V | yes | '+ | | '+ |
| 1093 | A73L, C174S, M204R, C220V, M227I, T230K, C267A, C356T, R396H, E437P, F442N, S447P, C464I, A467V | yes | '+ | | '+ |
| 1094 | A73R, C174S, M204R, C220V, M227I, T230K, C267A, C356T, R396H, E437P, F442N, S447T, C464I, A467V | yes | '+ | | '+ |
| 1095 | A73C, V163C, C174S, M204R, C220V, M227I, T230K, C267A, C356T, R396H, E437P, F442N, C464I, A467V | yes | '+ | | '+ |
| 1096 | V163C, C174S, M204R, C220V, M227I, T230K, C267A, C356T, R396H, E437P, F442N, S447E, C464I, A467V | yes | '+ | | '− |
| 1097 | A73W, V163C, C174S, M204R, C220V, M227I, T230K, C267A, C356T, R396H, E437P, F442N, S447K, C464I, A467V | yes | '+ | | '+ |
| 1098 | A73M, V163C, C174S, M204R, C220V, M227I, T230K, C267A, C356T, R396H, E437P, F442N, S447R, C464I, A467V | yes | '+ | | '+ |
| 1099 | V163C, C174S, M204R, C220V, M227I, T230K, C267A, C356T, R396H, E437P, F442N, S447P, C464I, A467V | yes | '+ | | '+ |
| 1100 | A73F, V163C, C174S, M204R, C220V, M227I, T230K, C267A, C356T, R396H, E437P, F442N, S447P, C464I, A467V | yes | '+ | | '− |
| 1101 | V163C, C174S, M204R, C220V, M227I, T230K, C267A, C356T, R396H, E437P, F442N, S447S, C464I, A467V | yes | '+++ | | '− |

[1] * active on other diols
[2] − = specificity < 1'
'+ = specificity between 1,0-2.0'
'++ = specificity between 2.0-3.0'
'+++ = specificity > 3.0
[3] − = relative activity < 1'
'+ = relative activity > 1'

Additional activities of exemplary ALD variants are shown in Table 3. Levels of 1,3-BDO production at 48 hours were obtained with ALD variants as high as greater than 50 g/liter, greater than 60 g/liter, greater than 70 g/liter, greater than 80 g/liter, and greater than 90 g/liter.

TABLE 3

Activities of Exemplary ALD Variants.

| Variant | Mutations Relative to Wild-Type Ald | Stable Enzyme Activity in Crude Lysates | Cofactor Preference | 3HBCoA/ AcCoA Specificity | R-3HB Aldehyde/ S-3HB Aldehyde | Increased 1,3-BDO produced in vivo | Increased enyzme activity in vitro |
|---|---|---|---|---|---|---|---|
| 45 | C174S, M204R, C220V, C267A, C356T, R396H, E437P, C464I, A467V | + | NADH | + | + | | + |
| 331 | K65A, I66M, C174S, M204R, C220V, A243Q, C267A, C356T, R396H, E437P, F442N, C464I, A467V | + | NADH | + | | | |
| 681 | K65A, I66M, A73S, C174S, M204R, C220V, M227I, T230C, A243P, C267A, C356T, R396H, E437P, F442N, S447P, C464I, A467V | + | NADH | + | | | |
| 687 | C174S, M204R, C220V, C267A, C356T, R396H, E437P, F442M, C464I, A467V | + | NADH | + | | | |
| 688 | K65A, C174S, M204R, C220V, A243Q, C267A, C356T, R396H, E437P, F442N, C464I, A467V | + | NADH | + | | | |
| 721 | 66M, C174S, M204R, C220V, A243Q, C267A, C356T, R396H, E437P, F442N, C464I, A467V | + | NADH | + | | | |
| 951 | C174S, M204R, C220V, C267A, C356T, R396H, F429H, E437P, F442H, C464I, A467V | + | NADH | + | + | | + |
| 952 | C174S, M204R, C220V, C267A, C356T, R396H, F429M, E437P, F442H, C464I, A467V | + | NADH | + | | | + |
| 953 | C174S, M204R, C220V, C267A, C356T, R396H, F429M, E437P, F442N, C464I, A467V | + | NADH | + | | | + |
| 954 | C174S, M204R, C220V, C267A, C356T, R396H, F429Q, E437P, C464I, A467V | + | NADH | + | | | + |
| 955 | C174S, M204R, C220V, C267A, C356T, R396H, E437P, F442N, C464I, A467V | + | NADH | + | + | | + |
| 956 | C174S, M204R, C220V, C267A, C356T, R396H, E437P, F442N, C464I, A467V | + | NADH | + | | | |
| 957 | C174S, M204R, C220V, C267A, C356T, R396H, E437P, F442Q, C464I, A467V | + | NADH | + | + | | + |
| 958 | C174S, M204R, C220V, C267A, C356T, R396H, E437P, I444V, C464I, A467V | + | NADH | + | + | | + |
| 959 | C174S, M204R, C220V, C267A, C356T, R396H, E437P, T440H, F442N, C464I, A467V | + | NADH | + | + | | + |
| 960 | V19I, D122N, C174S, M204R, C220V, C267A, C356T, R396H, F429D, E437P, F442Q, E450E, C464I, A467V | + | NADH | + | | | + |
| 961 | C174S, M204R, C220V, C267A, V315A, C356T, R396H, E437P, T440H, F442N, C464I, A467V | + | NADH | + | + | | + |
| 962 | A73S, C174S, M204R, C220V, C267A, C356T, R396H, E437P, F442M, S447M, C464I, A467V | + | | + | | + | |
| 963 | C174S, M204R, C220V, A254T, C267A, C356T, R396H, E437P, F442M, C464I, A467V | + | | + | | + | |
| 964 | V163C, C174S, M204R, C220V, C267A, C356T, R396H, E437P, F442M, C464I, A467V | + | | + | | + | |
| 965 | C174S, M204R, C220V, K229S, C267A, C356T, R396H, E437P, F442N, C464I, A467V | + | | + | | + | |
| 966 | C174S, M204R, C220V, C267A, C356L, R396H, E437P, F442N, C464I, A467V | + | | + | | + | |
| 967 | C174S, M204R, C220V, C267A, C356T, R396H, E437P, T441G, I44L, C464I, A467V | + | | + | | + | |
| 968 | C174S, M204R, C220V, C267A, C356T, R396H, E437P, F442M, C464I, A467V | + | | + | | + | |
| 969 | K65A, C174S, M204R, C220V, C267A, C356T, R396H, E437P, F442N, C464I, A467V | + | | + | | + | |
| 970 | V163C, C174S, M204R, C220V, C267A, C356T, R396H, E437P, F442N, C464I, A467V | + | | + | | + | |
| 971 | C174S, M204R, C220V, C267A, C356T, R396H, E437P, F442M, R460K, C464I, A467V | + | | + | | + | |
| 972 | C174S, M204R, C220V, C267A, C356T, R396H, E437P, F442M, S447M, C464I, A467V | + | | + | | + | |
| 598 | D12A, I139S, C174S, M204R, M227Q, T230R, A243P, C220V, C267A, C356T, R396H, F429Y, F442T, E437P, C464I, A467V | + | NADH/NADPH | + | | | + |
| 973 | C174S, M204R, C220V, C267A, A243K, C356T, R396H, E437P, F442N, C464I, A467V | + | NADH | + | | | + |
| 974 | Y107N, C174S, M204R, C220V, C267A, C356T, R396H, E437P, F442N, C464I, A467V | + | NADPH | + | | | + |
| 975 | D122G, C174S, M204R, C220V, C267A, C356T, R396H, E437P, F442N, C464I, A467V | + | NADPH | + | | | + |

TABLE 3-continued

Activities of Exemplary ALD Variants.

| Variant | Mutations Relative to Wild-Type Ald | Stable Enzyme Activity in Crude Lysates | Cofactor Preference | 3HBCoA/ AcCoA Specificity | R-3HB Aldehyde/ S-3HB Aldehyde | Increased 1,3-BDO produced in vivo | Increased enyzme activity in vitro |
|---|---|---|---|---|---|---|---|
| 976 | C174S, M204R, C220V, C267A, S349T, C356T, R396H, E437P, F442N, C464I, A467V | + | | + | | | + |
| 977 | C174S, N201D, M204R, C220V, C267A, C356T, R396H, E437P, F442N, C464I, A467V | + | | + | | | + |
| 978 | C174S, M204R, C220V, C267A, D313R, C356T, R396H, E437P, C464I, A467V | | NADH | + | | | + |
| 979 | C174S, M204R, C220V, C267A, P348G, C356T, R396H, E437P, C464I, A467V | | NADH | + | | | + |
| 980 | C174S, M204R, C220V, C267A, C356L, R396H, E437P, C464I, A467V | | NADH | + | | | + |
| 981 | C174S, M204R, C220V, C267A, C356T, A360K, R396H, E437P, C464I, A467V | | NADH | + | | | + |
| 982 | C174S, M204R, C220V, A243K, C267A, C356T, R396H, E437P, C464I, A467V | | NADH | + | | | + |
| 983 | C174S, M204R, C220V, K258W, C267A, C356T, R396H, E437P, C464I, A467V | | NADH | + | | | + |
| 984 | Y107N, C174S, M204R, C220V, C267A, C356T, R396H, E437P, C464I, A467V | | NADH | + | | | + |
| 985 | C174S, M204R, C220V, N223Q, C267A, C356T, R396H, E437P, C464I, A467V | | NADH | + | | | + |
| 986 | S131A, C174S, M204R, C220V, C267A, C356T, R396H, E437P, F442N, C464I, A467V | | NADH | + | | | + |
| 1011 | C174S, M204R, C220V, A243P, C267A, C356T, R396H, E437P, F442N, C464I, A467V | + | NADH | + | | | |
| 1062 | C174S, M204R, C220V, A243Q, C267A, C356T, R396H, E437P, F442N, C464I, A467V | + | NADH | + | | | |

Such aldehyde dehydrogenase variants as described above, which can act on the R form of 3-hydroxybutyraldehyde, can be used to produce a stereoisomer of R-3-hydroxybutyraldehyde or a mixture of R and S forms with a higher proportion of the R form. Such a stereoisomer can be utilized to make stereoisomers of downstream products, such as R-1,3-butanediol. Such stereoisomers have usefulness as pharmaceuticals or nutraceuticals.

These results demonstrate the production of aldehyde dehydrogenase variants having desirable properties, which are useful for commercial production of 3-hydroxybutyraldeyde, 1,3-butanediol, 4-hydroxybutyraldehyde or 1,4-butanediol or other desired products that are produced by metabolic pathways comprising an aldehyde dehydrogenase.

The variants described above are based on the ALD-1 parental sequence. It is understood that variant amino acid positions as shown in Tables 1, 2 or 3 can be applied to homologous aldehyde dehydrogenase sequences. Table 4 provides exemplary ALD sequences based on homology. One skilled in the art will readily understand that such sequences can be analyzed with routine and well known methods for aligning sequences (for example BLAST, blast.ncbi.nlm.nih.gov; Altschul et al., "J Mol. Biol. 215: 403-410 (1990)). Furthermore, additional homologous ALD sequences can be identified by searching publicly available sequence databases such as found at the National Center for Biotechnology Information (NCBI) GenBank database, European Molecular Biology Laboratory (EMBL), ExPasy Prosite, or other publicly available sequence databases using BLAST. Such alignments can provide information on conserved residues that can be utilized to identify a consensus sequence for preserving enzyme activity as well as positions for generating further enzyme variants.

TABLE 4

Exemplary Aldehyde Dehydrogenase (ALD) Sequences.

| | |
|---|---|
| butyraldehyde dehydrogenase [Clostridium saccharoperbutylacetonicum N1-4(HMT)] | AAP42563.1 GI:31075383 (SEQ ID NO: 7) |
| hypothetical protein ROSEINA2194_01708 [Roseburia inulinivorans DSM 16841] | EEG94445.1 (SEQ ID NO: 8) |
| aldehyde dehydrogenase [Bacillus sp. FJAT-21945] | KOP84001.1 (SEQ ID NO: 9) |
| aldehyde dehydrogenase [Bacillus solani] | KQL21940.1 (SEQ ID NO: 10) |
| aldehyde dehydrogenase [Terrisporobacter othiniensis] | WP_039679531.1 (SEQ ID NO: 11) |
| aldehyde dehydrogenase [Roseburia inulinivorans DSM 16841] | ABC25528.1 GI:83596371 (SEQ ID NO: 12) |
| propionaldehyde dehydrogenase [Clostridium sp. ASF502] | WP_004073235.1 (SEQ ID NO: 13) |

TABLE 4-continued

Exemplary Aldehyde Dehydrogenase (ALD) Sequences.

| Description | Accession |
|---|---|
| aldehyde dehydrogenase [[*Bacillus*] *selenitireducens*] | WP_013174003.1 (SEQ ID NO: 14) |
| aldehyde dehydrogenase [*Blautia obeum*] | WP_005427729.1 (SEQ ID NO: 15) |
| hypothetical protein CLOBOL_07248 [*Clostridium*] *bolteae* ATCC BAA-613] | EDP12494.1 (SEQ ID NO: 16) |
| aldehyde dehydrogenase [*Jeotgalibacillus alimentarius*] | WP_041123321.1 (SEQ ID NO: 17) |
| aldehyde dehydrogenase (NAD) family protein [[*Clostridium*] *hiranonis* DSM 13275] | EEA85935.1 SEQ ID NO: 18) |
| MULTISPECIES: aldehyde dehydrogenase [*Thermoanaerobacter*] | WP_003870148.1 (SEQ ID NO: 19) |
| MULTISPECIES: aldehyde dehydrogenase [*Clostridiales*] | WP_008705584.1 (SEQ ID NO: 20) |
| Aldehyde Dehydrogenase [*Sebaldella termitidis* ATCC 33386] | ACZ07905.1 SEQ ID NO: 21) |
| propionaldehyde dehydrogenase [*Eubacterium plexicaudatum*] | WP_004061597.1 (SEQ ID NO: 22) |
| MULTISPECIES: aldehyde dehydrogenase [*Escherichia*] | WP_000997839.1 SEQ ID NO: 23) |
| aldehyde dehydrogenase [*Rhodospirillum rubrum*] | WP_011388669.1 (SEQ ID NO: 24) |
| aldehyde dehydrogenase [*Clostridium beijerinckii*] | WP_012060202.1 SEQ ID NO: 25) |
| aldehyde dehydrogenase [[*Eubacterium*] *hallii*] | WP_005344386.1 (SEQ ID NO: 26) |
| aldehyde dehydrogenase [*Vibrio* sp. EJY3] | WP_014232054.1 (SEQ ID NO: 27) |
| aldehyde dehydrogenase [*Rhodopseudomonas palustris* BisB18] | ABD86737.1 SEQ ID NO: 28) |
| aldehyde dehydrogenase EutE [*Desulfatibacillum alkenivorans*] | WP_015949695.1 SEQ ID NO: 29) |
| aldehyde dehydrogenase Ald [*Clostridium saccharobutylicum*] | WP_022747467.1 SEQ ID NO: 30) |
| aldehyde dehydrogenase [*Clostridium* sp. DL-VIII] | WP_009171375.1 SEQ ID NO: 31) |
| aldehyde dehydrogenase EutE [*Clostridium taeniosporum*] | WP_069679818.1 SEQ ID NO: 32) |
| aldehyde dehydrogenase [*Clostridium botulinum*] | WP_012425099.1 SEQ ID NO: 33) |
| aldehyde dehydrogenase [*Clostridium botulinum*] | WP_035786720.1 (SEQ ID NO: 34) |
| aldehyde dehydrogenase [*Clostridium botulinum*] | WP_039308447.1 (SEQ ID NO: 35) |
| aldehyde dehydrogenase [*Clostridium botulinum*] | WP_035792132.1 (SEQ ID NO: 36) |
| aldehyde dehydrogenase [*Clostridium pasteurianum*] | WP_023973059.1 (SEQ ID NO: 37) |
| NAD-dependent aldehyde dehydrogenase [*Clostridium saccharoperbutylacetonicum*] | WP_015395720.1 (SEQ ID NO: 38) |
| MULTISPECIES: aldehyde dehydrogenase [*Clostridium*] | WP_023975647.1 (SEQ ID NO: 39) |
| aldehyde dehydrogenase [*Clostridium beijerinckii*] | WP_026888070.1 (SEQ ID NO: 40) |
| *Clostridium beijerinckii* strain NRRL B593 hypothetical protein, coenzyme A acylating aldehyde dehydrogenase (ald), acetoacetate:butyrate/acetate coenzyme A transferase (ctfA), acetoacetate:butyrate/acetate coenzyme A transferase (ctfB), and acetoacetate decarboxylase (adc) genes (AF157306 AF132754) | AF157306.2 (SEQ ID NO:41) |
| aldehyde dehydrogenase [*Clostridium beijerinckii*] | WP_012059995.1 (SEQ ID NO: 42) |
| aldehyde dehydrogenase [*Clostridium beijerinckii*] | WP_041898834.1 (SEQ ID NO: 43) |
| aldehyde dehydrogenase [*Clostridium beijerinckii*] | WP_017211959.1 (SEQ ID NO: 44) |
| aldehyde dehydrogenase EutE [*Clostridium beijerinckii*] | WP_065419149.1 (SEQ ID NO: 45) |
| NAD-dependent aldehyde dehydrogenase [*Clostridium saccharoperbutylacetonicum* N1-4(HMT)] > gb|AGF59413.1| NAD-dependent aldehyde dehydrogenase [*Clostridium saccharoperbutylacetonicum* N1-4(HMT)] | YP_007458667.1 GI:451822466 (WP_015395720.1) (SEQ ID NO: 46) |
| aldehyde dehydrogenase [*Clostridium beijerinckii* NCIMB 8052] > gb|AAQ12068.1| coenzyme A acylating aldehyde dehydrogenase [*Clostridium beijerinckii* NCIMB 8052] > gb|AAQ12072.1| coenzyme A acylating aldehyde dehydrogenase [*Clostridium beijerinckii*] > gb|AAT48939.1| aldehyde dehydrogenase [*Clostridium beijerinckii*] > gb|AAT66436.1| coenzyme A-acylating aldehyde dehydrogenase [*Clostridium beijerinckii*] > gb|ABR35947.1| aldehyde dehydrogenase [*Clostridium beijerinckii* NCIMB 8052] | YP_001310903.1 GI:150018649 (WP_012059995.1) (SEQ ID NO: 47) |
| coenzyme A acylating aldehyde dehydrogenase [*Clostridium beijerinckii*] | AAD31841.1 GI:4884855 (SEQ ID NO: 48) |

TABLE 4-continued

Exemplary Aldehyde Dehydrogenase (ALD) Sequences.

| | |
|---|---|
| Acetaldehyde dehydrogenase (acetylating) [*Clostridium* sp. DL-VIII] > gb\|EHJ00721.1\| Acetaldehyde dehydrogenase (acetylating) [*Clostridium* sp. DL-VIII] | ZP_09206127.1<br>GI:359413662<br>(SEQ ID NO: 49) |
| coenzyme A acylating aldehyde dehydrogenase [*Clostridium saccharobutylicum*] | CAQ57983.1<br>GI:189310620<br>(SEQ ID NO: 50) |
| ethanolamine utilization protein EutE [*Clostridium botulinum* B str. Eklund 17B] > gb\|ACD24339.1\| ethanolamine utilization protein EutE [*Clostridium botulinum* B str. Eklund 17B] | YP_001886323.1<br>GI:187934965<br>(WP_012425099.1)<br>(SEQ ID NO: 51) |
| Aldehyde Dehydrogenase [*Caldalkalibacillus thermarum* TA2.A1] > gb\|EGL82399.1\| Aldehyde Dehydrogenase [*Caldalkalibacillus thermarum* TA2.A1] | ZP_08533507.1<br>GI:335040377<br>(SEQ ID NO: 52) |
| Aldehyde Dehydrogenase [*Pelosinus fermentans* DSM 17108] > ref_ZP_15517111.1\| Aldehyde Dehydrogenase [*Pelosinus fermentans* B4] > ref ZP_15521980.1\| Aldehyde Dehydrogenase [*Pelosinus fermentans* B3] > ref_ZP_15526533.1\| Aldehyde Dehydrogenase [*Pelosinus fermentans* A12] > ref_ZP_15534416.1\| Aldehyde Dehydrogenase [*Pelosinus fermentans* A11] > gb \|EIW18982.1\| Aldehyde Dehydrogenase [*Pelosinus fermentans* B4] > gb\|EIW21808.1\| Aldehyde Dehydrogenase [*Pelosinus fermentans* A11] > gb\|EIW29163.1\| Aldehyde Dehydrogenase [*Pelosinus fermentans* DSM 17108] > gb\|EIW35484.1\| Aldehyde Dehydrogenase [*Pelosinus fermentans* B3] > gb\|EIW36902.1\| Aldehyde Dehydrogenase [*Pelosinus fermentans* A12] | ZP_10327808.1<br>GI:392962372<br>(SEQ ID NO: 53) |
| NAD-dependent aldehyde dehydrogenase [*Thermoanaerobacterium thermosaccharolyticum* M0795] > gb\|AGB19701.1\| NAD-dependent aldehyde dehydrogenase [*Thermoanaerobacterium thermosaccharolyticum* M0795] | YP_007299398.1<br>GI:433655690<br>(WP_015312185.1)<br>(SEQ ID NO: 54) |
| Aldehyde Dehydrogenase [*Pelosinus fermentans* JBW45] > gb\|EIW48189.1\| Aldehyde Dehydrogenase [*Pelosinus fermentans* JBW45] | ZP_15537951.1<br>GI:421076976<br>(SEQ ID NO: 55) |
| aldehyde dehydrogenase family protein [*Desulfosporosinus* sp. OT] > gb\|EGW35902.1\| aldehyde dehydrogenase family protein [*Desulfosporosinus* sp. OT] | ZP_08814704.1<br>GI:345862484<br>(SEQ ID NO: 56) |
| hypothetical protein CLOSTMETH_00016 [*Clostridium methylpentosum* DSM 5476] > gb\|EEG32278.1\| hypothetical protein CLOSTMETH_00016 [*Clostridium methylpentosum* DSM 5476]<br>aldehyde dehydrogenase | ZP_03705305.1<br>GI:225016072<br>(SEQ ID NO: 57)<br>GI:390933349<br>YP_006390854.1 |
| [*Thermoanaerobacterium saccharolyticum* JW/SL-YS485] > gb\|AFK85255.1\| Aldehyde Dehydrogenase [*Thermoanaerobacterium saccharolyticum* JW/SL-YS485] | (WP_014757178.1)<br>(SEQ ID NO: 58) |
| acetaldehyde dehydrogenase [*Thermoanaerobacterium xylanolyticum* LX-11] > gb\|AEF18105.1\| Acetaldehyde dehydrogenase (acetylating) [LX-11] | YP_004471777.1<br>GI:333897903<br>(WP_013788835.1)<br>(SEQ ID NO: 59) |
| aldehyde dehydrogenase EutE [*Acetonema longum* DSM 6540] > gb\|EGO64744.1\| aldehyde dehydrogenase EutE [*Acetonema longum* DSM 6540] | ZP_08623980.1<br>GI:338811775<br>(SEQ ID NO: 60) |
| ethanolamine utilization<br>protein eutE [*Geobacillus thermoglucosidans* TNO-09.020] > gb\|EID44455.1\| ethanolamine utilization protein eutE [*Geobacillus thermoglucosidans* TNO-09.020] | ZP_17694107.1<br>GI:423719925<br>(SEQ ID NO: 61) |
| aldehyde dehydrogenase [*Geobacillus* sp. Y4.1MC1] > gb\|ADP74637.1\| Aldehyde Dehydrogenase [*Geobacillus* sp. Y4.1MC1] | YP_003989248.1<br>GI:312110932<br>(WP_013400810.1)<br>(SEQ ID NO: 62) |
| acetaldehyde dehydrogenase<br>[*Geobacillus thermoglucosidasius* C56-YS93] > gb\|AEH47899.1\| Acetaldehyde dehydrogenase (acetylating) [*Geobacillus thermoglucosidasius* C56-YS93] | YP_004587980.1<br>GI:336235364<br>(WP_013876899.1)<br>SEQ ID NO: 63) |
| aldehyde dehydrogenase EutE [*Bacillus azotoformans* LMG 9581] > gb\|EKN64472.1\| aldehyde dehydrogenase EutE [*Bacillus azotoformans* LMG 9581] | ZP_11313951.1<br>GI:410460269<br>(SEQ ID NO: 64) |
| putative aldehyde dehydrogenase, ethanolamine utilization protein [[*Clostridium*] *sticklandii*] > emb\|CBH20800.1\| putative aldehyde dehydrogenase, ethanolamine utilization protein [*Clostridium*] *sticklandii*] | YP_003935705.1<br>GI:310657984<br>(WP_013360893.1)<br>(SEQ ID NO: 65) |
| Aldehyde Dehydrogenase [*Thermincola potens* JR] > gb\|ADG81503.1\| Aldehyde Dehydrogenase [*Thermincola potens* JR] | YP_003639404.1<br>GI:296132157<br>(WP_013119524.1)<br>(SEQ ID NO: 66) |
| CoA-dependent propionaldehyde dehydrogenase [*Clostridium* sp. D5] > gb\|EGB92558.1\| CoA-dependent propionaldehyde dehydrogenase [*Clostridium* sp. D5] | ZP_08130302.1<br>GI:325263568<br>(SEQ ID NO: 67) |
| acetaldehyde dehydrogenase<br>(acetylating) [*Fusobacterium* sp.<br>3_1_33] > gb\|EEW94895.1\| acetaldehyde dehydrogenase<br>(acetylating) [*Fusobacterium* sp. 3_1_33] | ZP_05815063.1<br>GI:260494934<br>(SEQ ID NO: 68) |
| ethanolamine utilization protein cutE [*Fusobacterium* sp. 7_1] > gb\|EEO43449.1\| ethanolamine utilization protein eutE [*Fusobacterium* sp. 7_1] | ZP_04573939.1<br>GI:237743458<br>(SEQ ID NO: 69) |

TABLE 4-continued

Exemplary Aldehyde Dehydrogenase (ALD) Sequences.

| Description | Accession |
|---|---|
| NAD-dependent aldehyde dehydrogenases [*Ruminococcus* sp. SR1/5] > emb\|CBL20089.1\| NAD-dependent aldehyde dehydrogenases [*Ruminococcus* sp. SR1/5] | YP_007783752.1<br>GI:479153977<br>(WP_015525955.1)<br>(SEQ ID NO: 70) |
| hypothetical protein HMPREF9942_01197 [*Fusobacterium nucleatum* subsp. animalis F0419] > gb\|EHO78009.1\| hypothetical protein HMPREF9942_01197 [*Fusobacterium nucleatum* subsp. *animalis* F0419] | ZP_17125059.1<br>GI:423 137416<br>(SEQ ID NO: 71) |
| possible aldehyde dehydrogenase [*Fusobacterium nucleatum* subsp. polymorphum ATCC 10953] > gb\|EDK87521.1\| possible aldehyde dehydrogenase [*Fusobacterium nucleatum* subsp. polymorphum ATCC 10953] | ZP_04969437.1<br>GI:254302079<br>(SEQ ID NO: 72) |
| ethanolamine utilization protein eutE [*Fusobacterium* sp. D11] > gb\|JEFD80567.1\| ethanolamine utilization protein eutE [*Fusobacterium* sp. D11] | ZP_06524378.1<br>GI:289765000<br>(SEQ ID NO: 73) |
| aldehyde dehydrogenase EutE [*Fusobacterium nucleatum* ChDC F128] > gb\|EJU08233.1\| aldehyde dehydrogenase EutE [*Fusobacterium nucleatum* ChDC F128] | ZP_15972610.1<br>GI:421526001<br>(SEQ ID NO: 74) |
| CoA-dependent propionaldehyde dehydrogenase [*Fusobacterium nucleatum* subsp. polymorphum F0401] > gb\|EHG19190.1\| CoA-dependent propionaldehyde dehydrogenase [*Fusobacterium nucleatum* subsp. polymorphum F0401] | ZP_16419680.1<br>GI:422338720<br>(SEQ ID NO: 75) |
| CoA-dependent propionaldehyde dehydrogenase [*Fusobacterium* sp. 11_3_2] > gb\|EGN65750.1\| CoA-dependent propionaldehyde dehydrogenase [*Fusobacterium* sp. 11_3_2] | ZP_08600044.1<br>GI:336419790<br>(SEQ ID NO: 76) |
| hypothetical protein CLOSTASPAR_02210 [*Clostridium asparagiforme* DSM 15981] > gb\|EEG55710.1\| hypothetical protein CLOSTASPAR_02210 [*Clostridium asparagiforme* DSM 15981] | ZP_03758198.1<br>GI:225388474<br>SEQ ID NO: 77) |
| aldehyde dehydrogenase [*Clostridium phytofermentans* ISDg] > gb\|ABX41556.1\| Aldehyde Dehydrogenase_[*Clostridium phytofermentans* ISDg] | YP_001558295.1<br>GI:160879327<br>(WP_012199204.1)<br>(SEQ ID NO: 78) |
| CoA-dependent propionaldehyde dehydrogenase [*Fusobacterium* sp. 1_1_41FAA] > gb\|EFG28139.1\| CoA-dependent propionaldehyde dehydrogenase [*Fusobacterium* sp. 1_1_41FAA] | ZP_06748808.1<br>GI:294783484<br>(SEQ ID NO: 79) |
| hypothetical protein HMPREF0991_01940 [*Lachnospiraceae bacterium* 2_1_58FAA] > gb\|EGN47419.1\| hypothetical protein HMPREF0991_01940 [*Lachnospiraceae bacterium* 2_1_58FAA] | ZP_08612821.1<br>GI:336432991<br>(SEQ ID NO: 80) |
| hypothetical protein RUMGNA_01022 [*Ruminococcus gnavus* ATCC 29149] > gb\|EDN78612.1\| aldehyde dehydrogenase (NAD) family protein [*Ruminococcus gnavus* ATCC 29149] | ZP_02040258.1<br>GI:154503198<br>(SEQ ID NO: 81) |
| NAD-dependent aldehyde dehydrogenases [*Ruminococcus obeum* A2-162] > emb\|CBL23217.1\| NAD-dependent aldehyde dehydrogenases [*Ruminococcus obeum* A2-162] | YP_007805199.1<br>GI:479177598<br>(WP_015542038.1)<br>(SEQ ID NO: 82) |
| aldehyde dehydrogenase [*Clostridium saccharolyticum* WM1] > gb\|ADL04402.1\| Aldehyde Dehydrogenase [*Clostridium saccharolyticum* WM1] | YP_003822025.1<br>GI:302386203<br>(WP_013272491.1)<br>(SEQ ID NO: 83) |
| aldehyde dehydrogenase family protein [*Flavonifractor plautii* ATCC 29863] > gb\|EHM40040.1\| aldehyde dehydrogenase family protein [*Flavonifractor plautii* ATCC 29863] | ZP_09385796.1<br>GI:365844997<br>(SEQ ID NO: 84) |
| hypothetical protein RUMOBE_00094 [*Ruminococcus obeum* ATCC 29174] > gb\|EDM88971.1\| aldehyde dehydrogenase (NAD) family protein [*Ruminococcus obeum* ATCC 29174] | ZP_01962381.1<br>GI:153809713<br>(SEQ ID NO: 85) |
| Aldehyde Dehydrogenase [*Clostridium carboxidivorans* P7] > ref_ZP_06856832.1\| aldehyde dehydrogenase (NAD) family protein [*Clostridium carboxidivorans* P7] > gb\|EET88516.1\| Aldehyde Dehydrogenase [*Clostridium carboxidivorans* P7] > gb \|EFG86154.1\| aldehyde dehydrogenase (NAD) family protein [*Clostridium carboxidivorans* P7] > gb\|ADO12117.1\| CoA-acylating aldehyde dehydrogenase [*Clostridium carboxidivorans* P7] | ZP_05391061.1<br>GI:255524100<br>(SEQ ID NO: 86) |
| hypothetical protein FUAG_00592 [*Fusobacterium ulcerans* ATCC 49185] > gb\|EFS25077.1\| hypothetical protein FUAG_00592 [*Fusobacterium ulcerans* ATCC 49185] | ZP_10974295.1<br>GI:404368948<br>(SEQ ID NO: 87) |
| hypothetical protein HMPREF0402_00608 [*Fusobacterium* sp. 12_1B] > gb\|JEHO83590.1\| hypothetical protein HMPREF0402 00608 [*Fusobacterium* sp. 12_1B] | ZP_09586735.1<br>GI:373496187<br>SEQ ID NO: 88) |
| Aldehyde Dehydrogenase [*Clostridium carboxidivorans* P7] > ref_ZP_06855343.1\| aldehyde dehydrogenase (NAD) family protein [*Clostridium carboxidivorans* P7] > gb\|EET85788.1\| Aldehyde Dehydrogenase [*Clostridium* carboxidivorans P7] > gb\|EFG87815.1\| aldehyde dehydrogenase (NAD) family protein [*Clostridium carboxidivorans* P7] | ZP_05393779.1<br>GI:255526882<br>(SEQ ID NO: 89) |
| NAD-dependent aldehyde dehydrogenases [*Clostridium* cf. *saccharolyticum* K10] > emb\|CBK77787.1\| NAD-dependent aldehyde dehydrogenases [*Clostridium* cf. *saccharolyticum* K10] | YP_007849785.1<br>GI:479338567<br>(WP_015574070.1)<br>(SEQ ID NO: 90) |
| ethanolamine utilization protein eutE [*Fusobacterium varium* ATCC 27725] > gb\|EES62817.1\| ethanolamine utilization protein eutE [*Fusobacterium varium* ATCC 27725] | ZP_08693593.1<br>GI:340756989<br>(SEQ ID NO: 91) |
| aldehyde dehydrogenase family protein [*Clostridium celatum* DSM 1785] > gb\|EKY29259.1\| aldehyde dehydrogenase family protein [*Clostridium celatum* DSM 1785] | ZP_19296595.1<br>GI:429764274<br>(SEQ ID NO: 92) |

TABLE 4-continued

Exemplary Aldehyde Dehydrogenase (ALD) Sequences.

| | |
|---|---|
| propionaldehyde dehydrogenase [*Clostridium* sp. ASF502] | EMZ20682.1<br>GI:476613570<br>(SEQ ID NO: 93) |
| hypothetical protein HMPREF0988_02063 [*Lachnospiraceae bacterium* 1_4_56FAA] > gb\|EGN36620.1\| hypothetical protein HMPREF0988_02063 [*Lachnospiraceae bacterium* 1_4_56FAA] | ZP_08616478.1<br>GI:336436768<br>(SEQ ID NO: 94) |
| hypothetical protein HMPREF0994_03038 [*Lachnospiraceae bacterium* 3_1_57FAA_CT1] > gb\|EGN40215.1\| hypothetical protein HMPREF0994_03038 [*Lachnospiraceae bacterium* 3_1_57FAA CT1] | ZP_08607032.1<br>GI:336427027<br>(SEQ ID NO: 95) |
| aldehyde dehydrogenase [*Ruminococcus* sp. 5_1_39B_FAA] > gb\|EES77009.1\| aldehyde dehydrogenase [*Ruminococcus* sp. 5_1_39BFAA] | ZP_04856816.1<br>GI:253579547<br>(SEQ ID NO: 96) |
| CoA-dependent propionaldehyde dehydrogenase PduP [*Acetobacterium woodii* DSM 1030] > gb\|AFA49334.1\| CoA-dependent propionaldehyde dehydrogenase PduP [*Acetobacterium woodii* DSM 1030] | YP_005270223.1<br>GI:379012411<br>(WP_014356934.1)<br>(SEQ ID NO: 97) |
| ethanolamine utilization protein EutE [*Clostridium botulinum* E1 str. 'BONT E Beluga'] > gb\|EES50221.1\| ethanolamine utilization protein EutE [*Clostridium botulinum* E1 str. 'BONT E Beluga'] | ZP_04822936.1<br>GI:251780016<br>(SEQ ID NO: 98) |
| ethanolamine utilization protein EutE [*Clostridium botulinum* B str. Eklund 17B] > gb\|ACD22415.1\| ethanolamine utilization protein EutE [*Clostridium botulinum* B str. Eklund 17B] | YP_001885942.1<br>GI:187933041<br>(WP_012423269.1)<br>(SEQ ID NO: 99) |
| ethanolamine utilization protein EutE [*Clostridium botulinum* E3 str. Alaska E43] > gb\|ACD53952.1\| ethanolamine utilization protein EutE [*Clostridium botulinum* E3 str. Alaska E43] | YP_001921227.1<br>GI:188590535<br>(WP_012451752.1)<br>(SEQ ID NO: 100) |
| propionaldehyde dehydrogenase [*Eubacterium plexicaudatum* ASF492] | EMZ27833.1<br>GI:476621007<br>(SEQ ID NO: 101) |
| Aldehyde Dehydrogenase [*Thermosediminibacter oceani* DSM 16646] > gb\|ADL07333.1\| Aldehyde Dehydrogenase [*Thermosediminibacter oceani* DSM 16646] | YP_003824956.1<br>GI:302389135<br>(WP_013275382.1)<br>(SEQ ID NO: 102) |
| hypothetical protein HMPREF1090_01637 [*Clostridium clostridioforme* 90A8] | ENZ17687.1<br>GI:480674262<br>(SEQ ID NO: 103) |
| hypothetical protein HMPREF9467_03550 [*Clostridium clostridioforme* 2_1_49FAA] > gb\|EHG29726.1\| hypothetical protein HMPREF9467 03550 [*Clostridium clostridioforme* 2_1 49FAA] | ZP_09116578.1<br>GI:357055510<br>SEQ ID NO: 104) |
| Aldehyde Dehydrogenase [*Ilyobacter polytropus* DSM 2926] > gb\|ADO84118.1\| Aldehyde Dehydrogenase [*Ilyobacter polytropus* DSM 2926] | YP_003968466.1<br>GI:310780134<br>(WP_013388777.1)<br>(SEQ ID NO: 105) |
| hypothetical protein GCWU000342_00651 [*Shuttleworthia satelles* DSM 14600] > gb\|EEP29295.1\| hypothetical protein GCWU000342 00651 [*Shuttleworthia satelles* DSM 14600] | ZP_04454656.1<br>GI:229828587<br>(SEQ ID NO: 106) |
| aldehyde dehydrogenase [*Clostridium beijerinckii* NCIMB 8052] >gb\|ABR36155.1\| aldehyde dehydrogenase [*Clostridium beijerinckii* NCIMB 8052] | YP_001311175.1<br>GI:150018857<br>(WP_012060202.1)<br>(SEQ ID NO: 107) |
| propionaldehyde dehydrogenase [*Clostridium clostridioforme* CM201] > gb\|ENZ04399.1\| propionaldehyde dehydrogenase [*Clostridium clostridioforme* 90B1] > gb\|ENZ17257.1\| propionaldehyde dehydrogenase [*Clostridium clostridioforme* 90A8] > gb\|ENZ22132.1\| propionaldehyde dehydrogenase [*Clostridium clostridioforme* 90A3] >gb\|ENZ29200.1\| propionaldehyde dehydrogenase [*Clostridium clostridioforme* 90A1] > gb\|ENZ64224.1\| propionaldehyde dehydrogenase [Clostridium clostridioforme 90A4] > gb\|ENZ70105.1\| propionaldehyde dehydrogenase [*Clostridium clostridioforme* 90A6] | ENY83847.1<br>GI:480639338<br>(SEQ ID NO: 108) |
| aldehyde dehydrogenase (NAD) domain protein [*Clostridium* sp. MSTE9] > gb\|EJF40077.1\| aldehyde dehydrogenase (NAD) domain protein [*Clostridium* sp. MSTE9] | ZP_14663848.1<br>GI:420157008<br>(SEQ ID NO: 109) |
| propionaldehyde dehydrogenase [*Clostridium bolteae* 90B8] > gb\|ENZ57487.1\| propionaldehyde dehydrogenase [*Clostridium bolteae* 90A5] > gb\|ENZ67775.1\| propionaldehyde dehydrogenase [*Clostridium bolteae* 90B7] | ENZ31577.1<br>GI:480688660<br>(SEQ ID NO: 110) |
| hypothetical protein EUBHAL_00514 [*Eubacterium hallii* DSM 3353] > gb\|EEG37590.1\| aldehyde dehydrogenase (NAD) family protein [*Eubacterium hallii* DSM 3353] | ZP_03715465.1<br>GI:225026273<br>(SEQ ID NO: 111) |
| CoA-acylating propionaldehyde dehydrogenase [*Halanaerobium saccharolyticum* subsp. *saccharolyticum* DSM 6643] > emb\|CCU77919.1\| CoA-acylating propionaldehyde dehydrogenase [*Halanaerobium saccharolyticum* subsp. *saccharolyticum* DSM 66431 | ZP_23773859.1<br>GI:470960332<br>(SEQ ID NO: 112) |
| hypothetical protein [*Eubacterium limosum* KIST612] > gb\|ADO39014.1\| hypothetical protein ELI_4072 [*Eubacterium limosum* KIST612] | YP_003961977.1<br>GI:310829620<br>(WP_013382321.1)<br>(SEQ ID NO: 113) |
| aldehyde dehydrogenase [*Thermoanaerobacter* sp. X514] > ref_ZP_07131928.1\| Aldehyde Dehydrogenase [*Thermoanaerobacter* sp. X561] > ref\|YP_003903905.1\| aldehyde dehydrogenase [*Thermoanaerobacter* sp. X513] >ref\|ZP_08212082.1\| Aldehyde Dehydrogenase [*Thermoanaerobacter ethanolicus* JW 200] > gb\|ABY93220.1\| aldehyde dehydrogenase [*Thermoanaerobacter* sp. X514] > gb\|EFK84693.1\| Aldehyde Dehydrogenase [Thermoanaerobacter sp. X561] > gb\|ADN54614.1\| Aldehyde Dehydrogenase [*Thermoanaerobacter* sp. X513] > gb\|EGD51928.1\| Aldehyde Dehydrogenase [*Thermoanaerobacter ethanolicus* JW 200] | YP_001663556.1<br>GI:167040571<br>(WP_003870148.1)<br>(SEQ ID NO: 114) |

TABLE 4-continued

Exemplary Aldehyde Dehydrogenase (ALD) Sequences.

| | |
|---|---|
| aldehyde dehydrogenase [*Rhodospirillum rubrum* ATCC 11170] > ref|YP_006047210.1| aldehyde dehydrogenase EutE [*Rhodospirillum rubrum* F11] > gb|ABC21715.1| Aldehyde dehydrogenase [*Rhodospirillum rubrum* ATCC 11170] > gb |AEO47413.1| aldehyde dehydrogenase EutE |*Rhodospirillum rubrum* F11] | YP_426002.1 GI:83592250 (SEQ ID NO: 115) |
| CoA-dependent propionaldehyde dehydrogenase [*Eubacterium yurii* subsp. *margaretiae* ATCC 43715] > gb|EFM39950.1| CoA-dependent propionaldehyde dehydrogenase [*Eubacterium yurii* subsp. *margaretiae* ATCC 43715] | ZP_07453625.1 GI:306819974 (SEQ ID NO: 116) |
| aldehyde dehydrogenase (NAD) domain protein [*Eubacterium* sp. AS15] > gb|EJP26117.1| aldehyde dehydrogenase (NAD) domain protein [*Eubacterium* sp. AS15] | ZP_10828060.1 GI:402309064 (SEQ ID NO: 117) |
| aldehyde dehydrogenase EutE [*Vibrio* sp. EJY3] > gb|AEX22176.1| aldehyde dehydrogenase EutE [*Vibrio* sp. EJY3] | YP_005023154.1 GI:375265711 (WP_014232054.1) (SEQ ID NO: 118) |
| hypothetical protein HMPREF9629_00032 [*Eubacteriaceae bacterium* ACC19a] > gb|EHL16790.1| hypothetical protein HMPREF9629 00032 [*Eubacteriaceae bacterium* ACC19a] | ZP_09320518.1 GI:363893420 (SEQ ID NO: 119) |
| aldehyde-alcohol dehydrogenase domain protein [*Propionibacterium propionicum* F0230a] > gb|AFN47240.1| aldehyde-alcohol dehydrogenase domain protein [*Propionibacterium propionicum* F0230a] | YP_006513121.1 GI:397671586 (WP_014847902.1) (SEQ ID NO: 120) |
| hypothetical protein HMPREF9628_01348 [*Eubacteriaceae bacterium* CM5] > gb|EHL19659.1| hypothetical protein HMPREF9628_01348 [*Eubacteriaceae bacterium* CM5] | ZP_09316712.1 GI:363889349 (SEQ ID NO: 121) |
| aldehyde dehydrogenase (NAD) family protein [*Eubacteriaceae bacterium* OBRC8] > gb|EJU23517.1| aldehyde dehydrogenase (NAD) family protein [*Eubacteriaceae bacterium* OBRC8] | ZP_10886417.1 GI:402837902 (SEQ ID NO: 122) |
| aldehyde dehydrogenase [*Clostridium beijerinckii*] | AAT48939.1 (SEQ ID NO:123) |

It is understood that the individual ALD variants such as those described above can be used alone, or can be combined with any other variant amino acid position, including 2, 3, 4, 5, 6, 7, 8, 9, 10, 11, 12, 13, 14, or 16, that is, up to all variant amino acid positions as disclosed herein (see Tables 1-3), to generate additional variants having desirable activities. Exemplary ALD variants include, but are not limited to, single substitutions, or a combination of one or more of the substitutions, at amino acid positions disclosed in any of Tables 1-3, for example, at amino acid position 12, 19, 33, 44, 65, 66, 72, 73, 107, 122, 129, 139, 143, 145, 155, 163, 167, 174, 189, 204, 220, 227, 229, 230, 243, 244, 254, 267, 315, 353, 356, 396, 429, 432, 437, 440, 441, 442, 444, 447, 450, 460, 464, or 467 corresponding to the amino acid sequence of ALD-1 (SEQ ID NO:1) (see Tables 1-3). For example, the ALD variants include, but are not limited to amino acid substitution, single substitutions, or a combination of one or more of the substitutions, at amino acid positions D12, V19, C33, I44, K65, I66, K72, A73, Y107, D122, E129, I139, T143, P145, G155, V163, G167, C174, C189, M204, C220, M227, K229, T230, A243, G244, A254, C267, V315, C353, C356, R396, F429, V432, E437, T440, T441, F442, I444, S447, E450, R460, C464, or A467 corresponding to the amino acid sequence of ALD-1 (SEQ ID NO:1) (see Tables 1-3). It is understood that any substitution of the other 19 amino acids can be done at one or more desired amino acid positions.

In one embodiment, the variant ALD comprises an amino acid substitution at position 12 that is D12A. In one embodiment, the variant ALD comprises an amino acid substitution at position 19 that is V19I. In one embodiment, the variant ALD comprises an amino acid substitution at position 33 that is C33R. In one embodiment, the variant ALD comprises an amino acid substitution at position 44 that is I44L. In one embodiment, the variant ALD comprises an amino acid substitution at position 65 that is K65A. In one embodiment, the variant ALD comprises an amino acid substitution at position 66 selected from I66M, I66Q, I66N, I66H, I66T and I66S. In one embodiment, the variant ALD comprises an amino acid substitution at position 72 that is K72N. In one embodiment, the variant ALD comprises an amino acid substitution at position 73 selected from A735, A73D, A73G, A73L, A73Q, A73F, A73E, A73W, A73R, A73C, and A73M. In one embodiment, the variant ALD comprises an amino acid substitution at position 107 that is Y107K. In one embodiment, the variant ALD comprises an amino acid substitution at position 122 that is D122N. In one embodiment, the variant ALD comprises an amino acid substitution at position 129 that is E129I. In one embodiment, the variant ALD comprises an amino acid substitution at position 139 selected from I139S, I139V, and I139L. In one embodiment, the variant ALD comprises an amino acid substitution at position 143 that is T143N or T143S. In one embodiment, the variant ALD comprises an amino acid substitution at position 163 selected from V163C, V163G and V163T. In one embodiment, the variant ALD comprises an amino acid substitution at position 167 that is G167S. In one embodiment, the variant ALD comprises an amino acid substitution at position 174 that is C174S. In one embodiment, the variant ALD comprises an amino acid substitution at position 189 that is C189A. In one embodiment, the variant ALD comprises an amino acid substitution at position 204 that is M204R. In one embodiment, the variant ALD comprises an amino acid substitution at position 220 that is C220V. In one embodiment, the variant ALD comprises an amino acid substitution at position 227 selected from M227K, M227Q, M227I, M227V, M227C, M227L, and M227A. In one embodiment, the variant ALD comprises an amino acid substitution at position 229 that is K 229S. In one embodiment, the variant ALD comprises an amino acid substitution at position 230 selected from T230R, T230K, T230H, T230A, T230M, T230C, T230L, T230S, T230Y, T230G, T230T, T230I, T230W, T230N, T230V, and T230Q. In one embodiment, the variant ALD comprises an amino acid substitution at position 243 selected from A243P, A243Q, A243E, A243S, A243N, A243K, A243L, A243C, A243M, and A243I. In one embodiment, the variant ALD comprises an amino acid substitution at position 254 that is A254T. In one embodiment, the variant ALD comprises an amino acid substitution at position 267 that is C267A. In one embodiment, the variant ALD comprises an amino acid substitution at position 315 that is V315A. In one embodiment, the variant ALD comprises an amino acid substitution at position 353 that is C353A. In one embodiment, the variant ALD comprises an amino acid substitution at position 356 that is C356T or C356L. In one embodiment, the variant ALD comprises an amino acid substitution at position 396 that is R396H. In one embodiment, the variant ALD comprises an amino acid substitution at position 429 selected from F429Y, F429Q, F429H, F429M, F429D, and F429L. In one embodiment, the variant ALD comprises an amino acid substitution at position 432 that is V432V or V432N. In one embodiment, the variant ALD comprises an amino acid substitution at position 437 that is E437P. In one embodiment, the variant ALD comprises an amino acid substitution at position 440 that is T440H. In one embodiment, the variant ALD comprises an amino acid substitution at position 441 that is T441G. In one embodiment, the variant ALD comprises an amino acid substitution at position 442 selected from F442T, F442Y, F442H, F442N, F442Q, F442M, and F442F. In one embodiment, the variant ALD comprises an amino acid substitution at position 444 that is I444V. In one embodiment, the variant ALD comprises an amino acid substitution at position 447 selected from S447M, S447P, S447H, S447K, S447R, S447T, S447E, and S447S. In one embodiment, the variant ALD comprises an amino acid substitution at position 460 that is R460K. In one embodiment, the variant ALD comprises an amino acid substitution at position 464 that is C464V or C464I. In one embodiment, the variant ALD comprises an amino acid substitution at position 467 that is A467V. Any of the above-described amino acid positions can be used for single amino acid substitutions, or a combination of one or more of the substitutions, to generate an ALD variant of the invention.

For example, an ALD variant can comprise two or more amino acid substitutions, such as D12 and I139; K65 and C174; M204 and C220; C464 and A467; R396 and F442; C356 and F442; C174 and A243; K65 and I66; I66 and A73; I66 and C174; I66 and M204; I66 and C220; I66 and M227; I66 and T230; I66 and A243; I66 and A243; I66 and C267; I66 and C356; I66 and R396; I66 and E437; I66 and F442; I66 and S447; I66 and C464; I66 and A467, and the like. For example, an ALD variant can comprise two or more amino acid substitutions, such as D12A and I139L; K65A and C174S; M204R and C220V; C464I and A467V; R396H and F442N; C356T and F442M; C174S and A243Q; K65A and I66H; I66H and A73S; I66H and C174S; I66H and M204R; I66H and C220V; I66H and M227I; I66H and T230C; I66H and A243Q; I66H and A243P; I66H and C267A; I66H and C356T; I66H and R396H; I66H and E437P; I66H and F442N; I66H and S447P; I66H and C464I; I66H and A467V; K65A and I66T; I66M and A73S; I66T and C174S; I66T and M204R; I66T and C220V; I66T and M227I; I66T and T230C; I66T and A243Q; I66T and A243P; I66T and C267A; I66T and C356T; I66T and R396H; I66T and E437P; I66T and F442N; I66T and S447P; I66T and C464I; I66T and A467V; K65A and I66M; I66M and A73S; I66M and C174S; I66M and M204R; I66M and C220V; I66M and M227I; I66M and T230C; I66M and A243Q; I66M and A243P; I66M and C267A; I66M and C356T; I66M and R396H; I66M and E437P; I66M and F442N; I66M and S447P; I66M and C464I; I66M and A467V; K65A and I66N; I66N and A73S; I66N and C174S; I66N and M204R; I66N and C220V; I66N and M227I; I66N and T230C; I66N and A243Q; I66N and A243P; I66N and C267A; I66N and C356T; I66N and R396H; I66N and E437P; I66N and F442N; I66N and S447P; I66N and C464I; I66N and A467V, K65A and I66Q; I66Q and A73S; I66Q and C174S; I66Q and M204R; I66Q and C220V; I66Q and M227I; I66Q and T230C; I66Q and A243Q; I66Q and A243P; I66Q and C267A; I66Q and C356T; I66Q and R396H; I66Q and E437P; I66Q and F442N; I66Q and S447P; I66Q and C464I; I66Q and A467V; K65A and I66S; I66S and A73S; I66S and C174S; I66S and M204R; I66S and C220V; I66S and M227I; I66S and T230C; I66S and A243Q; I66S and A243P; I66S and C267A; I66S and C356T; I66S and R396H; I66S and E437P; I66S and F442N; I66S and S447P; I66S and C464I; I66S and A467V, and the like.

An ALD variant can also comprise three or more amino acid substitutions such as D12, I139 and R396; K65, C174 and C356; M204, C220 and A243; C174, C464 and A467; A243, R396 and F442; C220, C356 and F442; C174, A243 and E437; K65, I66 and A243; I66, A73 and E437; I66, C174 and F442; I66, M204 and R396; I66, C220 and S447; I66, M227 and C267; I66, T230 and A243; I66, A243 and C464; I66, A243 and A467; I66, M204 and C267; I66, C356 and R396; I66, R396 and F442; I66, E437 and A467; I66, C220 and F442; I66, S447 and C464; I66, M204 and C464; I66, C174 and A467. For example, an ALD variant can comprise three or more amino acid substitutions, such as D12A, I139L and R396H; K65A, C174S and C356T; M204R, C220V and A243Q; C174S, C464I and A467V; A243P, R396H and F442N; C220V, C356T and F442M; C174S, A243Q and E437P; K65A, I66H and A243Q; I66H, A73S and E437P; I66H, C174S and F442N; I66H, M204R and R396H; I66H, C220V and S447P; I66H, M227I and C267A; I66H, T230C and A243P; I66H, A243Q and C464I; I66H, A243P and A467V; I66H, M204R and C267A; I66H, C356T and R396M; I66H, R396H and F442N; I66H, E437P and A467V; I66H, C220V and F442N; I66H, S447P and C464I; I66H, M204R and C464I; I66H, C174S and A467V; K65A, I66T and A243Q; I66M, A73S and E437P; I66T, C174S and F442N; I66T, M204R and R396H; I66T, C220V and S447P; I66T, M227I and C267A; I66T, T230C and A243P; I66T, A243Q and C464I; I66T, A243P and A467V; I66T, M204R and C267A; I66T, C356T and R396M; I66T, R396H and F442N; I66T, E437P and A467V; I66T, C220V and F442N; I66T, S447P and C464I; I66T, M204R and C464I; I66T, and C174S and A467V; K65A, I66M and A243Q; I66M, A73S and A437P; I66M, C174S and F442N; I66M, M204R and R396H; I66M, C220V and F442N; I66M, M227I and C267A; I66M, T230C and A243P; I66M, A243Q and C464I; I66M, A243P and A467V; I66M, M204R and C267A; I66M, C356T and R396M; I66M, R396H and F442N; I66M, E437P and A467V; I66M, C220V and F442N; I66M, S447P and C464I; I66M, M204R and C464I; I66M, C174S and A467V; K65A, I66N and A243Q; I66N, A73S and M227I; I66N, C174S and E437P; I66N, M204R and R396H; I66N, C220V and S447P; I66N, C174S and M227I; I66N, T230C and C356T; I66N, M204R and A243Q; I66N, A243P and S447P; I66N, C267A and C356T; I66N, C220V and C356T; I66N, R396H and E437P; I66N, M227I and E437P; I66N, F442N and A467V; I66N, M227I and S447P; I66N, M227I and C464I; I66N, A73S and A467V, K65A, I66Q and C220V; I66Q, A73S and M227I; I66Q, C174S and R396H; I66Q, M204R and C220V; I66Q, C220V and E437P; I66Q, M227I and F442N; I66Q, C174S and T230C; I66Q, A243Q and C356T; I66Q, A243P amd C267A; I66Q, C267A and C356T; I66Q, C220V and C356T; I66Q, R396H and E437P; I66Q, M204R and E437P; I66Q, M227I and F442N; I66Q, F442N and S447P; I66Q, C256A and C464I; I66Q, A73S and A467V; K65A, I66S and A73S; I66S, A73S and C220V; I66S, C174S and C267A; I66S, M204R and R396H; I66S, C220V and T230C; I66S, C220V and M227I; I66S, T230C and A243P; I66S, A243Q and C356T; I66S, M227I and A243P; I66S, C267A and F442N; I66S, M204R and C356T; I66S, T230C and R396H; I66S, M204R and E437P; I66S, C220V and F442N; I66S, A73S and S447P; I66S, C174S and C464I; I66S, C356T and A467V, and the like. It is understood that such combinations two or more, or three or more combinations of amino acid substitutions as described above are merely exemplary and that a person skilled in the art can readily determine desired combinations of amino acid substitutions for a desired ALD.

Based on the teachings herein, a person skilled in the art can readily identify amino acid positions corresponding to any of amino acid positions 12, 19, 33, 44, 65, 66, 72, 73, 107, 122, 129, 139, 143, 145, 155, 163, 167, 174, 189, 204, 220, 227, 229, 230, 243, 244, 254, 267, 315, 353, 356, 396, 429, 432, 437, 440, 441, 442, 444, 447, 450, 460, 464, or 467 corresponding to the amino acid sequence of ALD-1 (SEQ ID NO:1) in homologous ALD sequences. For example, as shown in the alignment in FIG. 4A, amino acid I139 of ALD-1 corresponds to amino acid I133 of SEQ ID NO:13 and 20. For SEQ ID NO:24, the corresponding position is V199. Using well known methods for aligning amino acid sequences, generally using default parameters as disclosed herein, a person skilled in the art can readily determine an amino acid position in another ALD sequence that corresponds to any of amino acid positions 12, 19, 33, 44, 65, 66, 72, 73, 107, 122, 129, 139, 143, 145, 155, 163, 167, 174, 189, 204, 220, 227, 229, 230, 243, 244, 254, 267, 315, 353, 356, 396, 429, 432, 437, 440, 441, 442, 444, 447, 450, 460, 464, or 467 corresponding to the amino acid sequence of ALD-1 (SEQ ID NO:1).

It is further understood that an ALD variant can contain 2, 3, 4, 5, 6, 7, 8, 9, 10, 11, 12, 13, 14, 15, or 16, that is, up to all variant amino acid positions as disclosed herein, for example, in Tables 1-3. A person skilled in the art can readily generate an ALD variant based on any single or combination of amino acid substitutions, as disclosed herein, such as the amino acid variant positions described above and in Tables 1-3. In a particular embodiment, the ALD variants are those disclosed in Tables 1-3.

Throughout this application various publications have been referenced. The disclosures of these publications in their entireties, including GenBank accession version designations and/or GI number publications, are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. An isolated nucleic acid molecule selected from:
   (a) a nucleic acid molecule encoding a polypeptide comprising an amino acid sequence that is a variant of SEQ ID NO: 1, wherein said amino acid sequence comprises the amino acid substitution I66M and F442N, wherein the amino acid sequence has at least 90% sequence identity to the amino acid sequence of SEQ ID NO: 1 and wherein said polypeptide has aldehyde dehydrogenase activity; and
   (b) a nucleic acid molecule that is complementary to (a).

2. The isolated nucleic acid molecule of claim 1, wherein the amino acid sequence, in addition to the substitution I66M and F442N, comprises one or more amino acid substitutions selected from the group consisting of K65A, A73S, C174S, M204R, C220V, M227I, T230C, A243P, A243Q, C267A, C356T, R396H, E437P, S447P, C464I and A467V, as compared to the amino acid sequence of SEQ ID NO: 1.

3. The isolated nucleic acid molecule of claim 1, wherein the amino acid sequence comprises at least 2, 3, 4, 5, 6, 7, 8, 9, 10, 11, 12, 13, 14, 15 or 16 of the amino acid substitutions selected from the group consisting of K65A, A73S, C174S, M204R, C220V, M227I, T230C, A243P, A243Q, C267A, C356T, R396H, E437P, S447P, C464I and A467V.

4. The isolated nucleic acid molecule of claim 1, wherein the amino acid sequence comprises one of the following groups of amino acid substitutions:
   A) K65A, C174S, M204R, C220V, A243Q, C267A, C356T, R396H, E437P, C464I and A467V;
   B) K65A, A73S, C174S, M204R, C220V, M227I, T230C, A243P, C267A, C356T, R396H, E437P, S447P, C464I and A467V;
   C) C174S, M204R, C220V, A243Q, C267A, C356T, R396H, E437P, C464I and A467V;
   D) C174S, M204R, C220V, A243P, C267A, C356T, R396H, E437P, C464I, and A467V and E) K65A, C174S, M204R, C220V, A243P, C267A, C356T, R396H, E437P, C4641 and A467V.

5. A vector containing the nucleic acid molecule of claim 1.

6. An isolated polypeptide comprising an amino acid sequence that is a variant of SEQ ID NO: 1, wherein said amino acid sequence comprises the amino acid substitution 166M and F442N, wherein the amino acid sequence has at least 90% sequence identity to the amino acid sequence of SEQ ID NO: 1 and wherein the isolated polypeptide has aldehyde dehydrogenase activity.

7. The isolated polypeptide of claim 6, wherein the amino acid sequence, in addition to the substitution 166M and F442N, comprises one or more amino acid substitutions selected from the group consisting of K65A, A73S, C174S, M204R, C220V, M2271, T230C, A243P, A243Q, C267A, C356T, R396H, E437P, S447P, C4641 and A467V, as compared to the amino acid sequence of SEQ ID NO: 1.

8. The isolated polypeptide of claim 6, wherein the amino acid sequence comprises at least 2, 3, 4, 5, 6, 7, 8, 9, 10, 11, 12, 13, 14, 15 or 16 of the amino acid substitutions selected from the group consisting of K65A, A73S, C174S, M204R, C220V, M2271, T230C, A243P, A243Q, C267A, C356T, R396H, E437P, S447P, C4641 and A467V.

9. The isolated polypeptide of claim 6, wherein the amino acid sequence comprises one of the following groups of amino acid substitutions:
A) K65A, C174S, M204R, C220V, A243Q, C267A, C356T, R396H, E437P, C4641 and A467V;
B) K65A, A73S, C174S, M204R, C220V, M2271, T230C, A243P, C267A, C356T, R396H, E437P, S447P, C4641 and A467V;
C) C174S, M204R, C220V, A243Q, C267A, C356T, R396H, E437P, C4641 and A467V;
D) C174S, M204R, C220V, A243P, C267A, C356T, R396H, E437P, C4641 and A467V and
E) K65A, C174S, M204R, C220V, A243P, C267A, C356T, R396H, E437P, C4641 and A467V.

10. The isolated polypeptide of claim 6, wherein the polypeptide:
(a) can convert 3-hydroxybutyryl-CoA to 3-hydroxybutyraldehyde;
(b) can convert 4-hydroxybutyryl-CoA to 4-hydroxybutyraldehyde;
(c) has higher activity relative to a polypeptide consisting of SEQ ID NO: 1;
(d) has higher activity for 3-hydroxy-(R)-butyryl-CoA over 3-hydroxy-(S)-butyryl-CoA;
(e) has higher specificity for 4-hydroxybutyryl-CoA over acetyl-CoA;
(f) produces decreased byproducts in a cell or cell extract relative to a cell or cell extract comprising a polypeptide consisting of SEQ ID NO: 1, wherein optionally the byproduct is ethanol or 4-hydroxy-2-butanone; and/or
(g) has a higher kcat relative to a polypeptide consisting of SEQ ID NO: 1.

11. A cell comprising the nucleic acid of claim 1.

12. The cell of claim 11, wherein the cell is a microbial organism.

13. The cell of claim 11, wherein said cell:
(a) comprises a pathway that produces 3-hydroxybutyraldehyde (3-HBal) and/or 1,3-butanediol (1,3-BDO), or an ester or amide thereof;
(b) comprises a pathway that produces 4-hydroxybutyraldehyde (4-HBal) and/or 1,4-butanediol (1,4-BDO), or an ester or amide thereof;
(c) is capable of fermentation;
(d) comprising at least one substrate for said polypeptide, wherein the substrate is 3-hydroxybutyryl-CoA or 3-hydroxy-(R)-butyryl-CoA; 4-hydroxybutyryl-CoA; or
(e) has higher activity for 3-hydroxy-(R)-butyryl-CoA over 3-hydroxy-(S)-butyryl-CoA.

14. A composition comprising the polypeptide of claim 6 and at least one substrate for said polypeptide.

15. A culture medium comprising the cell of claim 11.

16. A method of constructing a host strain comprising introducing the nucleic acid of claim 1 into a cell that is capable of fermentation.

17. A method for producing 3-hydroxybutyraldehyde (3-HBal) and/or 1,3-butanediol (1,3-BDO), or an ester or amide thereof, comprising culturing the cell of claim 11 to produce 3-HBal and/or 1,3-BDO, or an ester or amide thereof.

18. A method for producing 4-hydroxybutyraldehyde (4-HBal) and/or 1,4-butanediol (1,4-BDO), or an ester or amide thereof, comprising culturing the cell of claim 11 to produce 4-HBal and/or 1,4-BDO, or an ester or amide thereof.

19. A method for producing 3-hydroxybutyraldehyde (3-HBal) and/or 1,3-butanediol (1,3-BDO), or an ester or amide thereof, comprising providing a substrate to the polypeptide of claim 6 and converting the substrate to 3-HBal and/or 1,3-BDO, wherein the substrate is a racemic mixture of 1,3-hydroxybutyryl-CoA.

20. A method for producing 4-hydroxybutyraldehyde (4-HBal) and/or 1,4-butanediol (1,4-BDO), or an ester or amide thereof, comprising providing a substrate to the polypeptide of claim 6 and converting the substrate to 4-HBal and/or 1,4-BDO, wherein the substrate is 1,4-hydroxybutyryl-CoA.

21. A method for producing 3-HBal and/or 1,3-BDO, or 4-HBal and/or 1,4-BDO, comprising incubating a lysate of the cell of claim 11 to produce 3-HBal and/or 1,3-BDO, or 4-HBal and/or 1,4-BDO.

22. The isolated polypeptide of claim 6, wherein the amino acid sequence has at least 95% sequence identity to the amino acid sequence of SEQ ID NO: 1.

23. The isolated polypeptide of claim 6, wherein the amino acid sequence has at least 98% sequence identity to the amino acid sequence of SEQ ID NO: 1.

24. The isolated polypeptide of claim 6, wherein the amino acid sequence has at least 99% sequence identity to the amino acid sequence of SEQ ID NO: 1.

25. The isolated polypeptide of claim 6, wherein the amino acid sequence is identical to the amino acid sequence referenced as SEQ ID NO: 1 with the exception of the amino acid substitution 166M and F442N.

* * * * *

```
                              SEQUENCE LISTING

Sequence total quantity: 129
SEQ ID NO: 1           moltype = AA  length = 468
FEATURE                Location/Qualifiers
source                 1..468
                       mol_type = protein
                       organism = Clostridium saccharoperbutylacetonicum
SEQUENCE: 1
MIKDTLVSIT KDLKLKTNVE NANLKNYKDD SSCFGVFENV ENAISNAVHA QKILSLHYTK   60
EQREKIITEI RKAALENKEI LATMILEETH MGRYEDKILK HELVAKYTPG TEDLTTTAWS  120
GDNGLTVVEM SPYGVIGAIT PSTNPTETVI CNSIGMIAAG NTVVFNGHPG AKKCVAFAVE  180
MINKAIISCG GPENLVTTIK NPTMDSLDAI IKHPSIKLLC GTGGPGMVKT LLNSGKKAIG  240
AGAGNPPVIV DDTADIEKAG KSIIEGCSFD NNLPCIAEKE VFVFENVADD LISNMLKNNA  300
VIINEDQVSK LIDLVLQKNN ETQEYSINKK WVGKDAKLFL DEIDVESPSS VKCIICEVSA  360
SHPFVMTELM MPILPIVRVK DIDEAIEYAK IAEQNRKHSA YIYSKNIDNL NRFEREIDTT  420
IFVKNAKSFA GVGYEAEGFT TFTIAGSTGE GITSARNFTR QRRCVLAG              468

SEQ ID NO: 2           moltype = AA  length = 477
FEATURE                Location/Qualifiers
source                 1..477
                       mol_type = protein
                       organism = Lactobacillus brevis
SEQUENCE: 2
MNTENIEQAI RKILSEELSN PQSSTATNTT VPGKNGIFKT VNEAIAATKA AQENYADQPI   60
SVRNKVIDAI REGFRPYIED MAKRIHDETG MGTVSAKIAK LNNALYNTPG PEILQPEAET  120
GDGGLVMYEY APFGVIGAVG PSTNPSETVI ANAIMMLAGG NTLFFGAHPG AKNITRWTIE  180
KLNELVADAT GLHNLVVSLE TPSIESVQEV MQHPDVAMLS ITGGPAVVHQ ALISGKKAVG  240
AGAGNPPAMV DATANIALAA HNIVDSAAFD NNILCTAEKE VVVEAAVKDE LIMRMQQEGA  300
FLVTDSADIE KLAQMTIGPK GAPDRKFVGK DATYILDQAG ISYTGTPTLI ILEAAKDHPL  360
VTTEMLMPIL PVVCCPDFDS VLATATEVEG GLHHTASIHS ENLPHINKAA HRLNTSIFVV  420
NGPTYCGTGV ATNGAHSGAS ALTIATPTGE GTATSKTYTR RRRLNSPEGF SLRTWEA     477

SEQ ID NO: 3           moltype = AA  length = 462
FEATURE                Location/Qualifiers
source                 1..462
                       mol_type = protein
                       organism = Clostridium phytofermentans
SEQUENCE: 3
MTVNEQLVQD IIKNVVASMQ LTQTNKTELG VFDDMNQAIE AAKEAQLVVK KMSMDQREKI   60
ISAIRKKTIE HAETLARMAV EETGMGNVGH KILKHQLVAE KTPGTEDITT TAWSGDRGLT  120
LVEMGPFGVI GAITPCTNPS ETIICNTIGM LAGGNTVVFN PHPAAIKTSN FAVQLINEAS  180
LSAGGPVNIA CSVRKPTLDS SKIMMSHQDI PLIAATGGPG VVTAVLQSGK RGIGAGAGNP  240
PVLVDETADI RKAAEDIING CTFDNNLPCI AEKEVVAIDA IANELMNYMV KEQGCYAITK  300
EQQEKLTNLV ITPKGLNRNC VGKDARTLLG MIGIDVPSNI RCIIFEGEKE HPLISEELMM  360
```

```
PILGIVRAKS FDDAVEKAVW LEHGNRHSAH IHSKNVDRIT TYAKAIDTAI LVKNAPSYAA    420
IGFGGEGFCT FTIASRTGEG LTSASTFTKR RRCVMSDSLC IR                       462

SEQ ID NO: 4            moltype = AA  length = 468
FEATURE                 Location/Qualifiers
REGION                  1..468
                        note = source = /note="Description of Artificial Sequence:
                         Synthetic polypeptide"
source                  1..468
                        mol_type = protein
                        organism = synthetic construct
SEQUENCE: 4
MIKDTLVSIT KDLKLKTNVE NANLKNYKDD SSCFGVFENV ENAISNAVHA QKILSLHYTK    60
EQREKIITEI RKAALENKEI LATMILEETH MGRYEDKILK HELVAKYTPG TEDLTTTAWS    120
GDNGLTVVEM SPYGVIGAIT PSTNPTETVI CNSIGMIAAG NTVVFNGHPG AKKSVAFAVE    180
MINKAIISCG GPENLVTTIK NPTRDSLDAI IKHPSIKLLV GTGGPGMVKT LLNSGKKAIG    240
AGAGNPPVIV DDTADIEKAG KSIIEGASFD NNLPCIAEKE VFVFENVADD LISNMLKNNA    300
VIINEDQVSK LIDLVLQKNN ETQEYSINKK WVGKDAKLFL DEIDVESPSS VKCIITEVSA    360
SHPFVMTELM MPILPIVRVK DIDEAIEYAK IAEQNHKHSA YIYSKNIDNL NRFEREIDTT    420
IFVKNAKSFA GVGYEAPGFT TFTIAGSTGE GITSARNFTR QRRIVLVG                468

SEQ ID NO: 5            moltype = AA  length = 15
FEATURE                 Location/Qualifiers
VARIANT                 2
                        note = Any amino acid
VARIANT                 6..7
                        note = Any amino acid
VARIANT                 11
                        note = Any amino acid
REGION                  1..15
                        note = source = /note="Description of Artificial Sequence:
                         Synthetic peptide"
source                  1..15
                        mol_type = protein
                        organism = synthetic construct
SEQUENCE: 5
IXPKGXXNRK XVGKD                                                     15

SEQ ID NO: 6            moltype = AA  length = 18
FEATURE                 Location/Qualifiers
VARIANT                 5
                        note = Any amino acid
VARIANT                 7..9
                        note = Any amino acid
VARIANT                 13
                        note = Any amino acid
REGION                  1..18
                        note = source = /note="Description of Artificial Sequence:
                         Synthetic peptide"
source                  1..18
                        mol_type = protein
                        organism = synthetic construct
SEQUENCE: 6
SYAGXGXXXE GFXTFTIA                                                  18

SEQ ID NO: 7            moltype = AA  length = 468
FEATURE                 Location/Qualifiers
source                  1..468
                        mol_type = protein
                        organism = Clostridium saccharoperbutylacetonicum
SEQUENCE: 7
MIKDTLVSIT KDLKLKTNVE NANLKNYKDD SSCFGVFENV ENAISNAVHA QKILSLHYTK    60
EQREKIITEI RKAALENKEI LATMILEETH MGRYEDKILK HELVAKYTPG TEDLTTTAWS    120
GDNGLTVVEM SPYGVIGAIT PSTNPTETVI CNSIGMIAAG NTVVFNGHPG AKKCVAFAVE    180
MINKAIISCG GPENLVTTIK NPTMDSLDAI IKHPSIKLLC GTGGPGMVKT LLNSGKKAIG    240
AGAGNPPVIV DDTADIEKAG KSIIEGCSFD NNLPCIAEKE VFVFENVADD LISNMLKNNA    300
VIINEDQVSK LIDLVLQKNN ETQEYSINKK WVGKDAKLFL DEIDVESPSS VKCIICEVSA    360
RHPFVMTELM MPILPIVRVK DIDEAIEYAK IAEQNRKHSA YIYSKNIDNL NRFEREIDTT    420
IFVKNAKSFA GVGYEAEGFT TFTIAGSTGE GITSARNFTR QRRCVLAG                468

SEQ ID NO: 8            moltype = AA  length = 386
FEATURE                 Location/Qualifiers
source                  1..386
                        mol_type = protein
                        organism = Roseburia inulinivorans
SEQUENCE: 8
MGVNETGMGN VGDKILKHHL TADKVPGTED ISTIAWSGDR GLTLVEMGPF GVIGAITPAT    60
NPSETVICNC IGMLAGGNTV VFNPHPNAKK TTIYTINMIN EASIEAGGPD NIAVTVEAPT    120
LDTSAIMMKH PSIHLLVATG GPGVVTAVLS SGKRAIGAGA GNPPVLVDET ADIRKAAQDI    180
```

```
VNGCTFDNNL PCIAEKEIVA VDSVADELMN YMISENGCYL ASKEIQDKLV QTVFTPKGAL   240
NRKCVGRSAQ TLLAMVGVNV GPEIRCIVFE GQKEHPLIAE ELMMPILGMV RVKSFEEGVE   300
TAVWLEHGNR HSAHIHSKNV DHITTYARAL DTAILVKNGP SYAALGFGGE GYCTFTIASR   360
TGEGLTAAHS FTKSRRCTMS DSLCIR                                      386

SEQ ID NO: 9             moltype = AA   length = 467
FEATURE                  Location/Qualifiers
source                   1..467
                         mol_type = protein
                         organism = Bacillus sp.
SEQUENCE: 9
MNPAELPHQV HESGANGVFD RIEDAIEAGY IAQLNYVKQF QLKDREKIIT AIREAVIENK    60
EKLAQMVFEE TKLGRYEDKI AKHELVARKT PGTEDITTAA FSGDEGLTII EQAPFGLVGA   120
VTPVTNPTET IINNSISLLA AGNAVVLNVH PSSKASCAFV VNLINQAIKD TGGPENLVSM   180
VKDPTLETLN RIIESPKVKL LVGTGGLGMV KTLLKSGKKA IGAGAGNPPV IVDETADLKQ   240
AAKSIIEGAS FDNNLLCIAE KELFVIDSVA DDLIFHMLNE GAYMLDQQQL SKLMSFALEE   300
NVHQEAGGCS LDNKREYHVS KDWVGKDAVS FLRQLGIAHE EDIKLLICEV DPDHPFVQLE   360
QMMPVFPIVR VGNLDEAIEM ALLAEHGNRH TAIMHSKNVD HLTKFARAIE TTIFVKNASS   420
LAGVGFGGEG HTTMTIAGPT GEGITSAKTF TRQRRCVLAE GGFRIIG                467

SEQ ID NO: 10            moltype = AA   length = 467
FEATURE                  Location/Qualifiers
source                   1..467
                         mol_type = protein
                         organism = Bacillus solani
SEQUENCE: 10
MNPAELPHQV HESGANGVFD RIEDAIEAGY IAQLNYVKQF QLKDREKIIT AIREAVIENK    60
EKLAQMVFEE TKLGRYEDKI AKHELVARKT PGTEDITTAA FSGDEGLTII EQAPFGLVGA   120
VTPVTNPTET IINNSISLLA AGNAVVLNVH PSSKVSCAFV VNLINQAIKD TGGPENLVSM   180
VKDPTLETLN RIIESPKVKL LVGTGGPGMV KTLLKSGKKA IGAGAGNPPV IVDETADLKQ   240
AAKSIIEGAS FDNNLLCIAE KELFVIDSVA DDLIFHMLNE GAYMLDQQQL SKLMSFALEE   300
NVHQEAGGCS LDNKREYHVS KDWVGKDAVS FLRQLGIAHE EDIKLLICEV DPDHPFVQLE   360
QMMPVFPIVR VGNLDEAIEM ALLAEHGNRH TAIMHSKNVD HLTKFARAIE TTIFVKNASS   420
LAGVGFGGEG HTTMTIAGPT GEGITSAKTF TRQRRCVLAE GGFRIIG                467

SEQ ID NO: 11            moltype = AA   length = 473
FEATURE                  Location/Qualifiers
source                   1..473
                         mol_type = protein
                         organism = Terrisporobacter othiniensis
SEQUENCE: 11
MDIDVKLIEK MVSDALKEIK IENITQEVEK NSIEDNYGVF KTIEGAIDAS YVAQKELLFS    60
KISDRQKYVD AIRSAILNQE NLELISKLAV DETEIGCYEH KLIKNRLAAE KTPGTEDLIS   120
SVKTGDDGLT LVEYCPFGVI GAITPTTNPT ETIICNSIGM IAGGNTVVFS PHPRATKVSQ   180
TIIKILNKAL EEVGAPKNLI TMVEKPSIEN TNKMIENPKV RFLVATGGPS IVKKVLSSGK   240
KAIGAGAGNP PVVVDETADI RKAAKDIIDG CSFDNNVPCI AEKEVFAVAS ICDSLIENMK   300
LNGAYLVKDK KVIEQLLSVV AKENGAPKTN FVGKSAKYIL DKIGVTVDDN IKAIIMEVDK   360
DHTFVQEEMM MPILPIVRVE DVDKAIEYAQ EAEHGNRHTA IMHSKNIDKL SKMSKIMETT   420
IFVKNAPSYA GIGVGGEGHS TFTIAGPTGE GLTSPKSFCR IRRCVVSDSF SIR          473

SEQ ID NO: 12            moltype = AA   length = 457
FEATURE                  Location/Qualifiers
source                   1..457
                         mol_type = protein
                         organism = Roseburia inulinivorans
SEQUENCE: 12
MVHDIVQKVM ANMQISGSVS GMHGVFKDMN DAINASIEAQ KKVCTMTLDQ REQIISLIRK    60
KTHENAEILA NMGVNETGMG NVGDKILKHH LTADKVPGTE DISTIAWSGD RGLTLVEMGP   120
FGVIGAITPA TNPSETVICN CIGMLAGGNT VVFNPHPNAK KTTIYTINMI NEASIEAGGP   180
DNIAVTVEAP TLDTSAIMMK HPSIHLLVAT GGPGVVTAVL SSGKRAIGAG AGNPPVLVDE   240
TADIRKAAQD IVNGCTFDNN LPCIAEKEIV AVDSVADELM NYMISENGCY LASKEIQDKL   300
VQTVFTPKGA LNRKCVGRSA QTLLAMVGVN VGPEIRCIVF EGQKEHPLIA EELMMPILGM   360
VRVKSFEEGV ETAVWLEHGN RHSAHIHSKN VDHITTYARA LDTAILVKNG PSYAALGFGG   420
EGYCTFTIAS RTGEGLTAAH SFTKSRRCTM SDSLCIR                           457

SEQ ID NO: 13            moltype = AA   length = 462
FEATURE                  Location/Qualifiers
source                   1..462
                         mol_type = protein
                         organism = Clostridium sp.
SEQUENCE: 13
MSVNERMVQD IVQEVVAKMQ IASDVTGNHG VFQDMNAAIE AAKKTQKVVA RMSMDQREKI    60
ISNIRAKIKE HAEIFARMGV QETGMGNVGH KILKHQLVAE KTPGTEDIQT TAWSGDRGLT   120
LIEMGPFGVI GAITPCTNPS ETVLCNTIGM LAGGNTVVFN PHPAAIKTSI YAVNLINEAS   180
LEAGGPDNIA CTVENPTLES SNIMMKHKDI PLIAATGGPG VVTAVLSSGK RGIGAGAGNP   240
PALVDETADI RKAAEDIVNG CTFDNNLPCI AEKEIVAVDS IADELMHYMI SEQGCYLASK   300
EEQDALTEVV LKGGRLNRKC VGRDAKTLLG MIGVTVPDNI RCITFEGPKE HPLIAEELMM   360
PILGVVRAKD FDDAVEQAVW LEHGNRHSAH IHSKNVDNIT KYAKAIDTAI LVKNGPSYAA   420
IGFGGEGFCT FTIASRTGEG LTSASAFTKR RRCVMCDSLC IR                     462
```

```
SEQ ID NO: 14              moltype = AA  length = 509
FEATURE                    Location/Qualifiers
source                     1..509
                           mol_type = protein
                           organism = Bacillus selenitireducens
SEQUENCE: 14
MSISEDMLKQ IVKSVMNNVE KELGESPKPQ PRTIPVTVLN EVTPVKESRD PSPVHQHVLG    60
VPPDVDQAVH AAAGSQKEWV KRPVSERRVI LEAMKQTVDS QKERYSELAV EETGLGNVAD   120
KIAKHELIIT KTPGVEDLRT DAVSGDHGLT IEEDAPFGVI GAVTPVTNPT TTVIHNSLVM   180
LAAGNAVVFN VHPSSKATCQ RVVSDLNAAI KDAGGPQNLI TMIAEPTLDT LNQLAGHQEI   240
RLLVGTGGQG LVRSLLQSGK KAIGAGAGNP PVIVDETADI EAAAKAIILG ASFDNNILCI   300
AEKEVFALDV IYDDLIYHLL QEGAYMLSES ELSQVMKTVL VGDAPIEAAK SCSVSVRPDL   360
HIAKAWVGKE ASAILKAATG KDLPVKLLIC DVEATHPFVQ LEQMMPVLPI VRMPDFDAAV   420
EAAVKABKGN RHTAVIHSKN VDRLTQFARR IETTIFVKNA SSLAGVGFGG EGYATMTIAG   480
PTGEGITSPR TFTRKRRCVL AEGGFRIIG                                    509

SEQ ID NO: 15              moltype = AA  length = 462
FEATURE                    Location/Qualifiers
source                     1..462
                           mol_type = protein
                           organism = Blautia obeum
SEQUENCE: 15
MPISESMVQD IVQEVMAKMQ IADAPTGKHG IFKDMNDAIE AAKKSELIVK KMSMDQREKI    60
ITCIRKKIKE NAEVMARMGV DETGMGNVGD KILKHHLVAD KTPGTEDITT TAWSGDRGLT   120
LIEMGPFGVI GAITPCTNPS ETILCNTMGM LAGGNTVVFN PHPAAIKTSI FAINLVNEAS   180
LEAGGPDNIA VTVEKPTLET SNIMMKHKDI PLIAATGGPG VVTAVLSSGK RGIGAGAGNP   240
PAVVDETADI RKAAQDIVNG CTFDNNLPCI AEKEVVAVSS VVDELMHYML TENDCYLASK   300
EEQDKLTEVV LAGGKLNRKC VGRDARTLLS MIGVNAPANI RCIIFEGPKE HPLITTELMM   360
PILGIVRAKD FDDAVEQAVW LEHGNRHSAH IHSKNVDNIT KYAKAIDTAI LVKNGPSYSA   420
LGFGGEGYCT FTIASRTGEG LTSASTFTKR RRCVMSDSLC IR                     462

SEQ ID NO: 16              moltype = AA  length = 478
FEATURE                    Location/Qualifiers
source                     1..478
                           mol_type = protein
                           organism = Clostridium bolteae
SEQUENCE: 16
MKEGVIRLDM DIKVIEQLVE QALKEIKAEQ PLKFTAPKLE RYGVFKTMDE AIAASEEAQK    60
KLLFSKISDR QKYVDVIRST IIKRENLELI SRLSVEETEI GDYEHKLIKN RLAAEKTPGT   120
EDLLTEAITG DNGLTLVEYC PFGVIGAITP TTNPTETIIN NSISMIAGGN TVVFSPHPRA   180
KKVSQMTVKM LNKALIDNGA PPNLITMVEE PSIENTNKMI DNPSVRLLVA TGGPSIVKKV   240
LSSGKKAIGA GAGNPPVVVD ETADIDKAAK DIVDGCSFDN NVPCIAEKEV FAVDSICDYL   300
IHHMKENGAY QITDPMLLEQ LVALVTTEKG GPKTSFVGKS ARYILDKLGI TVDASVRVII   360
MEVPKDHLLV QEEMMMPILP VVRVSDVDTA IEYAHQAEHG NRHTAMMHSK NVEKLSKMAK   420
IMETTIFVKN APSYAGIGVG GEGYTTFTIA GPTGEGLTSP RTFCRKRKCV MTDAFSIR    478

SEQ ID NO: 17              moltype = AA  length = 515
FEATURE                    Location/Qualifiers
source                     1..515
                           mol_type = protein
                           organism = Jeotgalibacillus alimentarius
SEQUENCE: 17
MSISEETLQQ IIKSVVTQVE SELGHKHSAP ATGSQSATPV APVKMKAVTN KPVFKEHTYR    60
SSGEGIYTTV DEAVSRSAAA QKKYVKHFTM NDRVTVLNAI KQTVLNLSEM LSKMAVEETG   120
IGCYEDKIQK HELVCKKTPG IEDLKTEAMS GDDGLTIIEE APFGVIGAVT PVTNPTTTII   180
NNSLSMLAAG NTVVFNVHPS SKKVCSYLIR ELHQSIVQAG GPADLITMVA DPTLDTLNEL   240
AAHPDIRLLV GTGGPGLVKS LLQSGKKAIG AGAGNPPVIV DETADLVNAA KSIILGASFD   300
HNLLCIAEKE VFVLEEAANE LIYQMLDQGA YMLNNEELSR VMSLVLTEDS SSPVAGGCTG   360
KPSKKYHVKK EWIGQSAAAI ARAAGINKEN IKLLICETDP DHPFVVLEQM MPVLPIVKTQ   420
SFEEAVEWAV AAEKGNRHTA VIHSTNVDRM TAFARAIETT IFVKNASSLA GVGFGGEGHT   480
TMTIAGPTGE GVTSARSFTR KRRCVLAEGG FRIIG                             515

SEQ ID NO: 18              moltype = AA  length = 470
FEATURE                    Location/Qualifiers
source                     1..470
                           mol_type = protein
                           organism = Clostridium hiranonis
SEQUENCE: 18
MKMELDLIQE MIKQVLEEIK EEGVEVSSKE EYGYGVFDSM VEAIDASEKA QKELFECSVQ    60
QRDKFVDAIR AEILKKENLE MISYDAVEET KIGRVEDKII KNRVAAENTP GTEDLKTRAI   120
TGEDGLTIEE YCPFGVIGSI TPTTNPTETL INNSISMIAG GNTVVFSPHP RAKKVSIKLV   180
KMMNKALEEA GAPRNLITMV KEPSIENSKI MMESPKVRLL VATGCPAIVK QVLSAGKKAI   240
GAGAGNPPVV VDETADIEKA AKDIVSGASF DNNVPCIAEK EVFAVESVVD QLIYYMKKNG   300
AYEITSPEVL EQLDKAVSKE NGKPNPSLVG KSAKELLALV GINVDDDVKL VIARTNKDHH   360
LVTEEMLMPI LPIVSVSDVD TAIDWAYEAE AGNRHTAIMH SKNVDKLTKM AKKLEATIFV   420
KNAPSYAGIG VGGEGHTTFT IAGPTGEGIT SAKSFCRIRR CVMSEALSIR              470

SEQ ID NO: 19              moltype = AA  length = 466
```

```
FEATURE                 Location/Qualifiers
source                  1..466
                        mol_type = protein
                        organism = Thermoanaerobacter sp.
SEQUENCE: 19
MIDENLVVTI TKKILNEINL KEAEEKKEKD NPDLGIFNDV NEAVECAKEA QKKFALMDLE    60
KREEIIAAIR EACVNNARLL AEIACSETGR GRVEDKVAKN ILAAKKTPGT EDLKPTAWTG   120
DRGLTLVEMA PVGVIASITP VTNPTATIIN NTISMLAAGN AVVFNPHPSA KKTSNKAVEI   180
INEAILKVGA PNGLVCSINN PTIQTAQKLM EHPEVNMVVV TGGKAVVQTA LRCGKKVIGA   240
GAGNPPVVVD ETADIVKAAH DIACGASFDN NLPCIAEKEI IAVERIADTL LERMKREGAY   300
VLHGKDIDRM TELIFQGGAI NKDLIGRDAH FILSQIGIET GKDIRLVVMP VDVSHPLVYH   360
EQLMPVIPFV TVPTVEEAIN LAVKAEGGNR HTAMMHSKNV ENMTAFARAI QTTIFVKNAP   420
SYAGIGFGGE GYTTFTIAGP TGEGLTSART FTRQRRCVLV DAFRIV                  466

SEQ ID NO: 20           moltype = AA  length = 462
FEATURE                 Location/Qualifiers
source                  1..462
                        mol_type = protein
                        organism = Clostridiales sp.
SEQUENCE: 20
MPINENMVQE IVQEVMAKMQ IADAPTGKHG IFKEMNDAIE AAKKSQLIVK KMSMDQREKI    60
ITCIRKKIKE NAEVMARMGV EETGMGNVGD KILKHHLVAD KTPGTEVITT TAWSGDRGLT   120
LIEMGPFGVI GAITPCTNPS ETILCNTMGM LAGGNTVVFN PHPAAIKTSI YAINLLNEAS   180
LESGGPDNIA VTVEKPTLET SNVMMKHKDI PLIAATGGPG VVTAVLSSGK RGIGAGAGNP   240
PALVDETADI RKAATDIVNG CTFDNNLPCI AEKEIVAVSS IVDELMHYLV TENDCYLASK   300
EEQDKLTEVV LAGGKLNRKC VGRDARTLLS MIGVNAPANI RCIVFEGPKE HPLITTELMM   360
PILGVVRARD FDDAVEQAVW LEHGNRHSAH IHSKNIDNIT KYAKAIDTAI LVKNAPSYAA   420
LGFGGEGYCT FTIASRTGEG LTCASTFTKR RRCVMADSLC IR                     462

SEQ ID NO: 21           moltype = AA  length = 468
FEATURE                 Location/Qualifiers
source                  1..468
                        mol_type = protein
                        organism = Sebaldella termitidis
SEQUENCE: 21
MLDGLQLEDI IKKVINDVKN EKDINITNKE NSCGHGIFTN IETAVDKAYE AQQTYNSRSL    60
EERRNIISNI RKELLKYTEE MAEKTVAETK MGRIKDKILK NKLAIEKTPG VEDLGTEVFT   120
GDDGLTLVEL SAFGVLGSVT PVTNPTETII NNTIGALAGG NSIVFCPHPS AKNICLWLIK   180
KLNGIITEAG GPENLVTSAS EAKKENVDIL FSHEKINMLV ITGGTEIVKL ALKSGKKVIG   240
AGAGNPPVIV DETADIEKAA KDIVNGAGFD NNLPCIAEKE VLVLESVADY LIFNMEKAGA   300
FHITDKEDIK KLEDTVYKNG MVNKEFIGKD AGFILEKSGI KCSFDPALIT LETDINHVFV   360
QKELMPPVLA VVRQKNFEEA LKNAILTEHG LKHTAVMHSQ NVTRLSIAAR EMQTTIFVKN   420
APSYAALGFQ GEGYTTFTIA GPTGEGLTSA RNFTRKRRCV LGGSFSIR                468

SEQ ID NO: 22           moltype = AA  length = 462
FEATURE                 Location/Qualifiers
source                  1..462
                        mol_type = protein
                        organism = Eubacterium plexicaudatum
SEQUENCE: 22
MSVNDQMVQD IVRQVLANMR ISSDASGSRG VFSDMNEAVE AAKKAQAVIG KMPMDHREKI    60
ISSIRAKIME NAEILARMGV KETGMGNVGH KILKHQLVAE KTPGTEDITT KAWSGDRGLT   120
LIEMGPFGVI GAITPCTNPS ETILCNTIGM VAGGNTVVFN PHPAAIKTSI FAVNLVNEAS   180
VEAGGPDNIA CTVEHPTLDT SAIMMKHKDI HLIAATGGPG VVTAVLSSGK RGIGAGAGNP   240
PALVDETADI RKAAEDIVNG CTFDNNLPCI AEKEIVAVSS IADELMHYMI SEQGCYLASA   300
KEQEALISVV LKGGQLNRDC VGRDAKTLLG MIGVQAPDNI RCITFEGPKE HPLITEELMM   360
PILGVVRADS FEDAVEKAVW LEHGNRHSAH IHSKNVDHIT TYAKAIDTAI LVKNGPSYAA   420
IGFGGEGYCT FTIASRTGEG LTSASAFTKR RRCVMCDSLC IR                     462

SEQ ID NO: 23           moltype = AA  length = 505
FEATURE                 Location/Qualifiers
source                  1..505
                        mol_type = protein
                        organism = Escherichia sp.
SEQUENCE: 23
MNDIEIAQAV STILSKFTKA TPDEAPATSE AARVDGLDEI VAKALAQHSS VRDASAISQV    60
AKVANASTGA FDTMDEAISA AVLAQVQYRH CSMQDRASFI NGIRDVFLQE DVLCALSRMA   120
VEETGMGNYE DKLIKNRVAA LKTPGIEDLT TSAVSGDGGL TLIEYSAFGV IGSITPTTNP   180
TETIINNSIG MLAAGNTVVF SPHPRSRKVS LYAVELINNK LAQLGAPANM VVTVTKPSID   240
NTNVLINDPR INMLVATGGP AIVKTVMSSG KKAIGAGAGN PPAVVDETAD IEKAARDIIK   300
GCSFDNNLPC VAEKEVIVVN QVADYLIHCM KKSGAYLLCD KKLSQQLQSL VLNEKGTGPN   360
TAFVGKDARY ILQQLGIQVG DDIKVILIEA EKTHPFVVHE LMMPVLPVVR VDNVDEAIEL   420
AVKVEHGNRH TAVMHSTNVE KLTKMARLIQ TTIFVKNGPS YAGLGVGGEG HATFTIAGPT   480
GEGLTSARSF ARRRRCVMVE ALNIR                                         505

SEQ ID NO: 24           moltype = AA  length = 529
FEATURE                 Location/Qualifiers
source                  1..529
                        mol_type = protein
```

```
                        organism = Rhodospirillum rubrum
SEQUENCE: 24
MNDGQIAAAV  AKVLEAYGVP  ADPSAAAPAP  AAPVAPAAPT  AGSVSEMIAR  GIAKASSDDQ   60
IAQIVAKVVG  DYSAQAAKPA  VVPGAAASTE  AGDGVFDTMD  AAVDAAVLAQ  QQYLLCSMTD  120
RQRFVDGIRE  VILQKDTLEL  ISRMAAEETG  MGNYEHKLIK  NRLAAEKTPG  TEDLTTEAFS  180
GDDDGLTLVEY SPFGAIGAVA  PTTNPTETII  CNSIGMLAAG  NSVIFSPHPR  ATKVSLLTVK  240
LINQKLACLG  APANLVVTVS  KPSVENTNAM  MAHPKIRMLV  ATGGPGIVKA  VMSTGKKAIG  300
AGAGNPPVVV  DETADIEKAA  LDIINGCSFD  NNLPCIAEKE  IIAVAQIADY  LIFSMKKQGA  360
YQITDPAVLR  KLQDLVLTAK  GGPQTSCVGK  SAVWLLNKIG  IEVDSSVKVI  LMEVPKEHPF  420
VQEELMMPIL  PLVRVSDVDE  AIAVAIEVEH  GNRHTAIMHS  TNVRKLTKMA  KLIQTTIFVK  480
NGPSYAGLGV  GGEGYTTFTI  AGPTGEGLTS  AKSFARKRKC  VMVEALNIR               529

SEQ ID NO: 25           moltype = AA  length = 472
FEATURE                 Location/Qualifiers
source                  1..472
                        mol_type = protein
                        organism = Clostridium beijerinckii
SEQUENCE: 25
MDVDVVLVEK  LVRQAIEEVK  NKNLLNLDKF  ESVKNYGIFG  TMDAAVEASF  VAQKQLLNAS   60
MTDKQKYVDT  IKATILKKEN  LELISRMSVE  ETEIGKYEHK  LIKNRVAAEK  TPGIEDLTTE  120
AMTGDNGLTL  VEYCPFGVIG  AITPTTNPTE  TIICNSISMI  AGGNTVVFSP  HPRAKNVSIK  180
LVTMLNKALE  EAGAPDNLIA  TVKEPSIENT  NIMMEHPKIR  MLVATGGPAI  VNKVMSTGKK  240
AIGAGAGNPP  VVVDETADIE  KAAIDIVNGC  SFDNNVPCIA  EKEVFAVDQI  CDYLIHYMKL  300
NGAYEIKDRD  LIQKLLDLVT  NENGGPKVSF  VGKSAPYILN  KLGISVDENI  KVIIMEVEKN  360
HHFVLEEMMM  PILPIVRTKD  VDEAIECAYV  AEHGNRHTAI  MHSKNVDKLT  KMARLLETTI  420
FVKNAPSYAG  IGVGGEGTTT  FTIAGPTGEG  LTTARSFCRK  RRCVMVDAFN  IR          472

SEQ ID NO: 26           moltype = AA  length = 468
FEATURE                 Location/Qualifiers
source                  1..468
                        mol_type = protein
                        organism = Eubacterium hallii
SEQUENCE: 26
MNIDVELIEK  VVKKVLNDVE  TGSSESEYGY  GIFDTMDEAI  EASAKAQKEY  MNHSMADRQR   60
YVEGIREVVC  TKENLEYMSK  LAVEESGMGA  YEYKVIKNRL  AAVKSPGVED  LTTEALSGDD  120
GLTLVEYCPF  GVIGAIAPTT  NPTETVICNS  IAMLAGGNTV  VFSPHPRSKG  VSIWLIKKLN  180
AKLEELGAPR  NLIVTVKEPS  IENTNIMMNH  PKVRMLVATG  GPGIVKAVMS  TGKKAIGAGA  240
GNPPVVVDET  ADIEKAAKDI  VNGCSFDNNL  PCIAEKEVIA  VQDIADYLIF  NMKNNGAYEV  300
KDPEIIEKMV  DLVTKDRKKP  AVNFVGKSAQ  YILDKVGIKV  GPEVKCIIME  APKDHPFVQI  360
ELMMPILPIV  RVPNVDEAID  FAVEVEHGNR  HTAMMHSKNV  DKLTKMAKEI  ETTIFVKNGP  420
SYAGIGVGGM  GYTTFTIAGP  TGEGLTSAKS  FCRKRRCVLQ  DGLHIRMK                468

SEQ ID NO: 27           moltype = AA  length = 532
FEATURE                 Location/Qualifiers
source                  1..532
                        mol_type = protein
                        organism = Vibrio sp.
SEQUENCE: 27
MNEQEIAHAV  ENVLSKYTNV  TAQNAEPVSY  SSNASLENIV  SQALAGNMVK  QPETQTAPDL   60
NSNIENIVSQ  ILAENQAKPQ  SVQCQSANHG  TTEYLGCFAS  MEEAISAASH  AQVQYRHCTM  120
GDRASFVKGI  REVFTQDDVL  EKISRMAVEE  TGMGNYADKL  TKNRIAATKT  PGIEDLTTSA  180
LSGDSGLTLT  EFSAYGVIGS  ITPTTNPTET  IINNSIGMLA  AGNTVVYSPH  PRSRNVSLVA  240
VDLINRKLAE  LGAPANLVVT  VLEPSIDNTN  AMMNDPRVNM  LVATGGPSIV  KTVMSTGKKA  300
IGAGAGNPPA  VVDETANIEK  AAKDIINGCA  FDNNLPCIAE  KEVIVVNEVA  DYLIHCMKKS  360
GAYLLCDKQK  IQQLQSLVLN  EKGTGPNTSF  VGKGARYILD  KLNIQVSDDI  KVILIETERN  420
HPFVVHELMM  PILPLVRVEN  VDEAIDLAIK  VEHGNRHTAI  MHSTNVEKLS  KMARLIQTTI  480
FVKNGPSYSG  IGVGGEGHTT  FTIAGPTGEG  ITSARSFARY  RRCVMVEALN  IR          532

SEQ ID NO: 28           moltype = AA  length = 464
FEATURE                 Location/Qualifiers
source                  1..464
                        mol_type = protein
                        organism = Rhodopseudomonas palustris
SEQUENCE: 28
MVAKAIRDHA  GTAQPSGNAA  TSSAAVSDGV  FETMDAAVEA  AALAQQQYLL  CSMSDRARFV   60
QGIRDVILNQ  DTLEKMSRMA  VEETGMGNYE  HKLIKNRLAG  EKTPGIEDLT  TDAFSGDNGL  120
TLVEYSPFGV  IGAITPTTNP  TETIVCNSIG  MLAAGNSVVF  SPHPRARQVS  LLLVRLINQK  180
LAALGAPENL  VVTVEKPSIE  NTNAMMAHPK  VRMLVATGGP  AIVKAVLSTG  KKAIGAGAGN  240
PPVVVDETAN  IEKAACDIVN  GCSFDNNLPC  VAEKEIIAVA  QIADYLIFNL  KKNGAYEIKD  300
PAVLQQLQDL  VLTAKGGPQT  KCVGKSAVWL  LSQIGISVDA  SIKIILMEVP  REHPFVQEEL  360
MMPILPLVRV  ETVDDAIDLA  IEVEHDNRHT  AIMHSTDVRK  LTKMAKLIQT  TIFVKNGPSY  420
AGLGAGGEGY  STFTIAGPTG  EGLTSAKSFA  RRRKCVMVEA  LNIR                    464

SEQ ID NO: 29           moltype = AA  length = 468
FEATURE                 Location/Qualifiers
source                  1..468
                        mol_type = protein
                        organism = Desulfatibacillum alkenivorans
SEQUENCE: 29
```

```
MSVKEFALED MVASVIMEMM NKDDDSCQPT GDGIYETIDE AVAKAKAAQP RLISLSLEKR    60
EAILTAIRKI SLEKNEEWAK ATVAETGLGR VEDKIAENIL AATKTPGTED LDAKALSGDA   120
GLTLIEYAPF GVIGSLTPVT NATGTLINNT ISMLAGGNTV VYNVHPSALK ISTEVIRTFH   180
KVIVENGGPE GCVGMVATPT METAGEIMAH PDINVLVATG GAGVVKAVLS SGKKAIGAGA   240
GNPPVLVDET ACIRKAAEEI IAGHSINNNI FCISEKEVIA VDEVADNLLK FMEETGKAAI   300
LTPEEAQKVT ETVIHDNHVV KDYVGKNASV IIEGAGLTRL AGKKDLRCLV FEADCKHPMV   360
WIEQMMPVLP MVRVKDVWEG IDLAVKVEQG NRHTAMMHST NVEHLTALAR AIQTTIFVKN   420
GPSYSGIGLN GEGHATFTIA GPTGEGITSA KSFCRQRRCV LIDSFRIV                468

SEQ ID NO: 30           moltype = AA  length = 469
FEATURE                 Location/Qualifiers
source                  1..469
                        mol_type = protein
                        organism = Clostridium saccharobutylicum
SEQUENCE: 30
MNNNLFVSPE TKDLKLRTNV ENLKFKGCEG GSTYIGVFEN AETAIDEAVN AQKRLSLYYT    60
KEQREKIITE IRKVTLKNKE ILAQMILEET HMGRYEDKIL KHELVAKYTP GTEDLATTAW   120
SGDNGLTVVE MSPYGVIGAI TPSTNPTETI ICNSIGMIAS GNAVVFNGHP GAKKCVAFAV   180
DMINRAIISC GGPRNLVTAI KNPTMESLDA IIKHPAIKLL CGTGGPGMVK TLLSSGKKSI   240
GAGAGNPPVI VDDTADIEKA GKSIIEGCSF DNNLPCIAEK EVFVFENVAD DLIKNMLKNN   300
AVIINKDQVS RLVNLVLQKN NETSEYTINK KWVGKDAKLF LDEIDVESSS DVRCIICEVD   360
ADHPFVMTEL MMPILPIVRV KDIDEAIKYA KIAEQNRKHS AYIYSKNIEN LNRFEKEIDT   420
TIFVKNAKSF AGVGYGAEGF TTFTIAGCTG EGITSARNFT RQRRCVFVG               469

SEQ ID NO: 31           moltype = AA  length = 468
FEATURE                 Location/Qualifiers
source                  1..468
                        mol_type = protein
                        organism = Clostridium sp.
SEQUENCE: 31
MNKDTTISET ENLKFKTNIK NADLKNYENS TSYSGVFEDV EVAINKAITA QKEFSLYYTK    60
EQREKILTEI RKATLKNKKI LAKMILDETH MGRYEDKILK HELVAKYTPG IEDLTTTAWS   120
GDNGLTVVEM APYGVIGAIT PSTNPTETVI CNSIGMIAAG NAVVFNGHPS AKKCVAFAVD   180
MINKAIVSCG GPKNLITAVK NPTMESLDAI IKHPEIKLLC GTGGPGMVKT LLNSGKKAIG   240
AGAGNPPVIV DDTADIEKAG KNIIEGCSFD NNLPCIAEKE VFVFDNVADN LIDNMLKNNA   300
VIINKDITK LLNLILQKNN ETQEYNINKK WVGKDAKLFL NEIDVEAPSS VRCIICEVEP    360
DHPFVMTELM MPILPIVRVK NIDDAIQYAK IAEQSRKHSA YIYSKNIDNL NRFEKEIDTT   420
IFVKNAKSFA GVGYNAEGFT TFTIAGCTGE GITSARNFTR QRRCVLAG                468

SEQ ID NO: 32           moltype = AA  length = 467
FEATURE                 Location/Qualifiers
source                  1..467
                        mol_type = protein
                        organism = Clostridium taeniosporum
SEQUENCE: 32
MERNLSVLSQ KKNLKITRKV EGNKSINKES YLGVFEKVDN AITKAIYAQR KLSLYYTKED    60
RERIIEGIRK ATLENKEILA KMIVDETHMG RYEDKILKHE LVAKYTPGTE DLITTAWSGD   120
QGLTLVEMSP YGVIGAITPS TNPTETVICN SIGMIAAGNS VVFNGHPGAK KCVAFAVDMI   180
NKAIIKCGGP ENLVTTVENP TMDSLNVIMK HPYVKLLCGT GGPGLIKTLL NSGKAIGAG    240
AGNPPVIVDD SADIKHAAKS IIEGCSFDNN LPCIAEKEVF VFENVADDLI QNMLKNNAVL   300
INENEVSKLL DLVLIEKKDE PSGYVINKKW VGKDAKLFLG KIGKKVSDDV KCIICEVDN    360
HPFVMTELMM PILAIARVKD IDEAIECAKT AEQGKRHSAY MYSKNIDNLN RFEKEIDTTI   420
FVKNAKSFAG VGFGAEGFTT FTIAGPTGEG ITSARNFTRQ RRCVLAG                 467

SEQ ID NO: 33           moltype = AA  length = 467
FEATURE                 Location/Qualifiers
source                  1..467
                        mol_type = protein
                        organism = Clostridium botulinum
SEQUENCE: 33
MERNLSVLSQ TNDLKITKRT EGDKSNNKES YLGVFKKVEN AITKAIYAQK KLSLYYTKED    60
RERIIKSIRK ATLENKEILA KMIVDETHMG RYEDKILKHE LVAKYTPGTE DLITTAWSGD   120
QGLTLVEMSP YGVIGAITPS TNPTETVICN SIGMIAAGDS VVFNGHPGAK KCVAFAVDMI   180
NKAVIREGGP ENLVTTVENP TMESLNVIMK HPYIKLLCGT GGPGLIKTLL NSGKKAIGAG   240
AGNPPVIVDD SADIDKAAKN IIEGCSFDNN LPCIAEKEVF VFENVANDLI QNMIKNNAVL   300
INENQVSKLL DLVLLERKDE TLEYAINKKW VGKDAKLFLD KIGIKASDNV RCIICEVDAN   360
HPFVMTELMM PILPIVRVKD VDEAIECAKT AEQRKRHSAY MYSKNIDNLN RFEKEIDTTI   420
FVKNAKSFAG VGFGAEGFTT FTIAGPTGEG ITSARNFTRQ RRCVLAG                 467

SEQ ID NO: 34           moltype = AA  length = 467
FEATURE                 Location/Qualifiers
source                  1..467
                        mol_type = protein
                        organism = Clostridium botulinum
SEQUENCE: 34
MKRNLSVLLQ TNDLKITKRT EGDKSNNKES YLGVFKKVEN AITKAIYAQK KLSLYYTKED    60
RERIIKGIRK ATLENKEILA KMIVDETHMG RYEDKILKHE LVAKYTPGTE DLITTAWSGD   120
QGLTLVEMSP YGVIGAITPS TNPTETVICN SIGMIAAGDS VVFNGHPGAK KCVAFAVDMI   180
NKAVIKAGGP ENLVTTVENP TMESLNVIMK HPYIKLLCGT GGPGLIKTLL NSGKKAIGAG   240
```

```
AGNPPVIVDD SADINKAAKN IIEGCSFDNN SPCIAEKEVF VFENVANDLI QNMIKNNAVL     300
INENQVSKLL DLVLLERKDE TLEYAINKKW VGKDAKLFLD KIGIKSSDNV RCIIICEVDAN    360
HPFVMTELMM PILPIVRVKD VDEAIECAKT AEQRKRHSAY MYSKNIDNLN RFEKEIDTTI     420
FVKNAKSFAG VGFGAEGFTT FTIAGPTGEG ITSARNFTRQ RRCVLAG                   467

SEQ ID NO: 35           moltype = AA   length = 467
FEATURE                 Location/Qualifiers
source                  1..467
                        mol_type = protein
                        organism = Clostridium botulinum
SEQUENCE: 35
MKRNLSVLLQ TNDLKITKRT EGDKSNNKES YLGVFKKVEN AITEAIYAQK KLSLYYTKED     60
RERIIKGIRK ATLENKEILA KMIVDETHMG RYEDKILKHE LVAKYTPGTE DLITTAWSGD    120
QGLTLVEMSP YGVIGAITPS TNPTETVICN SIGMIAAGDS VVFNGHPGAK KCVAFAVDMI    180
NKAVIKAGGP ENLVTTVENP TMESLNVIMK HPYIKLLCGT GGPGLIKTLL NSGKKAIGAG    240
AGNPPVIVDD SADINKAAKN IIEGCSFDNN SPCIAEKEVF VFENVANDLI QNMIKNNAVL    300
INENQVSKLL DLVLLERKDE TLEYAINKKW VGKDAKLFLD KIGIKSSDNV RCIIICEVDAN   360
HPFVMTELMM PILPIVRVKD VDEAIECAKT AEQRKRHSAY MYSKNIDNLN RFEKEIDTTI    420
FVKNAKSFAG VGFGAEGFTT FTIAGPTGEG ITSARNFTRQ RRCVLAG                  467

SEQ ID NO: 36           moltype = AA   length = 467
FEATURE                 Location/Qualifiers
source                  1..467
                        mol_type = protein
                        organism = Clostridium botulinum
SEQUENCE: 36
MKRNLSVLLQ TNDLKITKRT EGDKSNNKES YLGVFKKVEN AITKAIYSQK KLSLYYTKED     60
RERIIKGIRK ATLENKEILA KMIVDETHMG RYEDKILKHE LVAKYTPGTE DLITTAWSGD    120
QGLTLVEMSP YGVIGAITPS TNPTETVICN SIGMIAAGDS VVFNGHPGAK KCVAFAVDMI    180
NKAVIKAGGP ENLVTTVENP TMESLNVIMK HPYIKLLCGT GGPGLIKTLL NSGKKAIGAG    240
AGNPPVIVDD SADINKAAKN IIEGCSFDNN SPCIAEKEVF VFENVANDLI QNMIKNNAVL    300
INENQVSKLL DLVLLERKDE TLEYAINKKW VGKDAKLFLD KIGIKSSDNV RCIIICEVDAN   360
HPFVMTELMM PILPIVRVKD VDEAIECAKT AEQRKRHSAY MYSKNIDNLN RFEKEIDTTI    420
FVKNAKSFAG VGFGAEGFTT FTIAGPTGEG ITSARNFTRQ RRCVLAG                  467

SEQ ID NO: 37           moltype = AA   length = 472
FEATURE                 Location/Qualifiers
source                  1..472
                        mol_type = protein
                        organism = Clostridium beijerinckii
SEQUENCE: 37
MDVDVVLVEK LVRQAIEEVK NKNLLNLDKF ESVKNYGIFG TMDAAVEASF VAQKQLLNAS     60
MTDKQKYVDT IKATILKKEN LELISRMSVE ETEIGKYEHK LIKNRVAAEK TPGIEDLTTE    120
AMTGDNGLTL VEYCPFGVIG AITPTTNPTE TIICNSISMI AGGNTVVFSP HPRAKNVSIK    180
LVTMLNKALE EAGAPDNLIA TVKEPSIENT NIMMEHPKIR MLVATGGPAI VNKVMSTGKK    240
AIGAGAGNPP VVVDETADIE KAAIDIVNGC SFDNNVPCIA EKEVFAVDQV CDYLIHYMKL    300
NGAYEIKDRD LIQKLLDLVT NENGGPKVSF VGKSAPYILN KLGISVDENI KVIIMEVEKN    360
HHFVLEEMMM PILPVRTKD VDEAIECAYV AEHGNRHTAI MHSKNVDKLT KMARLLETTI     420
FVKNSPSYAG IGVGGEGTTT FTIAGPTGEG LTTARSFCRK RRCVMVDAFN IR            472

SEQ ID NO: 38           moltype = AA   length = 468
FEATURE                 Location/Qualifiers
source                  1..468
                        mol_type = protein
                        organism = Clostridium saccharoperbutylacetonicum
SEQUENCE: 38
MIKDTLVSIT KDLKLKTNVE NANLKNYKDD SSCFGVFENV ENAISNAVHA QKILSLHYTK     60
EQREKIITEI RKAALENKEI LATMILEETH MGRYEDKILK HELVAKYTPG TEDLTTTAWS    120
GDNGLTVVEM SPYGVIGAIT PSTNPTETVI CNSIGMIAAG AKKCVAFAVE              180
MINKAIISCG GPENLVTTIK NPTMDSLDAI IKHPSIKLLC GTGGPGMVKT LLNSGKKAIG    240
AGAGNPPVIV DDTADIEKAG KSIIEGCSFD NNLPCIAEKE VFVFENVADD LISNMLKNNA    300
VIIINEDQVSK LIDLVLQKNN ETQEYSINKK WVGKDAKLFL DEIDVESPSS VKCIICEVSA   360
SHPFVMTELM MPILPIVRVK DIDEAIEYAK IAEQNRKHSA YIYSKNIDNL NRFEREIDTT    420
IFVKNAKSFA GVGYEAEGFT TFTIAGSTGE GITSARNFTR QRRCVLAG                 468

SEQ ID NO: 39           moltype = AA   length = 468
FEATURE                 Location/Qualifiers
source                  1..468
                        mol_type = protein
                        organism = Clostridium sp.
SEQUENCE: 39
MIKDTLVSVT KDLKLKTNVE NINLKNYKDN SSCFGVFENV ENAISSAVHA QKILSLHYTK     60
EQREKIITEI RKAALQNKEV LATMILEETH MGRCEDKILK HELVAKYTPG TEDLTTTAWS    120
GDNGLTVVEM SPYGVIGAIT PSTNPTETVI CNSIGMIAAG NAVVFNGHPG AKKCVAFAVE    180
MINKAIISCG GPENLVTTIK NPTMESLDAI IKHPSIKLLC GTGGPGMVKT LLNSGKKAIG    240
AGAGNPPVIV DDTADIEKAG RSIIEGCSFD NNLPCIAEKE VFVFENVADD LISNMLKNNA    300
VIIINEDQVSK LIDLVLQKNN ETQEYSINKK WVGKDAKLFL DEIDVESPSN VKCIICEVNA   360
NHPFVMTELM MPILPIVRVK DIDEAIKYAK IAEQNRKHSA YIYSKNIDNL NRFEREIDTT    420
IFVKNAKSFA GVGYEAEGFT TFTIAGSTGE GITSARNFTR QRRCVLAG                 468
```

```
SEQ ID NO: 40              moltype = AA  length = 468
FEATURE                    Location/Qualifiers
source                     1..468
                           mol_type = protein
                           organism = Clostridium beijerinckii
SEQUENCE: 40
MIKDTLVSVT KDLKLKTNVE NTNLKNYKDN SSCFGVFENA ENAISNAVHA QKILSLHYTK    60
EQREKIINEI RKAALENKEV LATMILEETH MGRYEDKILK HELVAKYTPG TEDLTTTAWS   120
GDNGLTVVEM SPYGVIGAIT PSTNPTETVL CNSIGMIAAG NAVVFNGHPG AKKCVAFAVE   180
MINKAIVSCG GPENLVTTIK NPTMESLNAI IKHPSIELLC GTGGPGMVKT LLNSGKKAIG   240
AGAGNPPVIV DDTADIEKAG KSIIEGCSFD NNLPCIAEKE VFVFENIADD LISNMLKNNA   300
VIINEDQVSK LIDLVLQKNN ETQEYSINKK WVGKDAKLFL DEIDVESPSN VKCIICEVNA   360
NHPFVMTELM MPILPIVRVK DIDEAIEYAK IAEQNRKHSA YIYSKNIDNL NRFEREIDTT   420
IFVKNAKSFA GVGYEAEGFT TFTIAGSTGE GITSARNFTR QRRCVLAG               468

SEQ ID NO: 41              moltype = AA  length = 468
FEATURE                    Location/Qualifiers
source                     1..468
                           mol_type = protein
                           organism = Clostridium beijerinckii
SEQUENCE: 41
MNKDTLIPTT KDLKLKTNVE NINLKNYKDN SSCFGVFENV ENAINSAVHA QKILSLHYTK    60
EQREKIITEI RKAALENKEV LATMILEETH MGRYEDKILK HELVAKYTPG TEDLTTTAWS   120
GDNGLTVVEM SPYGVIGAIT PSTNPTETVI CNSIGMIAAG NAVVFNGHPG AKKCVAFAIE   180
MINKAIISCG GPENLVTTIK NPTMESLDAI IKHPLIKLLC GTGGPGMVKT LLNSGKKAIG   240
AGAGNPPVIV DDTADIEKAG KSIIEGCSFD NNLPCIAEKE VFVFENVADD LISNMLKNNA   300
VIINEDQVSK LIDLVLQKNN ETQEYFINKK WVGKDAKLFS DEIDVESPSN IKCIVCEVNA   360
NHPFVMTELM MPILPIVRVK DIDEAVKYTK IAEQNRKHSA YIYSKNIDNL NRFEREIDTT   420
IFVKNAKSFA GVGYEAEGFT TFTIAGSTGE GITSARNFTR QRRCVLAG               468

SEQ ID NO: 42              moltype = AA  length = 468
FEATURE                    Location/Qualifiers
source                     1..468
                           mol_type = protein
                           organism = Clostridium beijerinckii
SEQUENCE: 42
MNKDTLIPTT KDLKVKTNGE NINLKNYKDN SSCFGVFENV ENAISSAVHA QKILSLHYTK    60
EQREKIITEI RKAALQNKEV LATMILEETH MGRYEDKILK HELVAKYTPG TEDLTTTAWS   120
GDNGLTVVEM SPYGVIGAIT PSTNPTETVI CNSIGMIAAG NAVVFNGHPC AKKCVAFAVE   180
MINKAIISCG GPENLVTTIK NPTMESLDAI IKHPSIKLLC GTGGPGMVKT LLNSGKKAIG   240
AGAGNPPVIV DDTADIEKAG RSIIEGCSFD NNLPCIAEKE VFVFENVADD LISNMLKNNA   300
VIINEDQVSK LIDLVLQKNN ETQEYFINKK WVGKDAKLFL DEIDVESPSN VKCIICEVNA   360
NHPFVMTELM MPILPIVRVK DIDEAIKYAK IAEQNRKHSA YIYSKNIDNL NRFEREIDTT   420
IFVKNAKSFA GVGYEAEGFT TFTIAGSTGE GITSARNFTR QRRCVLAG               468

SEQ ID NO: 43              moltype = AA  length = 468
FEATURE                    Location/Qualifiers
source                     1..468
                           mol_type = protein
                           organism = Clostridium beijerinckii
SEQUENCE: 43
MIKDTLVSVT KDLKLKTNVE NINLKNYKDN SSCFGVFENV ENAISSAVQA QKILSIHYTK    60
EQREKIITEI RKAALQNKEV LATMILEETH MGRYEDKILK HELVAKYTPG TEDLTTTAWS   120
GDNGLTVVEM SPYGVIGAIT PSTNPTETVI CNSIGMIAAG NAVVFNGHPG AKKCVAFAVE   180
MINKAIISCG GPENLVTTIK NPTMESLDAI IKHPSIKLLC GTGGPGMVKT LLNSGKKAIG   240
AGAGNPPVIV DDTADIEKAG RSIIEGCSFD NNLPCIAEKE VFVFENVADD LISNMLKNNA   300
VIINEDQVSK LIDLVLQKNN ETQEYFINKK WVGKDAKLFL DEIDVESPSN VKCIICEVNA   360
NHPFVMTELM MPILPIVRVK DIDEAIKYAK IAEQNRKHSA YIYSKNIDNL NRFEREIDTT   420
IFVKNAKSFA GVGYEAEGFT TFTIAGSTGE GITSARNFTR QRRCVLAG               468

SEQ ID NO: 44              moltype = AA  length = 468
FEATURE                    Location/Qualifiers
source                     1..468
                           mol_type = protein
                           organism = Clostridium beijerinckii
SEQUENCE: 44
MNKDTLIPTT KDLKVKTNGE NINLKNYKDN SSCFGVFENV ENAISSAVHA QKILSLHYTK    60
EQREKIITEI RKAALQNKEV LATMILEETH MGRYEDKILK HELVAKYTPG TEDLTTTAWS   120
GDNGLTVVEM SPYGVIGAIT PSTNPTETVI CNSIGMIAAG NAVVFNGHPG AKKCVAFAVE   180
MINKAIISCG GPENLVTTIK NPTMESLDAI IKHPSIKLLC GTGGPGMVKT LLNSGKKAIG   240
AGAGNPPVIV DDTADIEKAG RSIIEGCSFD NNLPCIAEKE VFVFENVADD LISNMLKNNA   300
VIINEDQISK LIDLVLQKNN ETQEYFINKK WVGKDAKLFL DEIDIESPSN VKCIICEVNE   360
NHPFVMTELM MPILPIVRVK DIDEAIRYAK IAEQNRKHSA YIYSKNIDNL NRFEREIDTT   420
IFVKNAKSFA GVGYEAEGFT TFTIAGSTGE GITSARNFTR QRRCVLAG               468

SEQ ID NO: 45              moltype = AA  length = 468
FEATURE                    Location/Qualifiers
source                     1..468
```

```
                          mol_type = protein
                          organism = Clostridium beijerinckii
SEQUENCE: 45
MNKDTLIPTT KDLKVKTNDE NINLKNYKDN SSCFGVFENV ENAISSAVHA QKILSIHYTK   60
EQREKIITEI RKAALQNKEA LATMILEETH MGRYEDKILK HELVAKYTPG TEDLTTTAWS  120
GDNGLTVVEM SPYGVIGAIT PSTNPTETVI CNSIGMIAAG NAVVFNGHPS AKKCVAFAVE  180
MINKAIISCG GPENLVTTIK NPTMESLDAI IKHPSIKLLC GTGGPGMVKT LLNSGKKAIG  240
AGAGANPPVIV DDTADIEKAG RSIIEGCSFD NNLPCIAEKE VFVFENVADD LISNMLKNNA  300
VIINEDQVSK LIDLVLQKNN ETQEYFINKK WVGKDAKLFL DEIDVESPSN VKCIICEVNA  360
NHPFVMTELM MPILPIVRVK DIDEAIKYAK IAEQNRKHSA YIYSKNIDNL NRFEREIDTT  420
IFVKNAKSFA GVGYEAEGFT TFTIAGSTGE GITSARNFTR QRRCVLAG              468

SEQ ID NO: 46             moltype = AA  length = 468
FEATURE                   Location/Qualifiers
source                    1..468
                          mol_type = protein
                          organism = Clostridium saccharoperbutylacetonicum
SEQUENCE: 46
MIKDTLVSIT KDLKLKTNVE NANLKNYKDD SSCFGVFENV ENAISNAVHA QKILSLHYTK   60
EQREKIITEI RKAALENKEI LATMILEETH MGRYEDKILK HELVAKYTPG TEDLTTTAWS  120
GDNGLTVVEM SPYGVIGAIT PSTNPTETVI CNSIGMIAAG NTVVFNGHPG AKKCVAFAVE  180
MINKAIISCG GPENLVTTIK NPTMDSLDAI IKHPSIKLLC GTGGPGMVKT LLNSGKKAIG  240
AGAGANPPVIV DDTADIEKAG KSIIEGCSFD NNLPCIAEKE VFVFENVADD LISNMLKNNA  300
VIINEDQVSK LIDLVLQKNN ETQEYSINKK WVGKDAKLFL DEIDVESPSS VKCIICEVSA  360
SHPFVMTELM MPILPIVRVK DIDEAIEYAK IAEQNRKHSA YIYSKNIDNL NRFEREIDTT  420
IFVKNAKSFA GVGYEAEGFT TFTIAGSTGE GITSARNFTR QRRCVLAG              468

SEQ ID NO: 47             moltype = AA  length = 468
FEATURE                   Location/Qualifiers
source                    1..468
                          mol_type = protein
                          organism = Clostridium beijerinckii
SEQUENCE: 47
MNKDTLIPTT KDLKVKTNGE NINLKNYKDN SSCFGVFENV ENAISSAVHA QKILSLHYTK   60
EQREKIITEI RKAALQNKEV LATMILEETH MGRYEDKILK HELVAKYTPG TEDLTTTAWS  120
GDNGLTVVEM SPYGVIGAIT PSTNPTETVI CNSIGMIAAG NAVVFNGHPC AKKCVAFAVE  180
MINKAIISCG GPENLVTTIK NPTMESLDAI IKHPSIKLLC GTGGPGMVKT LLNSGKKAIG  240
AGAGANPPVIV DDTADIEKAG RSIIEGCSFD NNLPCIAEKE VFVFENVADD LISNMLKNNA  300
VIINEDQVSK LIDLVLQKNN ETQEYFINKK WVGKDAKLFL DEIDVESPSN VKCIICEVNA  360
NHPFVMTELM MPILPIVRVK DIDEAIKYAK IAEQNRKHSA YIYSKNIDNL NRFEREIDTT  420
IFVKNAKSFA GVGYEAEGFT TFTIAGSTGE GITSARNFTR QRRCVLAG              468

SEQ ID NO: 48             moltype = AA  length = 468
FEATURE                   Location/Qualifiers
source                    1..468
                          mol_type = protein
                          organism = Clostridium beijerinckii
SEQUENCE: 48
MNKDTLIPTT KDLKLKTNVE NINLKNYKDN SSCFGVFENV ENAINSAVHA QKILSLHYTK   60
EQREKIITEI RKAALENKEV LATMILEETH MGRYEDKILK HELVAKYTPG TEDLTTTAWS  120
GDNGLTVVEM SPYGVIGAIT PSTNPTETVI CNSIGMIAAG NAVVFNGHPS AKKCVAFAVE  180
MINKAIISCG GPENLVTTIK NPTMESLDAI IKHPLIKLLC GTGGPGMVKT LLNSGKKAIG  240
AGAGANPPVIV DDTADIEKAG KSIIEGCSFD NNLPCIAEKE VFVFENVADD LISNMLKNNA  300
VIINEDQVSK LIDLVLQKNN ETQEYFINKK WVGKDAKLFS DEIDVESPSN IKCIVCEVNA  360
NHPFVMTELM MPILPIVRVK DIDEAVKYTK IAEQNRKHSA YIYSKNIDNL NRFEREIDTT  420
IFVKNAKSFA GVGYEAEGFT TFTIAGSTGE GITSARNFTR QRRCVLAG              468

SEQ ID NO: 49             moltype = AA  length = 468
FEATURE                   Location/Qualifiers
source                    1..468
                          mol_type = protein
                          organism = Clostridium sp.
SEQUENCE: 49
MNKDTTISET ENLKFKTNIK NADLKNYENS TSYSGVFEDV EVAINKAITA QKEFSLYYTK   60
EQREKILTEI RKATLKNKKI LAKMILDETH MGRYEDKILK HELVAKYTPG IEDLTTTAWS  120
GDNGLTVVEM APYGVIGAIT PSTNPTETVI CNSIGMIAAG NAVVFNGHPS AKKCVAFAVD  180
MINKAIVSCG GPKNLITAVK NPTMESLDAI IKHPEIKLLC GTGGPGMVKT LLNSGKKAIG  240
AGAGANPPVIV DDTADIEKAG KNIIEGCSFD NNLPCIAEKE VFVFDNVADN LIDNMLKNNA  300
VIINDKITK LLNLILQKNN ETQEYNINKK WVGKDAKLFL NEIDVEAPSS VRCIICEVEP  360
DHPFVMTELM MPILPIVRVK NIDDAIQYAK IAEQSRKHSA YIYSKNIDNL NRFEKEIDTT  420
IFVKNAKSFA GVGYNAEGFT TFTIAGCTGE GITSARNFTR QRRCVLAG              468

SEQ ID NO: 50             moltype = AA  length = 469
FEATURE                   Location/Qualifiers
source                    1..469
                          mol_type = protein
                          organism = Clostridium saccharobutylicum
SEQUENCE: 50
MNNNLFVSPE TKDLKLRTNV ENLKFKGCEG GSTYIGVFEN AETAIDEAVN AQKRLSLYYT   60
```

```
KEQREKIITE IRKVTLKNKE ILAQMILEET HMGRYEDKIL KHELVAKYTP GTEDLATTAW  120
SGDNGLTVVE MSPYGVIGAI TPSTNPTETI ICNSIGMIAS GNAVVFNGHP GAKKCVAFAV  180
DMINRAIISC GGPRNLVTAI KNPTMESLDA IIKHPAIKLL CGTGGPGMVK TLLSSGKKSI  240
GAGAGNPPVI VDDTADIEKA GKSIIEGCSF DNNLPCIAEK EVFVFENVAD DLIKNMLKNN  300
AVIINKDQVS RLVNLVLQKN NETSEYTINK KWVGKDAKLF LDEIDVESSS DVRCIICEVD  360
ADHPFVMTEL MMPILPIVRV KDIDEAIKYA KIAEQNRKHS AYIYSKNIEN LNRFEKEIDT  420
TIFVKNAKSF AGVGYGAEGF TTFTIAGCTG EGITSARNFT RQRRCVFVG             469

SEQ ID NO: 51              moltype = AA  length = 467
FEATURE                    Location/Qualifiers
source                     1..467
                           mol_type = protein
                           organism = Clostridium botulinum
SEQUENCE: 51
MERNLSVLSQ TNDLKITKRT EGDKSNNKES YLGVFKKVEN AITKAIYAQK KLSLYYTKED  60
RERIIKSIRK ATLENKEILA KMIVDETHMG RYEDKILKHE LVAKYTPGTE DLITTAWSGD  120
QGLTLVEMSP YGVIGAITPS TNPTETVICN SIGMIAAGDS VVFNGHPGAK KCVAFADMI  180
NKAVIREGGP ENLVTTVENP TMESLNVIMK HPYIKLLCGT GGPGLIKTLL NSGKKAIGAG  240
AGNPPVIVDD SADIDKAAKN IIEGCSFDNN LPCIAEKEVF VFENVANDLI QNMIKNNAVL  300
INENQVSKLL DLVLLERKDE TLEYAINKKW VGKDAKLFLD KIGIKASDNV RCIICEVDAN  360
HPFVMTELMM PILPIVRVKD VDEAIECAKT AEQRKRHSAY MYSKNIDLN RFEKEIDTTI  420
FVKNAKSFAG VGFGAEGFTT FTIAGPTGEG ITSARNFTRQ RRCVLAG                467

SEQ ID NO: 52              moltype = AA  length = 527
FEATURE                    Location/Qualifiers
source                     1..527
                           mol_type = protein
                           organism = Caldalkalibacillus thermarum
SEQUENCE: 52
MNMTEKDIEK IVQSVLHNVE SALGKSASAS PSVSAVSVAS GEGIKPVQFK QVPVFQQETV  60
KSPNRNRNLG GAEEKWGVFN HMEDAIEASY RAQMEFVKHF QLKDREKIIT AIREAVLREK  120
EVLARKVYEE TKIGRYEDKV AKHELAALKT PGTEDLKTEA FSGDNGLTIV ERAPYGLIGA  180
VTPVTNPTET IINNAIGMLA AGNAVVFNVH PSSKRSCAYA VQLINKAITE AGGPHHLVTM  240
VKEPTLDTLQ TLIDSPKVKL LVGTGGPGLV QTLLKSGKKA IGAGAGNPPV IVDDTADLEH  300
AARSIIEGAA FDNNLLCIAE KEVFVLESVA DDLIFHMLNH GAYMLGQHEV EQVMAFALEE  360
QGNEQNRGCG FNPQRHYQVS KDWIGQDARL FLEHIGVQPP TEVKLLICDV EFDHPFVQLE  420
QMMPVLPIVR VKTLDEAIEK AVMAEHGNRH TAIMHSKNVD HLTKFARAIQ TTLFVKNASS  480
LAGVGYGGEG HTTMTIAGPT GEGVTSAKTF TRERRCVLAE GGFRIIG                527

SEQ ID NO: 53              moltype = AA  length = 480
FEATURE                    Location/Qualifiers
source                     1..480
                           mol_type = protein
                           organism = Pelosinus fermentans
SEQUENCE: 53
MSIDQALIEK ITLEILTKMQ TGAKAAPAGY GDGIFETVDE AVAAARKAYQ ELKTLSLEKR  60
EVLIKAMRDV AYENATILAQ MAVDESGMGR VSDKIIKNQV AALKTPGTED LTTQAWSGDN  120
GLTLIEMGPY GVIGAITPTT NPTETVICNG IGMIAAGNTV FFSPHPTAKN TSMKIITLLN  180
QAIVKAGGPN NLLTSVANPS IKAANEMMKH PGINMLVATG GPGVVKAVLS SGKKAIGAGA  240
GNPPVIVDET ADIEKAARDI VAGCSFDNNL PCIAEKEVIA IGSIADRLIT YMQKYGAYLI  300
SGSNIDRLLD VIMTVQEEKI AEGCTDKPKR SYGINKDYVG KDAKYLLSKI GIDVPDSVRV  360
VLCETPADHP FVIEELMMPV LPVVQVKDID EAIEVAVRVE HGNRHTAAMH SKNVDHLTRF  420
ARAVETTIFV KNAPSYAGIG VGGEGFTSFT LAGPTGEGIT SPRSFTRQRR CVLVDAFSIV  480

SEQ ID NO: 54              moltype = AA  length = 479
FEATURE                    Location/Qualifiers
source                     1..479
                           mol_type = protein
                           organism = Thermoanaerobacterium thermosaccharolyticum
SEQUENCE: 54
MEINDNMISE IIERVLKEVQ KKSINDRYQN GIYDRMEDAI EAAYEAQKKL MKMSIEQRER  60
LISAMRKAIL DNAKSCAKLS VEETGMGRVD HKYLKLKLVA EKTPGTEVLT TKAYSGDKGL  120
TLVEMAPFGV IGSITPSTNP AETVCCNSIG MIAAGNTVVF SPHPGAIKSS LMAVEFLNKA  180
IIEAGGPENL ITSVRKPSIE FTDVMINHPK INLLVATGGP AIVKKVLSSG KKAIGAGAGN  240
PPCVVDETAD IKKAARDIIL GCTFDNNLPC IAEKEVIAVE SIYEELIENM KKNGAYEITD  300
DEAEKLADIV LTKKEELKAE GCSINRPKFE YSVNKKWVGK DAKVLLEQIG INVGDDIVCI  360
IYRCDKQHPF VQEELMMPIL PIVKKNIDE AINVAVEVEH GNHHTAEMHS KNIDNLTRFA  420
KAINTTIFVK NAPSYAGIGF GGEGYTTFTI AGPTGEGLTC AATFTRQRRC VMVDSFRIV  479

SEQ ID NO: 55              moltype = AA  length = 480
FEATURE                    Location/Qualifiers
source                     1..480
                           mol_type = protein
                           organism = Pelosinus fermentans
SEQUENCE: 55
MSIDQALIEK ITLEILTKMQ TGAKAAPAGY GDGIFETVDE AVAAARKAYQ ELKTLSLEKR  60
EVLIKAMRDV AYENATILAQ MAVDESGMGR VSDKIIKNQV AALKTPGTED LTTQAWSGDN  120
GLTLIEMGPY GVIGAITPTT NPTETVICNG IGMIAAGNTV FFSPHPTAKN TSMKIITLLN  180
QAIVKAGGPN NLLTSVANPS IKAANEMMKH PGINMLVATG GPGVVKAVLS SGKKAIGAGA  240
```

```
GNPPVIVDET ADIEKAARDI VAGCSFDNNL PCIAEKEVIA IGSIADRLIT YMQKYGAYLI    300
SGSNIDRLLN VIMTVQEEKI AEGCTDKPKR SYGINKDYVG KDAKYLLSKI GIDVPDSVRV    360
VLCETPADHP FVIEELMMPV LPVVQVKDID EAIEVAVRVE HGNRHTAAMH SKNVDHLTRF    420
ARAVETTIFV KNAPSYAGIG VGGEGFTSFT LAGPTGEGIT SPRSFTQRRR CVLVDAFSIV    480

SEQ ID NO: 56           moltype = AA   length = 479
FEATURE                 Location/Qualifiers
source                  1..479
                        mol_type = protein
                        organism = Desulfosporosinus sp.
SEQUENCE: 56
MSVDQALIRK ITSEILAKMQ NRTVSACQDC NGIFTTVDEA VAAARIAYQE LRTLSLEKRE     60
ELIKAMRNVA LENATMLAEM AVKESGMGRV EDKIIKHKLV AVKTPGTEDL RTEAWSGDSG    120
LTLVEMGPYG VIGAITPTTN PVATIICNGI GMIAAGNAVF FSPHPTAKNT SIKTITLLNE    180
AIVKAGGPMN LLTSVADPSI SAANAMMKHA GINLLVATGG PGVVKAVLSS GKKAIGAGAG    240
NPPVIVDETA DIEKAARDII AGCSFDNNLP CIAEKEVIAV GCIADRLISN MQKYGAYLIS    300
GSKIDQMLDV VMTATEEKMA EGCTAKPIKR YGINKDFVGK DAKYILTQIG LDVPDTIKVI    360
LCETPADHPF VIEELMMPIL PVVQVKDIDA AIELAVKVEH GNRHTAMMHS KNVDNMTRFA    420
KAIETTIFVK NAPSYAGIGV GGEGFCTFTI AGPTGEGLTT ARSFTQRRC VLVDSFSII      479

SEQ ID NO: 57           moltype = AA   length = 482
FEATURE                 Location/Qualifiers
source                  1..482
                        mol_type = protein
                        organism = Clostridium methylpentosum
SEQUENCE: 57
MEITPNQIDQ IVANVMAQLG GSAAPAASYD STQYSGRKYI GIYATMTEAI DAVADAYKVL     60
RSMTVDQREK IIEKIREFTR AEAEIMAKMG VEETGMGKVE HKTLKHHLVA DKTPGTEDIQ    120
TEAMSGDGGL TLLEMAPFGI IGAISPSTNP SETVLCNSMG MIAGANAVVF NPHPSAICTS    180
NYAVDLVNRA SLAAGGPANL CCSVVKPTMQ SADDMVKDPR VKMLVCTGGP GVVRAMLSSG    240
KKAIGAGAGN PPVIVDDTAD IRKAAKDIID GCTFDNNLPC IAEKEVFAFS NIADELMYYM    300
QQNGAYFISG EMADRLAKIV LVEKKNEKTG KISYSVSRDW VGRDAKKFLA ALDIEVGDDV    360
RCVICETDEN HLFVQTELMM PILPIVRVNN IDEAVRMAVR AEHGNRHTAH MHSKNIDNLT    420
KFARAVETTI FVKNAPSYAG IGFGSEGHTT FTIAGPTGEG LTSARSFTRK RRCVMSDSFN    480
IV                                                                    482

SEQ ID NO: 58           moltype = AA   length = 467
FEATURE                 Location/Qualifiers
source                  1..467
                        mol_type = protein
                        organism = Thermoanaerobacterium saccharolyticum
SEQUENCE: 58
MKVKEEDIEA IVKKVLSEFN FEKNTKSFRD FGVFQDMNDA IRAAKDAQKK LRNMSMESRE     60
KIIQNIRKKI MENKKILAEM GVSETGMGKV EHKIIKHELV ALKTPGTEDI VTTAWSGDKG    120
LTLVEMGPFG VIGTITPSTN PSETVLCNSI GMIAAGNSVV FNPHPGAVNV SNYAVKLVNE    180
AVMEAGGPEN LVASVEKPTL ETGNIMFKSP DVSLLVATGG PGVVTSVLSS GKRAIGAGAG    240
NPPVVVDETA DIKKAAKDIV DGATFDNNLP CIAEKEVVSV DKITDELIYY MQQNGCYKIE    300
GREIEKLIEL VLDHKGGKIT LNRKWVGKDA HLILKAIGID ADESVRCIIF EAEKDNPLVV    360
EELMMPILGI VRAKNVDEAI MIATELEHGN RHSAHMHSKN VDNLTKFGKI IDTAIFVKNA    420
PSYAALGYGG EGYCTFTIAS RTGEGLTSAR TFTKSRRCVL ADGLSIR                  467

SEQ ID NO: 59           moltype = AA   length = 467
FEATURE                 Location/Qualifiers
source                  1..467
                        mol_type = protein
                        organism = Thermoanaerobacterium xylanolyticum
SEQUENCE: 59
MKVKEEDIEA IVKKVLSEFN LEKTTSKYGD VGIFQDMNDA ISAAKDAQKK LRNMPMESRE     60
KIIQNIRKKI MENKKILAEM GVRETGMGRV EHKIVKHELV NLKTPGTEDI TTTAWSGDKG    120
LTLVEMGPFG VIGAITPSTN PSETVLCNSI GMIAAGNSVV FNPHPGAVNV SNYAVKLVNE    180
AAMEAGGPEN LVVSVEKPTL ETGNVMFKSS DVSLLVATGG PGVVTAVLSS GKRAIGAGAG    240
NPPVVVDETA DIKKAAKDII DGATFDNNLP CIAEKEVVSV DKITDELIYY MQKNGCYKIE    300
GREIEKLIEL VLDHEGGKTT LNRKWVGKDA HLILKAIGID ADESVRCIIF EAEKDNPLVV    360
EELMMPILGI VRAKNVDEAI MIATELEHGN RHSAHMHSKN IDNLTKFGKI IDTAIFVKNA    420
PSYAALGYGG EGYCTFTIAS RTGEGLTSAR TFTKSRRCVL ADGLSIR                  467

SEQ ID NO: 60           moltype = AA   length = 477
FEATURE                 Location/Qualifiers
source                  1..477
                        mol_type = protein
                        organism = Acetonema longum
SEQUENCE: 60
MVDQTLIEQI TRAVLTQMKA GKDAAVSGDG IFATVDQAVA ARQAYQELR LLTLEKRETL      60
IRAIRDAAFA NAAVIAQMAV QESGMGRVED KILKNQLAAR KTPGTEDLTS RAWSGDHGLT    120
LVEMAPYGVI GAITPTTNPS ETVICNSIGM IAAGNSIVFS PHPTAQNTSL TTIRLLNEAI    180
VKAGGPDNLL TAVAEPSIEA ANAMMRHPGI QMLVATGGPA VVKAVLSSGK KAIGAGAGNP    240
PAVVDETADI AKAAKDIVAG CSFDNNLPCI AEKEIIAVGR IADELISYLQ KYGAYLISGR    300
DIERLMEVVL TERTEEMAPG CVGKPRRVYG VNKDYIGKDA KFILSKINIQ APDHIRVILC    360
ETPADHPFVL EELMMPVLPL VSVRDIDAAI DLAVKVEHGN RHTAVMHSKN VDYMTRLAKA    420
```

```
IETTIFVKNA PSYAGIGVGG EGFTTFTIAG PTGEGLTSAR SFTRQRRCAL VDAFSIV      477

SEQ ID NO: 61              moltype = AA  length = 465
FEATURE                    Location/Qualifiers
source                     1..465
                           mol_type = protein
                           organism = Geobacillus thermoglucosidans
SEQUENCE: 61
MSVDAQKIEK LVRKILEEME EKKKPAETEC EWGIFDHMNQ AIEAAEIAQK ELVQLSLGQR   60
GKLIEAIRKA AKENAEKFAR MAVDETGMGK YEDKIVKNLL AAEKTPGIED LRTEVFSGDD  120
GLTLVELSPY GVIGAITPTT NPTETIICNS IGMIAAGNAV VFSPHPRAKN TSLYAIKIFN  180
QAIVEAGGPK NLITTVANPS IEQAEIMMKH KTIKMLVATG GPVVKAVLS SGKKAIGAGA   240
GNPPVVVDET ADIEKAAKDI IAGCSFDNNL PCVAEKEVIA VESIADRLID YMKKHGAYEI  300
TNKEQIQQLT DLVVENGHAN KEFVGKDAAY ILKHIGINVP PDIRVAIMEV DGKHPLVTVE  360
LMMPILPIVR VKNVDQAIEL AVEVEHGFRH TAIMHSKNVD HLTKFAKAIQ TTIFVKNAPS  420
YAGIGVGGEG YATFTIAGPT GEGLTSAKDF ARKRKCVLVD ALSIR                  465

SEQ ID NO: 62              moltype = AA  length = 463
FEATURE                    Location/Qualifiers
source                     1..463
                           mol_type = protein
                           organism = Geobacillus sp.
SEQUENCE: 62
MDAQKIEKLV RKILEEMEEK KKPAETECEW GIFDHMNQAI EAAEIAQKEL VQLSLGQRGK   60
LIEAIRKAAK ENAEKFARMA VDETGMGKYE DKIVKNLLAA EKTPGIEDLR TEVFSGDDGL  120
TLVELSPYGV IGAITPTTNP TETIICNSIG MIAAGNAVVF SPHPRAKNTS LYAIKIFNQA  180
IVEAGGPKNL ITTVANPSIE QAEIMMKHKT IKMLVATGGP GVVKAVLSSG KKAIGAGAGN  240
PPVVVDETAD IEKAAKDIIA GCSFDNNLPC VAEKEVIAVE SIADRLIDYM KKHGAYEITN  300
KEQIQQLTDL VVENGHANKE FVGKDAAYIL KHIGINVPPD TRVAIMEVDG KHPLVTVELM  360
MPILPIVRVK NVDQAIELAV EVEHGFRHTA IMHSKNVDHL TKFAKAIQTT IFVKNAPSYA  420
GIGVGGEGYA TFTIAGPTGE GLTSAKDFAR KRKCVLVDAL SIR                    463

SEQ ID NO: 63              moltype = AA  length = 463
FEATURE                    Location/Qualifiers
source                     1..463
                           mol_type = protein
                           organism = Geobacillus thermoglucosidasius
SEQUENCE: 63
MDAQKIEKLV RKILEEMEEK KKPAETECEW GIFDHMNQAI EAAEIAQKEF VQLSLGQRGK   60
LIEAIRKAAK ENAEKFARMA VDETGMGKYE DKIVKNLLAA EKTPGIEDLR TEVFSGDDGL  120
TLVELSPYGV IGAITPTTNP TETIICNSIG MIAAGNAVVF SPHPRAKNTS LYAIKIFNQA  180
IVEAGGPKNL ITTVANPSIE QAEIMMKHKT IKMLVATGGP GVVKAVLSSG KKAIGAGAGN  240
PPVVVDETAD IEKAAKDIIA GCSFDNNLPC VAEKEVIAVE SIADRLIDYM KKHGAYEITN  300
KEQIQQLTDL VVENGHANKE FVGKDAAYIL KHIGINVPPD IRVAIMEVDG KHPLVTVELM  360
MPILPIVRVK NVDQAIELAV EVEHGFRHTA IMHSKNVDHL TKFAKAIQTT IFVKNAPSYA  420
GIGVGGEGYA TFTIAGPTGE GLTSAKDFAR KRKCVLVDAL SIR                    463

SEQ ID NO: 64              moltype = AA  length = 463
FEATURE                    Location/Qualifiers
source                     1..463
                           mol_type = protein
                           organism = Bacillus azotoformans
SEQUENCE: 64
MAVEAKAIEE IVKKILEEMM IKKDACITGY GIFEDMNEAI EAATIAQKEL LKLSLEQRGN   60
LITAIRKAAK DNAETFAQMA VDETGMGNYG DKVIKNLIAA EKTPGIEDLT TEAFSGDHVL  120
TLVELSPYGV IGSITPTTNP TETVICNSIG MIAAGNAVVF SPHPTAKNTS LKAIEVINKA  180
IIKAGGPPNL ITSVANPTID QANIMMKHKK IKLLVATGGP GVVKAVLSSG KKAIGAGAGN  240
PPAVVDETAN LEKAARDIID GCSFDNNLPC TAEKEVIVVD SVADYLVSYM KKHGAFLITD  300
KEQIQKLTEL VVDNGHANKE LVGKSVAHIL QRIGIEVPSD ARVAILNVER NHPVLKAELM  360
MPILPVVRVE NVDAAIELAV EAEQGFRHTA IMHSTNIDNL TKFSKEIQTT IFVKNGPSYA  420
GIGIGGEGYA TFTIAGPTGE GLTSAKDFAR RRKCVLVDGL SIR                    463

SEQ ID NO: 65              moltype = AA  length = 503
FEATURE                    Location/Qualifiers
source                     1..503
                           mol_type = protein
                           organism = Clostridium sticklandii
SEQUENCE: 65
MKAGDIVQDF ITERDVEKII EQVLSKLEPV IEQVKPKEIN MLPNKTNIDF SQNANGIFES   60
IDLAVESALE AHIILTSYKL EDREKMIQSI RKEVLGDIEN IARLVYEETK LGKYEDKIAK  120
INLAASKTPG TEDIKTSAIS GDYGLTIEEM APFGVIGAVT PVTNPVETLI NNAISMISGG  180
NSVVFNVHPS SKKSSAYTVE LINKAVLKAG GPQNLVTMVK EPTIETVNQL SSHPRISMMV  240
GTGGPGLVKS LLKSGKKTIG AGAGNPPVVV DETADMNLAA KGIIEGASFD NNILCIAEKE  300
VFVVNEVADD LIYNMLSSGA YMLNQEELEK VMKLTVEDE DLGAKSCTLS PKKKYHVHKN   360
WVGKDASKIL SEIGITKQDV KLLICEVDSD HPYVTLEQMM PILPLVRCSD VDEAIKLAVK  420
AEGTNKHTAS IFSRNVDNMT KFARAINTTI FVKNAPTLAG VGYKGEGNAT FTIAGPTGEG  480
ITSAKTFTRV RRCVLAEGGF RIV                                          503

SEQ ID NO: 66              moltype = AA  length = 482
```

```
FEATURE             Location/Qualifiers
source              1..482
                    mol_type = protein
                    organism = Thermincola potens
SEQUENCE: 66
MAIEAYQIEK IVEEVMRKMV SGGSGDSFAG KAKGIFESVD EAVKAAKAAQ KELVAMRIEK   60
REMLLKAMRE AAIAHAEELA RLAVEETGMG RVTDKIIKNR VAAEKTPGTE NLQPSAVTGD  120
RGLTLIERAP YGVIGAITPS TNPCATVINN SISMVAAGNS VVFSVHPGAK KASLLTVEIL  180
NEAIEKAGGP ANVLTAVASP SLENTNALMK HPDIKLLVAT GGPGLVKAVL SSGKKAIGAG  240
AGNPPALVDE TADLERAAKS IVAGASFDNN LPCIAEKEVI VVDYVANQLI SYMKQNGAYL  300
ANDREIKALM DLVLTKNENL KAEGCTVKPE KLYGGINKEY VGKDAAYIMK KIGVDIPEDT  360
KLIICEVDED HPFVLEELMM PILPIVRVPN VQKAIEVGVR VEHGNRHTAV MHSQNIDNLS  420
AFARAVQTTI FVKNGPSYAG IGIGGEGYTT FTIAGPTGEG LTAASSFTRQ RRCVLVDGFS  480
IV                                                                482

SEQ ID NO: 67       moltype = AA  length = 462
FEATURE             Location/Qualifiers
source              1..462
                    mol_type = protein
                    organism = Clostridium sp.
SEQUENCE: 67
MSVNEQMIQD IVSEVMAKMQ IASEVSDNHG IFADMNEAIE AAKKAQKIVG RMSMDQREKI   60
ISNIRKKTVE NAEILARMGV QETGMGNVGH KILKHQLVAE KTPGTEDITT TAWSGDRGLT  120
LIEMGPFGVI GAITPCTNPS ETVLCNTIGM LAGGNTVVFN PHPGAIKTSI FAINMINEAS  180
LEAGGPDNIA CTVEKPTLES SNIMMKHKAI HLIAATGGPG VVTAVLSSGK RGIGAGAGNP  240
PALVDETADI RKAAEDIVNG CTFDNNLPCI AEKEIVADVS VADELMHYMV SEQGCYLASK  300
EEQEALTAVV LKDGRLNRNC VGRDAKTLLG MIGVSVPDNI RCITFEGPKE HPLIATELMM  360
PILGVVRAKD FDDAVEQSVW LEHGNRHSAH IHSKNVDNIT KYAKAIDTAI LVKNGPSYAA  420
IGFGGEGFCT FTIASRTGEG LTSASTFTKR RRCVMSDSLC IR                    462

SEQ ID NO: 68       moltype = AA  length = 470
FEATURE             Location/Qualifiers
source              1..470
                    mol_type = protein
                    organism = Fusobacterium sp.
SEQUENCE: 68
MRGELMEFEV NNIEKIVELI MKKMAESNIS TAGNSKNGVF DNVDEAIEEA KKAQAILFSS   60
KLELREKIIA SIRDTLKSHV TELAELAVKE TGMGRVSDKE LKNKIAIEKT PGLEDLKAFA  120
FSGDDGLTVM ELSPYGVIGA ITPSTNPSET VICNSIGMIA AGNAVIFAPH PGAKRTSIRT  180
VELINEAIRK VGGPDNLVVT IREPSIENTE KIIANPNIKM LVATGGPGVV KTVMSSGKKA  240
IGAGAGNPPV LVDETADIEK AAKDIIAGCS FDNNLPCTAE KEVVAVDSIV NYLIFEMQKN  300
GAYLLKDKKL IEKLLSLVLK NNSPDRKYVG RDAKYLLKQI GIEVGDEIKV IIVETDKNHP  360
FAVEELLMPI LPIVKVKDAL EGIKVAKELE RGLRHTAVIH SKNIDILTKY AREMETTILV  420
KNGPSYAGIG IGGEGHVTFT IAGPTGEGLT SAKSFARNRR CVLVGGFSIK            470

SEQ ID NO: 69       moltype = AA  length = 470
FEATURE             Location/Qualifiers
source              1..470
                    mol_type = protein
                    organism = Fusobacterium sp.
SEQUENCE: 69
MRGELMEFEV NNIEEIVELI MKKMAESNIS TAGNSKNGVF DNVDEAIEEA KKAQAILFSS   60
KLELREKIIA SIRDTLKNHV SELAELAVKE TGMGRVADKE LKNKIAIEKT PGLEDLKAFA  120
FSGDDGLTVM ELSPYGVIGA ITPSTNPSET VICNSIGMIA AGNAVIFAPH PGAKRTSIRT  180
VELINEAIRK VGGPDNLVVT IREPSIENTE KIIANPNIKM LVATGGPGVV KTVMSSGKKA  240
IGAGAGNPPV LVDETADIEK AAKDIIAGCS FDNNLPCTAE KEVVAVDSIV NYLIFEMQKN  300
GAYLLKDKEL IEKLLSLVLK NNSPDRKYVG RDAKYLLKQI GIEVGDEIKV IIVETDKNHP  360
FAVEELLMPI LPIVKVKDAL EGIKVAKELE RGLRHTAVIH SKNIDILTKY AREMETTILV  420
KNGPSYAGIG IGGEGHVTFT IAGPTGEGLT SAKSFARNRR CVLVGGFSIK            470

SEQ ID NO: 70       moltype = AA  length = 462
FEATURE             Location/Qualifiers
source              1..462
                    mol_type = protein
                    organism = Ruminococcus sp.
SEQUENCE: 70
MPISENMVQE IVQEVMAKMQ IADAPAGKHG VFKDMNDAIE AAKKAQLVVK TMSMDQREKI   60
ITCIRKKIKE NAEVLARMGV EETGMGNVGD KILKHHLVAE KTPGTEDITT TAWSGDRGLT  120
LIEMGPFGVI GAITPCTNPS ETVLCNTMGM LAGGNTVVFN PHPAAVKTSI YAINLLNEAS  180
LESGGPDNIA VTVEKPTLET SNIMMKHKDI HLIAATGGPG VVTAVLSSGK RGIGAGAGNP  240
PALVDDTADI RKAAQDIVNG CTFDNNLPCI AEKEVVAVSS VVDELMHYMI TENDCYLASK  300
EEQDKLVETV LAGGKLNRKC VGRDAKTLLS MIGVQAPANT RCIIFEGPKE HPLITTELMM  360
PILGIVRAKD FDDAVEQAVW LEHGNRHSAH IHSKNIDNIT KYAKAIDTAI LVKNGPSYSA  420
LGFGGEGFCT FTIASRTGEG LTSASTFTKR RRCVMTDSLC IR                    462

SEQ ID NO: 71       moltype = AA  length = 465
FEATURE             Location/Qualifiers
source              1..465
                    mol_type = protein
```

```
                        organism = Fusobacterium nucleatum
SEQUENCE: 71
MEFEVNNIEE IVELIMKKMA ESNISTAGNS KNGVFDNVDE AIEEAKKAQA ILFSSKLELR        60
EKIIASIRDT LKNHVTELAE LAVKETGMGR VADKELKNKI AIEKTPGLED LKAFAFSGDD       120
GLTVMELSPY GVIGAITPST NPSETVICNS IGMIAAGNAV IFAPHPGAKR TSIRTVELIN       180
EAIRKVGGPD NLVVTIREPS IENTEKIIAN PNIKMLVATG GPGVVKTVMS SGKKAIGAGA       240
GNPPVLVDET ADIEKAAKDI IAGCSFDNNL PCTAEKEVVA VDSIVNYLIF EMQKNGAYLL       300
KDKELIEKLL SLVLKNNSPD RKYVGRDAKY LLKQIGIEVG DEIKVIIVET DKNHPFAVEE       360
LLMPILPIVK VKDALEGIKV AKELERGLRH TAVIHSKNID ILTKYAREME TTILVKNGPS       420
YAGIGIGGEG HVTFTIAGPT GEGLTSAKSF ARNRRCVLVG GFSIK                       465

SEQ ID NO: 72           moltype = AA  length = 465
FEATURE                 Location/Qualifiers
source                  1..465
                        mol_type = protein
                        organism = Fusobacterium nucleatum
SEQUENCE: 72
MEFEVNNIEE IVELIMKKMT EGGVSTSNNS TNGVFKNVDE AIAEAKKAQT VLFSSKLELR        60
ERIIASIRDT LKSHITELSE LAVKETGMGR VADKELKNRI AIEKTPGLED LKAFAFSGDD       120
GLTVMELSPY GVIGAITPST NPSETVICNS IGMIAAGNAV IFAPHPGAKR TSIRAVELIN       180
EAIKKAGGPD NLVVTIAEPS IENTEKIIAN PNIKMVVATG GPGVVKTVMS SGKKAIGAGA       240
GNPPVLVDET ADIEKAAKDI IAGCSFDNNL PCTAEKEVIA VDSIVNYLIF EMQKNGAYLL       300
KDKELIEKLL SIVLKNNSPD RKYVGKDAKY LLKQIGIEVG DEIKVIIVET DKNHPFAVEE       360
LLMPILPIVK VKDALEGIKV AKELEKGLRH TAVIHSKNID ILSKYAREME TTILVKNGPS       420
YAGIGIGGEG HVTFTIAGPT GEGLTSARSF ARNRRCVLVG GFSIK                       465

SEQ ID NO: 73           moltype = AA  length = 470
FEATURE                 Location/Qualifiers
source                  1..470
                        mol_type = protein
                        organism = Fusobacterium sp.
SEQUENCE: 73
MRGELMEFEV NNIEEIVELI MKKMAESNIS TAGNSKNGVF DNVDGAIEEA KKAQAILFSS        60
KLELREKIIA SIRDTLKNHV TELAELAVKE TGMGRVADKE LKNKIAIEKT PGLEDLKAFA       120
FSGDDGLTVM ELSPYGVIGA ITPSTNPSET VICNSIGMIA AGNAVIFAPH PGAKRTSIRT       180
VELINEAIRK VGGPDNLIVT IREPSIENTE KIIANPNIKM LVATGGPGVV KTVMSSGKKA       240
IGAGAGNPPV LVDETADIEK AAKDIIAGCS FDNNLPCTAE KEVVAVDSIV NYLIFEMQKN       300
GAYLLKDKEL IEKLLSLVLK NNSPDRKYVG RDAKYLLKQI GIEVGDEIKV IIVETDKNHP       360
FAVEELLMPI LPIVKVKDAL EGIKVAKELE RGLRHTAVIH SKNIDILTKY AREMETTILV       420
KNGPSYAGIG IGGEGHVTFT IAGPTGEGLT SAKSFARNRR CVLVGGFSIK                  470

SEQ ID NO: 74           moltype = AA  length = 465
FEATURE                 Location/Qualifiers
source                  1..465
                        mol_type = protein
                        organism = Fusobacterium nucleatum
SEQUENCE: 74
MEFEVNNLEE IVELIMKKMS ESSISTSSNS KNGVFENVDE AIAEAKKAQT ILFSSKLELR        60
ERIIASIRDT LKPYITELSE LAVKETGMGR VSDKEIKNRI AIEKTPGLED LKAFAFSGDD       120
GLTVMELSPY GVIGAITPST NPSETVICNS IGMIAAGNAV IFAPHPGAKR TSIRAVELIN       180
EAIKKVGGPD NLIVTITEPS IENTEKIIAN PNIKMVVATG GPGVVKTVMS SGKKAIGAGA       240
GNPPVLVDET ADIEKAAKDI IAGCSFDNNL PCTAEKEVIA VDSIVNYLIF EMQKNGAYLL       300
KDKDLIEKLL SIVLKNNSPD RKYVGKDAKY LLKQIGIEVG DEIRVIIVET SKDHPFAVEE       360
LLMPILPIVK VKDALEGIKV AKELEKGLRH TAIIHSKNID ILSKYAREME TTILVKNGPS       420
YAGIGIGGEG HVTFTIAGPT GEGLTSARSF ARNRRCVLVG GFSIK                       465

SEQ ID NO: 75           moltype = AA  length = 465
FEATURE                 Location/Qualifiers
source                  1..465
                        mol_type = protein
                        organism = Fusobacterium nucleatum
SEQUENCE: 75
MEFEVNNIEE IVELIMKKMS ESGVSTSNNS TNGVFENVDE AIAEAKKAQT VLFSSKLELR        60
ERIIASIRDT LKTHITELSE LAVKETGMGR VADKELKNRI AIEKTPGLED LKAFAFSGDD       120
GLTVMELSPY GVIGAITPST NPSETVICNS IGMIAAGNAV IFAPHPGAKR TSIRAVELIN       180
EAIKKAGGPD NLVVTIAEPS IENTEKIIAN PNIKMVVATG GPGVVKTVMS SGKKAIGAGA       240
GNPPALVDET ADIEKAAKDI IAGCSFDNNL PCTAEKEVIA VDSIVNYLIF EMQKNGAYLL       300
KDKELIEKLL SIVLKNNSPD RKYVGKDAKY LLKQIGIEVG DEIKVIIVET DKNHPFAVEE       360
LLMPILPIVK VKDALEGIKV AKELEKGLRH TAVIHSKNID ILSKYAREME TTILVKNGPS       420
YAGIGIGGEG HVTFTIAGPT GEGLTSARSF ARNRRCVLVG GFSIK                       465

SEQ ID NO: 76           moltype = AA  length = 470
FEATURE                 Location/Qualifiers
source                  1..470
                        mol_type = protein
                        organism = Fusobacterium sp.
SEQUENCE: 76
MRGELMEFEV NNIEEIVELI MKKMAESNIS TAGNSKNGVF DNVDEAIEEA KKAQAILFSS        60
KLELREKIIA SIRDTLKNHV TELAELAVKE TGMGRVADKE LKNKIAIEKT PGLEDLKAFA       120
```

```
FSGDDDGLTVM ELSPYGVIGA ITPSTNPSET VICNSIGMIA AGNAVIFAPH PGAKRTSIRT    180
VELINEAIRK VGGPDNLIVT IREPSIENTE KIIANPNIKM LVATGGPVV KTVMSSGKKA    240
IGAGAGNPPV LVDETADIEK AAKDIIAGCS FDNNLPCTAE KEVVAVDSIV NYLIFEMQKN    300
GAYLLKDKEL IEKLLSLVLK NNSPDRKYVG RDAKYLLKQI GIEVGDEIKV IIVETDKNHP    360
FAVEELLMPI LPIVKVKDAL EGIKVAKELE RGLRHTAVIH SKNIDILTKY AREMETTILV    420
KNGPSYAGIG IGGEGHVTFT IAGPTGEGLT SAKSFARNRR CVLVGGFSIK               470

SEQ ID NO: 77              moltype = AA  length = 481
FEATURE                    Location/Qualifiers
source                     1..481
                           mol_type = protein
                           organism = Clostridium asparagiforme
SEQUENCE: 77
MEIETRDIER IVRQVMAAME QQGTIAGGAY PPAPGITAPR GDNGVFERVE DAIDAAWAAG     60
RVWAFHYKVE DRRRVIEAIR VMARENARTL AQMVRDETGM GRVEDKVEKH LAVADKTPGV    120
ECLTTDAISG DGGLMIEEYA PFGVIGAITP STNPTETVIH NTISMIAGGN SVVFNVHPGA    180
KKCCAFCLQL LNKTIVENGG PANLITMQRD PTMDAVNKMT SSPKIRLMVG TGGMGMVNAL    240
LRSGKKTIGA GAGNPPVIVD DTADVKLAAR ELYWGASFDN NLFCFAEKEV FVMEASADGL    300
IRGLVEQGAY LLTPAETEAI VKLALIQKDG KYEVNKKWVG KDAGLFLQAI GVSGHENTRL    360
LICDVPKCHP YVMVEQLMPV LPIVRCRTFD ECIQCSVEAE QGNRHTSSIF STNVYNMTKF    420
GKEIETTIYV KNGATLRGLG IGGEGHTTMT IAGPTGEGLT CARSFTRRRR CMLAEGGLRI    480
I                                                                   481

SEQ ID NO: 78              moltype = AA  length = 462
FEATURE                    Location/Qualifiers
source                     1..462
                           mol_type = protein
                           organism = Clostridium phytofermentans
SEQUENCE: 78
MTVNEQLVQD IIKNVVASMQ LTQTNKTELG VFDDMNQAIE AAKEAQLVVK KMSMDQREKI     60
ISAIRKKTIE HAETLARMAV EETGMGNVGH KILKHQLVAE KTPGTEDITT TAWSGDRGLT    120
LVEMGPFGVI GAITPCTNPS ETIICNTIGM LAGGNTVVFN PHPAAIKTSN FAVQLINEAS    180
LSAGGPVNIA CSVRKPTLDS SKIMMSHQDI PLIAATGGPG VVTAVLQSGK RGIGAGAGNP    240
PVLVDETADI RKAAEDIING CTFDNNLPCI AEKEVVAIDA IANELMNYMV KEQGCYAITK    300
EQQEKLTNLV ITPKGLNRNC VGKDARTLLG MIGIDVPSNI RCIIFEGEKE HPLISEELMM    360
PILGIVRAKS FDDAVEKAVW LEHGNRHSAH IHSKNVDRIT TYAKAIDTAI LVKNAPSYAA    420
IGFGGEGFCT FTIASRTGEG LTSASTFTKR RRCVMSDSLC IR                      462

SEQ ID NO: 79              moltype = AA  length = 470
FEATURE                    Location/Qualifiers
source                     1..470
                           mol_type = protein
                           organism = Fusobacterium sp.
SEQUENCE: 79
MRGELMELEV KNIEEIVDLI MKKMTESNVA VSYDSKNGVF DDVDVAIAEA KKAQTVLFSS     60
KLELRERIIA SIRETMRAHI TELSELAVKE TGMGRVKDKE QKNRVAIDRT PGLEDLKAFA    120
FSGDDDGLTVM EFSPYGVIGA ITPSTNPSET VICNSIGMIA AGNAVIFAPH PGAKRTSIRA    180
VELINEAIKK VGGPENLVVT ISEPSIENTE KIIANPNIKM LVATGGPVV KTVMSSGKKA    240
IGAGAGNPPV LVDETADIEK AAKDIIDGCS FDNNLPCTAE KEVIAVDSIV NYLIFEMQKN    300
GAYLLKDKEL IEKVSLVLK NNSPDRKYVG KDAKYILKQL GIEVGDEIRV IIVETDKNHP    360
FAVEELLMPV LPIVKVKDAL EGIKVAKELE RGLRHTAIIH SKNIDILSKY AREMETTILV    420
KNGPSYAGIG IGGEGHVTFT IAGPTGEGLT SARSFARNRR CVLVGGFSIK               470

SEQ ID NO: 80              moltype = AA  length = 462
FEATURE                    Location/Qualifiers
source                     1..462
                           mol_type = protein
                           organism = Lachnospiraceae bacterium
SEQUENCE: 80
MSVNEKMVQD IVQEVVAKMQ ISSDVSGKKG VFSDMNEAIE ASKKAQKIVA KMSMDQREAI     60
ISKIREKIKE NAEILARMGV EETGMGNVGH KILKHQLVAE KTPGTEDITT TAWSGDRGLT    120
LIEMGPFGVI GAITPCTNPS ETVLCNTIGM LAGGNTVVFN PHPAAIKTSI YAVNLLNEAS    180
VEVGGPENIA VTVEHPTMET SDVMMKHKDI HLIAATGGPG VVTAVLSSGK RGIGAGAGNP    240
PALVDETADI RKAAEDIVNG CTFDNNLPCI AEKEIVAVDS IADELLHYMV NEQGCYMISK    300
EEQDALTEVV LKGGRLNRKC VGRDAKTLLG MIGITVPDNI RCITFEGPKE HPLIAEELMM    360
PILGVVRAKD FDDAVEQAVW LEHGNRHSAH IHSKNVDNIT KYAKAIDTAI LVKNGPSYAA    420
LGFGGEGYCT FTIASRTGEG LTSASTFTKR RRCVMTDSLC IR                      462

SEQ ID NO: 81              moltype = AA  length = 462
FEATURE                    Location/Qualifiers
source                     1..462
                           mol_type = protein
                           organism = Ruminococcus gnavus
SEQUENCE: 81
MSVNEKMVQD IVQEVVAKMQ ISSDVSGKKG VFSDMNEAIE ASKKAQKIVA KMSMDQREAI     60
ISKIREKIKE NAEILARMGV EETGMGNVGH KILKHQLVAE KTPGTEDITT TAWSGDRGLT    120
LIEMGPFGVI GAITPCTNPS ETVLCNTIGM LAGGNTVVFN PHPAAIKTSI YAVNLLNEAS    180
VEVGGPENIA VTVEHPTMET SDIMMKHKDI HLIAATGGPG VVTAVLSSGK RGIGAGAGNP    240
PALVDETADI RKAAEDIVNG CTFDNNLPCI AEKEIVAVDS IADELLHYMV SEQGCYMISK    300
```

```
EEQDALTEVV LKGGRLNRKC VGRDAKTLLG MIGITVPDNI RCITFEGPKE HPLIAEELMM    360
PILGVVRAKD FDDAVEQAVW LEHGNRHSAH IHSKNVDNIT KYAKAIDTAI LVKNGPSYAA    420
LGFGGEGYCT FTIASRTGEG LTSASTFTKR RRCVMTDSLC IR                      462

SEQ ID NO: 82           moltype = AA   length = 462
FEATURE                 Location/Qualifiers
source                  1..462
                        mol_type = protein
                        organism = Ruminococcus obeum
SEQUENCE: 82
MPISESMVQD IVQEVMAKMQ IADAPTGKHG VFKEMNDAIE AAKKAELIVK KMSMDQREKI     60
ITCIRKKIKE NAEVMARMGV DETGMGNVGD KILKHHLVAD KTPGTEDITT TAWSGDRGLT    120
LIEMGPFGVI GAITPCTNPS ETVLCNTIGM LAGGNTVVFN PHPAAIKTSI FAINLVNEAS    180
LEAGGPDNIA VTVEKPTLET SNIMMKHKDI PLIAATGGPG VVTAVLSSGK RGIGAGAGNP    240
PAVVDETADI RKAAQDIVNG CTFDNNLPCI AEKEVVAVSS VVDELMHYML TENDCYLASK    300
EEQDKLTEVV LAGGKLNRKC VGRDAKTLLS MIGVNAPANT RCIIFEGPKE HPLITTELMM    360
PILGVVRARD FDDAVEQAVW LEHGNRHSAH IHSKNIDNIT KYAKAIDTAI LVKNGPSYSA    420
LGFGGEGYCT FTIASRTGEG LTSASTFTKR RRCVMSDSLC IR                      462

SEQ ID NO: 83           moltype = AA   length = 473
FEATURE                 Location/Qualifiers
source                  1..473
                        mol_type = protein
                        organism = Clostridium saccharolyticum
SEQUENCE: 83
MEIGAKEIEL IVREVLAGIE SRGPKLSYIP AQSDNGVFER VEDAIGAAHT AQREWVEHYR     60
VEDRRRIIEA IRMTAKSHAK TLAKLVWEET GMGRFEDKIQ KHMAVIEKTP GVECLTTDAI    120
SGDEGLMIEE YAPFGVIGAI TPSTNPTETI INNTISMIAG GNAVVFNVHP GAKKCCAHCL    180
KLLHQAIVEN GGPANLITMQ KEPTMEAVTK MTSDPRIRLM VGTGGMPVVN ALLRSGKKTI    240
GAGAGNPPVI VDDSADVSLA AREIYRGASF DNNILCELAEK EVPVMEKAAD ELVNNLVKEG    300
AYLLNPMELN EILKFAMIEK NGSCEVNKKW VGKDAGLFLE AIGVSGHKDV RLLICETDRN    360
HPFVMVEQLM PILPIVRLRT FEECVESAVA AESGNRHTAS MFSRNVENMT RPFGKVIETTI    420
FTKNGSTLKG VGIGGEGHTT MTIAGPTGEG LTCARSFTRR RRCMLAEGGL RII           473

SEQ ID NO: 84           moltype = AA   length = 471
FEATURE                 Location/Qualifiers
source                  1..471
                        mol_type = protein
                        organism = Flavonifractor plautii
SEQUENCE: 84
MNIDENVVES IVKRVVSQLS TETASAQTCP SGGDWGVFES MNDAVDAAVE AQREYLNRSM     60
HDRACYVQAI RDVVLDQENL EYISRLAVEE TGMGGYEYKL IKNRLAAVKT PGIEDLTTDA    120
MSGDDGLTLV EYSPFGVIGS ITPTTNPTET IICNSIGMLA AGNAVVFSPH PRAKKVSLHL    180
IQLINKALCK AGAPANLVVT VSAPSIENTN AMMSHPKIRM LVATGGPAIV KTVLSSGKKA    240
IGAGAGNPPV VVDETADIEK AAKDIVDGCS FDNNLPCIAE KEVIAVDSVA DYLIFNMKKN    300
GAYEVKDPAV ISQLVELVTK EGKSPKTEFV GKSAKYILDK IGITVGDDVK VILMEAKEDH    360
PFVQVELMMP ILPLVRVPDV DQAIEMAVRV EHGNRHTAMM HSRNVEKLTK MAKLIQTTIF    420
VKNGPSYAGI GVGGEGYTTF TIAGPTGEGL TSAKSFARRR RCVLVGGMDV R             471

SEQ ID NO: 85           moltype = AA   length = 462
FEATURE                 Location/Qualifiers
source                  1..462
                        mol_type = protein
                        organism = Ruminococcus obeum
SEQUENCE: 85
MPISESMVQD IVQEVMAKMQ IADAPTGKHG IFKDMNDAIE AAKKSELIVK KMSMDQREKI     60
ITCIRKKIKE NAEVMARMGV DETGMGNVGD KILKHHLVAD KTPGTEDITT TAWSGDRGLT    120
LIEMGPFGVI GAITPCTNPS ETILCNTMGM LAGGNTVVFN PHPAAIKTSI FAINLVNEAS    180
LEAGGPDNIA VTVEKPTLET SNIMMKHKDI PLIAATGGPG VVTAVLSSGK RGIGAGAGNP    240
PAVVDETADI RKAAQDIVNG CTFDNNLPCI AEKEVVAVSS VVDELMHYML TENDCYLASK    300
EEQDKLTEVV LAGGKLNRKC VGRDARTLLS MIGVNAPANI RCIIFEGPKE HPLITTELMM    360
PILGIVRAKD FDDAVEQAVW LEHGNRHSAH IHSKNVDNIT KYAKAIDTAI LVKNGPSYSA    420
LGFGGEGYCT FTIASRTGEG LTSASTFTKR RRCVMSDSLC IR                      462

SEQ ID NO: 86           moltype = AA   length = 469
FEATURE                 Location/Qualifiers
source                  1..469
                        mol_type = protein
                        organism = Clostridium carboxidivorans
SEQUENCE: 86
MELQSNELSL IIEKVLKEMN KKELKEEVSD GVFDTMEEAI EAAYEAQKKF SSYTIEQREK     60
LIAAMRKAII DNAMEIANLC VNESGMGRVD HKYLKLKLTA EKTPGTEVLQ TTAFTGDKGL    120
TLVENGAFGV IGSITPSTNP AATVACNGIG MLAAGGNTAVF SPHPGAFRSS LAMLRALNKA    180
IKEAGGPDNL LTSVKKPSIE STNSMMKNDK IRMVVATGGP GIVKMVLSSG RKAIGAGAGN    240
PPVVVDETAD IKKAARDIIA GCTFDNNLPC IAEKEALVVE AVYEELIKEM KNNRAVYELN    300
DEEEAAKVAEL VLVHNKEKNT YSINKAFVGK DAKYILQNIG KNDAEGVECL IYRAENSHPF    360
VQEELMMPIL PIVKTKDFEE ALKLAVQDEH GNRHTAIMHS KNVDNLTKMA RAIDTTIFVK    420
NAPSYAGIGF GGEGYTTFTI AGPTGEGLTN AVSFTKRRRC TMAESFRIV              469
```

```
SEQ ID NO: 87              moltype = AA   length = 469
FEATURE                    Location/Qualifiers
source                     1..469
                           mol_type = protein
                           organism = Fusobacterium ulcerans
SEQUENCE: 87
MNLEANNMDE IVALIMKELK KTDIKAGCQS CESPKNGVFS SMDEAIAAAK KAQEILFSSR     60
LEMREKIVAS IREVMKDYVV ELAELGVKET GMGRAADKAL KHQVTIEKTP GVEDLRAFAF    120
SGDDGLTVME LSPYGVIGAI TPSTNPSETI ICNSIGMISA GNSVVFAPHP GAKRTSIKTV    180
EIINEAVRKA GGPENLVVTI AEPSIENTNR MMENPDIKML VATGGPGVVK SVMSSGKKAI    240
GAGAGNPPVL VDETADIEKA ARDIVAGCSF DNNLPCIAEK EVVAVDSITD YLIFEMQKNG    300
AYLIKDKSVI DRLVAMVLKN GSPNRAYVGK DASYILKDLG INVGGEIRVI ITEADKDHPF    360
AVEELLMPIL PIIRVKNALE GIEVSKKLEH GLRHTAMIHS KNIDILTKYA RDMETTILVK    420
NGPSFAGIGV GGEGHTTFTI AGPTGEGLTS AKSFARNRRC VLVGGLSIK                469

SEQ ID NO: 88              moltype = AA   length = 469
FEATURE                    Location/Qualifiers
source                     1..469
                           mol_type = protein
                           organism = Fusobacterium sp.
SEQUENCE: 88
MNLEANNMDE IVALIMKELK KTDIKAGCQS CESLKNGVFS SMDEAIAAAK KAQEILFSSR     60
LEMREKIVAS IREVMKDYVV ELAELGVKET GMGRAADKAL KHQVTIEKTP GVEDLRAFAF    120
SGDDGLTVME LSPYGVIGAI TPSTNPSETI ICNSIGMISA GNSVVFAPHP GAKRTSIKTV    180
EIINEAVRRA GGPENLVVTI AEPSIENTNR MMENPDIKML VATGGPGVVK SVMSSGKKAI    240
GAGAGNPPVL VDETADIEKA ARDIVAGCSF DNNLPCIAEK EVVAVDSITD YLIFEMQKNG    300
AYLIKDKSVI DRLVAMVLKN GSPNRAYVGK DASYILKDLG INVGDEIRVI ITETDKDHPF    360
AVEELLMPIL PIIRVKNALE GIEVSKKLEH GLRHTAMIHS KNIDILTKYA RDMETTILVK    420
NGPSFAGIGV GGEGHTTFTI AGPTGEGLTS AKSFARNRRC VLVGGLSIK                469

SEQ ID NO: 89              moltype = AA   length = 469
FEATURE                    Location/Qualifiers
source                     1..469
                           mol_type = protein
                           organism = Clostridium carboxidivorans
SEQUENCE: 89
MELESNELSV IIEKVLKEMN KKEFGKKESD GIFDTMDEAV EASYEAQKKY SSYSLEQREK     60
LIQAMRKAIM DNAMEVANLC VKESGMGRVD HKYLKLKLIV EKTQGTEILR PEVYTGDNGL    120
TLIEHGAFGV IGAITPSTNP AATVACNSIC MLAGGNTVVF SPHPGALNSC LTMIRILNKA    180
IKEAGGPENL ITSVKAPSIE NTNIMINHKR IRLVVATGGP GIVKLVLSSG KKAIGAGAGN    240
PPVVVDETAD IPKAARDIIA GCSFDNNLPC IAEKEAIVVE SVYEELIKEF KKNRVVYELT    300
DEEEAEKLVGK VLNYDEKNKK YSINKKFVGK DAKYLLESIG KDAGTGVECL IYRAENSHPF    360
VQEELMMPIL PIVKVKNVDE AIETAVEDEH GNRHTAMMHS KNVVNLTKMA RAIDTTIFVK    420
NAPSYAGIGF GGEGHTTFTI AGPTGEGITN AVTFTRQRRC TMVDSFRIV                469

SEQ ID NO: 90              moltype = AA   length = 471
FEATURE                    Location/Qualifiers
source                     1..471
                           mol_type = protein
                           organism = Clostridium sp.
SEQUENCE: 90
MEMDMKVIEQ LVAQALKEMK AEEPAAFAEK KEENYGVFST MDEAIEASEK AQKALLFSKI     60
QDRQKYVDII RAAILKRENL ELISRMAVEE TEIGKYEHKL IKNRLAAEKT PGTEDLTTEA    120
QTGDHGLTLV EYCPFGVIGA ITPTTNPTET IICNSISMIA GGNTVVFSPH PRAKKVSQLL    180
VKMLNKALME GGAPANLITM VEEPSIENTN KMIEHPGVRL LVATGGPAIV KKVLSSGKKA    240
IGAGAGNPPV VVDETADIEK AARDIVDGCS FDNNVPCIAE KEVFAVDSIC DYLIQNMKLN    300
GAYEIRDAET IERLDALVTN EKGGPKTSFV GKSAKYILDK MGIPADDSVK VIIMEVRRDH    360
HLVTEEMMMP ILPIVRVSDV DTAIEYAHDA EHGNRHTAMM HSKNVEKLSK MAKLLETTIF    420
VKNAPSYAGI GAGGEGHATF TIAGPTGEGL TSARSFCRKR RCVMSDAFSI R              471

SEQ ID NO: 91              moltype = AA   length = 469
FEATURE                    Location/Qualifiers
source                     1..469
                           mol_type = protein
                           organism = Fusobacterium varium
SEQUENCE: 91
MNLEANNMDE IVALIMKELK KTDIKTVCQS CENPKNGVFS SMDEAITAAK KAQEILFSSR     60
LEMREKIVAS IREVMKDYVL ELAELGVKET GMGRVADKAL KHQVTIEKTP GVEDLKAFAF    120
SGDDGLTVME LSPYGVIGAI TPSTNPSETI ICNSIGMISA GNSIVFAPHP GAKRTSIKTV    180
EIINEAVRKV GGPENLVVTI AEPSIENTNK MMANPDIKML VATGGPGVVK SVMSSGKKAI    240
GAGAGNPPVL VDETADIEKA AKDIVAGCSF DNNLPCIAEK EVVAVDSITD YLIFEMQKNG    300
AYLIKDKAVI ERLAGMVLKN GSPNRAYVGK DASYILKDLG INVGDEIRVI IAETDKEHPF    360
AVEELLMPIL PIIRVKNALE GIEVSKKLEH GLRHTAMIHS KNIDVLTKYA RDMETTILVK    420
NGPSFAGIGV GGEGHTTFTI AGPTGEGLTS AKSFARNRRC VLVGGLSIK                469

SEQ ID NO: 92              moltype = AA   length = 482
FEATURE                    Location/Qualifiers
source                     1..482
                           mol_type = protein
```

```
                        organism = Clostridium celatum
SEQUENCE: 92
MDDNTKLIQD IVAKVISEIG TKEIEEEACC GNGSCGGSCG CNKEKYVFED VDSAVAAAKK      60
AYKELKQLTI KDRENIITKI REKCLTYSER LSIMAVDETG MGKVEDKITK HVLVARKTPG     120
TEDLTTTAWS GDGGLTLVER GAFGVIAAIT PSTNPTATIF CNSIGMIAAG NSVVFAPHPA     180
AKSCSKFAVK LINEASIEVG GPENIVVTFE NPSIEITSAL MKHKDIPFIS ATGGPGVVTQ     240
ACSSGKRAIG AGAGNPPVLV DETADIKHAA KSIIAGATFD NNLPCIAEKE VVALDSICDE     300
LIEDMQKEGA YFLNSTELIN RLIDTVLIRK DGKVTLNRNF VGRDAKIILD AIGVYADDSV     360
KCIIFEGCKS NLLIVEELMM PILGIVRVKD FNTAVDVAVE LEHGNRHSAH IHSKRIDRLT     420
YFAREIDTAI FVKNAPSYSA LGVEAEGYPT FTIASRTGEG LSSAKTFSKS RRCIMKDALS     480
IK                                                                   482

SEQ ID NO: 93           moltype = AA  length = 462
FEATURE                 Location/Qualifiers
source                  1..462
                        mol_type = protein
                        organism = Clostridium sp.
SEQUENCE: 93
MSVNERMVQD IVQEVVAKMQ IASDVTGNHG VFQDMNAAIE AAKKTQKVVA RMSMDQREKI      60
ISNIRAKIKE HAEIFARMGV QETGMGNVGH KILKHQLVAE KTPGTEDIQT TAWSGDRGLT     120
LIEMGPFGVI GAITPCTNPS ETVLCNTIGM LAGGNTVVFN PHPAAIKTSI YAVNLINEAS     180
LEAGGPDNIA CTVENPTLES SNIMMKHKDI PLIAATGGPG VVTAVLSSGK RGIGAGAGNP     240
PALVDETADI RKAAEDIVNG CTFDNNLPCI AEKEIVAVDS IADELMHYMI SEQGCYLASK     300
EEQDALTEVV LKGGRLNRKC VGRDAKTLLG MIGVTVPDNI RCITFEGKPE HPLIAEELMM     360
PILGVVRAKD FDDAVEQAVW LEHGNRHSAH IHSKNVDNIT KYAKAIDTAI LVKNGPSYAA     420
IGFGGEGFCT FTIASRTGEG LTSASAFTKR RRCVMCDSLC IR                        462

SEQ ID NO: 94           moltype = AA  length = 462
FEATURE                 Location/Qualifiers
source                  1..462
                        mol_type = protein
                        organism = Lachnospiraceae bacterium
SEQUENCE: 94
MSVNEQMVQD IVQEVMAKMQ ITSDVSGSHG VFKDMNEAIA AAKKTQKIVG KMSMDQREKI      60
ISNIRTKIKE NAEIMARMGV QETGMGNVGH KILKHVLVAE KTPGTEDITT TAWSGDRGLT     120
LIEMGPFGVI GAITPCTNPS ETVLCNTIGM LAGGNTVVFN PHPAAIKTSI FAINLLNEAS     180
LEAGGPDNIA CTVEKPTLAS SDIMMKHKDI PLIAATGGPG VVTAVLSSGK RGIGAGAGNP     240
PALVDETADI RKAAEDIVNG CTFDNNLPCI AEKEIVAVDS IADELMYYMV SEQGCYKITK     300
EEQDALTAVV LKDGKLNRKC VGRDAKTLLG MIGVTVPDNI RCITFEGKPE HPLIAEELMM     360
PILGVVRAKD FDDAVEQAVW LEHGNRHSAH IHSKNVDNIT TYAKAIDTAI LVKNGPSYAA     420
LGFGGEGYCT FTIASRTGEG LTSASTFTKR RRCVMTDSLC IR                        462

SEQ ID NO: 95           moltype = AA  length = 463
FEATURE                 Location/Qualifiers
source                  1..463
                        mol_type = protein
                        organism = Lachnospiraceae bacterium
SEQUENCE: 95
MPVSESMVQD IVKEVVARMQ LSGSAGTAQH GVFTDMNQAI EAAKEAEAKV RCMTMDQREQ      60
IVSNIRRKTH ENAELLARMG VEETGMGNVG DKILKHHLLA DKTPGTEDIT TTAWSGDRGL     120
TLIEMGPFGV IGAITPCTNP SETVLCNSMG MIAAGNTVVF NPHPQAIKTS IFAINMVNEA     180
SLEAGGPDNV ACTVSKPTLE TSNIMMKHKD IPLIAATGGP GVVTAVLSSG KRGIGAGAGN     240
PPALVDETAD VRKAAADIVN GCTFDNNLPC IAEKEIVAVD SVADELMNYM ISEQGCYLIS     300
KEEQDKLTAT VITPKGLNRK CVGRDARTLL SMIGIQAPEN IRCIVFEGEK EHPLIAEELM     360
MPILGVVRAK DFDDAVEKAV WLEHGNRHSA HIHSKNVDNI TKYAKAIDTA ILVKNAPSYA     420
ALGFGGEGFC TFTIASRTGE GLTSASTFTK RRRCVMSDSL CIR                       463

SEQ ID NO: 96           moltype = AA  length = 462
FEATURE                 Location/Qualifiers
source                  1..462
                        mol_type = protein
                        organism = Ruminococcus sp.
SEQUENCE: 96
MPINENMVQE IVQEVMAKMQ IADAPTGKHG IFKEMNDAIE AAKKSQLIVK KMSMDQREKI      60
ITCIRKKIKE NAEVMARMGV EETGMGNVGD KILKHHLVAD KTPGTEVITT TAWSGDRGLT     120
LIEMGPFGVI GAITPCTNPS ETILCNTMGM LAGGNTVVFN PHPAAIKTSI YAINLLNEAS     180
LESGGPDNIA VTVEKPTLET SNVMMKHKDI PLIAATGGPG VVTAVLSSGK RGIGAGAGNP     240
PALVDETADI RKAATDIVNG CTFDNNLPCI AEKEIVAVSS IVDELMHYLV TENDCYLASK     300
EEQDKLTEVV LAGGKLNRKC VGRDARTLLS MIGVNAPANI RCIVFEGPKE HPLITTELMM     360
PILGVVRARD FDDAVEQAVW LEHGNRHSAH IHSKNIDNIT KYAKAIDTAI LVKNAPSYAA     420
LGFGGEGYCT FTIASRTGEG LTCASTFTKR RRCVMADSLC IR                        462

SEQ ID NO: 97           moltype = AA  length = 469
FEATURE                 Location/Qualifiers
source                  1..469
                        mol_type = protein
                        organism = Acetobacterium woodii
SEQUENCE: 97
MNIDTTGIEY IVKKVMAEID CAEEGGKPLK DGELGIFNDM ENAIDAAFIA QKSFMRASMA      60
```

```
FRSKIIAAMR AEMLKKENME MICQMAVEET GMGNYEHKLL KHELAATKTP GVEDLVADAF  120
TGDDGLTLIE QSPFGVIGAV SPSTNPSETI ICNGIGMLAG GNTVVFAPHP SAKKTSALVV  180
KLLNKAILEA GGPENLIVTT VKPTIDSANT MFASPKITML CATGGPGVVK SVLQSGKKAI  240
GAGAGNPPAL VDETADIEKA GKDIIDGCCF DNNLPCIAEK EVVVVEQVAD YLIFNMKKNG  300
AYELKDAQKI KELEELVIPG GRLSRDYVGR SAKVILKGIG IEVDDSVRVV IIETSKDHIF  360
AVEELMMPIL AIVRVKDVAE GIDLAVSLEH GNRHTAIMHS TNINNLTEMA KRVQTTIFVK  420
NGPSYAGIGV GGEGYTTFTI AGPTGEGLTS AKTFTRKRRC VLVGGFTIK             469

SEQ ID NO: 98           moltype = AA  length = 497
FEATURE                 Location/Qualifiers
source                  1..497
                        mol_type = protein
                        organism = Clostridium botulinum
SEQUENCE: 98
MNDFNMIDIE SIVKNIVKEL TGNEKGQGAI TTATAPKEAN PLVDIEKKIM GFMNTPTMPV  60
GEYGVFEDIN DAIEQAWLAE QEYRKVGLDK RTEIIEAFKA EVRKNVEEIS RRTFEETGMG  120
RYEDKILKNN LALDKTPGVE DLEAGVKTGD GGLTLYEMSP FGVIGAIAPS TNPTETIINN  180
GISMLAGGNT VVFSPHPGAK DVSVFIVQLI NKAIERINGP KNLIVTVKNP NIESTNIMLA  240
HPKVNMICAT GGPGIVKVAL SSGKKAIGAG AGNPPVVVDE TADIEKAAVD IIDGCSFDNN  300
LPCICEKEVI VVDKVADYLK TCMSKYCALE ITDKNMLAQL EKLVLTENGT INKQFVGKNA  360
DYIMSKLGVN IDPSIRVIFA EVGANHPFAV EELMMPILPV IRVRNVDEAI DLGVELEHGN  420
RHTAIMHSKH IDNLSKFAKA VQTTIFVKNA PSYAGIGYGA EGHGTFTIAG PTGEGLTSAR  480
TFTRKRRCVM VDNFSIK                                                497

SEQ ID NO: 99           moltype = AA  length = 497
FEATURE                 Location/Qualifiers
source                  1..497
                        mol_type = protein
                        organism = Clostridium botulinum
SEQUENCE: 99
MNDFNMIDIE SIVKNIVKEL TGNEKEQGAI ITATAPKEVN PLVDIEKKIM GFMNTPTMQA  60
GEYGVFEDIN DAIEQAWLAE QEYRKVGLDK RTEIIEVFKA EVRKNVEEIS RRTFEETGMG  120
RYEDKILKNN LALDKTPGVE DLEAGVKTGD GGLTLYEMSP FGVIGAIAPS TNPTETIINN  180
GISMLAGGNT VVFSPHPGAK DVSVFIIQLI NKAIERVNGP KNLIVTVRNP NIESTNIMLS  240
HPKVNMICAT GGPGIVKVAL SSGKKAVGAG AGNPPVVVDE TADIEKAAVD IIDGCSFDNN  300
LPCICEKEVI VVDKVTDYLK TCMSKYCALE ITDKNMLAQL EKLVLTENGT INKKFVGKNA  360
DYIMSKLGIN IDPSIRVIFA EVGANHPFAV EELMMPILPI IRVRNVDEAI ELGVELEHGN  420
RHTAIMHSKH IDNLSKFAKA VQTTIFVKNA PSYAGIGYGA EGHGTFTIAG PTGEGLTSAR  480
TFTRKRRCVM VDNFSIK                                                497

SEQ ID NO: 100          moltype = AA  length = 497
FEATURE                 Location/Qualifiers
source                  1..497
                        mol_type = protein
                        organism = Clostridium botulinum
SEQUENCE: 100
MNDFNMIDIE SIVKNIVKEL TGNEKEQGTI TTAAVPKEVN PLVDIEKKIM GFVNTPTMPI  60
GEHGVFEDIN DAIEQAWIAE QEYRKVGLDK RTEIIEAFKA EVRKNVEEIS RRTFEETGMG  120
RYEDKILKNN LALDKTPGVE DLEAGVKTGD GGLTLYEMSP FGVIGAIAPS TNPTETIINN  180
GISMLAGGNT VVFSPHPGAK DVSVFIIQLI NKAIERVNGP KNLIVTVRNP NIESTNIMLA  240
HPKVNMICAT GGPGIVKVAL SSGKKAIGAG AGNPPVVVDE TADIEKAAVD IIDGCSFDNN  300
LPCICEKEVI VVDKVADYLK TCMSKYCALE ITDKNMLAQL EKLVLTENGT INKKFVGKNA  360
DYIMSKLGVN IDPSIRVIFA EVEANHPFAV EELMMPILPV IRVRNVDEAI DLGVELEHGN  420
RHTAIMHSKH IDNLSKFAKA VQTTIFVKNA PSYAGIGYGA EGHGTFTIAG PTGEGLTSAR  480
TFTRKRRCVM VDNFSIK                                                497

SEQ ID NO: 101          moltype = AA  length = 462
FEATURE                 Location/Qualifiers
source                  1..462
                        mol_type = protein
                        organism = Eubacterium plexicaudatum
SEQUENCE: 101
MSVNDQMVQD IVRQVLANMR ISSDASGSRG VFSDMNEAVE AAKKAQAVIG KMPMDHREKI  60
ISSIRAKIME NAEILARMGV KETGMGNVGH KILKHQLVAE KTPGTEDITT KAWSGDRGLT  120
LIEMGPFGVI GAITPCTNPS ETILCNTIGM VAGGNTVVFN PHPAAIKTSI FAVNLVNEAS  180
VEAGGPDNIA CTVEHPTLDT SAIMMKHKDI HLIAATGGPG VVTAVLSSGK RGIGAGAGNP  240
PALVDETADI RKAAEDIVNG CTFDNNLPCI AEKEIVAVDS IADELMHYMI SEQGCYLASA  300
KEQEALISVV LKGGQLNRDC VGRDAKTLLG MIGVQAPDNI RCITFEGPKE HPLITEELMM  360
PILGVVRADS FEDAVEKAVW LEHGNRHSAH IHSKNVDHIT TYAKAIDTAI LVKNGPSYAA  420
IGFGGEGYCT FTIASRTGEG LTSASAFTKR RRCVMCDSLC IR                    462

SEQ ID NO: 102          moltype = AA  length = 467
FEATURE                 Location/Qualifiers
source                  1..467
                        mol_type = protein
                        organism = Thermosediminibacter oceani
SEQUENCE: 102
MVDEKVVEAI AKRIIEELNL CESGSSGGES REELGIFDNL DDAVEAASQA QKRFAALDLE  60
KREEIIQAIR EACLNNARYL AELTVNETGI GRVEDKIVKN ILAAKKTPGT EDLRPSCWTG  120
```

```
DHGLTLVEMA PVGVIGSITP VTNPVATVIN NSISMLAAGN AVVFNPHPSA KRSSNKAVEI    180
INEAIMKVGG PRHLVNSVAE PTIETAKALM AHPKVNLVSV TGGKAVVSEA LRSGKKVIGA    240
GAGNPPVVVD ETADIVKAAH DIYCGASFDN NLPCIAEKEL IAVEAVADML LERLAREGAY    300
ILRGKDVEKI TEVVFDENHR INKKLVGKDA SFILEQIGIQ VGKDVRLVVV PVNPEHPLVH    360
HEQLMPVLPF VRVPNIQEAV ELAVRAEGGN RHTAVMHSKN VDNMTNFARA IQTTIFVKNA    420
PSYAGIGFGG EGYATFTIAG PTGEGLTSAR TFTRQRRCVL VDAFRII                 467

SEQ ID NO: 103             moltype = AA  length = 479
FEATURE                    Location/Qualifiers
source                     1..479
                           mol_type = protein
                           organism = Clostridium clostridioforme
SEQUENCE: 103
MEISEKEVEA IVRSVLSGLG QKSFQAEALH VKDKMCSDGE DGIFELVEDA IEAASKAQKE     60
WVHRYKLKDR KRIIEAIRVT SRAHAESLAR MVHEETGMGR YEDKITKHMA VIDKTPGVEC    120
LVTDAISGDE GLMIEEPAPF GVIGAITPST NPTETMINNT ISMIAGGNAV VFNVHPGAKK    180
CCAYCLQILH RAIVENGGPK NLITMQREPD MDAVHKLTSS PHIRLMVGTG GMGMVHALLC    240
SGKRTIGAGA GNPPVVVDDT ADLSLAAREL YRGASFDNNL LCLAEKEVFV MDNVAEELVD    300
RLVGEGAYLL DDLQLKKITE LAMVNKDGKY EVNKKWVGKD AGKFLEAIGI QEHREPRLLI    360
CVTDRSHPFV KVEQLMPVLP IVRCGSFEKC VEWAVDTEAG NRHTASIFSK NVEHMTLFGK    420
EIETTIYTKN GATLKGIGIG GEGHTTMTIA GPTGEGLTCA RSFTRRRRCM LAEGGLRII    479

SEQ ID NO: 104             moltype = AA  length = 471
FEATURE                    Location/Qualifiers
source                     1..471
                           mol_type = protein
                           organism = Clostridium clostridioforme
SEQUENCE: 104
MDMDIKVIEQ MVEQALKEIK AEQPQKFTMP KAELYGVFKT MDEAIAASEE AQKKLLFSKI     60
SDRQKYVDVI RRTILKRENL EMISRLSVEE TEIGDYENLV IKNRLAAEKT PGTEDLLTEA    120
MTGDNGLTLV EYCPFGVIGA ITPTTNPTET IINNSISMIA GGNTVVFSPH PRAKKVSQMT    180
VKLLNKALTE SGAPENLITM VEEPSIENTN KMIENPSVRL LVATGGPSIV KKVLSSGKKA    240
IGAGAGNPPV VVDETADIVK AAKDIVGCS FDNNVPCIAE KEVFAVDSIC DYLIHNMKEN     300
GAYQITDPAL LEKLVTLVTN EKGGPKTSFV GKSARYILDK IGTADASVR VIIMEVPKEH    360
LLVQEEMMMP ILPVVRVCDV DTAIEYARQA EHGNRHTAMM HSRNVEKLSK MAKIMETTIF    420
VKNAPSYAGI GVGGEGYTTF TIAGPTGEGL TSPRAFCRKR KCVMTDAFSI R            471

SEQ ID NO: 105             moltype = AA  length = 472
FEATURE                    Location/Qualifiers
source                     1..472
                           mol_type = protein
                           organism = Ilyobacter polytropus
SEQUENCE: 105
MNLDANNLNN IVSLIMKELD KNNNIDDTGQ GCGEEGKNG IFSSMDTAVS KAKEAQVTLF     60
ASKLELRERI IKAIREDVRE AAAELAEIAV EETGMGRVDD KTLKHYVTVD KTPGVEDLRA    120
FAYSGDNGLT VMELSPYGVI GSITPSTNPS ETIVCNAIGM IAAGNSVVFA PHPGAKKTSL    180
RAVEILNKAV ARAGGPNNLV VTIFEPSIEN TNKMVKNPDI KMVVATGGPG VVKSVMSSGK    240
KAIGAGAGNP PVLVDETADI EKAAKDIVNG CSFDNNLPCI TEKEVVAVDS ITDYLIFEMQ    300
KNGAYLVQDS KTIKKLCEMV INDGSPNRAY VGKNASYILK DLGIDVGDEI KVIIVETDAG    360
HPLAVLEMLM PVLPIVRVKD ALEGIKVCKK LEDGLRHTAM IHSKNIDILT KYARDMETTI    420
LVKNGPSYSG IGVGGEGYTT FTIAGPTGEG LTSAKSFARN RRCALVGGLS IK           472

SEQ ID NO: 106             moltype = AA  length = 462
FEATURE                    Location/Qualifiers
source                     1..462
                           mol_type = protein
                           organism = Shuttleworthia satelles
SEQUENCE: 106
MADEQLVQNV VREVVARMQI SAPARGMHGV FSDMEEAIEA ARTAQQTVRL LPMDQREKII     60
GAIRRKTREN AEIILARMAVN ETGMGNVGDK ILKHLLVADK VPGTEDISTR AFSGDRGLTL    120
IEMGPFGVIG AITPCTNPSE TVLCNTIGML AGGNTVVFNP HPQAIKTTLF TIQMVNEASL    180
EAGGPDNIAC TVDAPTLATS EIMMKSPHIK LLVATGGPGV VTAVLSSGKR AIGAGAGNPP    240
ALVDETADIR KAAEDIVNGC TFDNNLPCIA EKEIVAVDSI ADELLHYMLT EQGCYQASEE    300
ELDRLTKAVM DEKGRLNRKA VGRSARKLLS MIGVEVDANI RCITFFGPKE HPLITTELMM    360
PILGIVRVKD FAEGLETAAW LEHGNKHSAH IHSKNVDRIT EYARRLDTTI TVKNGPSYAA    420
LGFGGESYCT FTIASRTGEG LTSARSFIKS RHCVMTDSLC VR                     462

SEQ ID NO: 107             moltype = AA  length = 472
FEATURE                    Location/Qualifiers
source                     1..472
                           mol_type = protein
                           organism = Clostridium beijerinckii
SEQUENCE: 107
MDVDVVLVEK LVRQAIEEVK NKNLLNLDKF ESVKNYGIFG TMDAAVEASF VAQKQLLNAS     60
MTDKQKYVDT IKATILKKEN LELISRMSVE ETEIGKYEHK LIKNRVAAEK TPGIEDLTTE    120
AMTGDNGLTL VEYCPFGVIG AITPTTNPTE TIICNSISMI AGGNTVVFSP HPRAKNVSIK    180
LVTMLNKALE EAGAPDNLIA TVKEPSIENT NIMMEHPKIR MLVATGGPAI VNKVMSTGKK    240
AIGAGAGNPP VVVDETADIE KAAIDIVNGC SFDNNVPCIA EKEVFAVDQI CDYLIHYMKL    300
NGAYEIKDRD LIQKLLDLVT NENGGPKVSF VGKSAPYILN KLGISVDENI KVIIMEVEKN    360
```

```
HHFVLEEMMM PILPIVRTKD VDEAIECAYV AEHGNRHTAI MHSKNVDKLT KMARLLETTI    420
FVKNAPSYAG IGVGGEGTTT FTIAGPTGEG LTTARSFCRK RRCVMVDAFN IR           472

SEQ ID NO: 108              moltype = AA  length = 471
FEATURE                     Location/Qualifiers
source                      1..471
                            mol_type = protein
                            organism = Clostridium clostridioforme
SEQUENCE: 108
MDMDIKVIEQ MVEQALKEIK AEQPQKFTMP KAELYGVFKT MDEAIAASEE AQKKLLFSKI    60
SDRQKYVDVI RRTILKRENL EMISRLSVEE TEIGDYEHKL IKNRLAAEKT PGTEDLLTEA   120
MTGDNGLTLV EYCPFGVIGA ITPTTNPTET IINNSISMIA GGNTVVFSPH PRAKKVSQMT   180
VKLLNKALTE SGAPENLITM VEEPSIENTN KMIENPSVRL LVATGGPSIV KKVLSSGKKA   240
IGAGAGNPPV VVDETADIVK AAKDIVDGCS FDNNVPCIAE KEVFAVDSIC DYLIHNMKEN   300
GAYQITDPAL LEKLVTLVTN EKGGPKTSFV GKSARYILDK LGITADASVR VIIMEVPKEH   360
LLVQEEMMMP ILPVVRVCDV DTAIEYARQA EHGNRHTAMM HSRNVEKLSK MAKIMETTIF   420
VKNAPSYAGI GVGGEGYTTF TIAGPTGEGL TSPKAFCRKR KCVMTDAFSI R            471

SEQ ID NO: 109              moltype = AA  length = 473
FEATURE                     Location/Qualifiers
source                      1..473
                            mol_type = protein
                            organism = Clostridium sp.
SEQUENCE: 109
MKLDDKLIEQ VARLVMEEMK SGSAAACEEN GTCGDSYGIF DSMDDAVQAS EAAQRKYLFS    60
TMEDRQKYVD VIRQTVLEPE MLQKISRMAV EETGMGNYEH KLIKNRLAAE KSPGTEDLVT   120
EAMTGDRGLT LVEYCPFGVI GAVTPATNPT ETIICNSIAM LAGGNTVVFS PHPRAKNVTH   180
VLVTALNQAL EKVGAPTNLI VTVREPSVEN TNLMIKHPKI RVLVATGPGP GIVKMVMSTGK  240
KAIGAGAGNP PVVVDETADI EKAAKDIVDG CSFDNNLPCI AEKEVIAVDT IADCLIWHMK   300
RVGAFELKEE SAISRLLQLV TNEKGGPKVE FVGKSAPYIL NKLGISGGEN ARVILMETQK   360
DHPFVMEELM MPILPIVRAA DVDEAIEIAL VAERGNRHTA MMHSKNVDKL TKMAKLLQTT   420
IFVKNAPSYA GIGVGGEGCT TFTIAGPTGE GLTTARSFCR KRRCVMSDAL HIR          473

SEQ ID NO: 110              moltype = AA  length = 471
FEATURE                     Location/Qualifiers
source                      1..471
                            mol_type = protein
                            organism = Clostridium bolteae
SEQUENCE: 110
MDMDIKVIEQ LVEQALKEIK AEQPLKFTAP KLERYGVFKT MDEAIAASEE AQKKLLFSKI    60
SDRQKYVDVI RSTIIKRENL ELISRLSVEE TEIGDYEHKL IKNRLAAEKT PGTEDLLTEA   120
ITGDNGLTLV EYCPFGVIGA ITPTTNPTET IINNSISMIA GGNTVVFSPH PRAKKVSQMT   180
VKMLNKALID NGAPPNLITM VEEPSIENTN KMIDNPSVRL LVATGGPSIV KKVLSSGKKA   240
IGAGAGNPPV VVDETADIDK AAKDIVDGCS FDNNVPCIAE KEVFAVDSIC DYLIHHMKEN   300
GAYQITDPML LEQLVALVTT EKGGPKTSFV GKSARYILDK LGITVDASVR VIIMEVPKDH   360
LLVQEEMMMP ILPVVRVSDV DTAIEYAHQA EHGNRHTAMM HSKNVEKLSK MAKIMETTIF   420
VKNAPSYAGI GVGGEGYTTF TIAGPTGEGL TSPRTFCRKR KCVMTDAFSI R            471

SEQ ID NO: 111              moltype = AA  length = 468
FEATURE                     Location/Qualifiers
source                      1..468
                            mol_type = protein
                            organism = Eubacterium hallii
SEQUENCE: 111
MNIDVELIEK VVKKVLNDVE TGSSESEYGY GIFDTMDEAI EASAKAQKEY MNHSMADRQR    60
YVEGIREVVC TKENLEYMSK LAVEESGMGA YEYKVIKNRL AAVKSPGVED LTTEALSGDD   120
GLTLVEYCPF GVIGAIAPTT NPTETVICNS IAMLAGGNTV VFSPHPRSKG VSIWLIKKLN   180
AKLEELGAPR NLIVTVKEPS IENTNIMMNH PKVRMLVATG GPGIVKAVMS TGKKAIGAGA   240
GNPPVVVDET ADIEKAAKDI VNGCSFDNNL PCIAEKEVIA PQIADYLIF NMKNNGAYEV    300
KDPEIIEKMV DLVTKDRKKP AVNFVGKSAQ YILDKVGIKV GPEVKCIIME APKDHPFVQI   360
ELMMPILPIV RVPNVDEAID FAVEVEHGNR HTAMMHSKNV DKLTKMAKEI ETTIFVKNGP   420
SYAGIGVGGM GYTTFTIAGP TGEGLTSAKS FCRKRRCVLQ DGLHIRMK                468

SEQ ID NO: 112              moltype = AA  length = 467
FEATURE                     Location/Qualifiers
source                      1..467
                            mol_type = protein
                            organism = Halanaerobium saccharolyticum
SEQUENCE: 112
MKIKENELDK IVNQVISSLN NKQNSNDFNT KINYGIFSTM DEAIAEAVKA QACLQLNYST    60
EAREKIIKSI RKNVSKHVEK ISEMAVEETD MGRIEDKIIK NNLAINKTPG TEDLRTEAFS   120
GKKGLTIVEE APFGVICSIA PVTNPTETII SNAISMIASC NGVVFNSHPG AKKVSKYIIE   180
VLNKVIMEAG GPENLLTAVN EPTLQTVESC MRDDRIAMIV ATGGPGVVNA ALSSGKKAIG   240
AGAGNPPVLV DDTVDLKRVA KDIINGASFD NNLPCTSEKA IVALESIADS LLNEMTNQNA   300
QLVHDIKALE RVILNDDGSI NKALVGKDAA FILNKAGLKA KSEDLRLVIV DVDLRHPFVQ   360
KEQLMPVIPL VRAKNFNEAM EMGVDIEEGN RHTAIIHSKN VDNLTKFAKK IETTIYVKNA   420
PSYAGIGAGG EGYATFTIAG PTGEGLTSAR SFTRKRRCVL VDGFSII                 467

SEQ ID NO: 113              moltype = AA  length = 469
```

```
FEATURE                 Location/Qualifiers
source                  1..469
                        mol_type = protein
                        organism = Eubacterium limosum
SEQUENCE: 113
MNIDTTGIEY IVKKVMDQID YAEETGAPVV DGKDGVFQTM DAAIEAAAVA QKEYMKKPLA    60
LRRQMIAAMR EIMLKKENIE TICAMVVEES GMGNYEHKLA KHRLATTGTP GVEDLLTEAW   120
AGDDGCTLLE LSPFGVIGAI TPTTNPNETI VNNSIGMLAA GNAVVFSPHP KALKTSFLCI   180
KLLNEAIVSV GGPRNLIVTC ANPTIEAANE MMVHPKIRML VATGGPGVVK AVLSSGKKAI   240
GAGAGNPPAL VDETADIEKA AKDIIDGCSF DNNLPCIAEK EVVVVDQVAD YLIFNMKKNG   300
AYEITDKKAI DALADLVCPE GRLSRDFVGK SAKYIAAAAG LDVPEDTRVL ICETSKDHLL   360
AVEELMMPIL PIVRVANVDE GIDVAVELEH GNRHTAIMHS KNVDKLTEMA KRIQTTIFVK   420
NGPSYAGIGF GGEGYPTFTI AGPTGEGLTS AKSFARRRRC VLVGGFDIK              469

SEQ ID NO: 114          moltype = AA   length = 466
FEATURE                 Location/Qualifiers
source                  1..466
                        mol_type = protein
                        organism = Thermoanaerobacter sp.
SEQUENCE: 114
MIDENLVVTI TKKILNEINL KEAEEKKEKD NPDLGIFNDV NEAVECAKEA QKKFALMDLE    60
KREEIIAAIR EACVNNARLL AEIACSETGR GRVEDKVAKN ILAAKKTPGT EDLKPTAWTG   120
DRGLTLVEMA PVGVIASITP VTNPTATIIN NTISMLAAGN AVVFNPHPSA KKTSNKAVEI   180
INEAILKVGA PNGLVCSINN PTIQTAQKLM EHPEVNMVVV TGGKAVVQTA LRCGKKVIGA   240
GAGNPPVVVD ETADIVKAAH DIACGASFDN NLPCIAEKEI IAVERIADTL LERMKREGAY   300
VLHGKDIDRM TELIFQGGAI NKDLIGRDAH FILSQIGIET GKDIRLVVMP VDVSHPLVYH   360
EQLMPVIPFV TVPTVEEAIN LAVKAEGGNR HTAMMHSKNV ENMTAFARAI QTTIFVKNAP   420
SYAGIGFGGE GYTTFTIAGP TGEGLTSART FTRQRRCVLV DAFRIV                 466

SEQ ID NO: 115          moltype = AA   length = 529
FEATURE                 Location/Qualifiers
source                  1..529
                        mol_type = protein
                        organism = Rhodospirillum rubrum
SEQUENCE: 115
MNDGQIAAAV AKVLEAYGVP ADPSAAAPAP AAPVAPAAPT AGSVSEMIAR GIAKASSDDQ    60
IAQIVAKVVG DYSAQAAKPA VVPGAAASTE AGDGVFDTMD AAVDAAVLAQ QQYLLCSMTD   120
RQRFVDGIRE VILQKDTLEL ISRMAAEETG MGNYEHKLIK NRLAAEKTPG TEDLTTEAFS   180
GDDGLTLVEY SPFGAIGAVA PTTNPTETII CNSIGMLAAG NSVIFSPHPR ATKVSLLTVK   240
LINQKLACLG APANLVVTVS KPSVENTNAM MAHPKIRMLV ATGGPGIVKA VMSTGKKAIG   300
AGAGNPPVVV DETADIEKAA LDIINGCSFD NNLPCIAEKE IIAVAQIADY LIFSMKKQGA   360
YQITDPAVLR KLQDLVLTAK GGPQTSCVGK SAVWLLNKIG IEVDSSVKVI LMEVPKEHPF   420
VQEELMMPIL PLVRVSDVDE AIAVAIEVEH GNRHTAIMHS TNVRKLTKMA KLIQTTIFVK   480
NGPSYAGLGV GGEGYTTFTI AGPTGEGLTS AKSFARKRKC VMVEALNIR              529

SEQ ID NO: 116          moltype = AA   length = 466
FEATURE                 Location/Qualifiers
source                  1..466
                        mol_type = protein
                        organism = Eubacterium yurii
SEQUENCE: 116
MNPELLEDVV RQVLSEMKLE SSKMVDIYNY GIFDSVDDAI NASEIAQRQL FECSVQKRNE    60
YVNAIRQIIL KKDNLEMMSR DAVEETGIGR YEDKILKNKL AAEKTPGMED LITRAVSGQD   120
GLTLEEYCPF GVIGSITPTT NPTETFISNS ISMIVGGNTV VFSPHPRAKN TSIKLVKLMN   180
KALEQVGAPR NLISMVKEPS IENTNLMMNH PKIKMLVATG GPAIVKTVLS SGKKAIGAGA   240
GNPPVVVDET ADIEKAAKDI VAGSSFDNNV PCIAEKEVFA VESICDQLIY HMKKNGAYEI   300
TSYEMIEKLD KLVSQENGKP NTDFVGKSAK YILEKLGISV DDSIRLIICR TNKDHHLVQE   360
EMLMPILPIV SVSDVDVAIE YAYEAEHRNR HTAIMHSRNV EKLSKMAKKL EATIFVKNAP   420
SYAGIGVGGE GYTTFTIAGP TGEGLTSPKS FCRVRRCTMS DSFSIR                 466

SEQ ID NO: 117          moltype = AA   length = 466
FEATURE                 Location/Qualifiers
source                  1..466
                        mol_type = protein
                        organism = Eubacterium sp.
SEQUENCE: 117
MNPELLEDVV RQVLSEMKLE SSKMVDIYNY GIFDSVDDAI NASEIAQRQL FECSVQKRNE    60
YVNAIRQIIL KKDNLEMMSR DAVEETGIGR YEDKILKNKL AAEKTPGMED LITRAVSGQD   120
GLTLEEYCPF GVIGSITPTT NPTETFISNS ISMIVGGNTV VFSPHPRAKN TSIKLVKLMN   180
KALEQVGAPR NLISMVKEPS IENTNLMMNH PKIKMLVATG GPAIVKTVLS SGKKAIGAGA   240
GNPPVVVDET ADIEKAAKDI VAGSSFDNNV PCIAEKEVFA VESICDQLIY HMKKNGAYEI   300
TSYEMIEKLD KLVSQENGKP NTDFVGKSAK YILEKLGINV DDSIRLIICR TNKDHHLVQE   360
EMLMPILPIV SVSDVDVAIE YAYEAEHRNR HTAIMHSRNV EKLSKMAKKL EATIFVKNAP   420
SYAGIGVGGE GYTTFTIAGP TGEGLTSPKS FCRVRRCTMS DSFSIR                 466

SEQ ID NO: 118          moltype = AA   length = 532
FEATURE                 Location/Qualifiers
source                  1..532
                        mol_type = protein
```

```
                           organism = Vibrio sp.
SEQUENCE: 118
MNEQEIAHAV ENVLSKYTNV TAQNAEPVSY SSNASLENIV SQALAGNMVK QPETQTAPDL     60
NSNIENIVSQ ILAENQAKPQ SVQCQSANHG TTEYLGCFAS MEEAISAASH AQVQYRHCTM    120
GDRASFVKGI REVFTQDDVL EKISRMAVEE TGMGNYADKL TKNRIAATKT PGIEDLTTSA    180
LSGDSGLTLT EFSAYGVIGS ITPTTNPTET IINNSIGMLA AGNTVVYSPH PRSRNVSLVA    240
VDLINRKLAE LGAPANLVVT VLEPSIDNTN AMMNDPRVNM LVATGGPSIV KTVMSTGKKA    300
IGAGAGANPPA VVDETANIEK AAKDIINGCA FDNNLPCIAE KEVIVVNEVA DYLIHCMKKS   360
GAYLLCDKQK IQQLQSLVLN EKGTGPNTSF VGKGARYILD KLNIQVSDDI KVILIETERN    420
HPFVVHELMM PILPVVRVEN VDEAIDLAIK VEHGNRHTAI MHSTNVEKLS KMARLIQTTI    480
FVKNGPSYSG IGVGGEGHTT FTIAGPTGEG ITSARSFARY RRCVMVEALN IR            532

SEQ ID NO: 119             moltype = AA  length = 467
FEATURE                    Location/Qualifiers
source                     1..467
                           mol_type = protein
                           organism = Eubacteriaceae bacterium
SEQUENCE: 119
MNAELLQDVV RQVLSEMKLE SSNILSNEYN YGIFDDMEAA INASETAQRK LFECSVQQRN     60
EFANVIRKEI LKKDNLEMIS RDAVEETEIG RFEDKILKNK VAAEKTPGME DLTTRAISGK    120
DGLMIEEYCP FGVIGSITPT TNPTETLINN SISMIVGGNT VVFSPHPRAK NVSIKLVKMM    180
NKALEEHGAP RNMITMVKEP SIENTNLMMS NPKVKLLVAT GGPFIVNTVL SSGKKAIGAG    240
AGNPPVVVDE TADIEKAAID IVSGASFDNN VPCIAEKEVF AVDSISDMLI YHMKKNGAYE    300
IVSQDMIEKL DKLVSQENGK PKTEFVGKSA KYILEKLGIY VDDSIRLIIC RTSKNHHLVQ    360
EEMLMPILPI VSVSDVDIAI EYAYEAEHGN RHTAIMHSKN VEKLSKMAKK LEATIFVKNA    420
PSYSGIGVGG EGHTTFTIAG PTGEGITSAK SFCRIRRCVM HDSFSIR                  467

SEQ ID NO: 120             moltype = AA  length = 473
FEATURE                    Location/Qualifiers
source                     1..473
                           mol_type = protein
                           organism = Propionibacterium propionicum
SEQUENCE: 120
MKIDPAQLEA TIREVLAAML PGNDNQTEAP ATQQEAPGDG VFADMDSAVE AAHLAQREYL     60
SHPMADRRRY VAAIREAMLA PEALDYMSEQ AVAQSGMGDV GHKYLKNKVA AAETPGVEDL    120
VTEAWSGDDG LTTIEYSPYG VIGAITPTTN PTETITCNSI GMLAAGNAVV FSPHPRVAKL    180
SCWQVRRINR ALRAAGAPDN LVVTVTAPSL ENTNAMMAHP KVRMLVATGG PGIVKAVLSS    240
GKKAIGAGAG NPPAVVDETA DIEHAAKCIV DGASFDNNLP CTAEKEIIAV DSIADMLKFC    300
MIKHGAYEAT ASEVAELEKL LVNGDKPRTE WVGKPAAKIL EAIGVTPPPG VRLIVCEASA    360
THPFVVHELM MPVLGLVRVP DVDAAIDLAV ELEHGNRHTA VMHSLNVSKL TKMGKLIQTT    420
IFVKNGPSYN GIGIGGEGYP TFTIAGPTGE GLTSARSFTR KRRCVLVGDL NVR           473

SEQ ID NO: 121             moltype = AA  length = 467
FEATURE                    Location/Qualifiers
source                     1..467
                           mol_type = protein
                           organism = Eubacteriaceae bacterium
SEQUENCE: 121
MNAELLQDVV RQVLSEMKLE SSNILSNEYN YGIFDDMEAA INASETAQRK LFECSVQQRN     60
EFANVIRKEI LKKDNLEMIS RDAVEETEIG RFEDKILKNK VAAEKTPGME DLTTRALTGK    120
DGLMIEEYCP FGVIGSITPT TNPTETLINN SISMIVGGNT VVFSPHPRAK NVSIKLVKMM    180
NKALEEYGAP RNMITMVKEP SIENTNLMMS NPKVKLLVAT GGPFIVNTVL SSGKKAIGAG    240
AGNPPVVVDE TADIEKAAID IVSGASFDNN VPCIAEKEVF AVDSISDMLI YHMKKNGAYE    300
IVSQDMIEKL DKLVSQENGK PKTEFVGKSA KYILEKLGIY VDDSIRLIIC RTSKNHHLVQ    360
EEMLMPILPI VSVSDVDIAI EYAYEAEHGN RHTAIMHSKN VEKLSKMAKK LEATIFVKNA    420
PSYSGIGVGG EGHTTFTIAG PTGEGITSAK SFCRIRRCVM HDSFSIR                  467

SEQ ID NO: 122             moltype = AA  length = 467
FEATURE                    Location/Qualifiers
source                     1..467
                           mol_type = protein
                           organism = Eubacteriaceae bacterium
SEQUENCE: 122
MNAELLQDVV RQVLSEMKLE SSNILSNEYN YGIFDDMEAA INASETAQRK LFECSVQQRN     60
EFANVIRREV LKKDNLEMIS RDAVEETEIG RFEDKILKNK VAAEKTPGME DLTTRALTGK    120
DGLMIEEYCP FGVIGSITPT TNPTETLINN SISMIVGGNT VVFSPHPRAK NVSIKLVKMM    180
NKALEEYGAP RNMITMVKEP SIENTNLMMS NPKVKLLVAT GGPFIVNTVL SSGKKAIGAG    240
AGNPPVVVDE TADIEKAAID IVSGASFDNN VPCIAEKEVF AVDSISDMLI YHMKKNGAYE    300
IVSQDMIEKL DKLVSQENGK PKTEFVGKSA KYILEKLGIY VDDSIRLIIC RTSKNHHLVQ    360
EEMLMPILPI VSVSDVDIAI EYAYEAEHGN RHTAIMHSKN VEKLSKMAKK LEATIFVKNA    420
PSYSGIGVGG EGHTTFTIAG PTGEGITSAK SFCRIRRCVM HDSFSIR                  467

SEQ ID NO: 123             moltype = AA  length = 468
FEATURE                    Location/Qualifiers
source                     1..468
                           mol_type = protein
                           organism = Clostridium beijerinckii
SEQUENCE: 123
MNKDTLIPTT KDLKVKTNGE NINLKNYKDN SSCFGVFENV ENAISSAVHA QKILSLHYTK     60
```

```
EQREKIITEI RKAALQNKEV LATMILEETH MGRYEDKILK HELVAKYTPG TEDLTTTAWS    120
GDNGLTVVEM SPYGVIGAIT PSTNPTETVI CNSIGMIAAG NAVVFNGHPC AKKCVAFAVE    180
MINKAIISCG GPENLVTTIK NPTMESLDAI IKHPSIKLLC GTGGPGMVKT LLNSGKKAIG    240
AGAGNPPVIV DDTADIEKAG RSIIEGCSFD NNLPCIAEKE VFVFENVADD LISNMLKNNA    300
VIINEDQVSK LIDLVLQKNN ETQEYFINKK WVGKDAKLFL DEIDVESPSN VKCIICEVNA    360
NHPFVMTELM MPILPIVRVK DIDEAIKYAK IAEQNRKHSA YIYSKNIDNL NRFEREIDTT    420
IFVKNAKSFA GVGYEAEGFT TFTIAGSTGE GITSARNFTR QRRCVLAG                468

SEQ ID NO: 124         moltype = AA  length = 20
FEATURE                Location/Qualifiers
source                 1..20
                       mol_type = protein
                       organism = Clostridium saccharoperbutylacetonicum
SEQUENCE: 124
LQKNNETQEY SINKKWVGKD                                                20

SEQ ID NO: 125         moltype = AA  length = 15
FEATURE                Location/Qualifiers
source                 1..15
                       mol_type = protein
                       organism = Lactobacillus brevis
SEQUENCE: 125
IGPKGAPDRK FVGKD                                                     15

SEQ ID NO: 126         moltype = AA  length = 14
FEATURE                Location/Qualifiers
source                 1..14
                       mol_type = protein
                       organism = Clostridium phytofermentans
SEQUENCE: 126
ITPKGLNRNC VGKD                                                      14

SEQ ID NO: 127         moltype = AA  length = 18
FEATURE                Location/Qualifiers
source                 1..18
                       mol_type = protein
                       organism = Clostridium saccharoperbutylacetonicum
SEQUENCE: 127
SFAGVGYEAE GFTTFTIA                                                  18

SEQ ID NO: 128         moltype = AA  length = 22
FEATURE                Location/Qualifiers
source                 1..22
                       mol_type = protein
                       organism = Lactobacillus brevis
SEQUENCE: 128
TYCGTGVATN GAHSGASALT IA                                             22

SEQ ID NO: 129         moltype = AA  length = 18
FEATURE                Location/Qualifiers
source                 1..18
                       mol_type = protein
                       organism = Clostridium phytofermentans
SEQUENCE: 129
SYAAIGFGGE GFCTFTIA                                                  18
```